US012558149B2

(12) United States Patent
Shelton, IV

(10) Patent No.: US 12,558,149 B2
(45) Date of Patent: Feb. 24, 2026

(54) SURGICAL END EFFECTOR JAW AND ELECTRODE CONFIGURATIONS

(71) Applicant: Cilag GmbH International, Zug (CH)

(72) Inventor: Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 1330 days.

(21) Appl. No.: 17/030,989

(22) Filed: Sep. 24, 2020

(65) Prior Publication Data

US 2021/0068889 A1     Mar. 11, 2021

Related U.S. Application Data

(63) Continuation of application No. 15/392,265, filed on Dec. 28, 2016, now abandoned, which is a
(Continued)

(51) Int. Cl.
*A61B 18/14*          (2006.01)
*A61B 18/12*          (2006.01)
(Continued)

(52) U.S. Cl.
CPC ...... *A61B 18/1442* (2013.01); *A61B 18/1206* (2013.01); *A61B 34/37* (2016.02);
(Continued)

(58) Field of Classification Search
CPC . A61B 18/1442; A61B 18/1206; A61B 34/37; A61B 34/71; A61B 90/10;
(Continued)

(56) References Cited

U.S. PATENT DOCUMENTS

| 2,366,274 A | 1/1945 | Luth et al. |
| 2,458,152 A | 1/1949 | Eakins |
| | (Continued) | |

FOREIGN PATENT DOCUMENTS

| CN | 201223445 Y | 4/2009 |
| CN | 102274074 A | 12/2011 |
| | (Continued) | |

OTHER PUBLICATIONS

International Search Report, Application No. PCT/US2013/046777, dated Oct. 1, 2013 (4 pages).
(Continued)

*Primary Examiner* — Michael F Peffley
*Assistant Examiner* — Bo Ouyang
(74) *Attorney, Agent, or Firm* — Lempia Summerfield Katz LLC

(57) ABSTRACT

A surgical end effector may comprise first and second jaw members. The second jaw member may comprise an offset proximal supply electrode that is positioned to contact an opposing member of the first jaw member when the first and second jaw members are in the closed position. The second jaw member may also comprise a distal supply electrode that is positioned distal of the offset proximal electrode and is aligned with a conductive surface of the first jaw member when the first and second jaw members are in the closed position. When the first and second jaw members are in the closed position, the proximal supply electrode may be in contact with the opposing member and the distal supply electrode is not in contact with the conductive surface of the first jaw member.

21 Claims, 128 Drawing Sheets

Related U.S. Application Data continuation of application No. 13/536,393, filed on Jun. 28, 2012, now abandoned.

(51) Int. Cl.

| | |
|---|---|
| *A61B 34/00* | (2016.01) |
| *A61B 34/37* | (2016.01) |
| *A61B 90/10* | (2016.01) |
| *A61B 90/50* | (2016.01) |
| *A61B 17/00* | (2006.01) |
| *A61B 18/00* | (2006.01) |
| *A61B 34/30* | (2016.01) |

(52) U.S. Cl.
CPC .............. *A61B 34/71* (2016.02); *A61B 90/10* (2016.02); *A61B 90/50* (2016.02); *A61B 2017/00477* (2013.01); *A61B 2018/00083* (2013.01); *A61B 2018/00345* (2013.01); *A61B 2018/00619* (2013.01); *A61B 2018/00982* (2013.01); *A61B 2018/00988* (2013.01); *A61B 2018/1226* (2013.01); *A61B 2018/126* (2013.01); *A61B 2018/1455* (2013.01); *A61B 2018/1467* (2013.01); *A61B 2034/254* (2016.02); *A61B 2034/303* (2016.02); *A61B 2034/306* (2016.02); *A61B 2034/743* (2016.02); *A61B 2090/506* (2016.02)

(58) Field of Classification Search
CPC .............. A61B 90/50; A61B 2034/254; A61B 2034/303; A61B 2034/306; A61B 2034/743; A61B 2090/506; A61B 2018/00477; A61B 2018/00083; A61B 2018/00345; A61B 2018/00619; A61B 2018/00982; A61B 2018/0988; A61B 2018/1266; A61B 2018/126; A61B 2018/1455; A61B 2018/1467
See application file for complete search history.

(56) References Cited

U.S. PATENT DOCUMENTS

| | | | |
|---|---|---|---|
| 2,510,693 | A | 6/1950 | Green |
| 2,867,039 | A | 1/1959 | Zach |
| 3,166,971 | A | 1/1965 | Stoecker |
| 3,525,912 | A | 8/1970 | Wallin |
| 3,580,841 | A | 5/1971 | Cadotte et al. |
| 3,703,651 | A | 11/1972 | Blowers |
| 3,777,760 | A | 12/1973 | Essner |
| 4,005,714 | A | 2/1977 | Hiltebrandt |
| 4,034,762 | A | 7/1977 | Cosens et al. |
| 4,058,126 | A | 11/1977 | Leveen |
| 4,220,154 | A | 9/1980 | Semm |
| 4,237,441 | A | 12/1980 | van Konynenburg et al. |
| 4,281,785 | A | 8/1981 | Brooks |
| 4,304,987 | A | 12/1981 | van Konynenburg |
| 4,463,759 | A | 8/1984 | Garito et al. |
| 4,492,231 | A | 1/1985 | Auth |
| 4,535,773 | A | 8/1985 | Yoon |
| 4,545,926 | A | 10/1985 | Fouts, Jr. et al. |
| 4,550,870 | A | 11/1985 | Krumme et al. |
| 4,582,236 | A | 4/1986 | Hirose |
| 4,617,927 | A | 10/1986 | Manes |
| 4,633,874 | A | 1/1987 | Chow et al. |
| 4,735,603 | A | 4/1988 | Goodson et al. |
| 4,761,871 | A | 8/1988 | O'Connor et al. |
| 4,830,462 | A | 5/1989 | Karny et al. |
| 4,849,133 | A | 7/1989 | Yoshida et al. |
| 4,860,745 | A | 8/1989 | Farin et al. |
| 4,878,493 | A | 11/1989 | Pasternak et al. |
| 4,910,389 | A | 3/1990 | Sherman et al. |
| 4,920,978 | A | 5/1990 | Colvin |
| 4,936,842 | A | 6/1990 | D'Amelio et al. |

| | | | |
|---|---|---|---|
| 5,061,269 | A | 10/1991 | Muller |
| 5,099,840 | A | 3/1992 | Goble et al. |
| 5,104,025 | A | 4/1992 | Main et al. |
| 5,106,538 | A | 4/1992 | Barma et al. |
| 5,108,383 | A | 4/1992 | White |
| 5,156,633 | A | 10/1992 | Smith |
| 5,160,334 | A | 11/1992 | Billings et al. |
| 5,190,541 | A | 3/1993 | Abele et al. |
| 5,196,007 | A | 3/1993 | Ellman et al. |
| 5,205,459 | A | 4/1993 | Brinkerhoff et al. |
| 5,217,460 | A | 6/1993 | Knoepfler |
| 5,234,428 | A | 8/1993 | Kaufman |
| 5,258,004 | A | 11/1993 | Bales et al. |
| 5,258,006 | A | 11/1993 | Rydell et al. |
| 5,285,945 | A | 2/1994 | Brinkerhoff et al. |
| 5,290,286 | A | 3/1994 | Parins |
| 5,293,863 | A | 3/1994 | Zhu et al. |
| 5,309,927 | A | 5/1994 | Welch |
| 5,318,564 | A | 6/1994 | Eggers |
| 5,318,589 | A | 6/1994 | Lichtman |
| 5,330,471 | A | 7/1994 | Eggers |
| 5,339,723 | A | 8/1994 | Huitema |
| 5,342,359 | A | 8/1994 | Rydell |
| 5,361,583 | A | 11/1994 | Huitema |
| 5,383,860 | A | 1/1995 | Lau |
| 5,383,874 | A | 1/1995 | Jackson et al. |
| 5,383,880 | A | 1/1995 | Hooven |
| 5,383,888 | A | 1/1995 | Zvenyatsky et al. |
| 5,387,207 | A | 2/1995 | Dyer et al. |
| 5,389,098 | A | 2/1995 | Tsuruta et al. |
| 5,395,033 | A | 3/1995 | Byrne et al. |
| 5,395,312 | A | 3/1995 | Desai |
| 5,395,363 | A | 3/1995 | Billings et al. |
| 5,395,364 | A | 3/1995 | Anderhub et al. |
| 5,396,900 | A | 3/1995 | Slater et al. |
| 5,403,312 | A | 4/1995 | Yates et al. |
| 5,417,709 | A | 5/1995 | Slater |
| 5,428,504 | A | 6/1995 | Bhatla |
| 5,429,131 | A | 7/1995 | Scheinman et al. |
| 5,443,463 | A | 8/1995 | Stern et al. |
| 5,445,638 | A | 8/1995 | Rydell et al. |
| 5,451,227 | A | 9/1995 | Michaelson |
| 5,458,598 | A | 10/1995 | Feinberg et al. |
| 5,465,895 | A | 11/1995 | Knodel et al. |
| 5,472,443 | A | 12/1995 | Cordis et al. |
| 5,476,479 | A | 12/1995 | Green et al. |
| 5,480,409 | A | 1/1996 | Riza |
| 5,484,436 | A | 1/1996 | Eggers et al. |
| 5,486,189 | A | 1/1996 | Mudry et al. |
| 5,496,317 | A | 3/1996 | Goble et al. |
| 5,504,650 | A | 4/1996 | Katsui et al. |
| 5,509,922 | A | 4/1996 | Aranyi et al. |
| 5,511,556 | A | 4/1996 | DeSantis |
| 5,520,704 | A | 5/1996 | Castro et al. |
| 5,522,839 | A | 6/1996 | Pilling |
| 5,524,643 | A | 6/1996 | Faries, Jr. et al. |
| 5,529,235 | A | 6/1996 | Boiarski et al. |
| 5,531,744 | A | 7/1996 | Nardella et al. |
| 5,542,916 | A | 8/1996 | Hirsch et al. |
| 5,558,671 | A | 9/1996 | Yates |
| 5,563,179 | A | 10/1996 | Stone et al. |
| 5,571,121 | A | 11/1996 | Heifetz |
| 5,573,534 | A | 11/1996 | Stone |
| 5,584,830 | A | 12/1996 | Ladd et al. |
| 5,599,350 | A | 2/1997 | Schulze et al. |
| 5,611,813 | A | 3/1997 | Lichtman |
| 5,618,307 | A | 4/1997 | Donlon et al. |
| 5,624,452 | A | 4/1997 | Yates |
| 5,647,871 | A | 7/1997 | Levine et al. |
| 5,658,281 | A | 8/1997 | Heard |
| 5,662,615 | A | 9/1997 | Blake, III |
| 5,662,667 | A | 9/1997 | Knodel |
| 5,665,085 | A | 9/1997 | Nardella |
| 5,665,100 | A | 9/1997 | Yoon |
| 5,674,219 | A | 10/1997 | Monson et al. |
| 5,674,220 | A | 10/1997 | Fox et al. |
| 5,688,270 | A | 11/1997 | Yates et al. |
| 5,693,051 | A | 12/1997 | Schulze et al. |
| 5,709,680 | A | 1/1998 | Yates et al. |

(56)        References Cited

U.S. PATENT DOCUMENTS

| | | | |
|---|---|---|---|
| 5,713,896 A | 2/1998 | Nardella |
| 5,716,366 A | 2/1998 | Yates |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,776,130 A | 7/1998 | Buysse et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,807,393 A | 9/1998 | Williamson, IV et al. |
| 5,810,811 A | 9/1998 | Yates et al. |
| 5,817,033 A | 10/1998 | DeSantis et al. |
| 5,817,084 A | 10/1998 | Jensen |
| 5,817,093 A | 10/1998 | Williamson, IV et al. |
| 5,836,909 A | 11/1998 | Cosmescu |
| 5,836,943 A | 11/1998 | Miller, III |
| 5,853,412 A | 12/1998 | Mayenberger |
| 5,876,325 A | 3/1999 | Mizuno et al. |
| 5,876,401 A | 3/1999 | Schulze et al. |
| 5,878,193 A | 3/1999 | Wang et al. |
| 5,880,668 A | 3/1999 | Hall |
| 5,891,142 A | 4/1999 | Eggers et al. |
| 5,906,625 A | 5/1999 | Bito et al. |
| 5,980,493 A | 11/1999 | Smith et al. |
| 5,984,938 A | 11/1999 | Yoon |
| 6,003,517 A | 12/1999 | Sheffield et al. |
| 6,013,052 A | 1/2000 | Durman et al. |
| 6,024,741 A | 2/2000 | Williamson, IV et al. |
| 6,024,744 A | 2/2000 | Kese et al. |
| 6,033,399 A | 3/2000 | Gines |
| 6,039,734 A | 3/2000 | Goble |
| 6,050,996 A | 4/2000 | Schmaltz et al. |
| 6,063,098 A | 5/2000 | Houser et al. |
| 6,068,629 A | 5/2000 | Haissaguerre et al. |
| 6,074,389 A | 6/2000 | Levine et al. |
| 6,091,995 A | 7/2000 | Ingle et al. |
| 6,099,483 A | 8/2000 | Palmer et al. |
| 6,099,550 A | 8/2000 | Yoon |
| 6,113,598 A | 9/2000 | Baker |
| H1904 H | 10/2000 | Yates et al. |
| 6,132,368 A | 10/2000 | Cooper |
| 6,144,402 A | 11/2000 | Norsworthy et al. |
| 6,152,923 A | 11/2000 | Ryan |
| 6,174,309 B1 | 1/2001 | Wrublewski et al. |
| 6,190,386 B1 | 2/2001 | Rydell |
| 6,206,876 B1 | 3/2001 | Levine et al. |
| 6,228,080 B1 | 5/2001 | Gines |
| 6,231,565 B1 | 5/2001 | Tovey et al. |
| 6,241,724 B1 | 6/2001 | Fleischman et al. |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,364,888 B1 | 4/2002 | Niemeyer et al. |
| 6,387,094 B1 | 5/2002 | Eitenmuller |
| 6,391,026 B1 | 5/2002 | Hung et al. |
| 6,398,779 B1 | 6/2002 | Buysse et al. |
| H2037 H | 7/2002 | Yates et al. |
| 6,419,675 B1 | 7/2002 | Gallo, Sr. |
| 6,430,446 B1 | 8/2002 | Knowlton |
| 6,443,968 B1 | 9/2002 | Holthaus et al. |
| 6,458,128 B1 | 10/2002 | Schulze |
| 6,458,130 B1 | 10/2002 | Frazier et al. |
| 6,461,363 B1 | 10/2002 | Gadberry et al. |
| 6,464,702 B2 | 10/2002 | Schulze et al. |
| 6,475,211 B2 | 11/2002 | Chess et al. |
| 6,491,690 B1 | 12/2002 | Goble et al. |
| 6,500,112 B1 | 12/2002 | Khouri |
| 6,500,176 B1 | 12/2002 | Truckai et al. |
| 6,503,248 B1 | 1/2003 | Levine |
| 6,506,208 B2 | 1/2003 | Hunt et al. |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,290 B2 | 3/2003 | Adams et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,602,252 B2 | 8/2003 | Mollenauer |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,695,840 B2 | 2/2004 | Schulze |
| 6,709,445 B2 | 3/2004 | Boebel et al. |
| 6,719,765 B2 | 4/2004 | Bonutti |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,775,575 B2 | 8/2004 | Bommannan et al. |
| 6,783,524 B2 | 8/2004 | Anderson et al. |
| 6,789,939 B2 | 9/2004 | Schrodinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,814,731 B2 | 11/2004 | Swanson |
| 6,817,974 B2 | 11/2004 | Cooper et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,004,951 B2 | 2/2006 | Gibbens, III |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,134,587 B2 | 11/2006 | Schwemberger et al. |
| 7,137,980 B2 | 11/2006 | Buysse et al. |
| 7,143,925 B2 | 12/2006 | Shelton, IV et al. |

(56) References Cited

U.S. PATENT DOCUMENTS

| | | | |
|---|---|---|---|
| 7,147,138 | B2 | 12/2006 | Shelton, IV |
| 7,156,846 | B2 | 1/2007 | Dycus et al. |
| 7,160,296 | B2 | 1/2007 | Pearson et al. |
| 7,169,146 | B2 | 1/2007 | Truckai et al. |
| 7,169,156 | B2 | 1/2007 | Hart |
| 7,186,253 | B2 | 3/2007 | Truckai et al. |
| 7,189,233 | B2 | 3/2007 | Truckai et al. |
| 7,195,631 | B2 | 3/2007 | Dumbauld |
| 7,207,471 | B2 | 4/2007 | Heinrich et al. |
| 7,208,005 | B2 | 4/2007 | Frecker et al. |
| 7,220,951 | B2 | 5/2007 | Truckai et al. |
| 7,225,964 | B2 | 6/2007 | Mastri et al. |
| 7,226,448 | B2 | 6/2007 | Bertolero et al. |
| 7,232,440 | B2 | 6/2007 | Dumbauld et al. |
| 7,235,073 | B2 | 6/2007 | Levine et al. |
| 7,241,294 | B2 | 7/2007 | Reschke |
| 7,251,531 | B2 | 7/2007 | Mosher et al. |
| 7,252,667 | B2 | 8/2007 | Moses et al. |
| 7,267,677 | B2 | 9/2007 | Johnson et al. |
| 7,267,685 | B2 | 9/2007 | Butaric et al. |
| 7,287,682 | B1 | 10/2007 | Ezzat et al. |
| 7,300,450 | B2 | 11/2007 | Vleugels et al. |
| 7,303,557 | B2 | 12/2007 | Wham et al. |
| 7,307,313 | B2 | 12/2007 | Ohyanagi et al. |
| 7,309,849 | B2 | 12/2007 | Truckai et al. |
| 7,311,709 | B2 | 12/2007 | Truckai et al. |
| 7,329,257 | B2 | 2/2008 | Kanehira et al. |
| 7,354,440 | B2 | 4/2008 | Truckal et al. |
| 7,357,287 | B2 | 4/2008 | Shelton, IV et al. |
| 7,364,577 | B2 | 4/2008 | Wham et al. |
| 7,367,976 | B2 | 5/2008 | Lawes et al. |
| 7,371,227 | B2 | 5/2008 | Zeiner |
| RE40,388 | E | 6/2008 | Gines |
| 7,381,209 | B2 | 6/2008 | Truckai et al. |
| 7,384,420 | B2 | 6/2008 | Dycus et al. |
| 7,396,356 | B2 | 7/2008 | Mollenauer |
| 7,403,224 | B2 | 7/2008 | Fuller et al. |
| 7,404,508 | B2 | 7/2008 | Smith et al. |
| 7,407,077 | B2 | 8/2008 | Ortiz et al. |
| 7,422,139 | B2 | 9/2008 | Shelton, IV et al. |
| 7,435,582 | B2 | 10/2008 | Zimmermann et al. |
| 7,442,193 | B2 | 10/2008 | Shields et al. |
| 7,445,621 | B2 | 11/2008 | Dumbauld et al. |
| 7,451,904 | B2 | 11/2008 | Shelton, IV |
| 7,464,846 | B2 | 12/2008 | Shelton, IV et al. |
| 7,473,253 | B2 | 1/2009 | Dycus et al. |
| 7,488,319 | B2 | 2/2009 | Yates |
| 7,491,201 | B2 | 2/2009 | Shields et al. |
| 7,491,202 | B2 | 2/2009 | Odom et al. |
| 7,494,501 | B2 | 2/2009 | Ahlberg et al. |
| 7,498,080 | B2 | 3/2009 | Tung et al. |
| 7,510,107 | B2 | 3/2009 | Timm et al. |
| 7,510,556 | B2 | 3/2009 | Nguyen et al. |
| 7,513,025 | B2 | 4/2009 | Fischer |
| 7,517,349 | B2 | 4/2009 | Truckai et al. |
| 7,524,320 | B2 | 4/2009 | Tierney et al. |
| 7,540,872 | B2 | 6/2009 | Schechter et al. |
| 7,550,216 | B2 | 6/2009 | Ofer et al. |
| 7,559,452 | B2 | 7/2009 | Wales et al. |
| 7,582,086 | B2 | 9/2009 | Privitera et al. |
| 7,586,289 | B2 | 9/2009 | Andruk et al. |
| 7,588,176 | B2 | 9/2009 | Timm et al. |
| 7,594,925 | B2 | 9/2009 | Danek et al. |
| 7,597,693 | B2 | 10/2009 | Garrison |
| 7,604,150 | B2 | 10/2009 | Boudreaux |
| 7,608,083 | B2 * | 10/2009 | Lee .................... B25J 9/104 |
| | | | 606/1 |
| 7,625,370 | B2 | 12/2009 | Hart et al. |
| 7,628,791 | B2 | 12/2009 | Garrison et al. |
| 7,628,792 | B2 | 12/2009 | Guerra |
| 7,632,267 | B2 | 12/2009 | Dahla |
| 7,632,269 | B2 | 12/2009 | Truckai et al. |
| 7,637,410 | B2 | 12/2009 | Marczyk |
| 7,641,653 | B2 | 1/2010 | Dalla Betta et al. |
| 7,641,671 | B2 | 1/2010 | Crainich |
| 7,644,848 | B2 | 1/2010 | Swayze et al. |
| 7,645,277 | B2 | 1/2010 | McClurken et al. |
| 7,648,499 | B2 | 1/2010 | Orszulak et al. |
| 7,658,311 | B2 | 2/2010 | Boudreaux |
| 7,662,151 | B2 | 2/2010 | Crompton, Jr. et al. |
| 7,665,647 | B2 | 2/2010 | Shelton, IV et al. |
| 7,666,206 | B2 | 2/2010 | Taniguchi et al. |
| 7,691,098 | B2 | 4/2010 | Wallace et al. |
| 7,703,459 | B2 | 4/2010 | Saadat et al. |
| 7,708,735 | B2 | 5/2010 | Chapman et al. |
| 7,708,751 | B2 | 5/2010 | Hughes et al. |
| 7,708,758 | B2 | 5/2010 | Lee et al. |
| 7,717,312 | B2 | 5/2010 | Beetel |
| 7,717,914 | B2 | 5/2010 | Kimura |
| 7,722,527 | B2 | 5/2010 | Bouchier et al. |
| 7,722,607 | B2 | 5/2010 | Dumbauld et al. |
| 7,727,244 | B2 | 6/2010 | Orban, III et al. |
| 7,753,904 | B2 | 7/2010 | Shelton, IV et al. |
| 7,753,908 | B2 | 7/2010 | Swanson |
| 7,762,445 | B2 | 7/2010 | Heinrich et al. |
| 7,766,910 | B2 | 8/2010 | Hixson et al. |
| 7,776,037 | B2 | 8/2010 | Odom |
| 7,780,663 | B2 | 8/2010 | Yates et al. |
| 7,784,663 | B2 | 8/2010 | Shelton, IV |
| 7,789,883 | B2 | 9/2010 | Takashino et al. |
| 7,803,156 | B2 | 9/2010 | Eder et al. |
| 7,806,891 | B2 | 10/2010 | Nowlin et al. |
| 7,815,641 | B2 | 10/2010 | Dodde et al. |
| 7,819,298 | B2 | 10/2010 | Hall et al. |
| 7,819,299 | B2 | 10/2010 | Shelton, IV et al. |
| 7,819,872 | B2 | 10/2010 | Johnson et al. |
| 7,824,401 | B2 | 11/2010 | Manzo et al. |
| 7,832,408 | B2 | 11/2010 | Shelton, IV et al. |
| 7,832,612 | B2 | 11/2010 | Baxter, III et al. |
| 7,841,980 | B2 | 11/2010 | Minosawa et al. |
| 7,846,159 | B2 | 12/2010 | Morrison et al. |
| 7,846,160 | B2 | 12/2010 | Payne et al. |
| 7,850,688 | B2 | 12/2010 | Hafner |
| 7,867,228 | B2 | 1/2011 | Nobis et al. |
| 7,879,035 | B2 | 2/2011 | Garrison et al. |
| 7,879,070 | B2 | 2/2011 | Ortiz et al. |
| 7,896,875 | B2 | 3/2011 | Heim et al. |
| 7,901,400 | B2 | 3/2011 | Wham et al. |
| 7,919,184 | B2 | 4/2011 | Mohapatra et al. |
| 7,931,649 | B2 | 4/2011 | Couture et al. |
| 7,935,114 | B2 | 5/2011 | Takashino et al. |
| 7,935,130 | B2 | 5/2011 | Williams |
| 7,955,322 | B2 | 6/2011 | Devengenzo et al. |
| 7,955,331 | B2 | 6/2011 | Truckai et al. |
| 7,963,963 | B2 | 6/2011 | Francischelli et al. |
| 7,967,602 | B2 | 6/2011 | Lindquist |
| 7,980,443 | B2 | 7/2011 | Scheib et al. |
| 7,981,113 | B2 | 7/2011 | Truckai et al. |
| 7,982,776 | B2 | 7/2011 | Dunki-Jacobs et al. |
| 7,995,045 | B2 | 8/2011 | Dunki-Jacobs |
| 7,997,278 | B2 | 8/2011 | Utley et al. |
| 8,016,855 | B2 | 9/2011 | Whitman et al. |
| 8,020,743 | B2 | 9/2011 | Shelton, IV |
| 8,048,070 | B2 | 11/2011 | O'Brien et al. |
| 8,054,184 | B2 | 11/2011 | Cline et al. |
| 8,058,771 | B2 | 11/2011 | Giordano et al. |
| 8,066,167 | B2 | 11/2011 | Measamer et al. |
| 8,070,036 | B1 | 12/2011 | Knodel |
| 8,070,731 | B2 | 12/2011 | Wenchell et al. |
| 8,075,555 | B2 | 12/2011 | Truckai et al. |
| 8,075,558 | B2 | 12/2011 | Truckai et al. |
| 8,100,894 | B2 | 1/2012 | Mucko et al. |
| 8,105,323 | B2 | 1/2012 | Buysse et al. |
| 8,105,324 | B2 | 1/2012 | Palanker et al. |
| 8,128,624 | B2 | 3/2012 | Couture et al. |
| 8,136,712 | B2 | 3/2012 | Zingman |
| 8,141,762 | B2 | 3/2012 | Bedi et al. |
| 8,147,508 | B2 | 4/2012 | Madan et al. |
| 8,152,825 | B2 | 4/2012 | Madan et al. |
| 8,157,145 | B2 | 4/2012 | Shelton, IV et al. |
| 8,161,977 | B2 | 4/2012 | Shelton, IV et al. |
| 8,186,560 | B2 | 5/2012 | Hess et al. |
| 8,187,267 | B2 | 5/2012 | Pappone et al. |
| 8,197,446 | B2 | 6/2012 | Beardsley |

(56)  References Cited

U.S. PATENT DOCUMENTS

| | | | |
|---|---|---|---|
| 8,197,472 B2 | 6/2012 | Lau et al. |
| 8,197,479 B2 | 6/2012 | Olson et al. |
| 8,210,411 B2 | 7/2012 | Yates et al. |
| 8,221,415 B2 | 7/2012 | Francischelli |
| 8,241,235 B2 | 8/2012 | Kahler et al. |
| 8,241,283 B2 | 8/2012 | Guerra et al. |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |
| 8,277,447 B2 | 10/2012 | Garrison et al. |
| 8,277,471 B2 | 10/2012 | Wiener et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,292,888 B2 | 10/2012 | Whitman |
| 8,298,232 B2 | 10/2012 | Unger |
| 8,303,583 B2 | 11/2012 | Hosier et al. |
| 8,308,040 B2 | 11/2012 | Huang et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,834 B2 | 12/2012 | Isaacs et al. |
| 8,343,146 B2 | 1/2013 | Godara et al. |
| 8,343,171 B2 | 1/2013 | Farritor et al. |
| 8,348,126 B2 | 1/2013 | Olson et al. |
| 8,357,144 B2 | 1/2013 | Whitman et al. |
| 8,357,158 B2 | 1/2013 | McKenna et al. |
| 8,377,059 B2 | 2/2013 | Deville et al. |
| 8,388,646 B2 | 3/2013 | Chojin |
| 8,397,971 B2 | 3/2013 | Yates et al. |
| 8,403,926 B2 | 3/2013 | Nobis et al. |
| 8,414,577 B2 | 4/2013 | Boudreaux et al. |
| 8,423,182 B2 | 4/2013 | Robinson et al. |
| 8,425,410 B2 | 4/2013 | Murray et al. |
| 8,430,811 B2 | 4/2013 | Hess et al. |
| 8,430,876 B2 | 4/2013 | Kappus et al. |
| 8,453,906 B2 | 6/2013 | Huang et al. |
| 8,454,599 B2 | 6/2013 | Inagaki et al. |
| 8,460,288 B2 | 6/2013 | Tamai et al. |
| 8,460,292 B2 | 6/2013 | Truckai et al. |
| 8,484,833 B2 | 7/2013 | Cunningham et al. |
| 8,485,970 B2 | 7/2013 | Widenhouse et al. |
| 8,486,057 B2 | 7/2013 | Behnke, II |
| 8,491,533 B2 | 7/2013 | Parihar et al. |
| 8,491,625 B2 | 7/2013 | Horner |
| 8,496,682 B2 | 7/2013 | Guerra et al. |
| 8,512,364 B2 | 8/2013 | Kowalski et al. |
| 8,529,437 B2 | 9/2013 | Taylor et al. |
| 8,535,311 B2 | 9/2013 | Schall |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,579,176 B2 | 11/2013 | Smith et al. |
| 8,579,937 B2 | 11/2013 | Gresham |
| 8,591,459 B2 | 11/2013 | Clymer et al. |
| 8,591,506 B2 | 11/2013 | Wham et al. |
| 8,613,383 B2 | 12/2013 | Beckman et al. |
| 8,613,727 B2 | 12/2013 | Hart et al. |
| 8,616,431 B2 | 12/2013 | Timm et al. |
| 8,622,274 B2 | 1/2014 | Yates et al. |
| 8,623,016 B2 | 1/2014 | Fischer |
| 8,623,044 B2 | 1/2014 | Timm et al. |
| 8,628,529 B2 | 1/2014 | Aldridge et al. |
| 8,632,461 B2 | 1/2014 | Glossop |
| 8,636,736 B2 | 1/2014 | Yates et al. |
| 8,640,788 B2 | 2/2014 | Dachs, II et al. |
| 8,647,350 B2 | 2/2014 | Mohan et al. |
| 8,652,120 B2 | 2/2014 | Giordano et al. |
| 8,663,222 B2 | 3/2014 | Anderson et al. |
| 8,668,691 B2 | 3/2014 | Heard |
| 8,684,253 B2 | 4/2014 | Giordano et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,734,443 B2 | 5/2014 | Hixson et al. |
| 8,747,238 B2 | 6/2014 | Shelton, IV et al. |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,758,342 B2 | 6/2014 | Bales et al. |
| 8,764,747 B2 | 7/2014 | Cummings et al. |
| 8,784,418 B2 | 7/2014 | Romero |
| 8,790,342 B2 | 7/2014 | Stulen et al. |
| 8,795,274 B2 | 8/2014 | Hanna |
| 8,795,276 B2 | 8/2014 | Dietz et al. |
| 8,795,327 B2 | 8/2014 | Dietz et al. |
| 8,801,752 B2 | 8/2014 | Fortier et al. |
| 8,814,856 B2 | 8/2014 | Elmouelhi et al. |
| 8,827,995 B2 | 9/2014 | Schaller et al. |
| 8,828,023 B2 | 9/2014 | Neff et al. |
| 8,834,466 B2 | 9/2014 | Cummings et al. |
| 8,834,518 B2 | 9/2014 | Faller et al. |
| 8,851,354 B2 | 10/2014 | Swensgard et al. |
| 8,864,757 B2 | 10/2014 | Klimovitch et al. |
| 8,864,761 B2 | 10/2014 | Johnson et al. |
| 8,888,776 B2 | 11/2014 | Dietz et al. |
| 8,888,809 B2 | 11/2014 | Davison et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,912,746 B2 | 12/2014 | Reid et al. |
| 8,926,607 B2 | 1/2015 | Norvell et al. |
| 8,926,608 B2 | 1/2015 | Bacher et al. |
| 8,931,682 B2 | 1/2015 | Timm et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,961,515 B2 | 2/2015 | Twomey et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,992,422 B2 | 3/2015 | Spivey et al. |
| 8,992,526 B2 | 3/2015 | Brodbeck et al. |
| 9,002,518 B2 | 4/2015 | Manzo et al. |
| 9,005,199 B2 | 4/2015 | Beckman et al. |
| 9,011,437 B2 | 4/2015 | Woodruff et al. |
| 9,017,326 B2 | 4/2015 | DiNardo et al. |
| 9,017,333 B2 | 4/2015 | Beale et al. |
| 9,028,494 B2 | 5/2015 | Shelton, IV et al. |
| 9,028,519 B2 | 5/2015 | Yates et al. |
| 9,039,695 B2 | 5/2015 | Giordano et al. |
| 9,039,705 B2 | 5/2015 | Takashino |
| 9,044,243 B2 | 6/2015 | Johnson et al. |
| 9,044,245 B2 | 6/2015 | Condie et al. |
| 9,050,093 B2 | 6/2015 | Aldridge et al. |
| 9,050,098 B2 | 6/2015 | Deville et al. |
| 9,055,961 B2 | 6/2015 | Manzo et al. |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,072,535 B2 | 7/2015 | Shelton, IV et al. |
| 9,072,536 B2 | 7/2015 | Shelton, IV et al. |
| 9,089,360 B2 | 7/2015 | Messerly et al. |
| 9,095,362 B2 | 8/2015 | Dachs, II et al. |
| 9,101,385 B2 | 8/2015 | Shelton, IV et al. |
| 9,106,270 B2 | 8/2015 | Puterbaugh et al. |
| 9,107,684 B2 | 8/2015 | Ma |
| 9,113,900 B2 | 8/2015 | Buysse et al. |
| 9,119,657 B2 | 9/2015 | Shelton, IV et al. |
| 9,119,957 B2 | 9/2015 | Gantz et al. |

(56)                  References Cited

U.S. PATENT DOCUMENTS

| | | | |
|---|---|---|---|
| 9,125,662 | B2 | 9/2015 | Shelton, IV |
| 9,125,667 | B2 | 9/2015 | Stone et al. |
| 9,149,324 | B2 | 10/2015 | Huang et al. |
| 9,161,803 | B2 | 10/2015 | Yates et al. |
| 9,168,054 | B2 | 10/2015 | Turner et al. |
| 9,168,089 | B2 | 10/2015 | Buysse et al. |
| 9,179,912 | B2 | 11/2015 | Yates et al. |
| 9,192,431 | B2 | 11/2015 | Woodruff et al. |
| 9,198,715 | B2 | 12/2015 | Livneh |
| 9,204,879 | B2 | 12/2015 | Shelton, IV |
| 9,220,559 | B2 | 12/2015 | Worrell et al. |
| 9,226,751 | B2 | 1/2016 | Shelton, IV et al. |
| 9,237,891 | B2 | 1/2016 | Shelton, IV |
| 9,254,165 | B2 | 2/2016 | Aronow et al. |
| 9,259,265 | B2 | 2/2016 | Harris et al. |
| 9,259,277 | B2 | 2/2016 | Rogers et al. |
| 9,265,567 | B2 | 2/2016 | Orban, III et al. |
| 9,265,926 | B2 | 2/2016 | Strobl et al. |
| 9,282,974 | B2 | 3/2016 | Shelton, IV |
| 9,283,027 | B2 | 3/2016 | Monson et al. |
| 9,289,256 | B2 | 3/2016 | Shelton, IV et al. |
| 9,295,514 | B2 | 3/2016 | Shelton, IV et al. |
| 9,308,014 | B2 | 4/2016 | Fischer |
| 9,314,292 | B2 | 4/2016 | Trees et al. |
| 9,320,563 | B2 | 4/2016 | Brustad et al. |
| 9,333,025 | B2 | 5/2016 | Monson et al. |
| 9,339,323 | B2 | 5/2016 | Eder et al. |
| 9,339,342 | B2 | 5/2016 | Prisco et al. |
| 9,345,481 | B2 | 5/2016 | Hall et al. |
| 9,364,230 | B2 | 6/2016 | Shelton, IV et al. |
| 9,375,232 | B2 | 6/2016 | Hunt et al. |
| 9,386,983 | B2 | 7/2016 | Swensgard et al. |
| 9,402,682 | B2 | 8/2016 | Worrell et al. |
| 9,408,606 | B2 | 8/2016 | Shelton, IV |
| 9,408,660 | B2 | 8/2016 | Strobl et al. |
| 9,414,880 | B2 | 8/2016 | Monson et al. |
| 9,421,060 | B2 | 8/2016 | Monson et al. |
| 9,456,864 | B2 | 10/2016 | Witt et al. |
| 9,492,224 | B2 | 11/2016 | Boudreaux et al. |
| 9,504,524 | B2 | 11/2016 | Behnke, II |
| 9,526,407 | B2 | 12/2016 | Hoeg et al. |
| 9,526,565 | B2 | 12/2016 | Strobl |
| 9,554,846 | B2 | 1/2017 | Boudreaux |
| 9,554,854 | B2 | 1/2017 | Yates et al. |
| 9,561,038 | B2 | 2/2017 | Shelton, IV et al. |
| 9,572,552 | B1 | 2/2017 | Bodor et al. |
| 9,597,104 | B2 | 3/2017 | Nicholas et al. |
| 9,597,143 | B2 | 3/2017 | Madan et al. |
| 9,610,091 | B2 | 4/2017 | Johnson et al. |
| 9,642,669 | B2 | 5/2017 | Takashino et al. |
| 9,649,110 | B2 | 5/2017 | Parihar et al. |
| 9,649,111 | B2 | 5/2017 | Shelton, IV et al. |
| 9,668,806 | B2 | 6/2017 | Unger et al. |
| 9,707,027 | B2 | 7/2017 | Ruddenklau et al. |
| 9,737,355 | B2 | 8/2017 | Yates et al. |
| 9,737,358 | B2 | 8/2017 | Beckman et al. |
| 9,757,128 | B2 | 9/2017 | Baber et al. |
| 9,757,186 | B2 | 9/2017 | Boudreaux et al. |
| 9,763,661 | B2 | 9/2017 | Zergiebel et al. |
| 9,782,214 | B2 | 10/2017 | Houser et al. |
| 9,795,436 | B2 | 10/2017 | Yates et al. |
| 9,808,308 | B2 | 11/2017 | Faller et al. |
| 9,814,514 | B2 | 11/2017 | Shelton, IV et al. |
| 9,820,740 | B2 | 11/2017 | Zemlok et al. |
| 9,820,771 | B2 | 11/2017 | Norton et al. |
| 9,861,428 | B2 | 1/2018 | Trees et al. |
| 9,877,776 | B2 | 1/2018 | Boudreaux |
| 9,888,942 | B1 | 2/2018 | Savage et al. |
| 9,913,680 | B2 | 3/2018 | Voegele et al. |
| 9,913,694 | B2 | 3/2018 | Brisson |
| 9,937,626 | B2 | 4/2018 | Rockrohr |
| 9,987,008 | B2 | 6/2018 | Scirica et al. |
| 10,016,207 | B2 | 7/2018 | Suzuki et al. |
| 10,070,916 | B2 | 9/2018 | Artale |
| 10,092,310 | B2 | 10/2018 | Boudreaux et al. |
| 10,098,527 | B2 | 10/2018 | Weisenburgh, II et al. |
| 10,164,466 | B2 | 12/2018 | Calderoni |
| 10,166,060 | B2 | 1/2019 | Johnson et al. |
| 10,166,080 | B2 | 1/2019 | Balicki et al. |
| 10,166,082 | B1 | 1/2019 | Hariri et al. |
| 10,172,669 | B2 | 1/2019 | Felder et al. |
| 10,172,687 | B2 | 1/2019 | Garbus et al. |
| 10,179,413 | B2 | 1/2019 | Rockrohr |
| 10,194,976 | B2 | 2/2019 | Boudreaux |
| 10,213,266 | B2 | 2/2019 | Zemlok et al. |
| 10,231,775 | B2 | 3/2019 | Shelton, IV et al. |
| 10,251,672 | B2 | 4/2019 | Meglan |
| 10,258,359 | B2 | 4/2019 | Kapadia |
| 10,265,118 | B2 | 4/2019 | Gerhardt |
| 10,278,721 | B2 | 5/2019 | Dietz et al. |
| 10,321,964 | B2 | 6/2019 | Grover et al. |
| 10,368,838 | B2 | 8/2019 | Williams et al. |
| 10,376,338 | B2 | 8/2019 | Taylor et al. |
| 10,390,895 | B2 | 8/2019 | Henderson et al. |
| 10,398,517 | B2 | 9/2019 | Eckert et al. |
| 10,420,620 | B2 | 9/2019 | Rockrohr |
| 10,426,516 | B2 | 10/2019 | Racenet et al. |
| 10,463,421 | B2 | 11/2019 | Boudreaux et al. |
| 10,470,830 | B2 | 11/2019 | Hill et al. |
| 10,507,068 | B2 | 12/2019 | Kopp et al. |
| 10,517,686 | B2 | 12/2019 | Vokrot et al. |
| 10,537,351 | B2 | 1/2020 | Shelton, IV et al. |
| 10,548,504 | B2 | 2/2020 | Shelton, IV et al. |
| 10,561,470 | B2 | 2/2020 | Hourtash et al. |
| 10,588,706 | B2 | 3/2020 | Limon |
| 10,624,691 | B2 | 4/2020 | Wiener et al. |
| 10,639,111 | B2 | 5/2020 | Kopp |
| 10,653,489 | B2 | 5/2020 | Kopp |
| 10,667,877 | B2 | 6/2020 | Kapadia |
| 10,675,104 | B2 | 6/2020 | Kapadia |
| 10,716,639 | B2 | 7/2020 | Kapadia et al. |
| 10,736,219 | B2 | 8/2020 | Seow et al. |
| 10,743,872 | B2 | 8/2020 | Leimbach et al. |
| 10,751,087 | B2 | 8/2020 | Morgan et al. |
| 10,765,484 | B2 | 9/2020 | Bonutti et al. |
| 10,772,688 | B2 | 9/2020 | Peine et al. |
| 10,779,849 | B2 | 9/2020 | Shelton, IV et al. |
| 10,779,897 | B2 | 9/2020 | Rockrohr |
| 10,779,900 | B2 | 9/2020 | Pedros et al. |
| 10,799,304 | B2 | 10/2020 | Kapadia et al. |
| 10,806,454 | B2 | 10/2020 | Kopp |
| 10,813,703 | B2 | 10/2020 | Swayze et al. |
| 10,849,700 | B2 | 12/2020 | Kopp et al. |
| 10,881,399 | B2 | 1/2021 | Shelton, IV et al. |
| 10,893,884 | B2 | 1/2021 | Stoddard et al. |
| 10,898,280 | B2 | 1/2021 | Kopp |
| 10,912,616 | B2 | 2/2021 | Dachs, II et al. |
| 10,932,772 | B2 | 3/2021 | Shelton, IV et al. |
| 10,959,788 | B2 | 3/2021 | Grover et al. |
| 10,980,610 | B2 | 4/2021 | Rosenberg et al. |
| 11,013,563 | B2 | 5/2021 | Shelton, IV et al. |
| 11,013,569 | B2 | 5/2021 | Shelton, IV et al. |
| 11,026,764 | B2 | 6/2021 | Kopp |
| 11,045,265 | B2 | 6/2021 | Seow et al. |
| 11,058,504 | B2 | 7/2021 | Blanco et al. |
| 11,090,125 | B2 | 8/2021 | Peine et al. |
| 11,109,866 | B2 | 9/2021 | Shelton, IV et al. |
| 11,160,623 | B2 | 11/2021 | Hagn |
| 11,207,146 | B2 | 12/2021 | Shelton, IV et al. |
| 11,229,471 | B2 | 1/2022 | Shelton, IV et al. |
| 11,278,362 | B2 | 3/2022 | Shelton, IV et al. |
| 11,298,128 | B2 | 4/2022 | Messerly et al. |
| 11,364,067 | B2 | 6/2022 | Murrell et al. |
| 11,510,747 | B2 | 11/2022 | Zemlok et al. |
| 11,813,746 | B2 | 11/2023 | Overmyer et al. |
| 11,839,420 | B2 | 12/2023 | Shelton, IV et al. |
| 2002/0022836 | A1 | 2/2002 | Goble et al. |
| 2002/0072736 | A1 | 6/2002 | Tierney et al. |
| 2003/0014053 | A1 | 1/2003 | Nguyen et al. |
| 2003/0114851 | A1 | 6/2003 | Truckai et al. |
| 2003/0130693 | A1 | 7/2003 | Levin et al. |
| 2003/0139741 | A1 | 7/2003 | Goble et al. |
| 2003/0158548 | A1 | 8/2003 | Phan et al. |
| 2003/0229344 | A1 | 12/2003 | Dycus et al. |

(56)  References Cited

U.S. PATENT DOCUMENTS

| | | |
|---|---|---|
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0249374 A1 | 12/2004 | Tetzlaff et al. |
| 2004/0260273 A1 | 12/2004 | Wan |
| 2005/0006432 A1* | 1/2005 | Racenet ............... A61B 17/105 |
| | | 227/176.1 |
| 2005/0015125 A1 | 1/2005 | Mioduski et al. |
| 2005/0033278 A1 | 2/2005 | McClurken et al. |
| 2005/0090817 A1 | 4/2005 | Phan |
| 2005/0131390 A1 | 6/2005 | Heinrich et al. |
| 2005/0165429 A1 | 7/2005 | Douglas et al. |
| 2005/0171522 A1 | 8/2005 | Christopherson |
| 2005/0267464 A1 | 12/2005 | Truckai et al. |
| 2006/0064086 A1 | 3/2006 | Odom |
| 2006/0069306 A1 | 3/2006 | Banik et al. |
| 2006/0135978 A1 | 6/2006 | Franer |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0032704 A1 | 2/2007 | Gandini et al. |
| 2007/0073185 A1 | 3/2007 | Nakao |
| 2007/0073341 A1 | 3/2007 | Smith et al. |
| 2007/0078395 A1 | 4/2007 | Valaie |
| 2007/0135826 A1 | 6/2007 | Zaver et al. |
| 2007/0173803 A1 | 7/2007 | Wham et al. |
| 2007/0173813 A1 | 7/2007 | Odom |
| 2007/0185474 A1 | 8/2007 | Nahen |
| 2007/0191713 A1 | 8/2007 | Eichmann et al. |
| 2007/0203483 A1 | 8/2007 | Kim et al. |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0260242 A1 | 11/2007 | Dycus et al. |
| 2007/0265613 A1 | 11/2007 | Edelstein et al. |
| 2007/0282358 A1 | 12/2007 | Remiszewski et al. |
| 2008/0015575 A1 | 1/2008 | Odom et al. |
| 2008/0064921 A1 | 3/2008 | Larkin et al. |
| 2008/0071269 A1 | 3/2008 | Hilario et al. |
| 2008/0081948 A1 | 4/2008 | Weisenburgh et al. |
| 2008/0114355 A1 | 5/2008 | Whayne et al. |
| 2008/0125794 A1 | 5/2008 | Brock et al. |
| 2008/0147058 A1 | 6/2008 | Horrell et al. |
| 2008/0147062 A1 | 6/2008 | Truckai et al. |
| 2008/0188755 A1 | 8/2008 | Hart |
| 2008/0281315 A1 | 11/2008 | Gines |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0182327 A1 | 7/2009 | Unger |
| 2009/0182332 A1 | 7/2009 | Long et al. |
| 2009/0248021 A1 | 10/2009 | McKenna |
| 2009/0248037 A1 | 10/2009 | Prisco |
| 2009/0248041 A1 | 10/2009 | Williams et al. |
| 2010/0036370 A1 | 2/2010 | Mirel et al. |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0168520 A1 | 7/2010 | Poll et al. |
| 2010/0222752 A1 | 9/2010 | Collins, Jr. et al. |
| 2010/0228264 A1 | 9/2010 | Robinson et al. |
| 2010/0274278 A1 | 10/2010 | Fleenor et al. |
| 2011/0028964 A1 | 2/2011 | Edwards |
| 2011/0230719 A1 | 9/2011 | Katakura et al. |
| 2011/0251609 A1* | 10/2011 | Johnson ............. A61B 18/1445 |
| | | 606/46 |
| 2011/0251612 A1* | 10/2011 | Faller ................. A61B 18/1445 |
| | | 606/52 |
| 2011/0290856 A1 | 12/2011 | Shelton, IV et al. |
| 2011/0295295 A1 | 12/2011 | Shelton, IV et al. |
| 2011/0301414 A1 | 12/2011 | Hotto et al. |
| 2011/0306840 A1 | 12/2011 | Allen et al. |
| 2011/0306967 A1 | 12/2011 | Payne et al. |

| | | |
|---|---|---|
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0041358 A1 | 2/2012 | Mann et al. |
| 2012/0078244 A1 | 3/2012 | Worrell et al. |
| 2012/0109186 A1 | 5/2012 | Parrott et al. |
| 2012/0111920 A1 | 5/2012 | Kostrzewski |
| 2012/0116222 A1 | 5/2012 | Sawada et al. |
| 2012/0116265 A1 | 5/2012 | Houser et al. |
| 2012/0132018 A1 | 5/2012 | Tang et al. |
| 2012/0238827 A1 | 9/2012 | Berry et al. |
| 2012/0303025 A1* | 11/2012 | Garrison ........... A61B 18/1447 |
| | | 606/51 |
| 2013/0023915 A1 | 1/2013 | Mueller |
| 2013/0023925 A1 | 1/2013 | Mueller |
| 2013/0085510 A1 | 4/2013 | Stefanchik et al. |
| 2013/0123776 A1 | 5/2013 | Monson et al. |
| 2013/0331730 A1 | 12/2013 | Fenech et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005718 A1 | 1/2014 | Shelton, IV et al. |
| 2014/0066944 A1 | 3/2014 | Taylor et al. |
| 2014/0207135 A1 | 7/2014 | Winter |
| 2014/0246477 A1 | 9/2014 | Koch, Jr. et al. |
| 2014/0263552 A1 | 9/2014 | Hall et al. |
| 2014/0276944 A1 | 9/2014 | Farritor et al. |
| 2014/0343569 A1 | 11/2014 | Turner |
| 2014/0371763 A1 | 12/2014 | Poll et al. |
| 2015/0038981 A1 | 2/2015 | Kilroy et al. |
| 2015/0080876 A1 | 3/2015 | Worrell et al. |
| 2015/0114404 A1 | 4/2015 | Czop et al. |
| 2015/0272659 A1 | 10/2015 | Boudreaux et al. |
| 2016/0015261 A1 | 1/2016 | Kishi et al. |
| 2016/0051316 A1 | 2/2016 | Boudreaux |
| 2016/0113728 A1 | 4/2016 | Piron et al. |
| 2016/0175028 A1 | 6/2016 | Trees et al. |
| 2016/0346930 A1 | 12/2016 | Hares |
| 2016/0361122 A1 | 12/2016 | Seeber |
| 2016/0361127 A1 | 12/2016 | Dachs et al. |
| 2017/0028562 A1 | 2/2017 | Yamazaki et al. |
| 2017/0079708 A1 | 3/2017 | Gilbert et al. |
| 2017/0079730 A1 | 3/2017 | Azizian et al. |
| 2017/0105785 A1 | 4/2017 | Shelton, IV et al. |
| 2017/0135771 A1 | 5/2017 | Auld et al. |
| 2017/0188802 A1 | 7/2017 | Lawrence et al. |
| 2017/0224428 A1 | 8/2017 | Kopp |
| 2017/0296213 A1 | 10/2017 | Swensgard et al. |
| 2017/0296257 A1 | 10/2017 | Shelton, IV et al. |
| 2017/0333145 A1 | 11/2017 | Griffiths et al. |
| 2018/0085175 A1 | 3/2018 | Steinle et al. |
| 2018/0125568 A1 | 5/2018 | Shelton, IV et al. |
| 2018/0192862 A1 | 7/2018 | Ide |
| 2018/0289427 A1 | 10/2018 | Griffiths et al. |
| 2018/0296286 A1 | 10/2018 | Peine et al. |
| 2019/0053866 A1 | 2/2019 | Seow et al. |
| 2019/0059986 A1 | 2/2019 | Shelton, IV et al. |
| 2019/0083182 A1 | 3/2019 | Roach et al. |
| 2019/0094084 A1 | 3/2019 | Swinehart et al. |
| 2019/0104919 A1 | 4/2019 | Shelton, IV et al. |
| 2019/0125457 A1 | 5/2019 | Parihar et al. |
| 2019/0133703 A1 | 5/2019 | Seow et al. |
| 2019/0167267 A1 | 6/2019 | Kobayashi et al. |
| 2019/0183596 A1 | 6/2019 | Dachs, II |
| 2019/0200844 A1 | 7/2019 | Shelton, IV et al. |
| 2019/0200981 A1 | 7/2019 | Harris et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201120 A1 | 7/2019 | Shelton, IV et al. |
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201142 A1 | 7/2019 | Shelton, IV et al. |
| 2019/0201594 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |

(56) References Cited

U.S. PATENT DOCUMENTS

| | | | |
|---|---|---|---|
| 2019/0206569 A1 | 7/2019 | Shelton, IV et al. | |
| 2019/0208641 A1 | 7/2019 | Yates et al. | |
| 2019/0298471 A1 | 10/2019 | Holop | |
| 2019/0314107 A1 | 10/2019 | Worrell et al. | |
| 2019/0321112 A1 | 10/2019 | Cecil | |
| 2019/0328469 A1 | 10/2019 | Ando et al. | |
| 2019/0357884 A1 | 11/2019 | Williams et al. | |
| 2020/0000536 A1 | 1/2020 | Yakimovich et al. | |
| 2020/0054412 A1 | 2/2020 | Fuerst et al. | |
| 2020/0078109 A1 | 3/2020 | Steger et al. | |
| 2020/0093554 A1 | 3/2020 | Schuh et al. | |
| 2020/0197108 A1 | 6/2020 | Usui | |
| 2020/0214776 A1 | 7/2020 | Hingwe et al. | |
| 2020/0246063 A1 | 8/2020 | Shelton, IV et al. | |
| 2020/0281675 A1 | 9/2020 | Meglan | |
| 2020/0315715 A1 | 10/2020 | Rockrohr et al. | |
| 2020/0315721 A1 | 10/2020 | Rabindran et al. | |
| 2020/0405375 A1 | 12/2020 | Shelton, IV et al. | |
| 2020/0405401 A1 | 12/2020 | Shelton, IV et al. | |
| 2020/0405403 A1 | 12/2020 | Shelton, IV et al. | |
| 2020/0405404 A1 | 12/2020 | Shelton, IV et al. | |
| 2020/0405405 A1 | 12/2020 | Shelton, IV et al. | |
| 2020/0405406 A1 | 12/2020 | Harris et al. | |
| 2020/0405408 A1 | 12/2020 | Shelton, IV et al. | |
| 2020/0405414 A1 | 12/2020 | Shelton, IV et al. | |
| 2020/0405415 A1 | 12/2020 | Shelton, IV et al. | |
| 2020/0405416 A1 | 12/2020 | Shelton, IV et al. | |
| 2020/0405417 A1 | 12/2020 | Shelton, IV et al. | |
| 2020/0405421 A1 | 12/2020 | Luck | |
| 2021/0015519 A1 | 1/2021 | Meglan et al. | |
| 2021/0059777 A1 | 3/2021 | Overmyer et al. | |
| 2021/0093409 A1 | 4/2021 | Overmyer et al. | |
| 2021/0196356 A1 | 7/2021 | Shelton, IV et al. | |
| 2021/0212777 A1 | 7/2021 | Cheng | |
| 2021/0401524 A1 | 12/2021 | Suresh et al. | |
| 2022/0031350 A1 | 2/2022 | Witte | |
| 2022/0054208 A1 | 2/2022 | Cooper et al. | |
| 2022/0202437 A1 | 6/2022 | Overmyer et al. | |
| 2022/0202514 A1 | 6/2022 | Boudreaux | |
| 2022/0202517 A1 | 6/2022 | Overmyer et al. | |
| 2022/0287782 A1 | 9/2022 | Shelton, IV et al. | |
| 2023/0000491 A1 | 1/2023 | Wise et al. | |
| 2023/0000542 A1 | 1/2023 | Murrell | |
| 2023/0000578 A1 | 1/2023 | Moubarak | |
| 2023/0001579 A1 | 1/2023 | Overmyer et al. | |
| 2023/0320776 A1 | 10/2023 | Shelton, IV et al. | |

FOREIGN PATENT DOCUMENTS

| | | |
|---|---|---|
| DE | 29623113 U1 | 10/1997 |
| DE | 20004812 U1 | 9/2000 |
| DE | 10201569 A1 | 7/2003 |
| EP | 0705571 A1 | 4/1996 |
| EP | 2060238 A1 | 5/2009 |
| EP | 1747761 B1 | 10/2009 |
| JP | H08229050 A | 9/1996 |
| SU | 578972 A1 | 11/1977 |
| WO | WO-8103272 A1 | 11/1981 |
| WO | WO-9800069 A1 | 1/1998 |
| WO | WO-9923960 A1 | 5/1999 |
| WO | WO-0024330 A1 | 5/2000 |
| WO | WO-0128444 A1 | 4/2001 |
| WO | WO-2004078051 A2 | 9/2004 |
| WO | WO-2010104755 A1 | 9/2010 |
| WO | WO-2012044606 A2 | 4/2012 |

OTHER PUBLICATIONS

International Preliminary Report on Patentability, Application No. PCT/US2013/046777, dated Dec. 31, 2014 (5 pages).
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-induced changes in the mechanics of a collagenous tissue: pseudoelastic behavior at 37° C.," Journal of Biomechanics, 31, pp. 211-216 (1998).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
Kurt Gieck & Reiner Gieck, Engineering Formulas § Z.7 (7th ed. 1997).
National Semiconductors Temperature Sensor Handbook—http://www.national.com/appinfo/tempsensors/files/temphb.pdf; accessed online: Apr. 1, 2011.
Glaser and Subak-Sharpe,Integrated Circuit Engineering, Addison-Wesley Publishing, Reading, MA (1979). (book—not attached).
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).

(56) References Cited

OTHER PUBLICATIONS

Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.

Jang, J. et al. "Neuro-fuzzy and Soft Computing." Prentice Hall, 1997, pp. 13-89, 199-293, 335-393, 453-496, 535-549.

Douglas, S.C. "Introduction to Adaptive Filter". Digital Signal Processing Handbook. Ed. Vijay K. Madisetti and Douglas B. Williams. Boca Raton: CRC Press LLC, 1999.

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

Sullivan, "Optimal Choice for Number of Strands in a Litz-Wire Transformer Winding," IEEE Transactions on Power Electronics, vol. 14, No. 2, Mar. 1999, pp. 283-291.

Covidien Brochure, The LigaSure Precise ™ Instrument, dated Mar. 2011 (2 pages).

"ATM-MPLS Network Interworking Version 2.0, af-aic-0178.001" ATM Standard, The ATM Forum Technical Committee, published Aug. 2003.

IEEE Std 802.3-2012 (Revision of IEEE Std 802.3-2008, published Dec. 28, 2012.

* cited by examiner

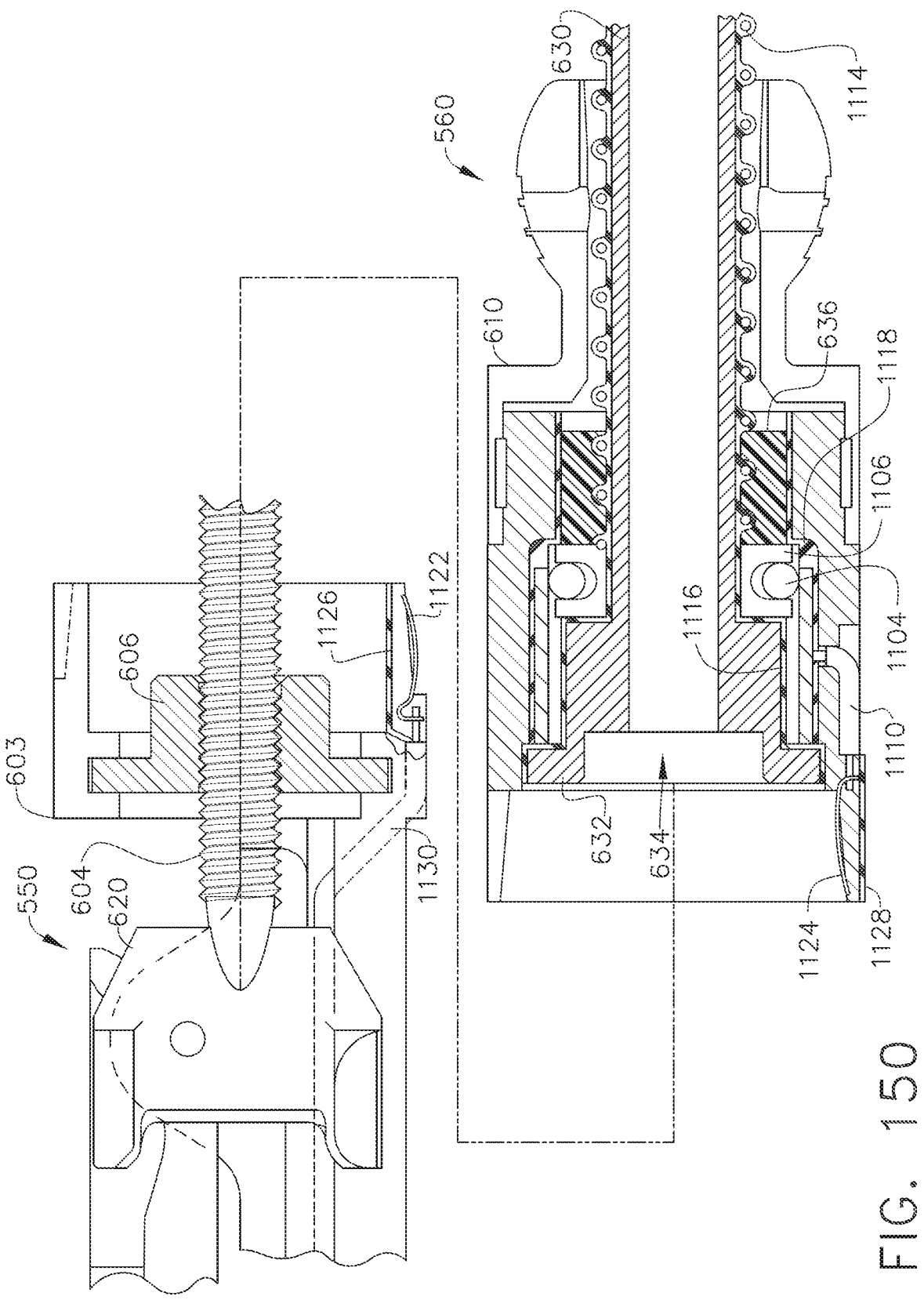
F I G. 1 5 0

SURGICAL END EFFECTOR JAW AND ELECTRODE CONFIGURATIONS

CROSS-REFERENCE TO RELATED APPLICATIONS

This application is a continuation application claiming priority under 35 U.S.C. § 120 to U.S. patent application Ser. No. 15/392,265, entitled SURGICAL END EFFECTOR JAW AND ELECTRODE CONFIGURATIONS, filed on Dec. 28, 2016, now U.S. Patent Application Publication No. 2017/0105785, which is a continuation application claiming priority under 35 U.S.C. § 120 to U.S. patent application Ser. No. 13/536,393, entitled SURGICAL END EFFECTOR JAW AND ELECTRODE CONFIGURATIONS, filed on Jun. 28, 2012, now U.S. Patent Application Publication No. 2014/0005640, the entire disclosures of which are hereby incorporated by reference herein.

BACKGROUND

Over the years a variety of minimally invasive robotic (or "telesurgical") systems have been developed to increase surgical dexterity as well as to permit a surgeon to operate on a patient in an intuitive manner. Many of such systems are disclosed in the following U.S. patents which are each herein incorporated by reference in their respective entirety: U.S. Pat. No. 5,792,135, entitled ARTICULATED SURGICAL INSTRUMENT FOR PERFORMING MINIMALLY INVASIVE SURGERY WITH ENHANCED DEXTERITY AND SENSITIVITY, U.S. Pat. No. 6,231,565, entitled ROBOTIC ARM DLUS FOR PERFORMING SURGICAL TASKS, U.S. Pat. No. 6,783,524, entitled ROBOTIC SURGICAL TOOL WITH ULTRASOUND CAUTERIZING AND CUTTING INSTRUMENT, U.S. Pat. No. 6,364,888, entitled ALIGNMENT OF MASTER AND SLAVE IN A MINIMALLY INVASIVE SURGICAL APPARATUS, U.S. Pat. No. 7,524,320, entitled MECHANICAL ACTUATOR INTERFACE SYSTEM FOR ROBOTIC SURGICAL TOOLS, U.S. Pat. No. 7,691,098, entitled PLATFORM LINK WRIST MECHANISM, U.S. Pat. No. 7,806,891, entitled REPOSITIONING AND REORIENTATION OF MASTER/SLAVE RELATIONSHIP IN MINIMALLY INVASIVE TELESURGERY, and U.S. Pat. No. 7,824,401, entitled ROBOTIC TOOL WITH WRISTED MONOPOLAR ELECTROSURGICAL END EFFECTORS. Many of such systems, however, have in the past been unable to generate the magnitude of forces required to effectively cut and fasten tissue. In addition, existing robotic surgical systems are limited in the number of different types of surgical devices that they may operate.

BRIEF DESCRIPTION OF THE DRAWINGS

The features and advantages of this invention, and the manner of attaining them, will become more apparent and the invention itself will be better understood by reference to the following description of example embodiments of the invention taken in conjunction with the accompanying drawings, wherein:

Various example embodiments are described herein by way of example in conjunction with the following FIGS. wherein:

FIG. 117 is another perspective view of the surgical end effector shown in FIG. 116 including a cross sectional perspective view of a jaw member in accordance with certain embodiments described herein.

FIG. 118 is cross sectional view of a first jaw member and a second jaw member of a surgical end effector in accordance with certain embodiments described herein.

FIG. 119 is cross sectional view of a first jaw member and a second jaw member of a surgical end effector in accordance with certain embodiments described herein FIG. 120 is a perspective view of a first jaw member and a second jaw member of a surgical end effector in accordance with certain embodiments described herein.

FIG. 121 is a prospective view of a distal portion of a jaw member of a surgical end effector in accordance with certain embodiments described herein.

FIG. 122 is a top view of a gripping portion in accordance with certain embodiments described herein.

FIG. 123 is a top view of a gripping portion in accordance with certain embodiments described herein.

FIG. 124 is a top view of a gripping portion in accordance with certain embodiments described herein.

FIG. 125 is a top view of a gripping portion in accordance with certain embodiments described herein.

FIG. 126 is a top view of a gripping portion in accordance with certain embodiments described herein.

FIG. 127 is a top view of a gripping portion in accordance with certain embodiments described herein.

FIG. 128 is a top view of a gripping portion in accordance with certain embodiments described herein.

FIG. 129 is a top view of a gripping portion in accordance with certain embodiments described herein.

Figures 129, 130, 131:
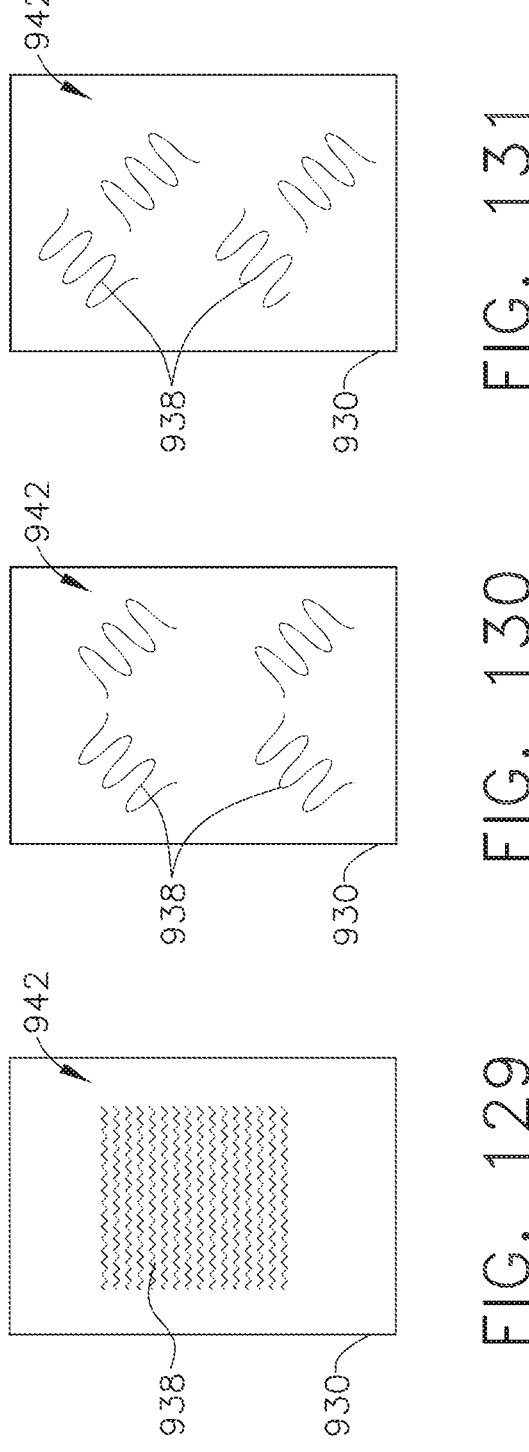

FIG. 130 is a top view of a gripping portion in accordance with certain embodiments described herein.

FIG. 131 is a top view of a gripping portion in accordance with certain embodiments described herein.

Figures 132, 133:
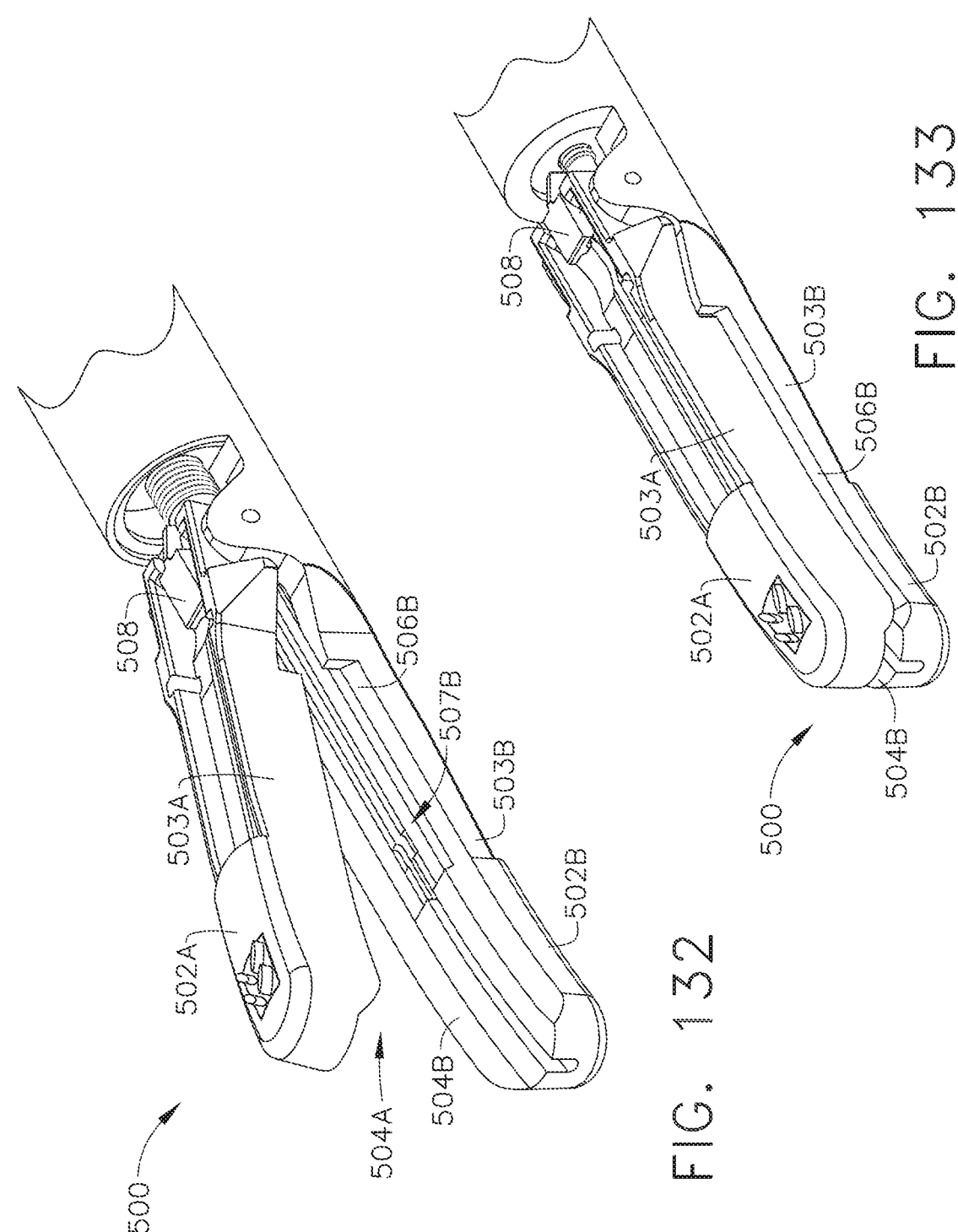

FIG. 132 is a perspective view of one embodiment of an end effector having first and second jaw members in an open position and angled tissue-contacting surfaces along substantially the entire length of the jaw members.

FIG. 133 is another perspective view of one embodiment of the end effector shown in FIG. 132 with the first and second jaw members in a closed position.

Figure 134:
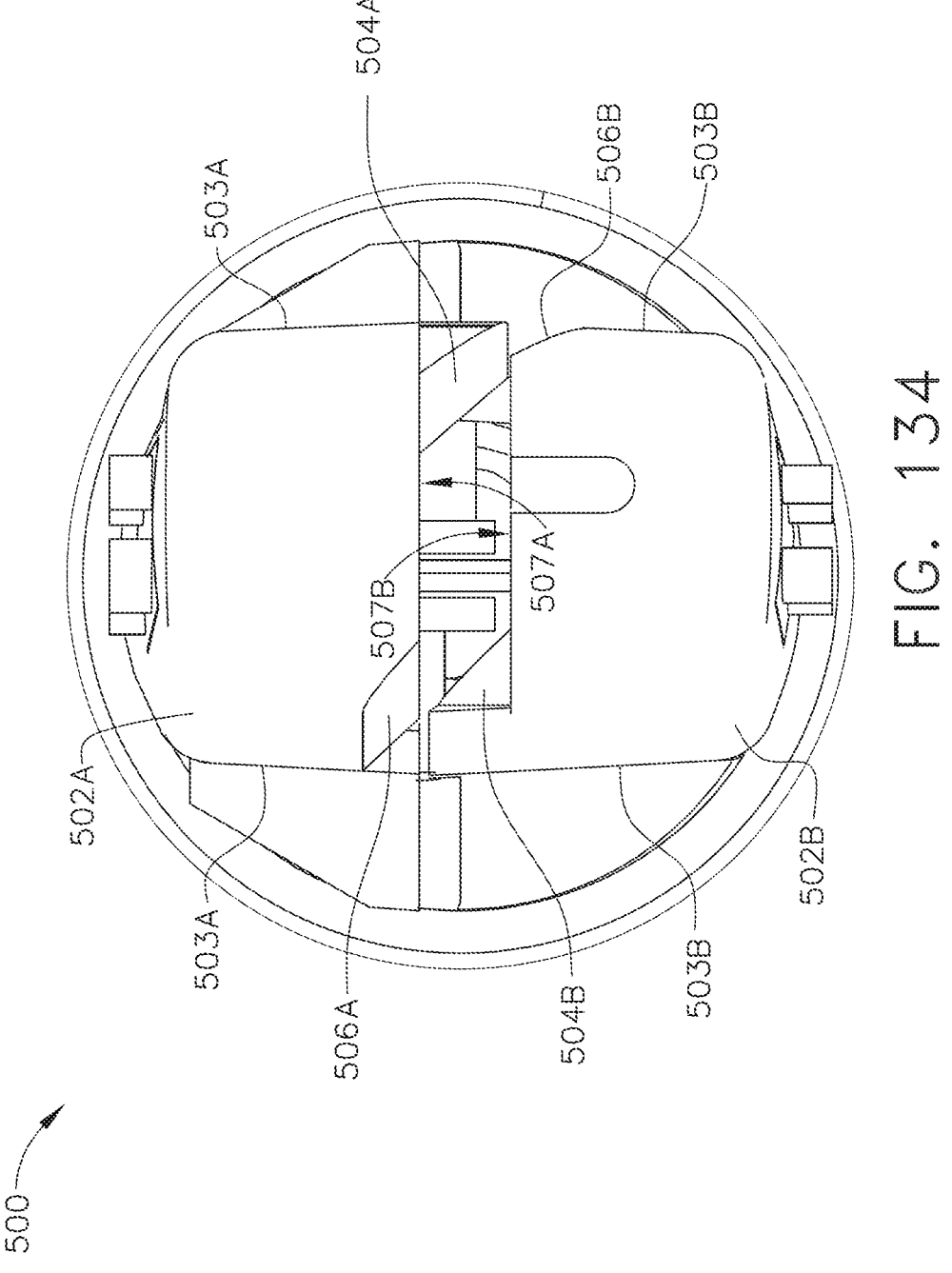

FIG. 134 is a front view of one embodiment of the end effector shown in FIG. 133.

Figure 135:
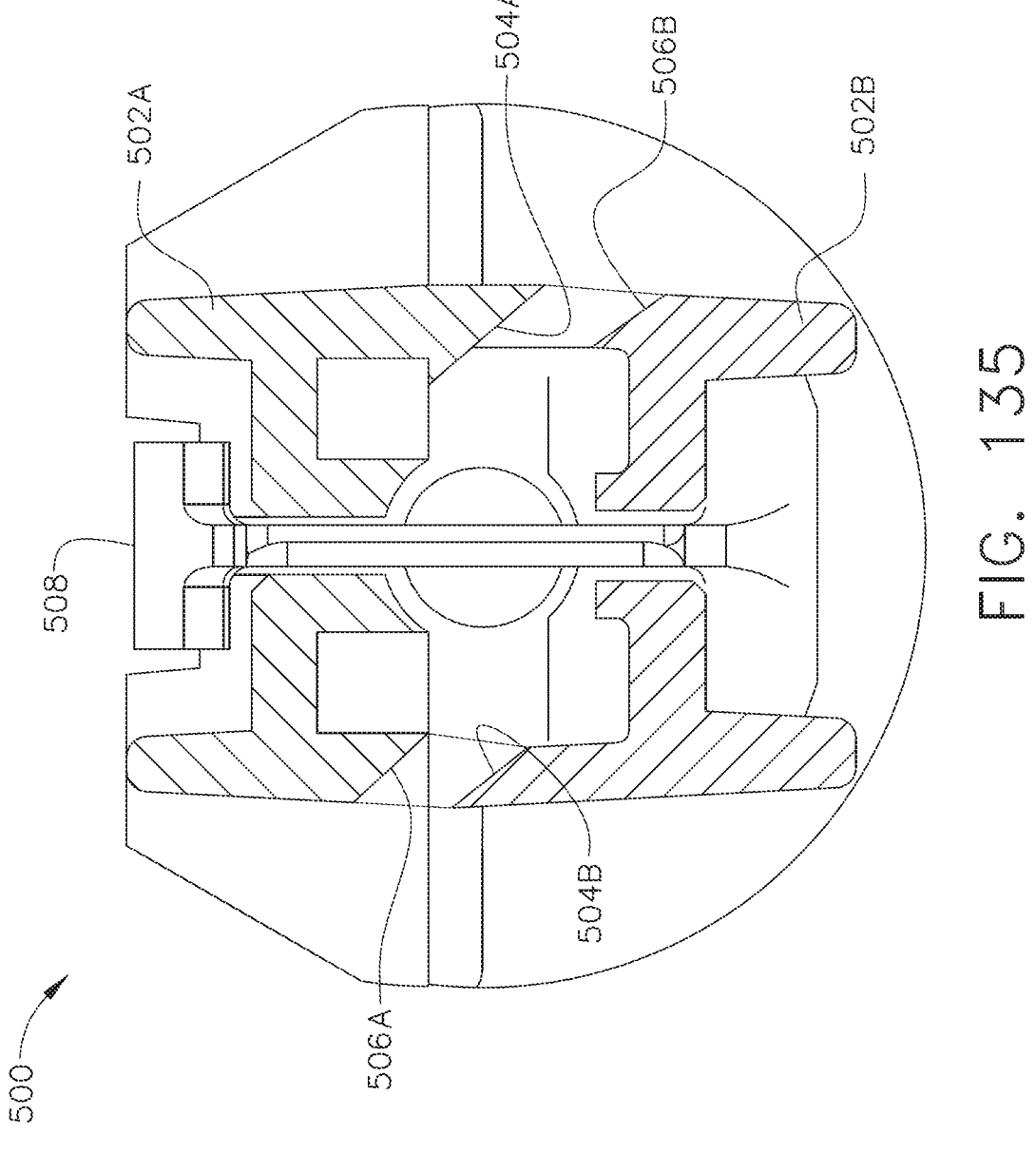

FIG. 135 is a cross-sectional view of one embodiment of the end effector shown in FIG. 134.

Figures 136, 137:
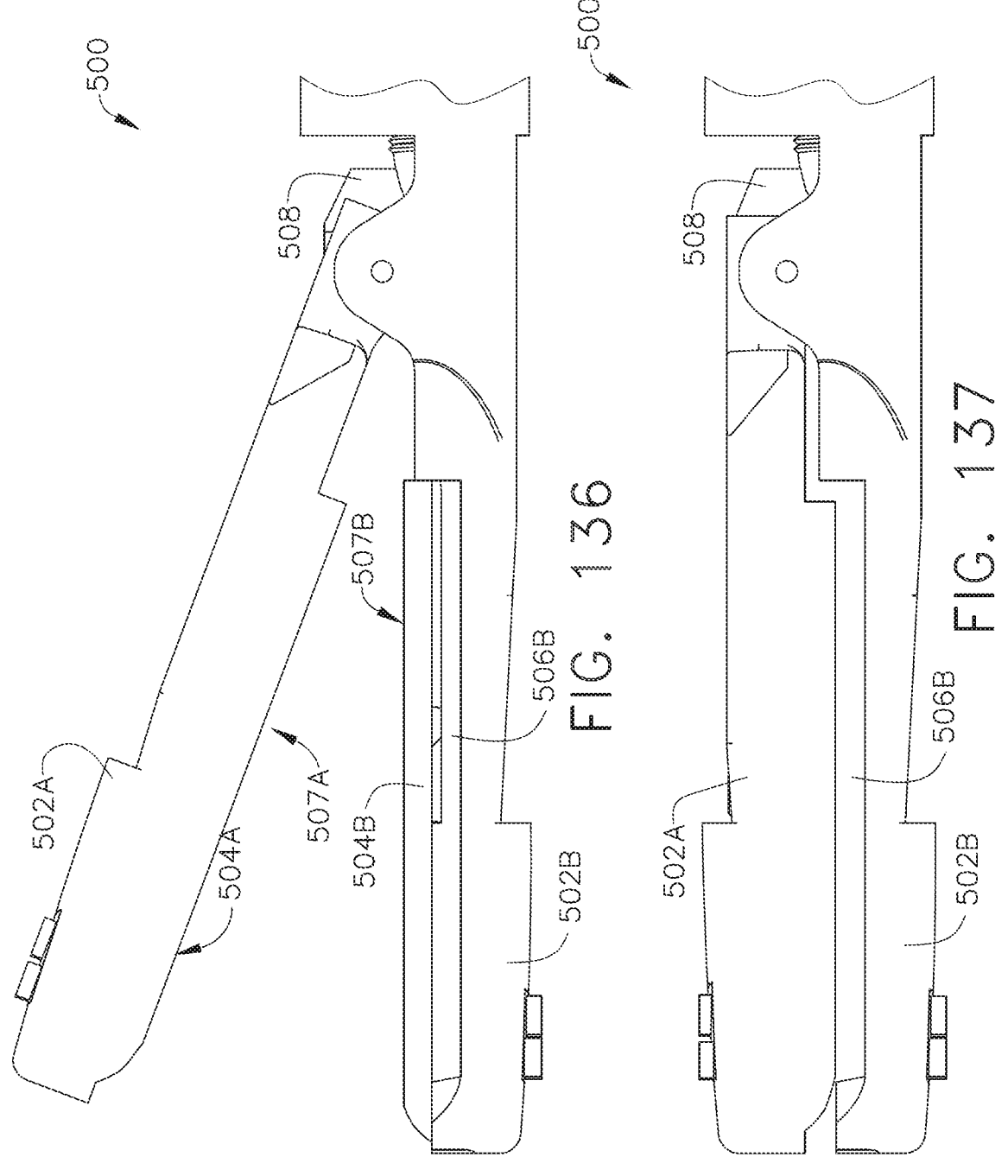

FIG. 136 is a side view of one embodiment of the end effector shown in FIG. 132.

FIG. 137 is a side view of one embodiment of the end effector shown in FIG. 133.

Figure 138:
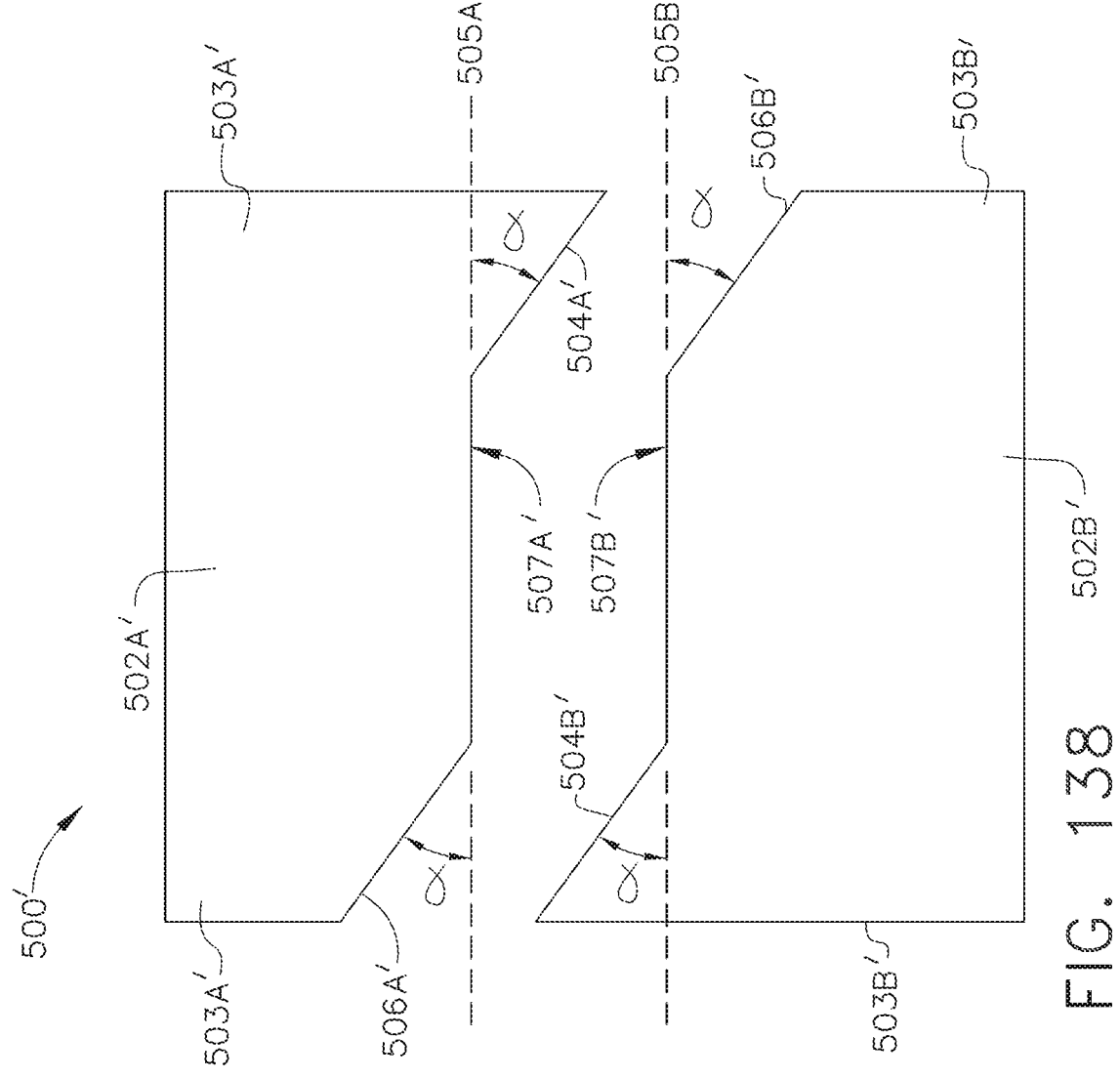

FIG. 138 is a schematic diagram showing a front view of one embodiment of an end effector having first and second jaw members, wherein each jaw member has two oppositely-angled tissue-contacting surfaces.

Figure 139:
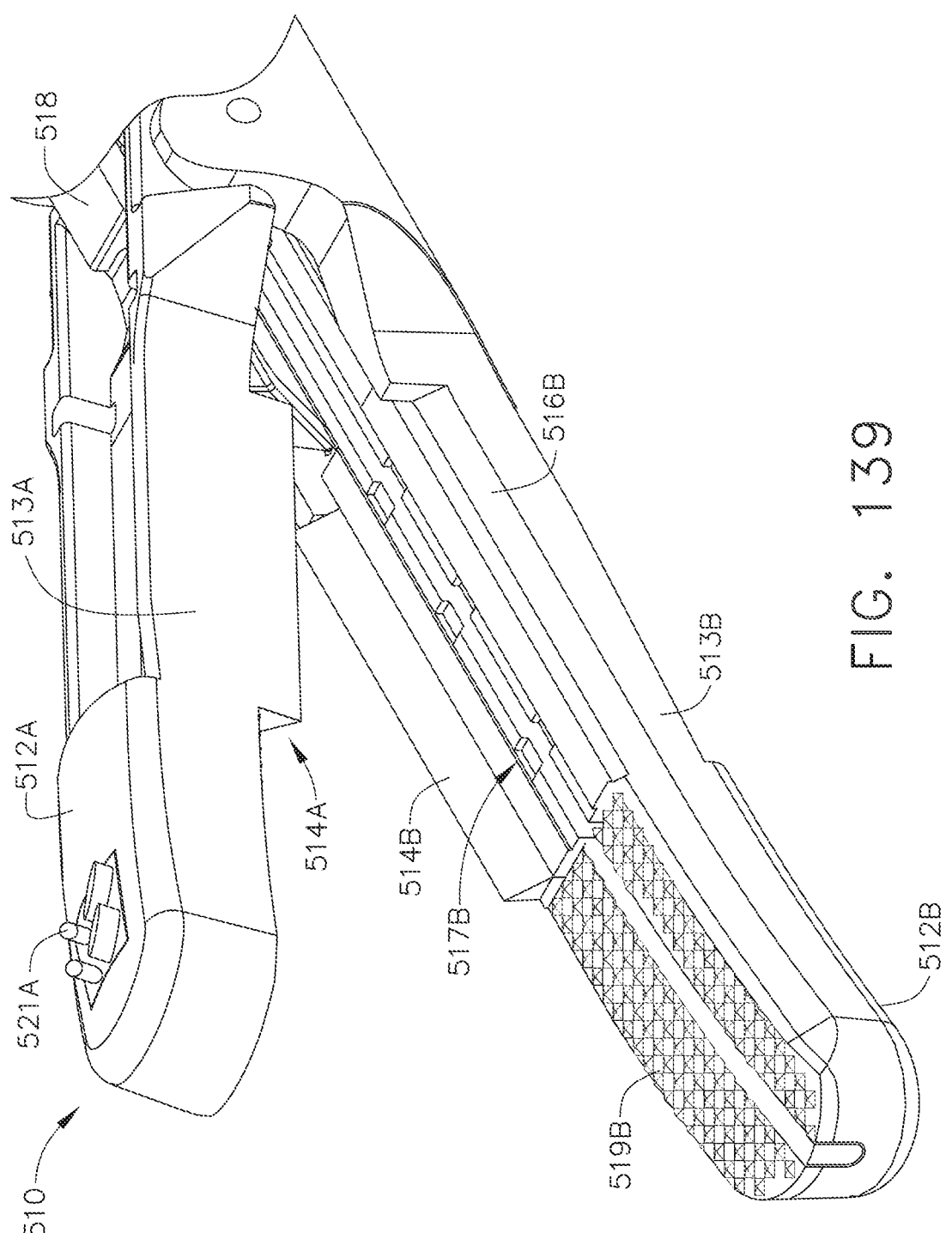

FIG. 139 is a perspective view of one embodiment of an end effector having first and second jaw members in an open position and angled tissue-contacting surfaces along a portion of the length of the jaw members.

Figure 140:
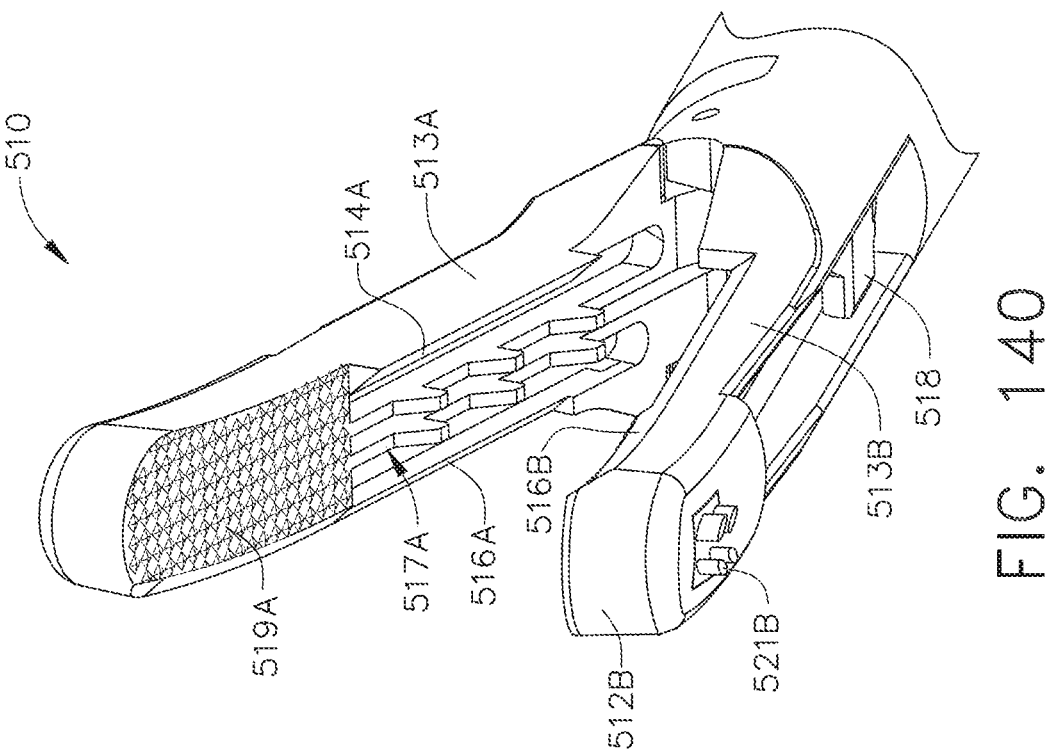

FIG. 140 is another perspective view of one embodiment of the end effector shown in FIG. 139.

Figure 141:
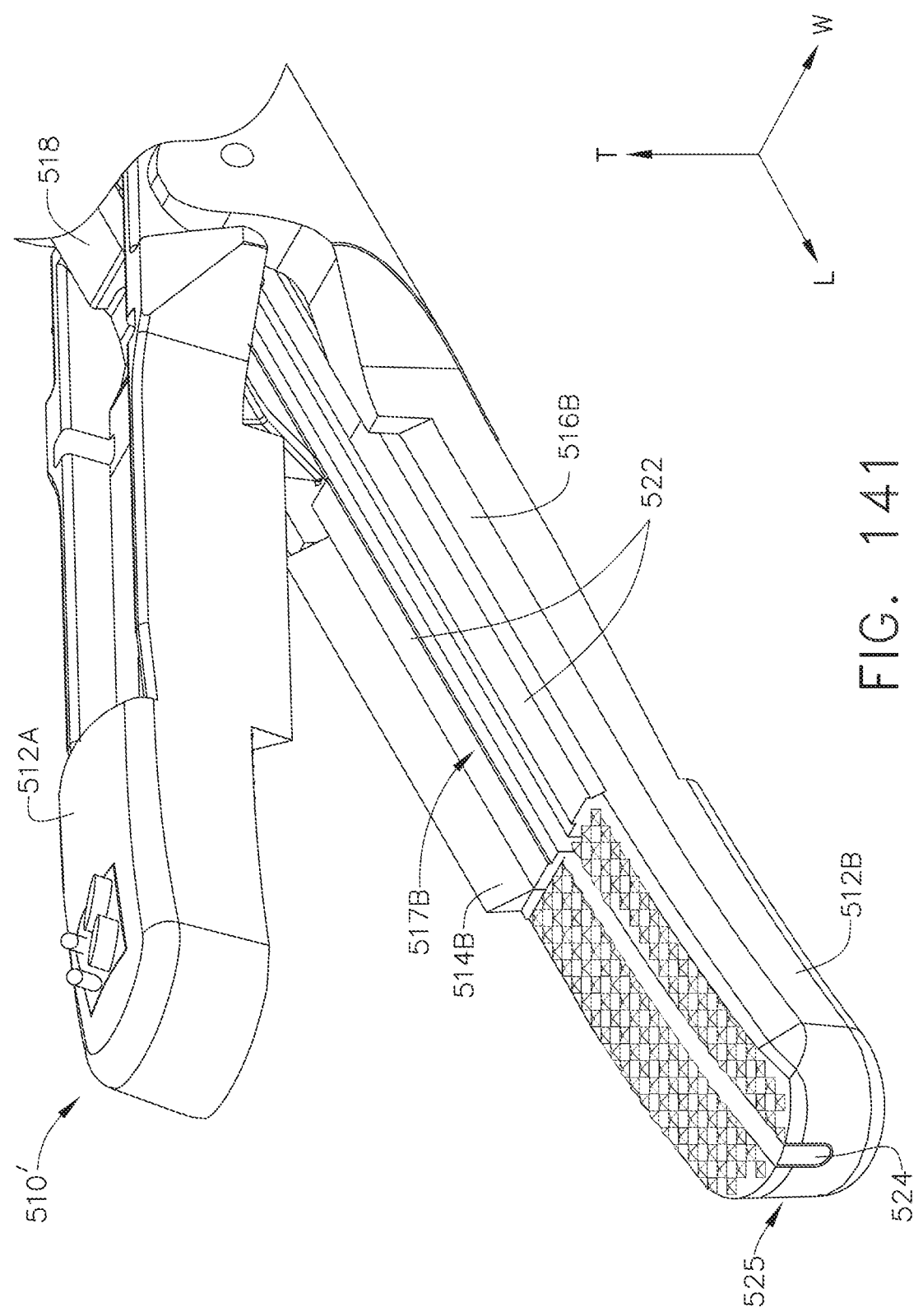

FIG. 141 is a perspective view of one embodiment of an end effector having first and second jaw members in an open position, angled tissue-contacting surfaces along a portion of the length of the jaw members, and electrodes positioned between the two angled tissue-contacting surfaces on the second jaw member.

Figure 142:
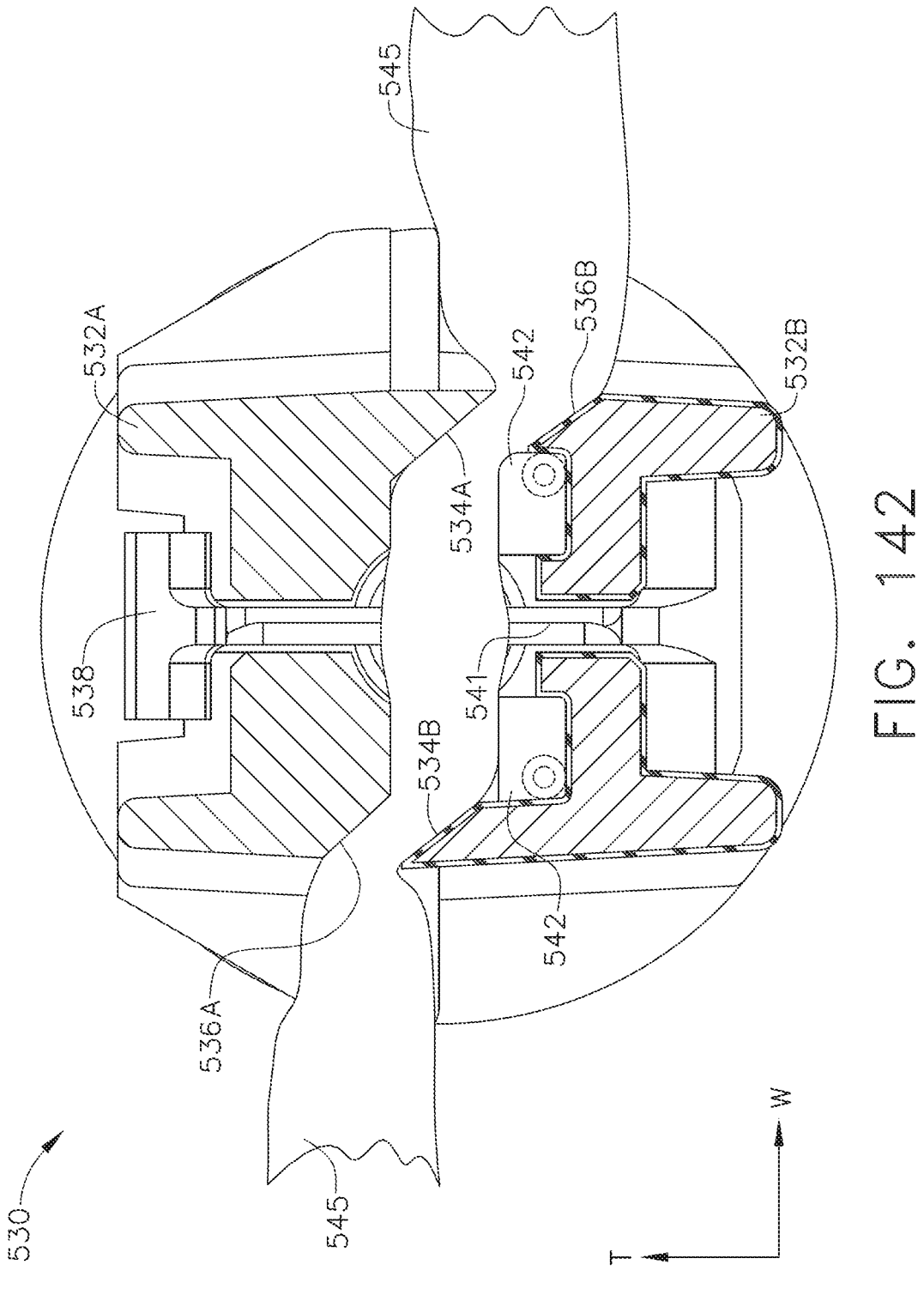

FIG. 142 is a cross-sectional view of one embodiment of an end effector having first and second jaw members in a closed position clamping tissue between the jaw members, wherein the first and second jaw members have opposed angled tissue-contacting surfaces.

Figure 143:
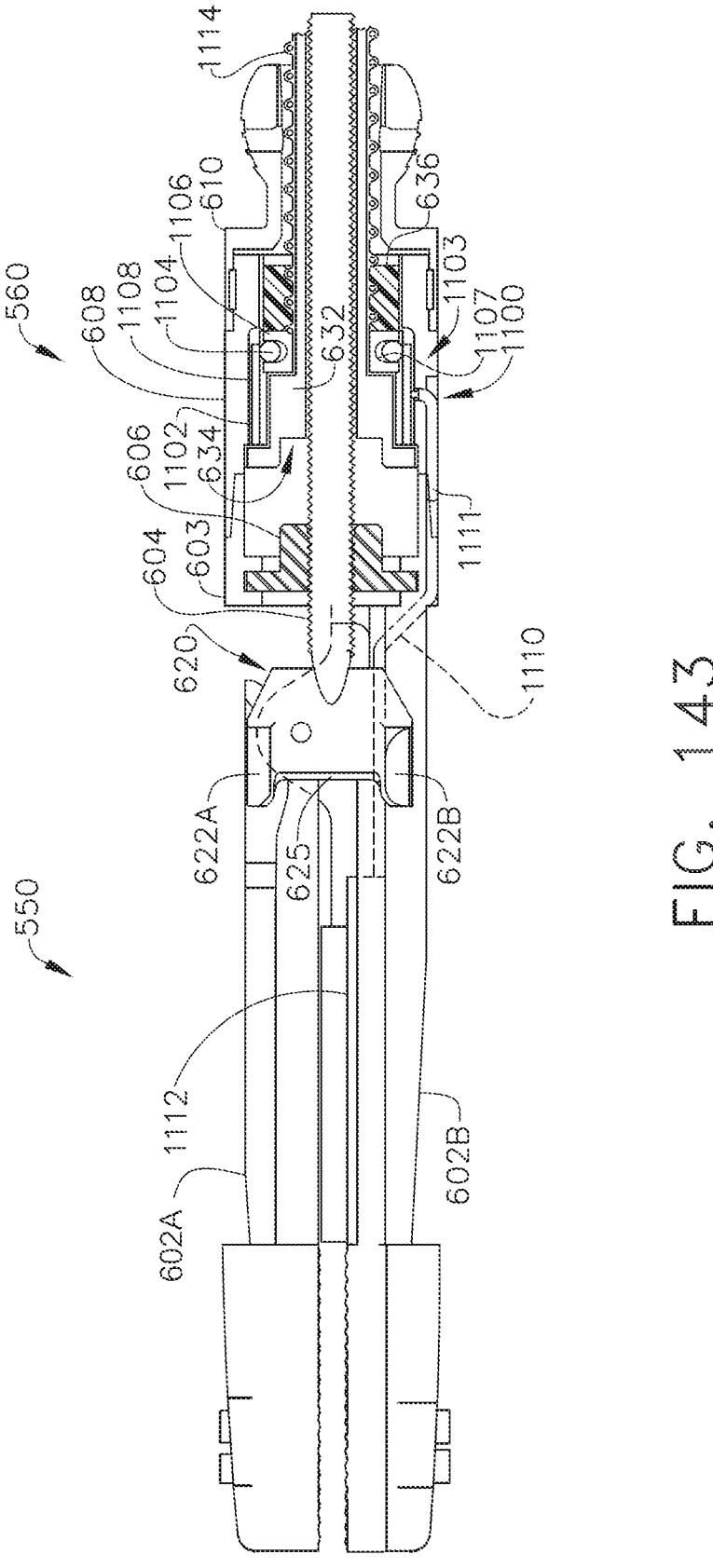

FIG. 143 is a cross-sectional view of one embodiment of the end effector and shaft assembly of FIGS. 64-82 illustrating an example installation of a rotary electrode assembly.

Figure 144:
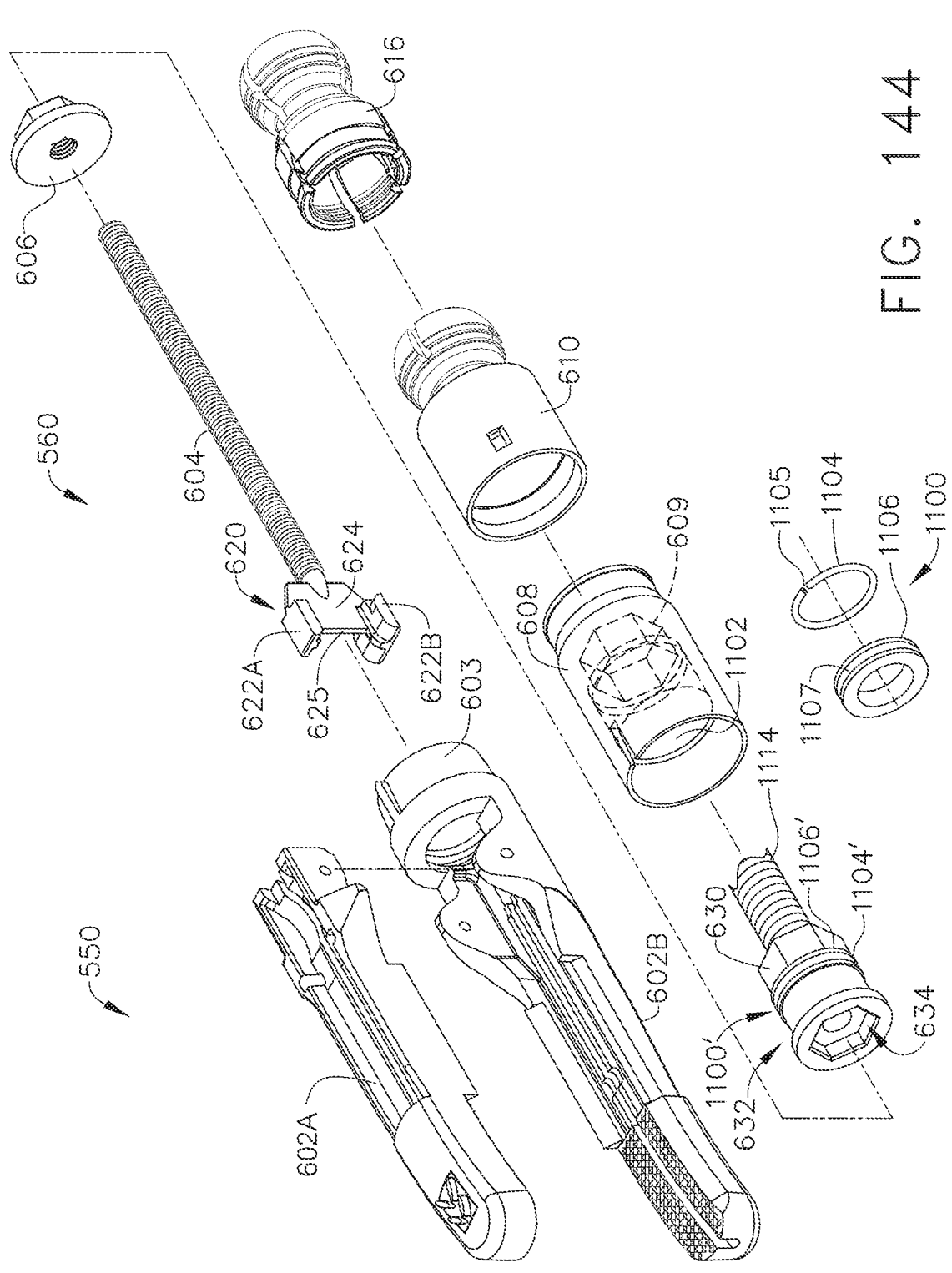

FIG. 144 is an exploded view of one embodiment of the end effector and shaft assembly of FIG. 143 showing the rotary electrode assembly both installed and exploded.

Figure 145:
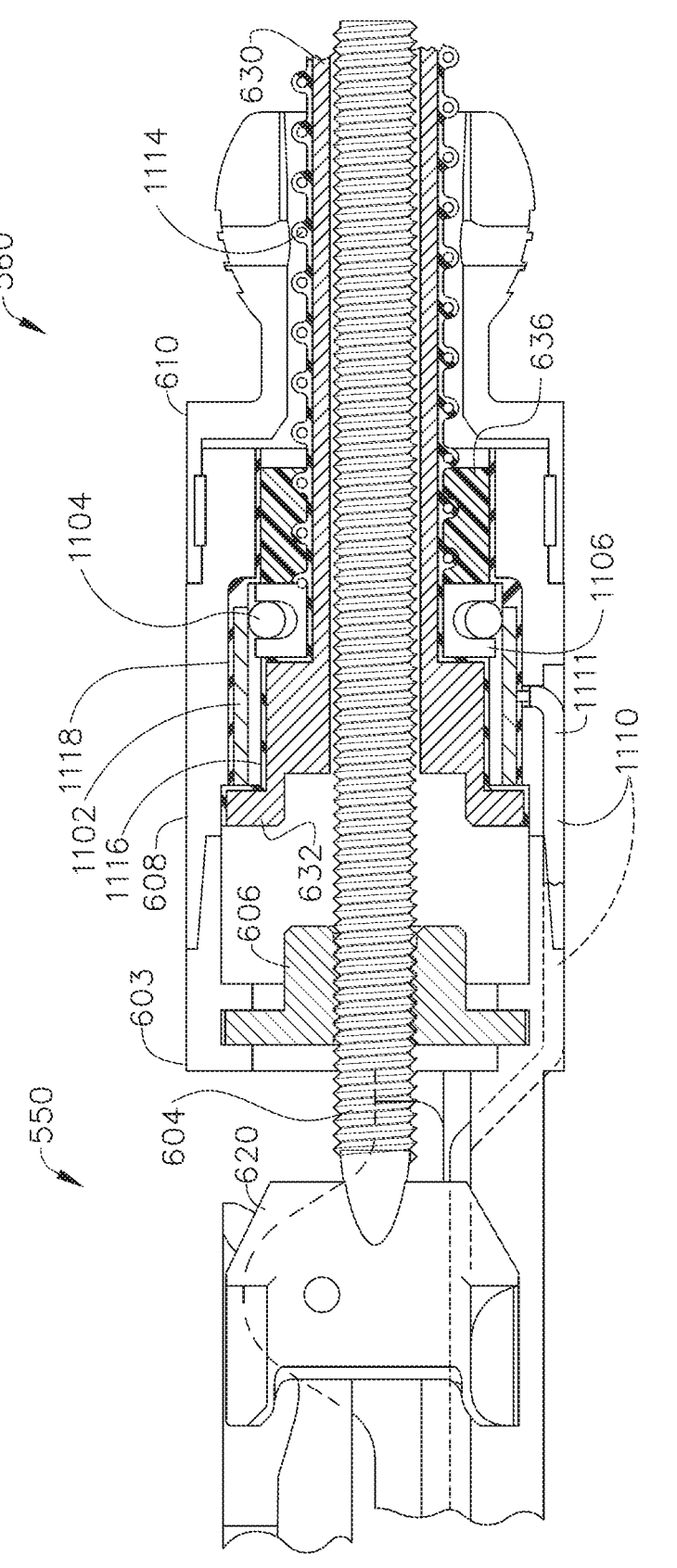

FIG. 145 is a cross-sectional view of one embodiment of the end effector and shaft assembly of FIG. 143 showing the rotary electrode assembly with a rotary drive head in a proximal position.

Figure 146:
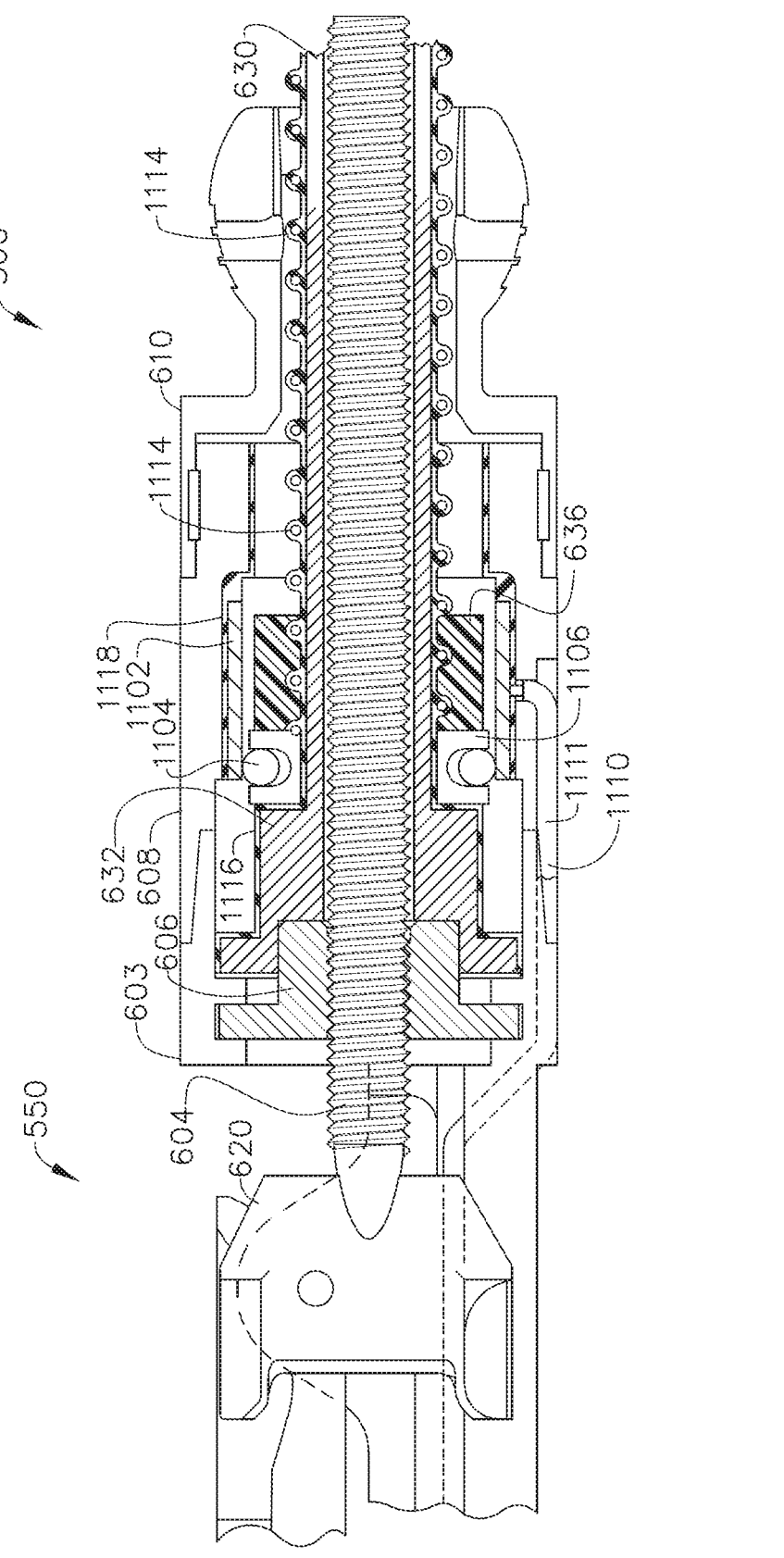

FIG. 146 is a cross-sectional view of one embodiment of the end effector and shaft assembly of FIG. 143 showing the rotary electrode assembly with the rotary drive head in a distal position.

Figure 147:
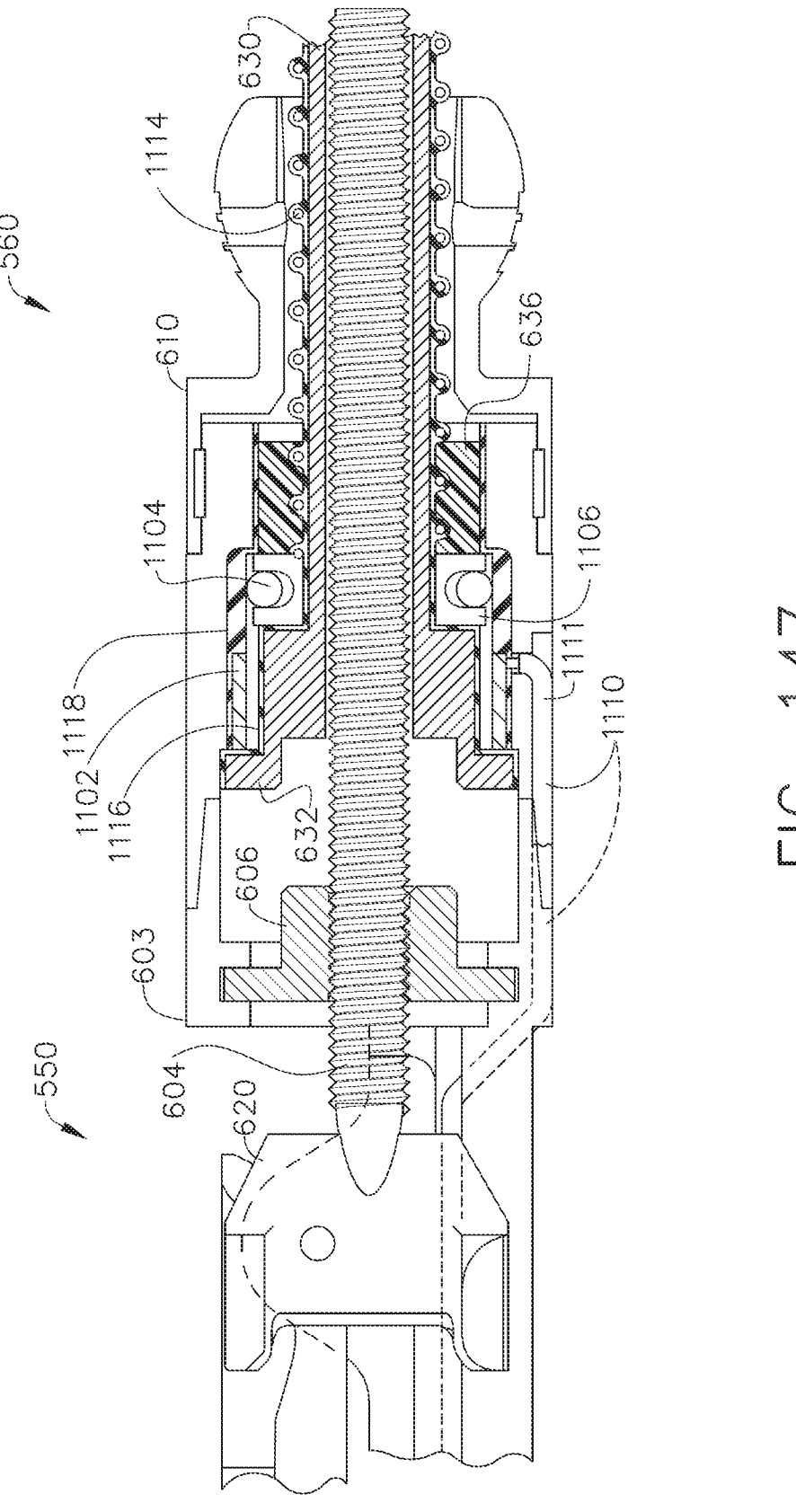
Figure 148:
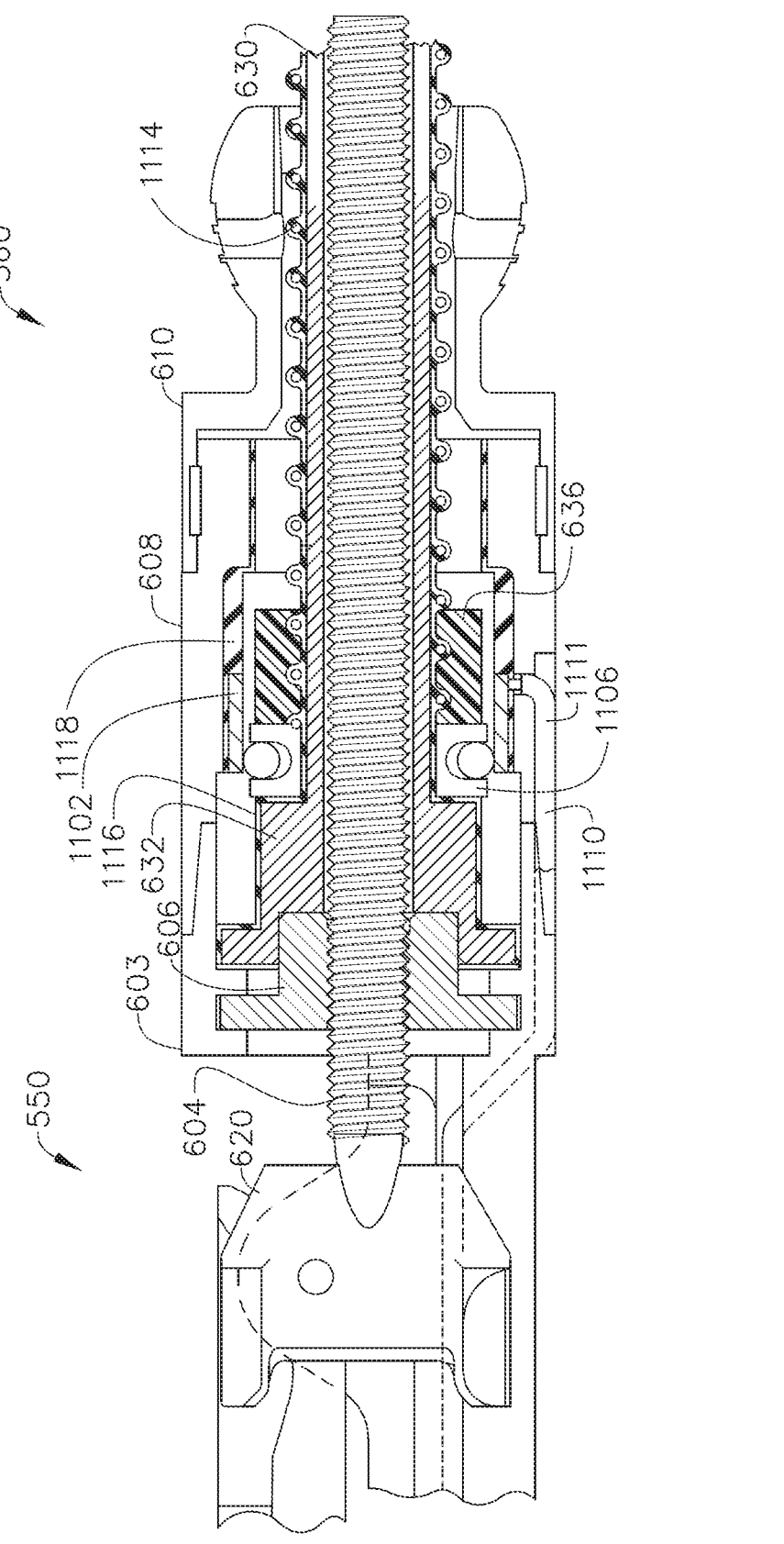

FIGS. 147-148 are cross-sectional views of one embodiment of the end effector and shaft assembly of FIG. 143 where a longitudinal length of the outer contact is selected such that the rotary connector assembly alternately creates and breaks an electrical connection limited by the longitudinal position of the brush assembly.

Figure 149:
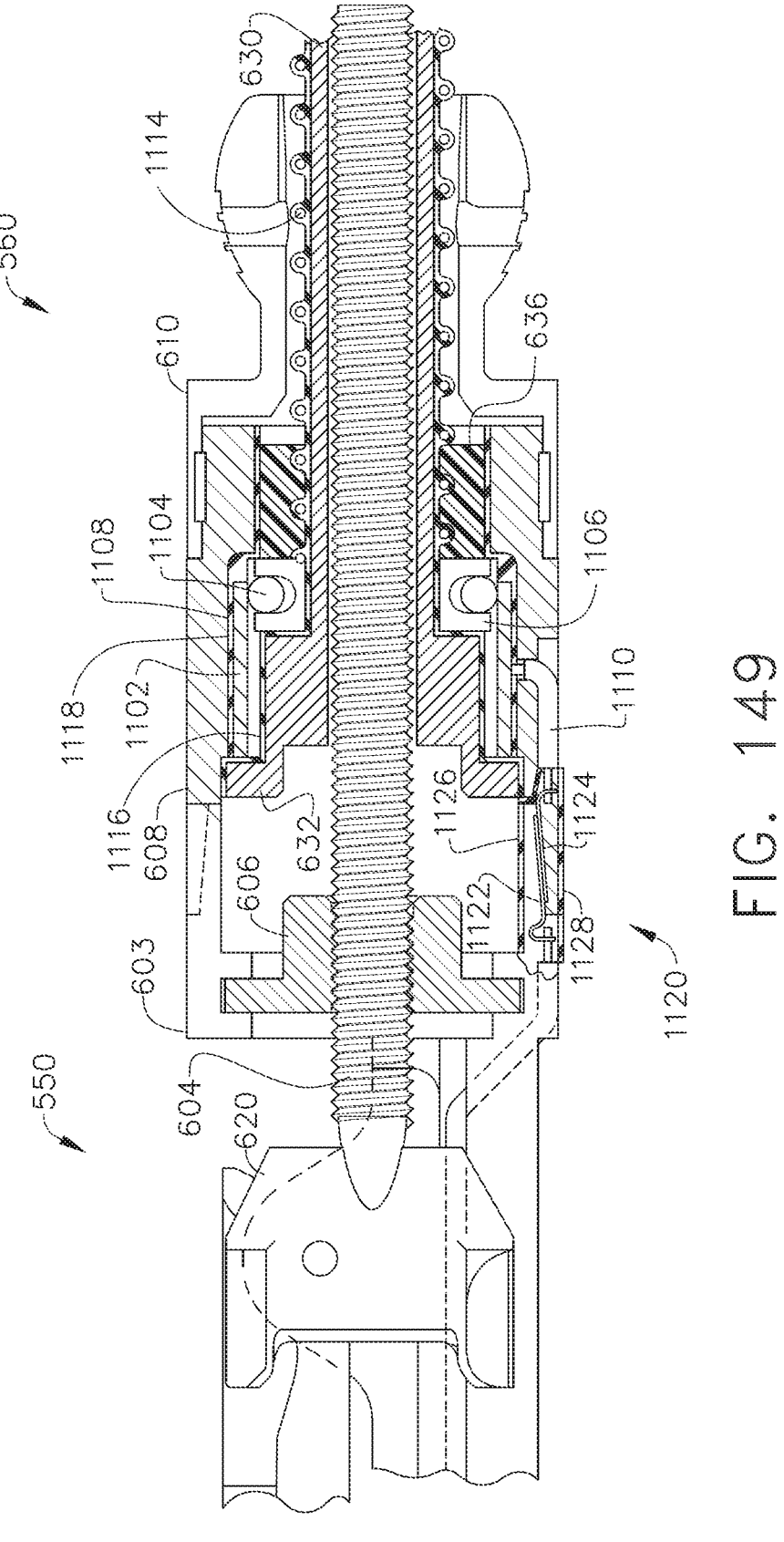

FIGS. 149-150 illustrate one embodiment of the end effector and shaft assembly of FIG. 143 showing a configuration including lead portions and connector assembly between the end effector and the shaft assembly.

Figure 151:
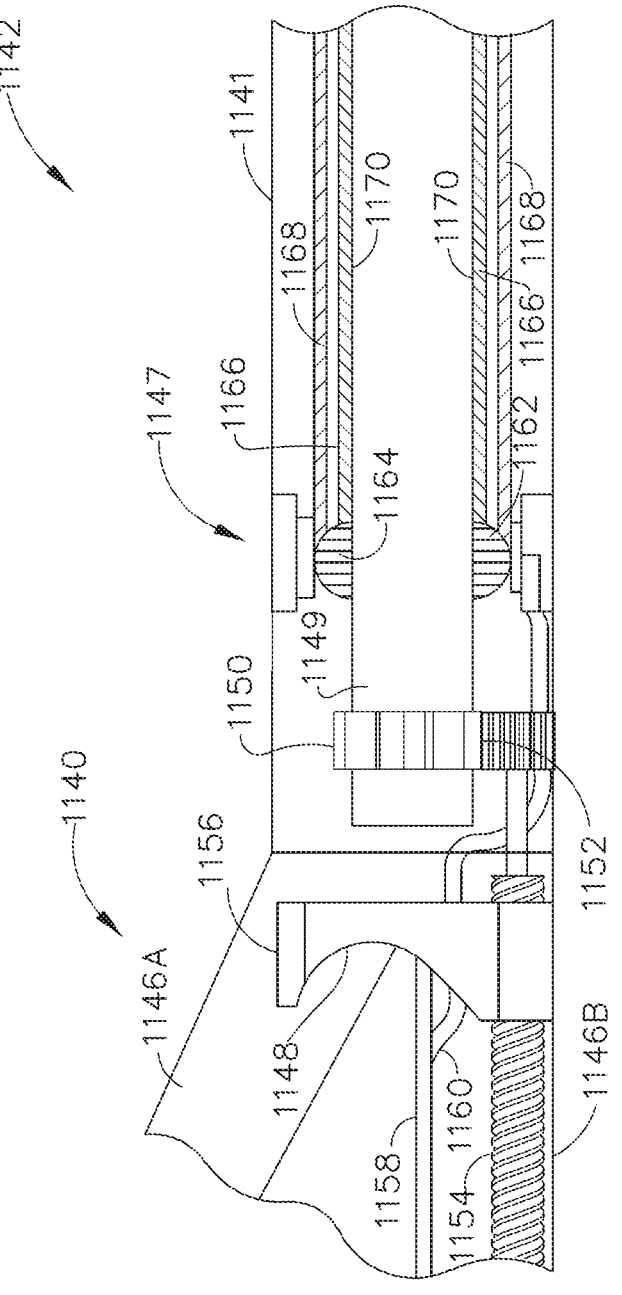

FIG. 151 illustrates a cross-sectional view one embodiment of an end effector and shaft assembly showing another context in which a rotary connector assembly may utilized.

Figure 152:
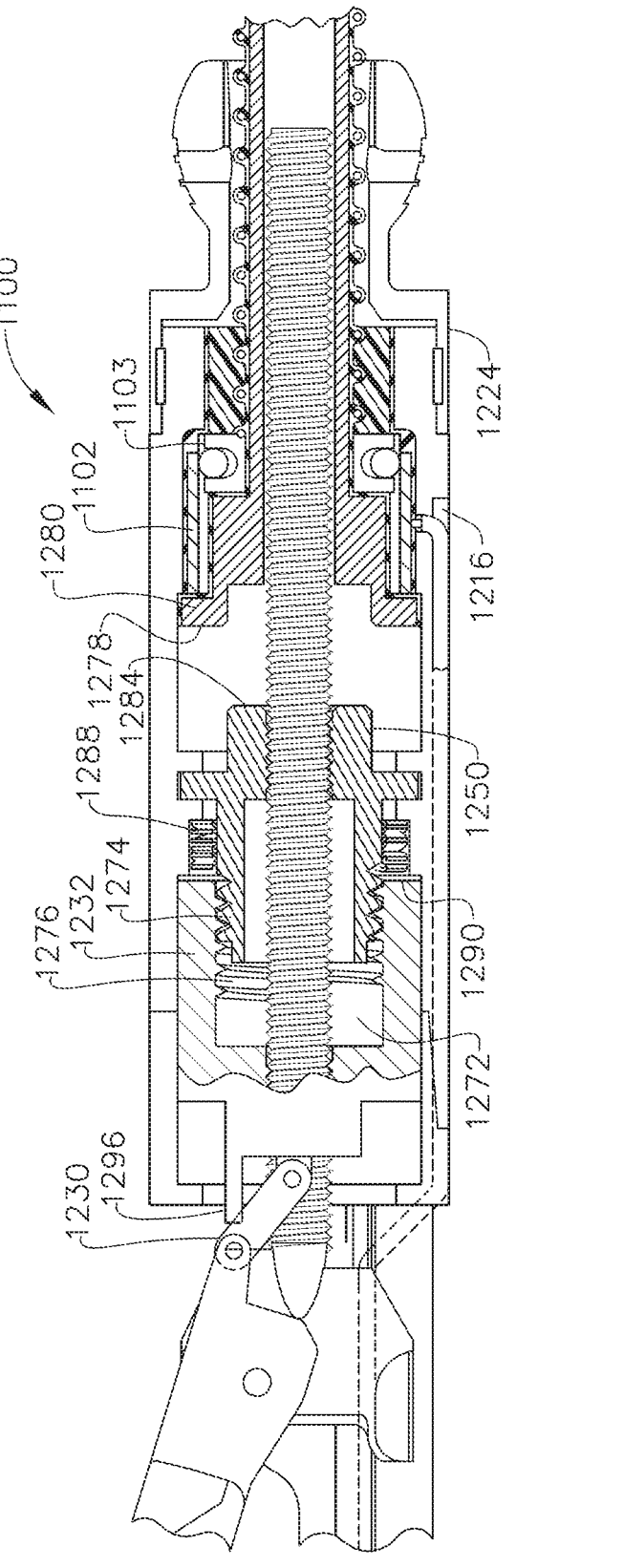

FIG. 152 illustrates a cross-sectional view of one embodiment of the end effector and shaft assembly of FIGS. 83-91 illustrating another example installation of a rotary electrode assembly.

Figure 153:
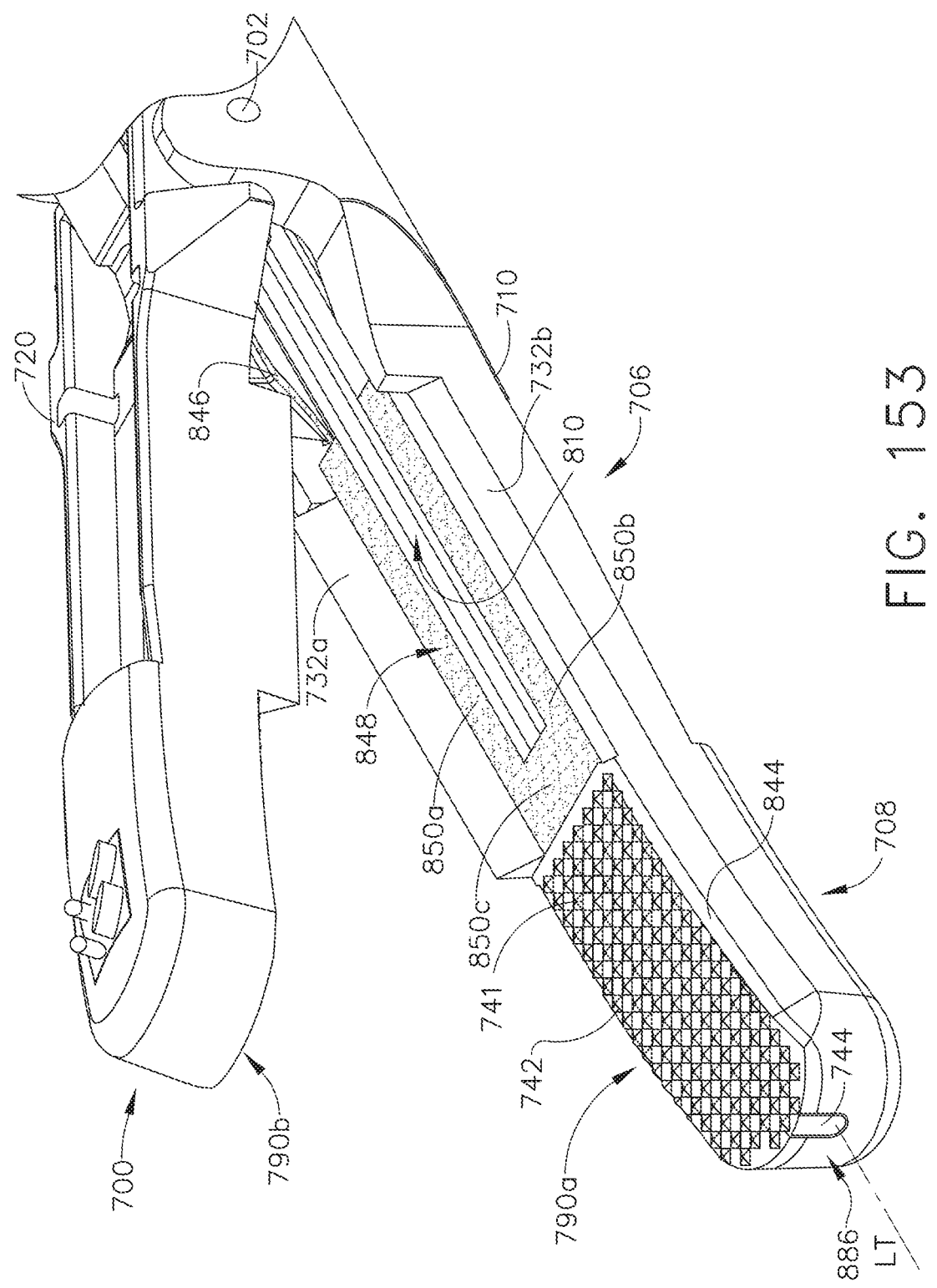

FIG. 153 illustrates one embodiment of an end effector that may be utilized with various surgical tools, including those described herein.

Figure 154:
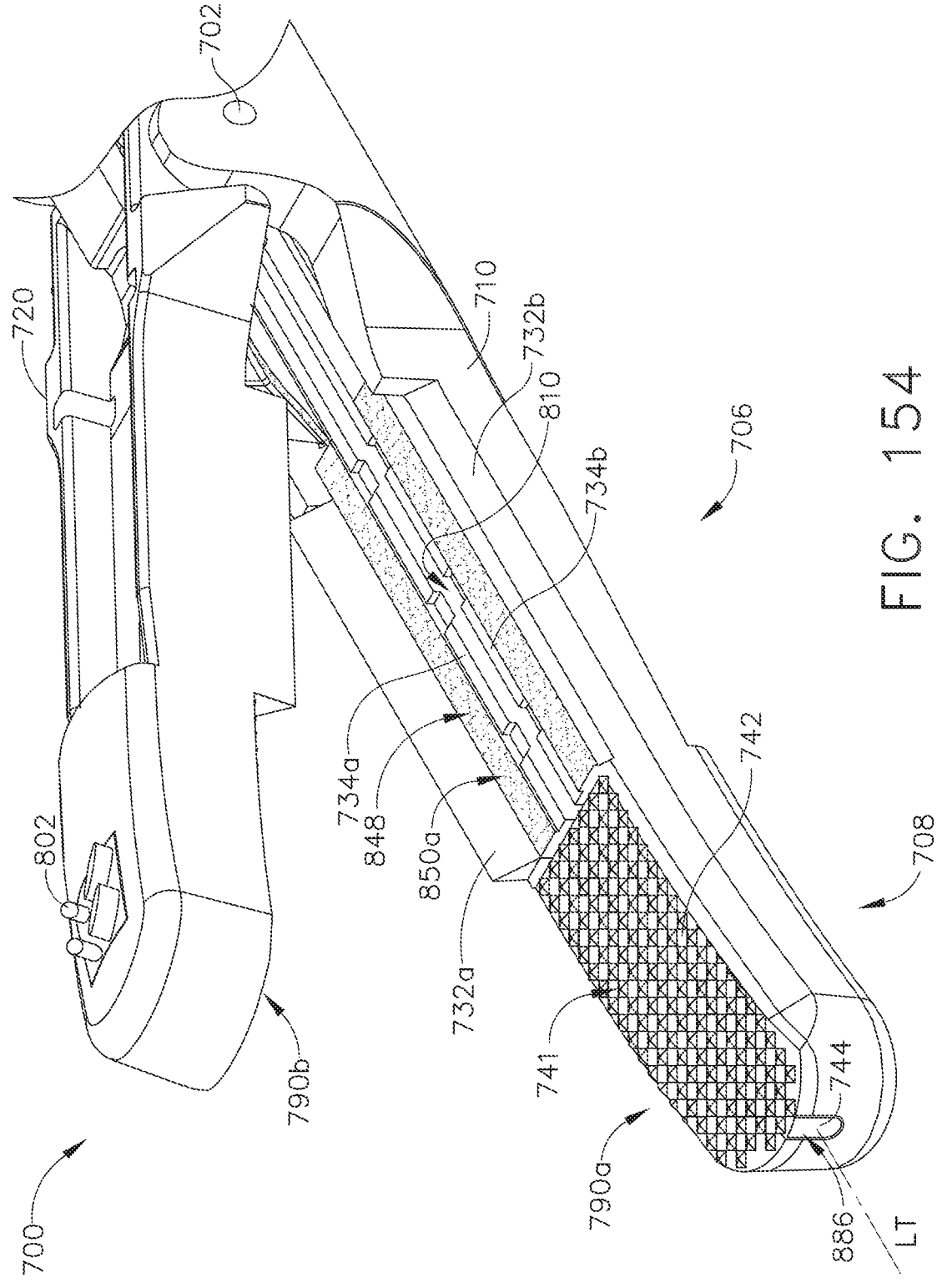

FIG. 154 illustrates one embodiment of the end effector of FIG. 153 showing a tissue contacting portion adjacent a longitudinal channel of the second jaw member of the end effector.

Figure 155:
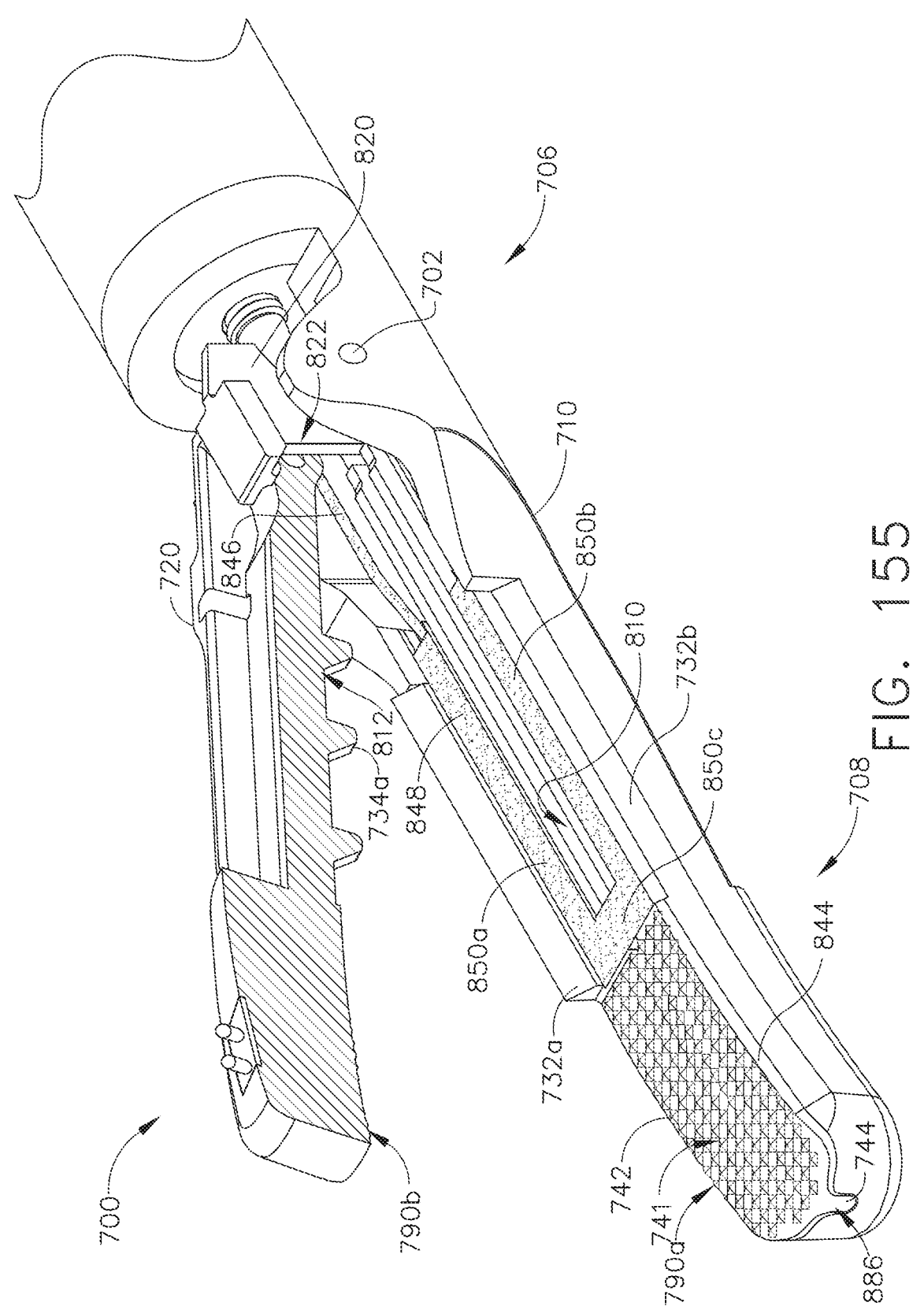

FIG. 155 illustrates one embodiment of the end effector of FIG. 153 showing an axial cross-section along a midline of the first jaw member showing a tissue-contacting portion disposed adjacent to a longitudinal channel of the first jaw member.

Figure 156:
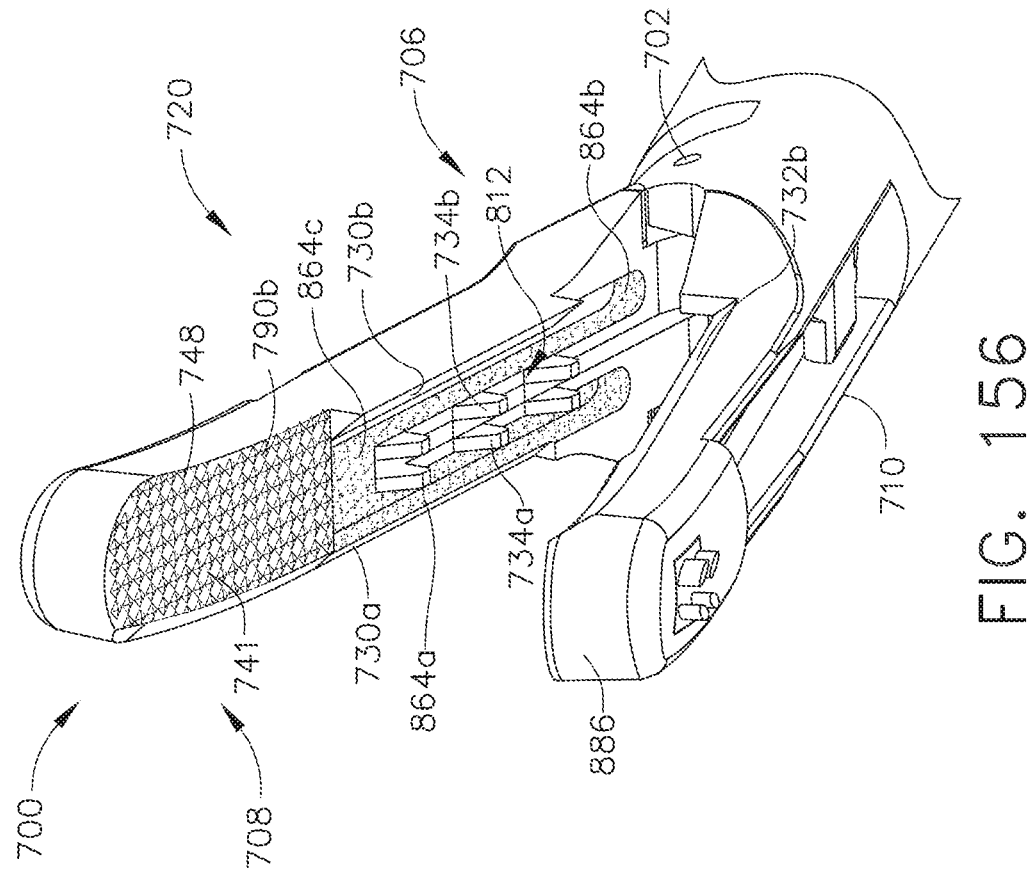

FIG. 156 illustrates a perspective view of one embodiment of the end effector of FIG. 153 in an open position.

Figure 157:
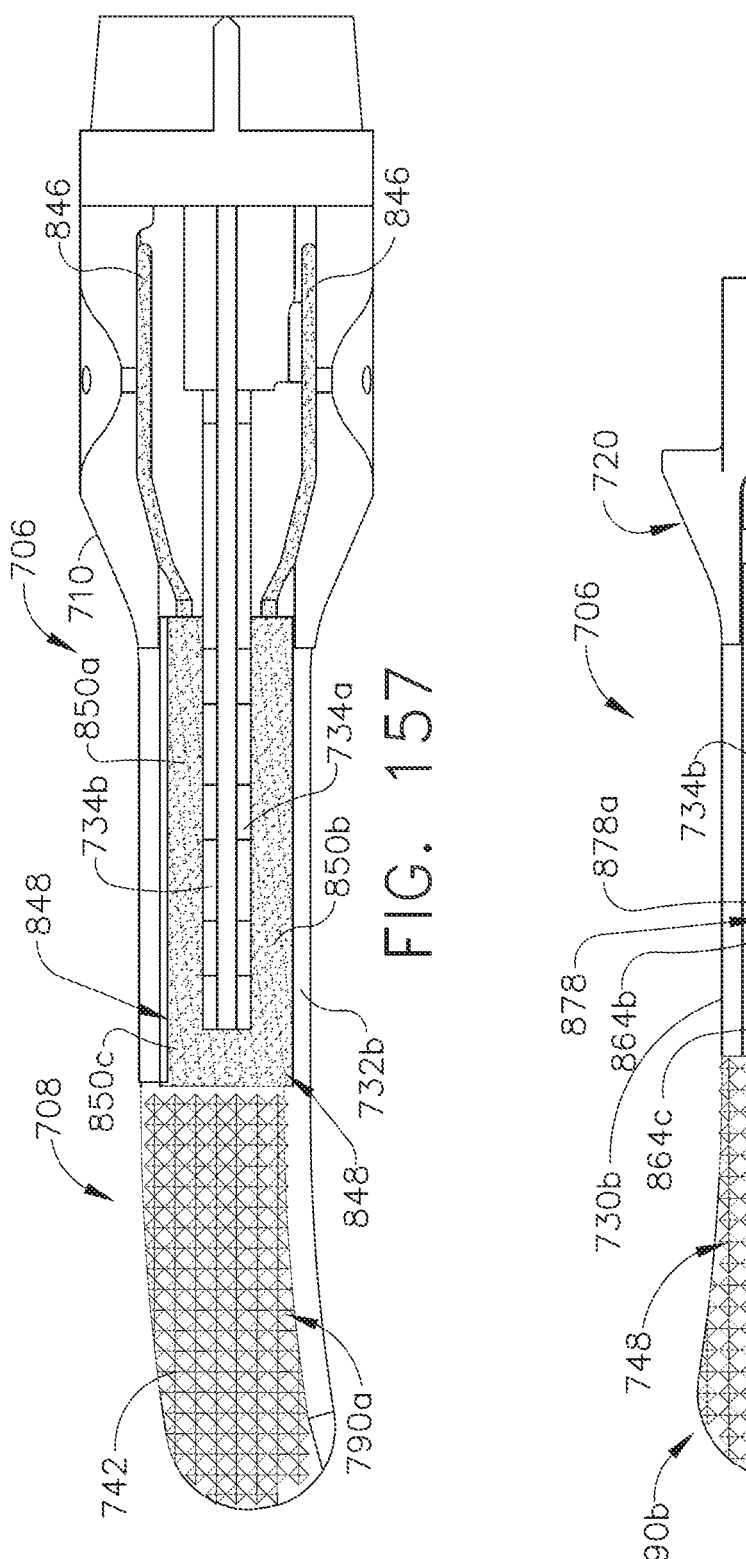

FIG. 157 illustrates a top view of one embodiment of a second jaw member suitable for use with the end effector of FIG. 153.

Figure 158:
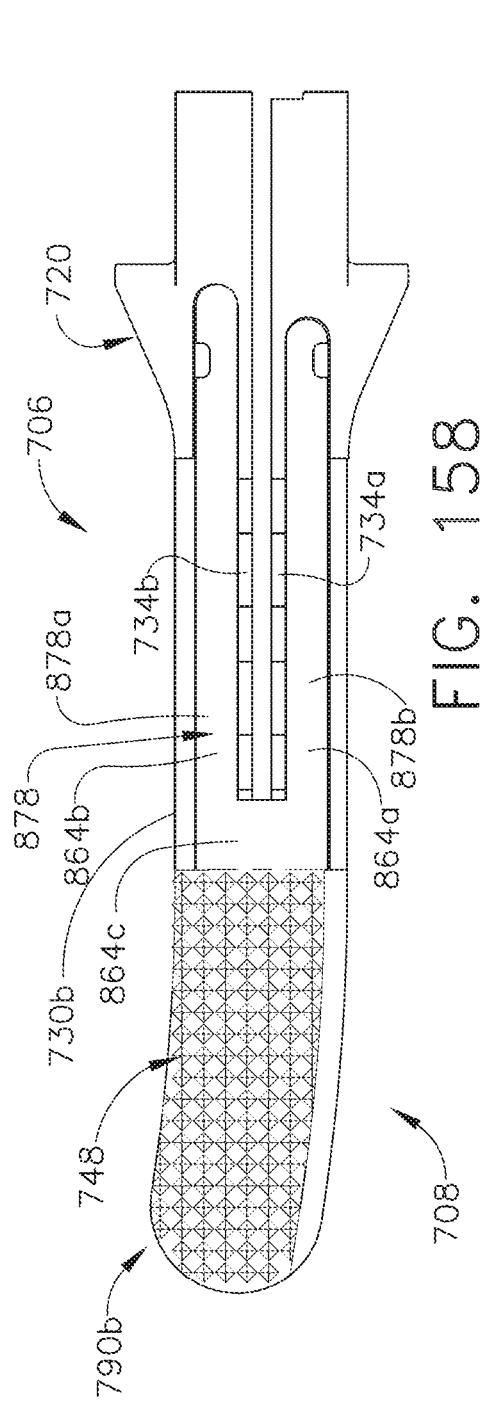

FIG. 158 illustrates a bottom view of one embodiment of a first jaw member suitable for use with the end effector of FIG. 153.

Figure 159:
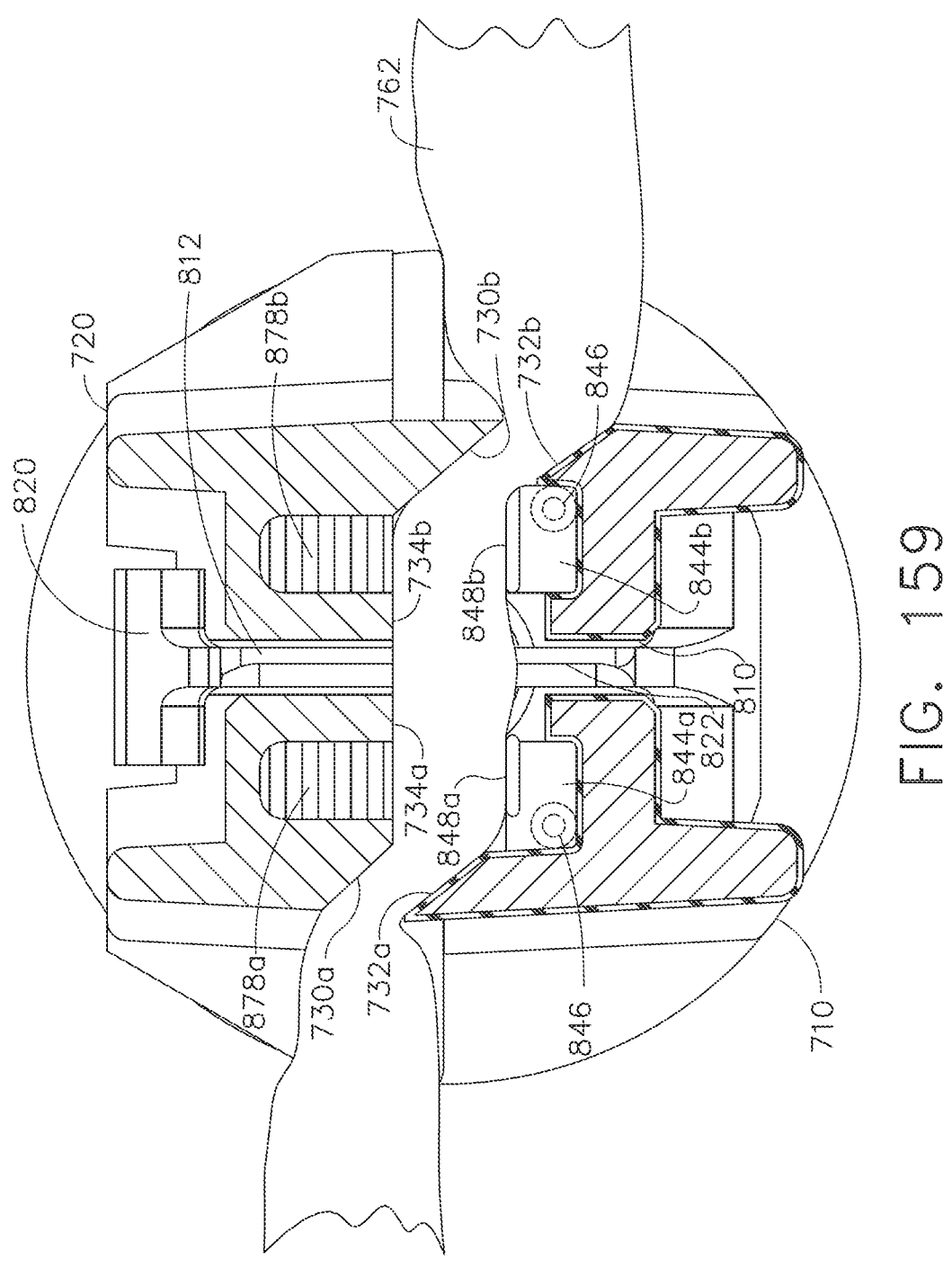

FIG. 159 illustrates a front cross-sectional view of another embodiment of the end effector of FIG. 153 in a closed position.

FIGS. 160-165 illustrates side cross-sectional views of various embodiments of the end effector of FIG. 153

Figure 166:
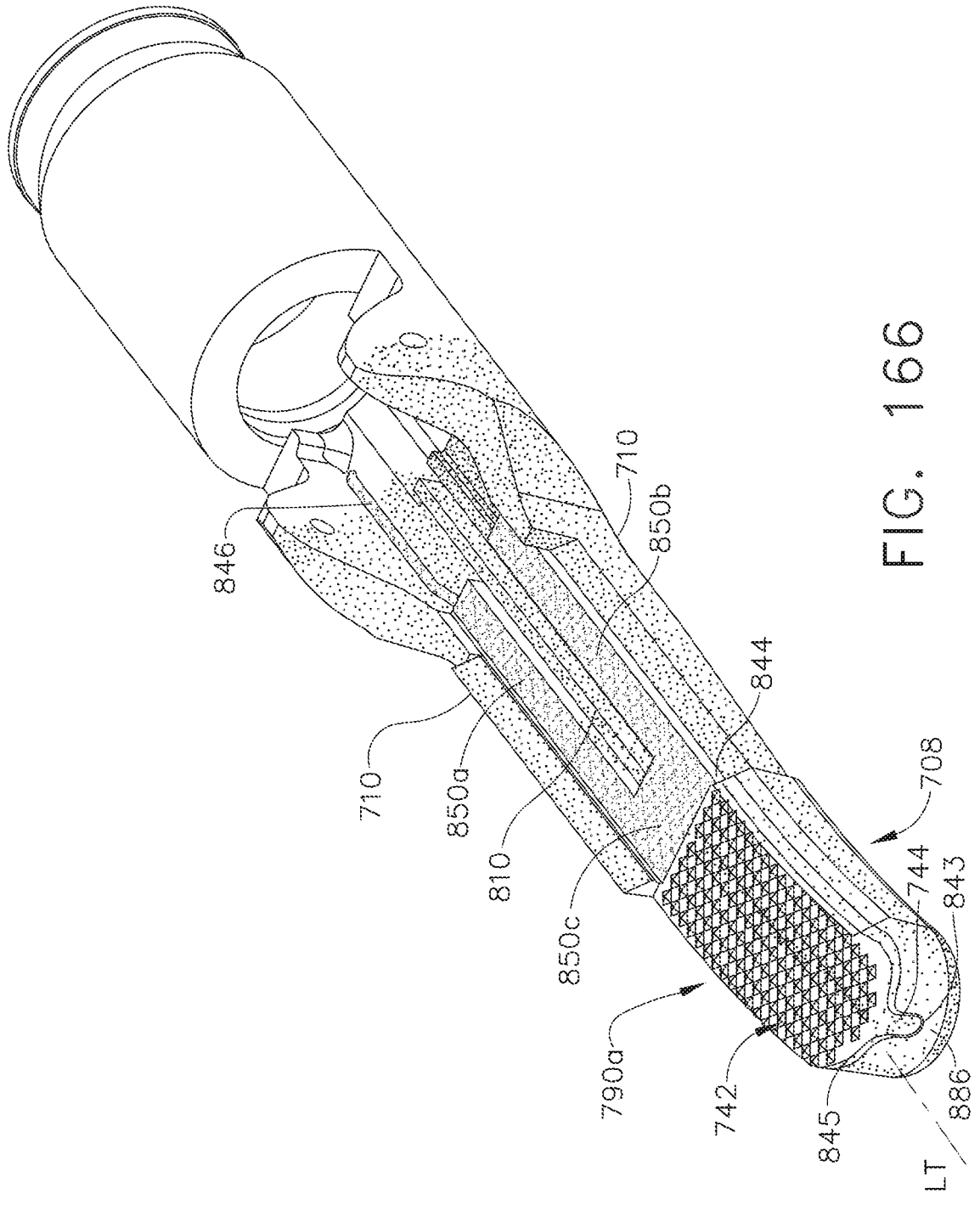

FIG. 166 illustrates another embodiment of the second jaw member suitable for use with the end effector of FIG. 153, in a closed position holding a surgical implement.

Figure 167:
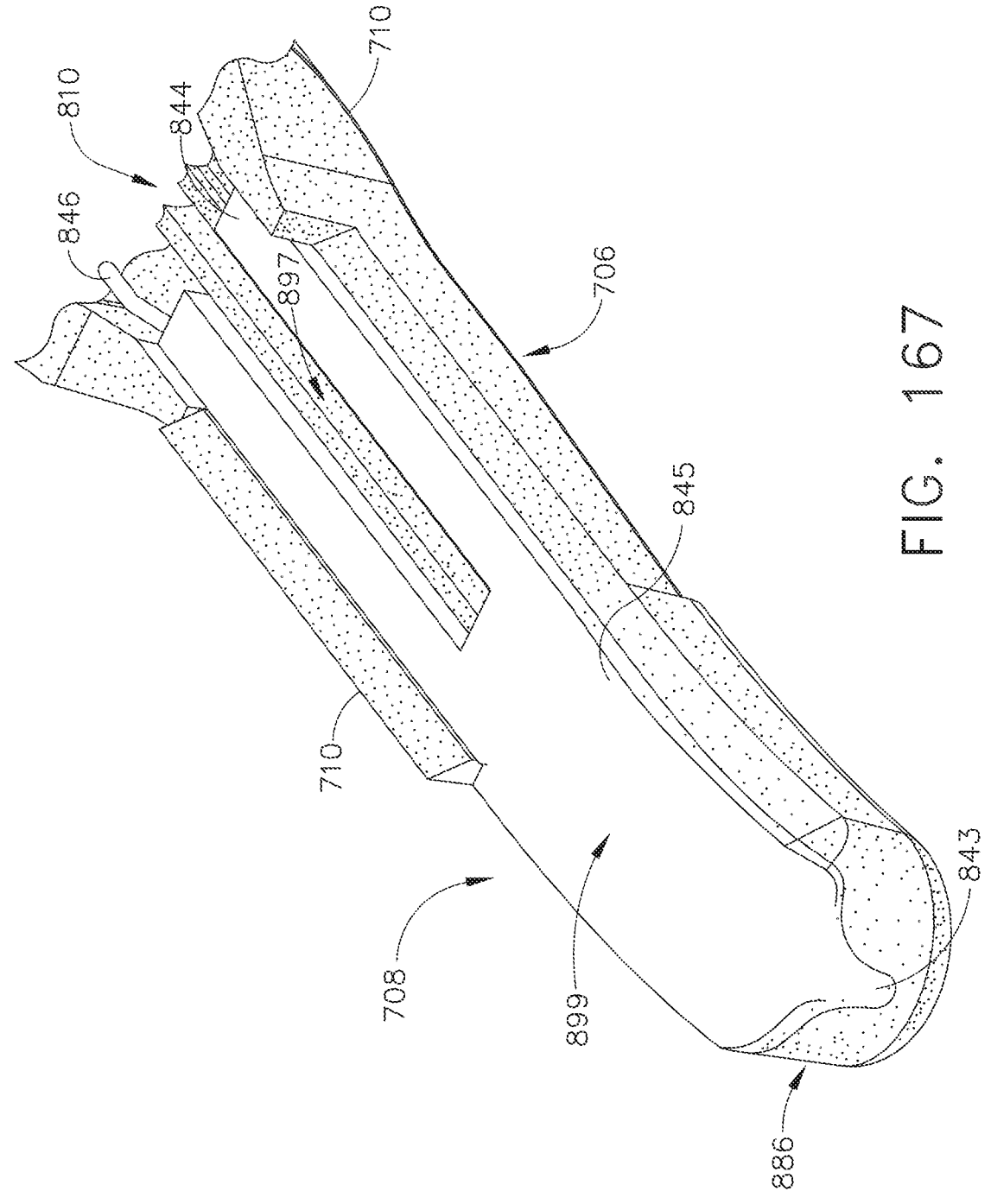

FIG. 167 illustrates one embodiment of the second jaw member suitable for use with the end effector of FIG. 153.

Figure 168:
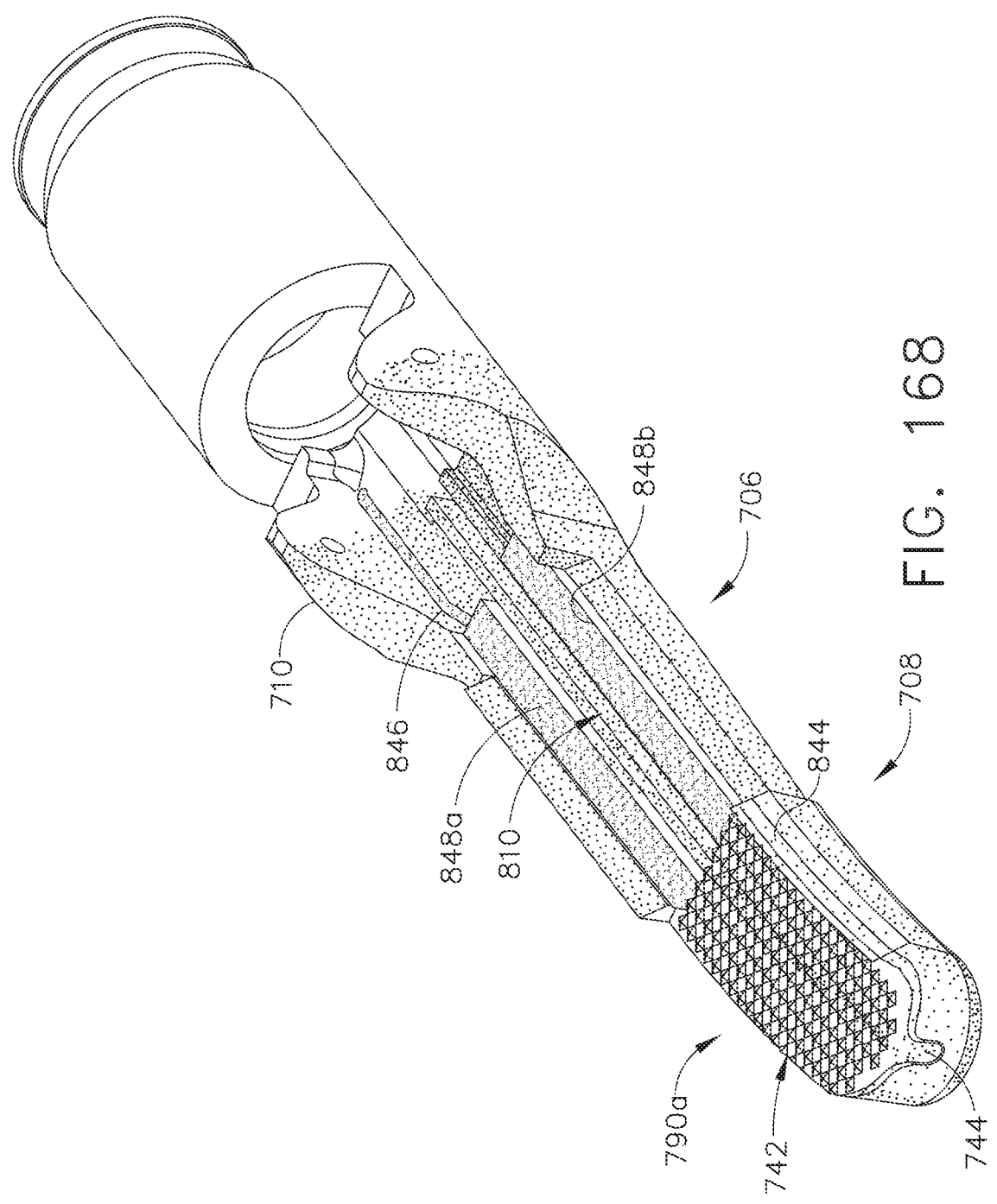

FIG. 168 illustrates another embodiment of the second jaw member suitable for use with the end effector of FIG. 153.

DETAILED DESCRIPTION

Applicant of the present application also owns the following patent applications that have been filed on Jun. 28, 2012 and which are each herein incorporated by reference in their respective entireties:

1. U.S. patent application Ser. No. 13/536,271, entitled FLEXIBLE DRIVE MEMBER, now U.S. Pat. No. 9,204,879.
2. U.S. patent application Ser. No. 13/536,288, entitled MULTI-FUNCTIONAL POWERED SURGICAL DEVICE WITH EXTERNAL DISSECTION FEATURES, now U.S. Patent Application Publication No. 2014-0005718 A1.
3. U.S. patent application Ser. No. 13/536,277, entitled COUPLING ARRANGEMENTS FOR ATTACHING SURGICAL END EFFECTORS TO DRIVE SYSTEMS THEREFOR, now U.S. Patent Application Publication No. 2014-0001234 A1.
4. U.S. patent application Ser. No. 13/536,295, entitled ROTARY ACTUATABLE CLOSURE ARRANGEMENT FOR SURGICAL END EFFECTOR, now U.S. Pat. No. 9,119,657.
5. U.S. patent application Ser. No. 13/536,326, entitled SURGICAL END EFFECTORS HAVING ANGLED TISSUE-CONTACTING SURFACES, now U.S. Pat. No. 9,289,256.
6. U.S. patent application Ser. No. 13/536,303, entitled INTERCHANGEABLE END EFFECTOR COUPLING ARRANGEMENT, now U.S. Pat. No. 9,028,494.
7. U.S. patent application Ser. No. 13/536,362, entitled MULTI-AXIS ARTICULATING AND ROTATING SURGICAL TOOLS, now U.S. Pat. No. 9,125,662.
8. U.S. patent application Ser. No. 13/536,284, entitled DIFFERENTIAL LOCKING ARRANGEMENTS FOR ROTARY POWERED SURGICAL INSTRUMENTS, now U.S. Pat. No. 9,072,536.
9. U.S. patent application Ser. No. 13/536,374, entitled INTERCHANGEABLE CLIP APPLIER, now U.S. Pat. No. 9,561,038.
10. U.S. patent application Ser. No. 13/536,292, entitled FIRING SYSTEM LOCKOUT ARRANGEMENTS FOR SURGICAL INSTRUMENTS, now U.S. Patent Application Publication No. 2014-0001231 A1.
11. U.S. patent application Ser. No. 13/536,301, entitled ROTARY DRIVE SHAFT ASSEMBLIES FOR SURGICAL INSTRUMENTS WITH ARTICULATABLE END EFFECTORS, now U.S. Pat. No. 8,747,238.
12. U.S. patent application Ser. No. 13/536,313, entitled ROTARY DRIVE ARRANGEMENTS FOR SURGICAL INSTRUMENTS, now U.S. Patent Application Publication No. 2014-0005678 A1.
13. U.S. patent application Ser. No. 13/536,323, entitled ROBOTICALLY POWERED SURGICAL DEVICE WITH MANUALLY-ACTUATABLE REVERSING SYSTEM, now U.S. Pat. No. 9,408,606.
14. U.S. patent application Ser. No. 13/536,379, entitled REPLACEABLE CLIP CARTRIDGE FOR A CLIP APPLIER, now U.S. Pat. No. 9,649,111.
15. U.S. patent application Ser. No. 13/536,386, entitled EMPTY CLIP CARTRIDGE LOCKOUT, now U.S. Pat. No. 9,282,974.
16. U.S. patent application Ser. No. 13/536,360, entitled SURGICAL INSTRUMENT SYSTEM INCLUDING REPLACEABLE END EFFECTORS, now U.S. Pat. No. 9,226,751.

17. U.S. patent application Ser. No. 13/536,335, entitled ROTARY SUPPORT JOINT ASSEMBLIES FOR COUPLING A FIRST PORTION OF A SURGICAL INSTRUMENT TO A SECOND PORTION OF A SURGICAL INSTRUMENT, now U.S. Pat. No. 9,364, 230.

18. U.S. patent application Ser. No. 13/536,417, entitled ELECTRODE CONNECTIONS FOR ROTARY DRIVEN SURGICAL TOOLS, now U.S. Pat. No. 9,101,385.

Applicant also owns the following patent applications that are each incorporated by reference in their respective entireties:

U.S. patent application Ser. No. 13/118,259, entitled SURGICAL INSTRUMENT WITH WIRELESS COMMUNICATION BETWEEN A CONTROL UNIT OF A ROBOTIC SYSTEM AND REMOTE SENSOR, now U.S. Pat. No. 8,684,253;

U.S. patent application Ser. No. 13/118,210, entitled ROBOTICALLY-CONTROLLED DISPOSABLE MOTOR DRIVEN LOADING UNIT, now U.S. Pat. No. 8,752,749;

U.S. patent application Ser. No. 13/118,194, entitled ROBOTICALLY-CONTROLLED ENDOSCOPIC ACCESSORY CHANNEL, now U.S. Pat. No. 8,992, 422;

U.S. patent application Ser. No. 13/118,253, entitled ROBOTICALLY-CONTROLLED MOTORIZED SURGICAL INSTRUMENT, now U.S. Pat. No. 9,386, 983;

U.S. patent application Ser. No. 13/118,278, entitled ROBOTICALLY-CONTROLLED SURGICAL STA-PLING DEVICES THAT PRODUCE FORMED STAPLES HAVING DIFFERENT LENGTHS, now U.S. Pat. No. 9,237,891;

U.S. patent application Ser. No. 13/118,190, entitled ROBOTICALLY-CONTROLLED MOTORIZED CUTTING AND FASTENING INSTRUMENT, now U.S. Pat. No. 9,179,912;

U.S. patent application Ser. No. 13/118,223, entitled ROBOTICALLY-CONTROLLED SHAFT BASED ROTARY DRIVE SYSTEMS FOR SURGICAL INSTRUMENTS, now U.S. Pat. No. 8,931,682;

U.S. patent application Ser. No. 13/118,263, entitled ROBOTICALLY-CONTROLLED SURGICAL INSTRUMENT HAVING RECORDING CAPABILI-TIES, now U.S. Patent Application Publication No. 2011-0295295 A1;

U.S. patent application Ser. No. 13/118,272, entitled ROBOTICALLY-CONTROLLED SURGICAL INSTRUMENT WITH FORCE FEEDBACK CAPA-BILITIES, U.S. Patent Application Publication No. 2011-0290856 A1;

U.S. patent application Ser. No. 13/118,246, entitled ROBOTICALLY-DRIVEN SURGICAL INSTRU-MENT WITH E-BEAM DRIVER, Now U.S. Pat. No. 9,060,770; and U.S. patent application Ser. No. 13/118,241, entitled SURGICAL STAPLING INSTRUMENTS WITH ROTATABLE STAPLE DEPLOYMENT ARRANGE-MENTS, now U.S. Pat. No. 9,072,535.

Certain example embodiments will now be described to provide an overall understanding of the principles of the structure, function, manufacture, and use of the devices and methods disclosed herein. One or more examples of these example embodiments are illustrated in the accompanying drawings. Those of ordinary skill in the art will understand that the devices and methods specifically described herein and illustrated in the accompanying drawings are non-limiting example embodiments and that the scope of the various example embodiments of the present invention is defined solely by the claims. The features illustrated or described in connection with one example embodiment may be combined with the features of other example embodiments. Such modifications and variations are intended to be included within the scope of the present invention.

Figure 1:
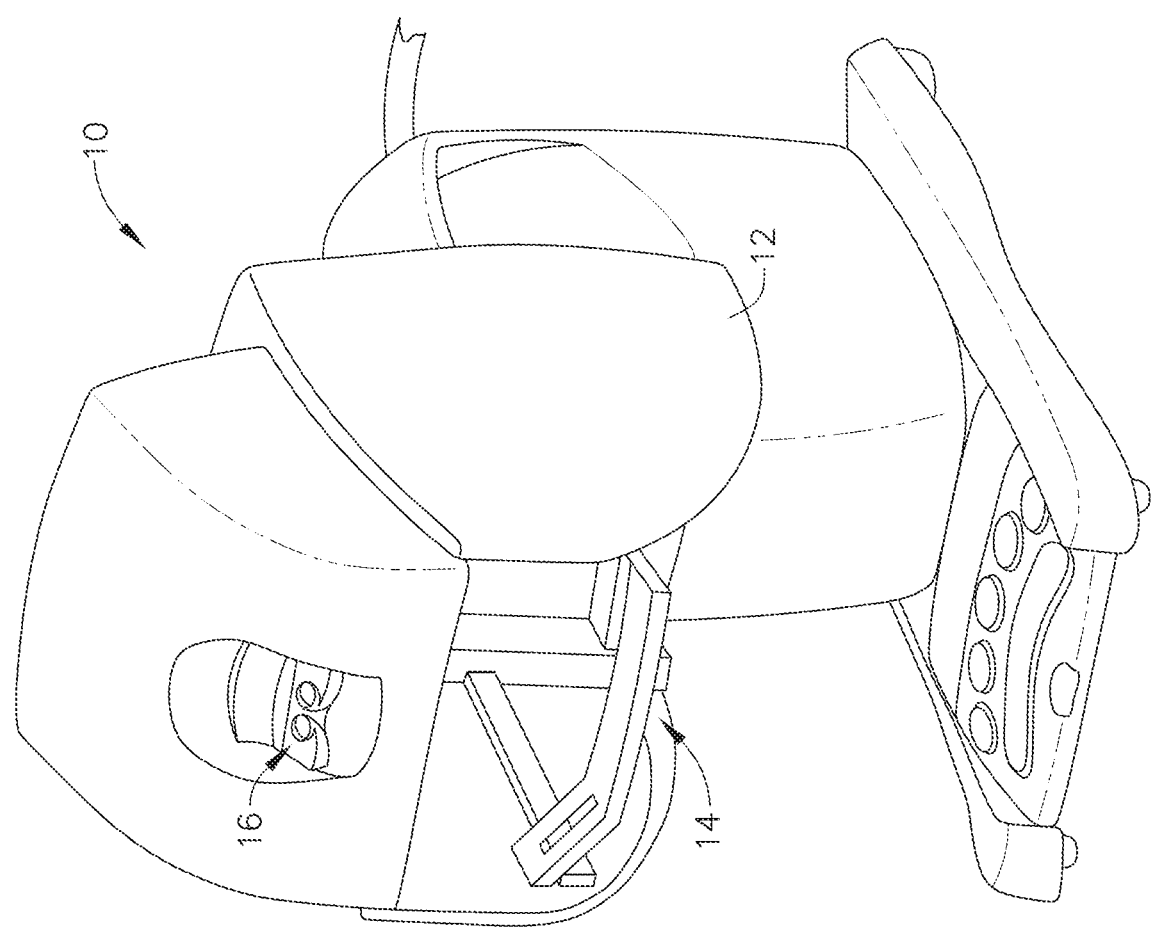
FIG. 1 is a perspective view of one embodiment of a robotic controller.
Figure 2:
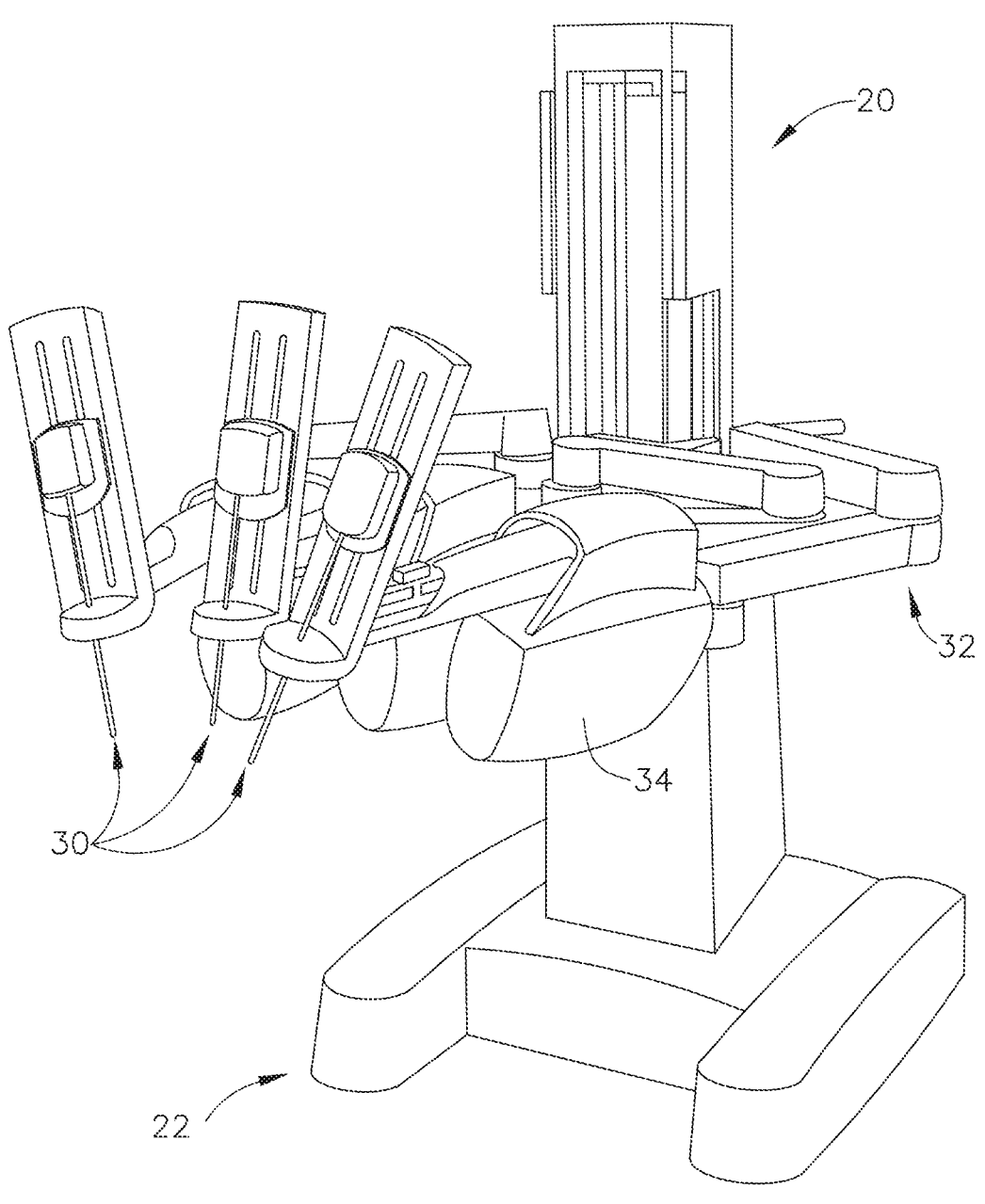
FIG. 2 is a perspective view of a robotic surgical arm cart/manipulator of a robotic system operably supporting a plurality of surgical tool embodiments.

FIG. 1 depicts a master controller 12 that is used in connection with a robotic arm slave cart 20 of the type depicted in FIG. 2. Master controller 12 and robotic arm slave cart 20, as well as their respective components and control systems are collectively referred to herein as a robotic system 10. Examples of such systems and devices are disclosed in U.S. Pat. No. 7,524,320 which has been herein incorporated by reference. Thus, various details of such devices will not be described in detail herein beyond that which may be necessary to understand various example embodiments disclosed herein. As is known, the master controller 12 generally includes master controllers (generally represented as 14 in FIG. 1) which are grasped by the surgeon and manipulated in space while the surgeon views the procedure via a stereo display 16. The master controllers 12 generally comprise manual input devices which preferably move with multiple degrees of freedom, and which often further have an actuatable handle for actuating tools (for example, for closing grasping jaws, applying an electrical potential to an electrode, or the like).

As can be seen in FIG. 2, the robotic arm cart 20 is configured to actuate a plurality of surgical tools, generally designated as 30. Various robotic surgery systems and methods employing master controller and robotic arm cart arrangements are disclosed in U.S. Pat. No. 6,132,368, entitled MULTI-COMPONENT TELEPRESENCE SYS-TEM AND METHOD, the full disclosure of which is incorporated herein by reference. As shown, the robotic arm cart 20 includes a base 22 from which, in the illustrated embodiment, three surgical tools 30 are supported. The surgical tools 30 are each supported by a series of manually articulatable linkages, generally referred to as set-up joints 32, and a robotic manipulator 34. These structures are herein illustrated with protective covers extending over much of the robotic linkage. These protective covers may be optional, and may be limited in size or entirely eliminated to minimize the inertia that is encountered by the servo mechanisms used to manipulate such devices, to limit the volume of moving components so as to avoid collisions, and to limit the overall weight of the cart 20. The cart 20 generally has dimensions suitable for transporting the cart 20 between operating rooms. The cart 20 is configured to typically fit through standard operating room doors and onto standard hospital elevators. The cart 20 would preferably have a weight and include a wheel (or other transportation) system that allows the cart 20 to be positioned adjacent an operating table by a single attendant.

Figure 3:
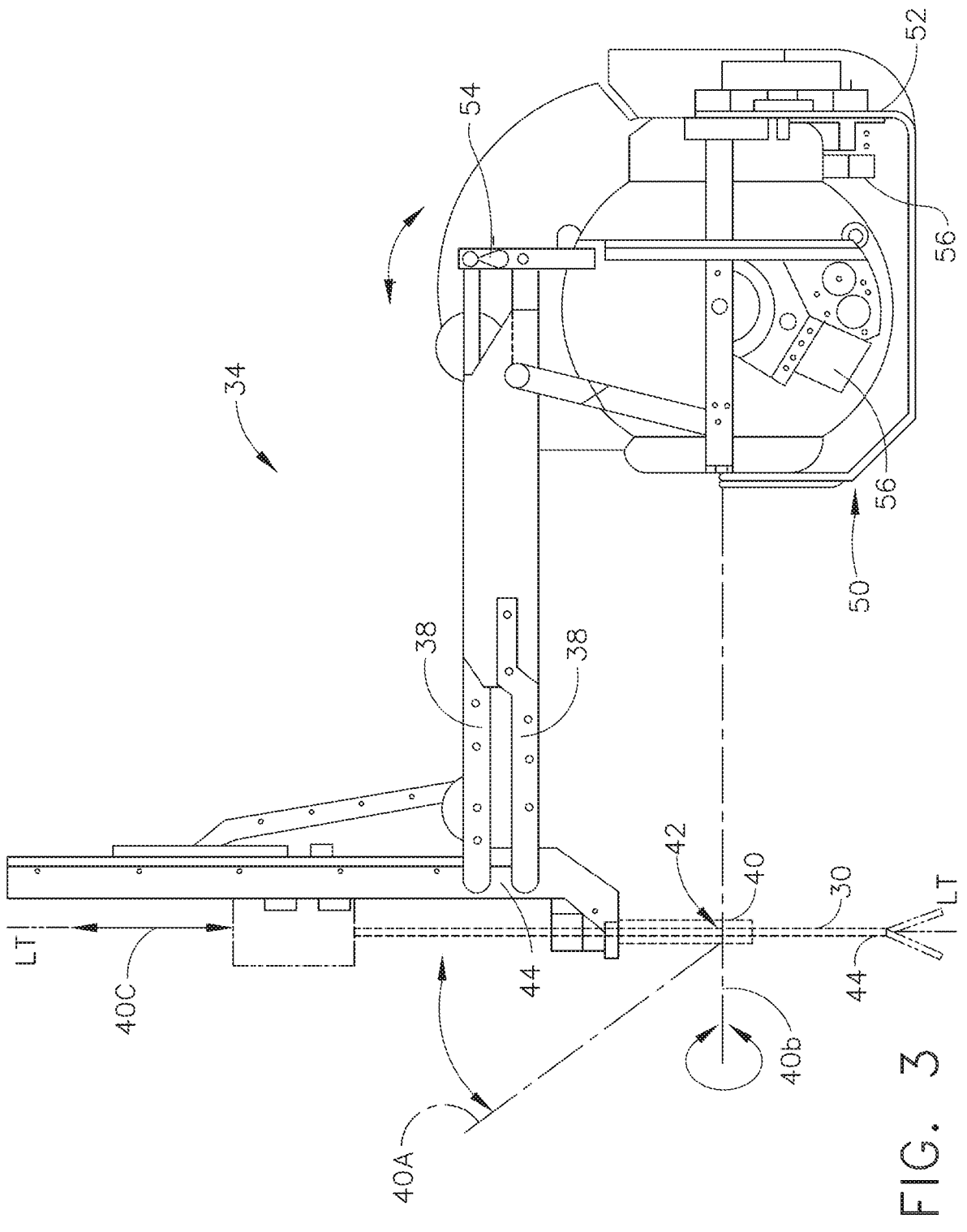
FIG. 3 is a side view of one embodiment of the robotic surgical arm cart/manipulator depicted in FIG. 2.
Figure 4:
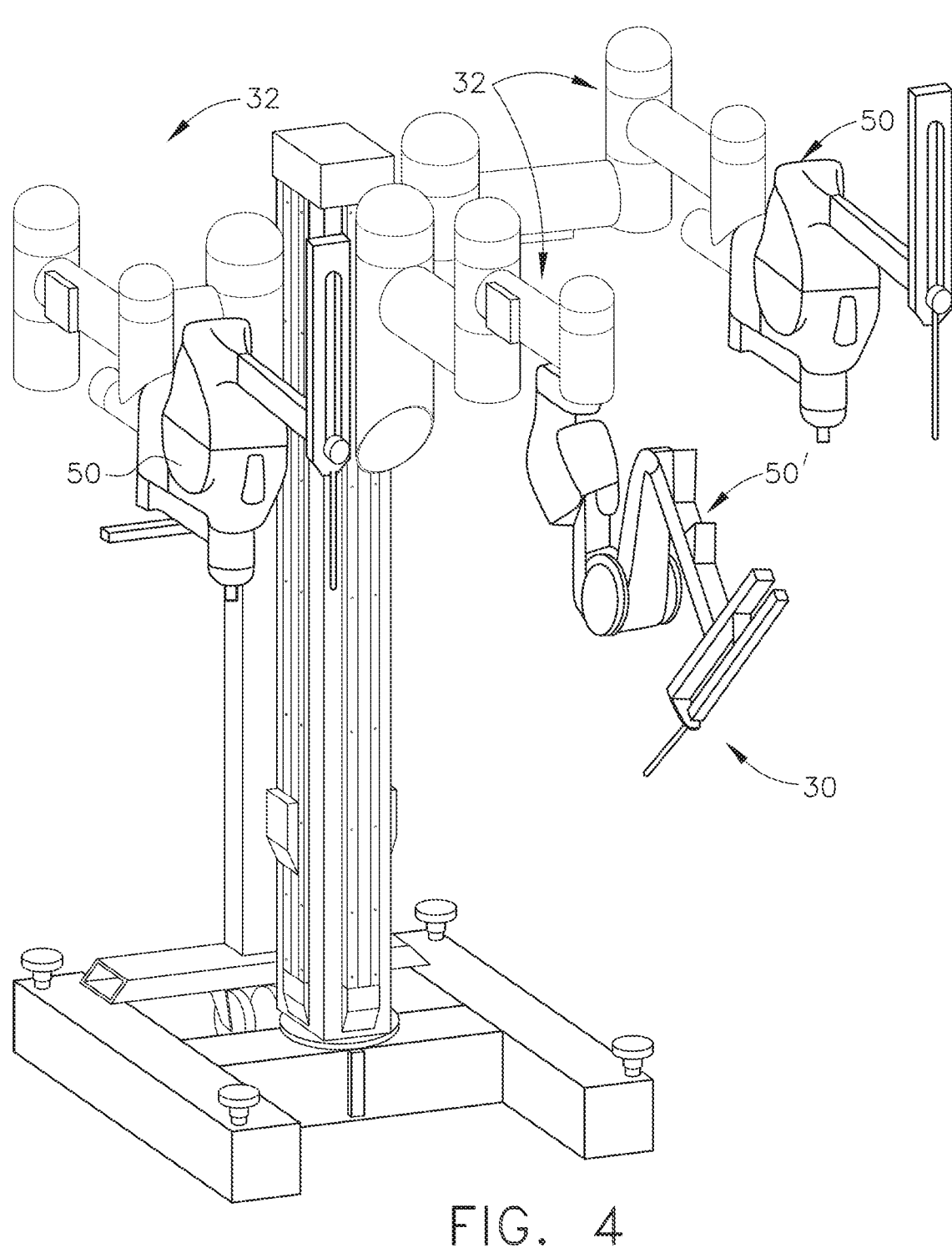
FIG. 4 is a perspective view of a cart structure with positioning linkages for operably supporting robotic manipulators that may be used with surgical tool embodiments.

Referring now to FIG. 3, robotic manipulators 34 as shown include a linkage 38 that constrains movement of the surgical tool 30. Linkage 38 includes rigid links coupled together by rotational joints in a parallelogram arrangement so that the surgical tool 30 rotates around a point in space 40, as more fully described in U.S. Pat. No. 5,817,084, the full disclosure of which is herein incorporated by reference. The parallelogram arrangement constrains rotation to pivoting about an axis 40a, sometimes called the pitch axis. The links supporting the parallelogram linkage are pivotally mounted to set-up joints 32 (FIG. 2) so that the surgical tool 30 further rotates about an axis 40b, sometimes called the yaw axis. The pitch and yaw axes 40a, 40b intersect at the remote center 42, which is aligned along a shaft 44 of the surgical tool 30. The surgical tool 30 may have further degrees of driven freedom as supported by manipulator 50, including sliding motion of the surgical tool 30 along the longitudinal tool axis "LT-LT". As the surgical tool 30 slides along the tool axis LT-LT relative to manipulator 50 (arrow 40c), remote center 42 remains fixed relative to base 52 of manipulator 50. Hence, the entire manipulator is generally moved to re-position remote center 42. Linkage 54 of manipulator 50 is driven by a series of motors 56. These motors actively move linkage 54 in response to commands from a processor of a control system. Motors 56 are also employed to manipulate the surgical tool 30. An alternative set-up joint structure is illustrated in FIG. 4. In this embodiment, a surgical tool 30 is supported by an alternative manipulator structure 50' between two tissue manipulation tools.

Other embodiments may incorporate a wide variety of alternative robotic structures, including those described in U.S. Pat. No. 5,878,193, entitled AUTOMATED ENDOSCOPE SYSTEM FOR OPTIMAL POSITIONING, the full disclosure of which is incorporated herein by reference. Additionally, while the data communication between a robotic component and the processor of the robotic surgical system is described with reference to communication between the surgical tool 30 and the master controller 12, similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

Figure 5:
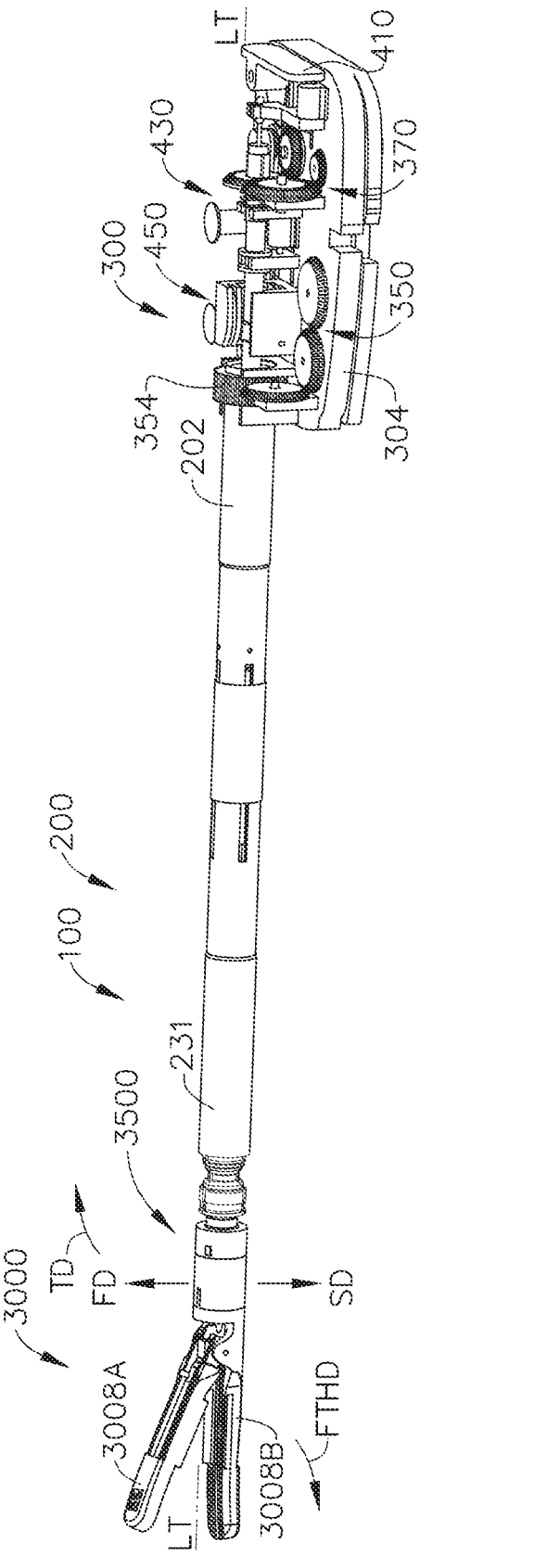
FIG. 5 is a perspective view of a surgical tool embodiment and a surgical end effector embodiment.
Figure 6:
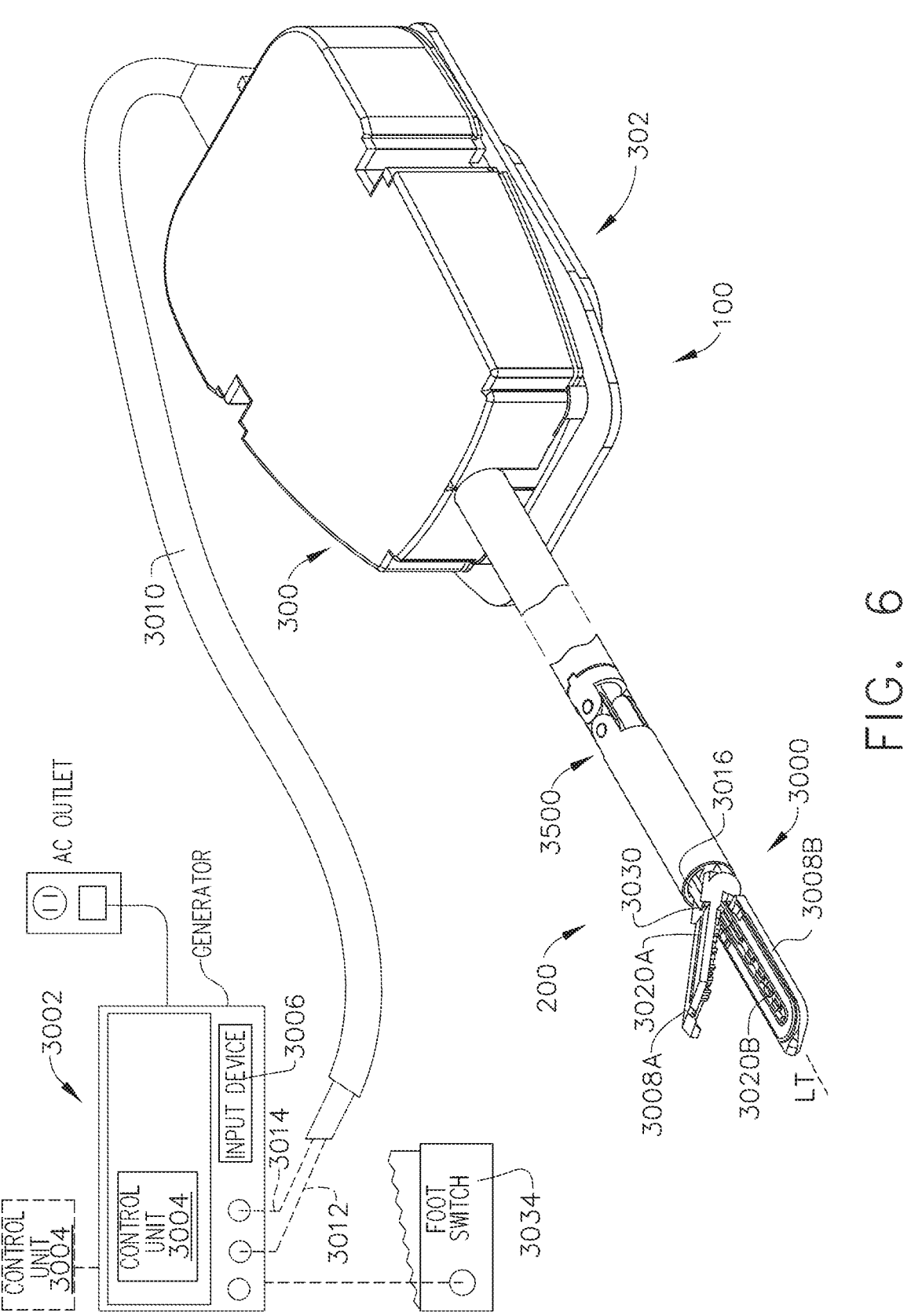
FIG. 6 is a perspective view of one embodiment of an electrosurgical tool in electrical communication with a generator

A surgical tool 100 that is well-adapted for use with a robotic system 10 is depicted in FIGS. 5-6. FIG. 5 illustrates an additional embodiment of the surgical tool 100 and electrosurgical end effector 3000. As can be seen in FIG. 5, the surgical tool 100 includes an electrosurgical end effector 3000. The electrosurgical end effector 3000 may utilize electrical energy to treat and/or destroy tissue. The electrosurgical end effector 3000 generally comprises first and second jaw members 3008A, 3008B which may be straight, as shown in FIGS. 6-10, or curved as shown in various other figures described herein. One or both of the jaw members 3008A, 3008B generally comprise various electrodes for providing electrosurgical energy to tissue. The surgical tool 100 generally includes an elongate shaft assembly 200 that is operably coupled to the manipulator 50 by a tool mounting portion, generally designated as 300. Electrosurgical tools (e.g., surgical tools that include an electrosurgical end effector, such at the tool 100 and end effector 3000) may be used in any suitable type of surgical environment including, for example, open, laparoscopic, endoscopic, etc.

Generally, electrosurgical tools comprise one or more electrodes for providing electric current. The electrodes may be positioned against and/or positioned relative to tissue such that electrical current can flow through the tissue. The electrical current may generate heat in the tissue that, in turn, causes one or more hemostatic seals to form within the tissue and/or between tissues. For example, tissue heating caused by the electrical current may at least partially denature proteins within the tissue. Such proteins, such as collagen, for example, may be denatured into a proteinaceous amalgam that intermixes and fuses, or "welds", together as the proteins renature. As the treated region heals over time, this biological "weld" may be reabsorbed by the body's wound healing process.

Electrical energy provided by electrosurgical tools may be of any suitable form including, for example, direct or alternating current. For example, the electrical energy may include high frequency alternating current such as radio frequency or "RF" energy. RF energy may include energy in the range of 300 kilohertz (kHz) to 1 megahertz (MHz). When applied to tissue, RF energy may cause ionic agitation or friction, increasing the temperature of the tissue. Also, RF energy may provide a sharp boundary between affected tissue and other tissue surrounding it, allowing surgeons to operate with a high level of precision and control. The low operating temperatures of RF energy enables surgeons to remove, shrink or sculpt soft tissue while simultaneously sealing blood vessels. RF energy works particularly well on connective tissue, which is primarily comprised of collagen and shrinks when contacted by heat.

In certain arrangements, some bi-polar (e.g., two-electrode) electrosurgical tools can comprise opposing first and second jaw members, where the face of each jaw can comprise a current path and/or electrode. In use, the tissue can be captured between the jaw faces such that electrical current can flow between the electrodes in the opposing jaw members and through the tissue positioned therebetween. Such tools may have to coagulate, seal or "weld" many types of tissues, such as anatomic structures having walls with irregular or thick fibrous content, bundles of disparate anatomic structures, substantially thick anatomic structures, and/or tissues with thick fascia layers such as large diameter blood vessels, for example. Some embodiments may include a knife or cutting edge to transect the tissue, for example, during or after the application of electrosurgical energy. With particular regard to cutting and sealing large diameter blood vessels, for example, such applications may require a high strength tissue weld immediately post-treatment.

FIG. 6 is a perspective view of one embodiment of the electrosurgical tool 100 in electrical communication with a generator 3002. The electrosurgical tool 100 in conjunction with the generator 3002 can be configured to supply energy, such as electrical energy, ultrasonic energy, and/or heat energy, for example, to the tissue of a patient. In the illustrated embodiment and in functionally similar embodiments, the generator 3002 is connected to electrosurgical tool 100 via a suitable transmission medium such as a cable 3010. In one embodiment, the generator 3002 is coupled to a controller, such as a control unit 3004, for example. In various embodiments, the control unit 3004 may be formed integrally with the generator 3002 or may be provided as a separate circuit module or device electrically coupled to the generator 3002 (shown in phantom to illustrate this option). Although in the presently disclosed embodiment, the generator 3002 is shown separate from the electrosurgical tool 100, in one embodiment, the generator 3002 (and/or the control unit 3004) may be formed integrally with the electrosurgical tool 100 to form a unitary electrosurgical system. For example, in some embodiments a generator or equivalent circuit may be present within the tool mounting portion 300 and/or within a handle in suitable manual embodiments (as described herein).

The generator 3002 may comprise an input device 3006 located on a front panel of the generator 3002 console. The input device 3006 may comprise any suitable device that generates signals suitable for programming the operation of the generator 3002, such as a keyboard, or input port, for example. In one embodiment, various electrodes in the first jaw member 3008A and the second jaw member 3008B may be coupled to the generator 3002. A cable 3010 connecting the tool mounting portion 300 to the generator 3002 may comprise multiple electrical conductors for the application of electrical energy to positive (+) and negative (−) electrodes of the electrosurgical tool 100. The control unit 3004 may be used to activate the generator 3002, which may serve as an electrical source. In various embodiments, the generator 3002 may comprise an RF source, an ultrasonic source, a direct current source, and/or any other suitable type of electrical energy source, for example.

In various embodiments, surgical tool 100 may comprise at least one supply conductor 3012 and at least one return conductor 3014, wherein current can be supplied to electrosurgical tool 100 via the supply conductor 3012 and wherein the current can flow back to the generator 3002 via return conductor 3014. In various embodiments, the supply conductor 3012 and the return conductor 3014 may comprise insulated wires and/or any other suitable type of conductor. In certain embodiments, as described below, the supply conductor 3012 and the return conductor 3014 may be contained within and/or may comprise the cable 3010 extending between, or at least partially between, the generator 3002 and the end effector 3000 of the electrosurgical tool 100. In any event, the generator 3002 can be configured to apply a sufficient voltage differential between the supply conductor 3012 and the return conductor 3014 such that sufficient current can be supplied to the end effector 3000.

Figure 7:
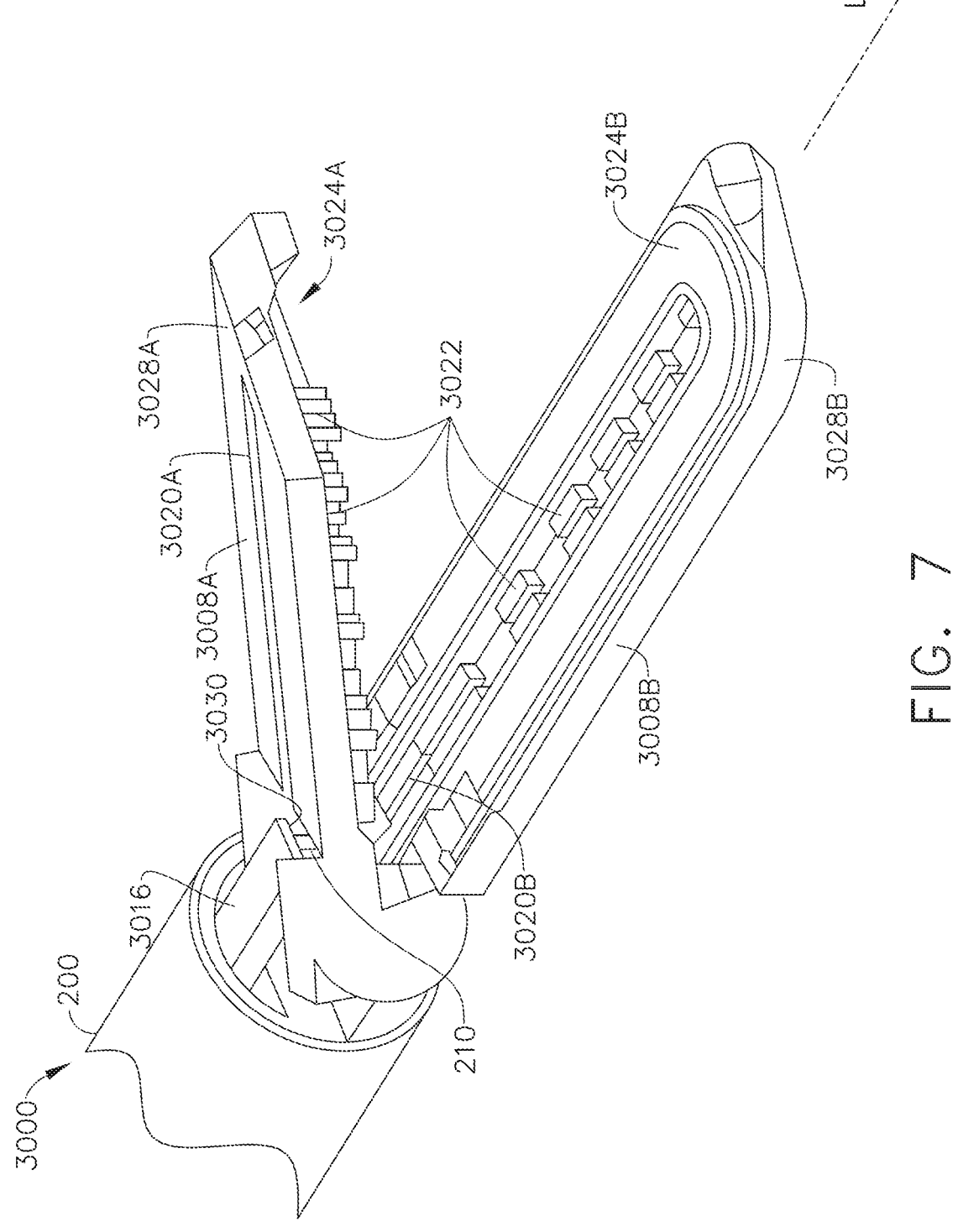
FIG. 7 shows a perspective view of one embodiment of the end effector of the surgical tool of FIG. 6 with the jaw members open and the distal end of an axially movable member in a retracted position.
Figure 8:
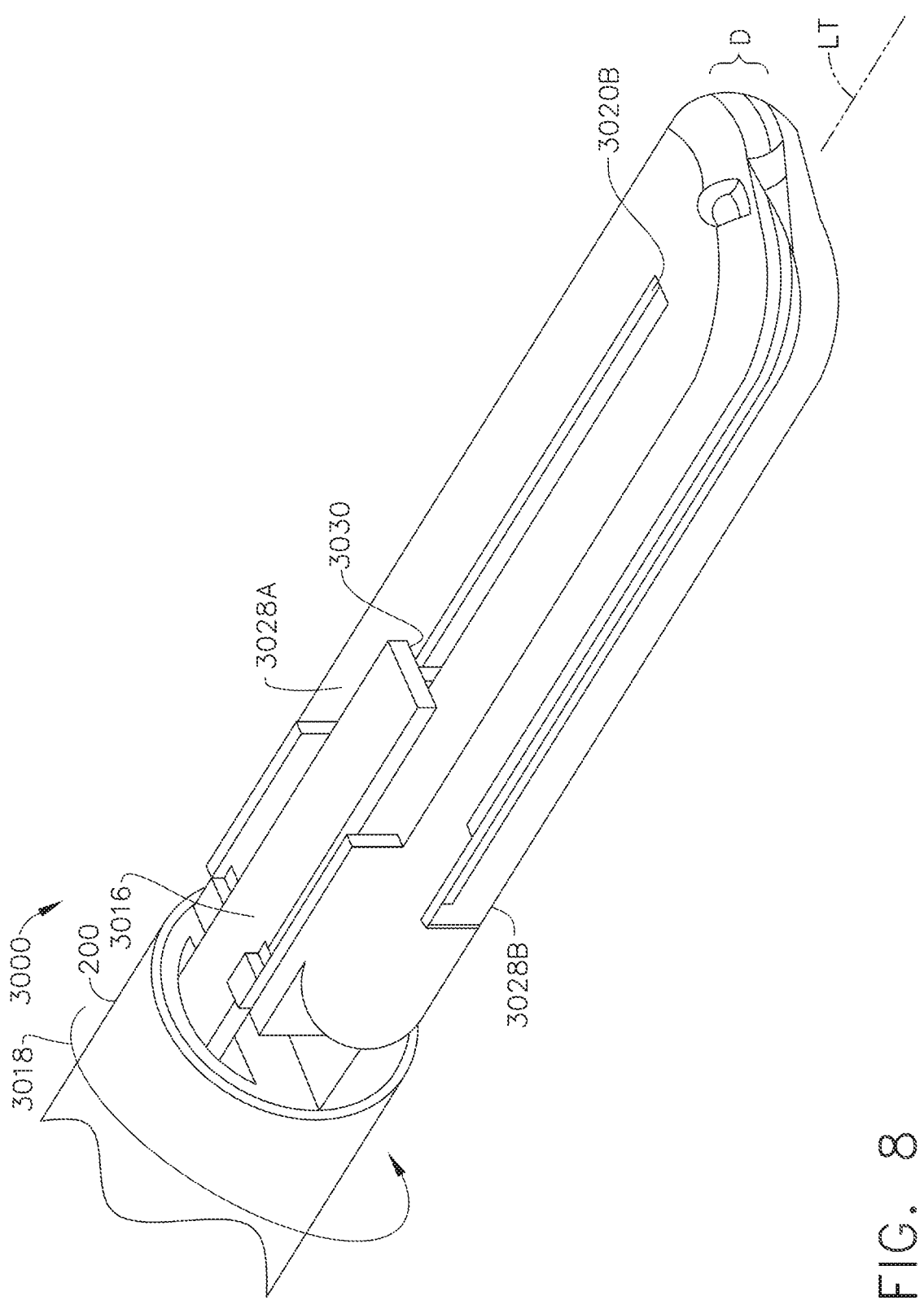
FIG. 8 shows a perspective view of one embodiment of the end effector of the surgical tool of FIG. 6 with the jaw members closed and the distal end of an axially movable member in a partially advanced position.

The electrosurgical end effector 3000 may be adapted for capturing and transecting tissue and for the contemporaneously welding the captured tissue with controlled application of energy (e.g., RF energy). FIG. 7 illustrates one embodiment of the electrosurgical end effector 3000 with the jaw members 3008A, 3008B open and an axially movable member 3016 in a proximally retracted position. FIG. 8 illustrates one embodiment of the electrosurgical end effector 3000 with the jaw members 3008A, 3008B closed and the axially movable member 3016 in a partially advanced position.

In use, the jaw members 3008A, 3008B close to thereby capture or engage tissue about a longitudinal tool axis LT-LT defined by the axially moveable member 3016 (or a distal portion thereof). The first jaw member 3008A and second jaw member 3008B may also apply compression to the tissue. In some embodiments, the elongate shaft 200, along with first jaw member 3008A and second jaw member 3008B, can be rotated a full 360° degrees, as shown by arrow 3018 (see FIG. 8), relative to tool mounting portion 300.

The first jaw member 3008A and the second jaw member 3008B may each comprise an elongate slot or channel 3020A and 3020B (FIG. 7), respectively, disposed outwardly along their respective middle portions. Further, the first jaw member 3008A and second jaw member 3008B may each have tissue-gripping elements, such as teeth 3022, disposed on the inner portions of first jaw member 3008A and second jaw member 3008B. The lower jaw member 3008B may define a jaw body with an energy delivery surface or electrode 3024B. For example, the electrode 3024B may be in electrical communication with the generator 3002 via the supply conductor 3012. An energy delivery surface 3024A on the upper first jaw member 3008 may provide a return path for electrosurgical energy. For example, the energy delivery surface 3024A may be in electrical communication with the return conductor 3014. In the illustrated embodiment and in functionally similar embodiments, other conductive parts of the surgical tool 100 including, for example the jaw members 3008A, 3008B, the shaft 200, etc. may form all or a part of the return path. Various configurations of electrodes and various configurations for coupling the energy delivery surfaces 3024A, 3024B to the conductors 3012, 3014 are described herein. Also, it will be appreciated that the supply electrode 3024B may be provided on the lower jaw member 3008B as shown or on the upper jaw member 3008A.

Figures 9, 10:
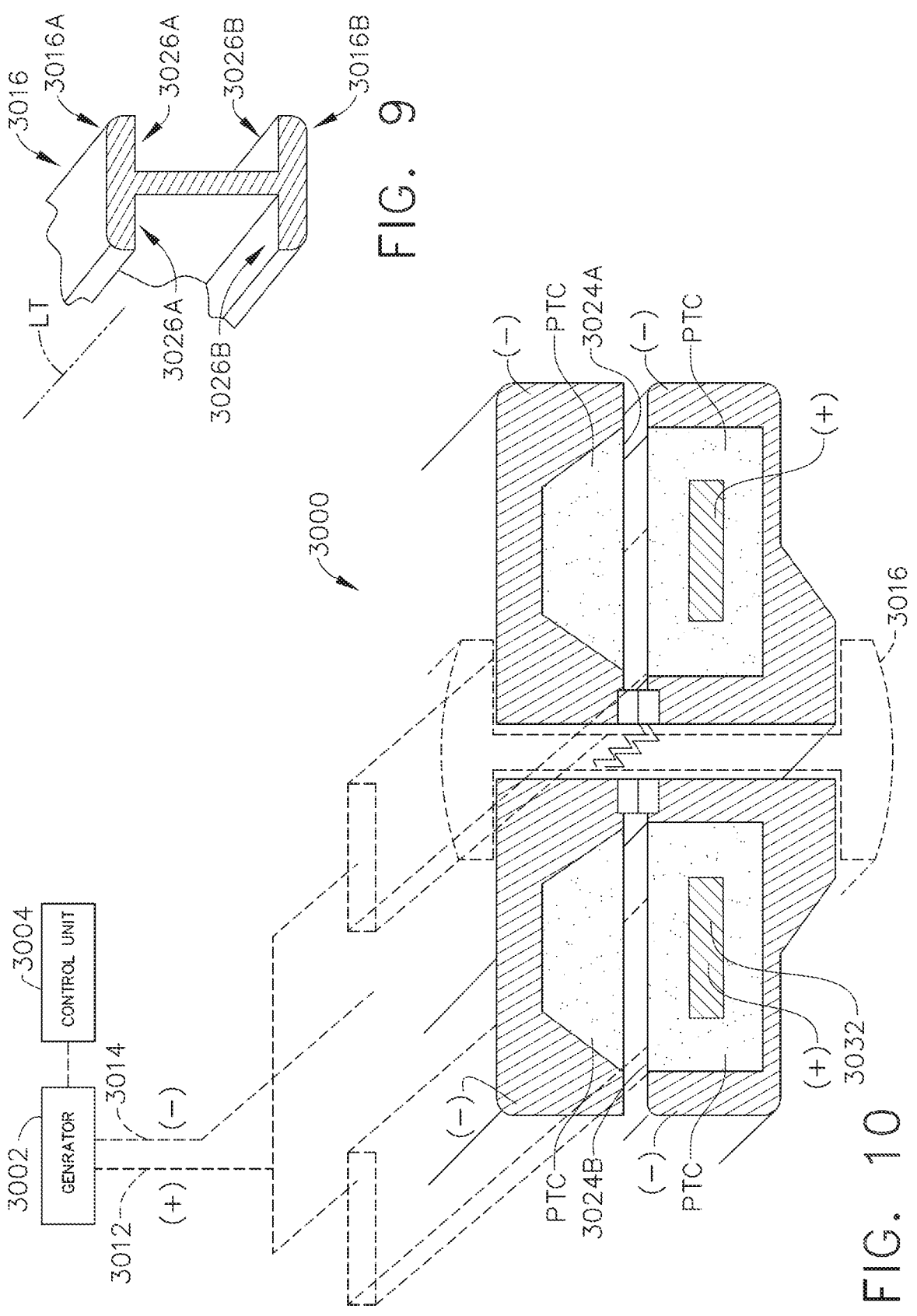
FIG. 9 is a perspective view of one embodiment of the axially moveable member of the surgical tool of FIG. 6.
FIG. 10 is a section view of one embodiment of the electrosurgical end effector of the surgical tool of FIG. 6.

Distal and proximal translation of the axially moveable member 3016 may serve to open and close the jaw members 3008A, 3008B and to sever tissue held therebetween. FIG. 9 is a perspective view of one embodiment of the axially moveable member 3016 of the surgical tool 100. The axially moveable member 3016 may comprise one or several pieces, but in any event, may be movable or translatable with respect to the elongate shaft 200 and/or the jaw members 3008A, 3008B. Also, in at least one embodiment, the axially moveable member 3016 may be made of 17-4 precipitation hardened stainless steel. The distal end of axially moveable member 3016 may comprise a flanged "I"-beam configured to slide within the channels 3020A and 3020B in jaw members 3008A and 3008B. The axially moveable member 3016 may slide within the channels 3020A, 3020B to open and close first jaw member 3008A and second jaw member 3008B. The distal end of the axially moveable member 3016 may also comprise an upper flange or "c"-shaped portion 3016A and a lower flange or "c"-shaped portion 3016B. The flanges 3016A and 3016B respectively define inner cam surfaces 3026A and 3026B for engaging outward facing surfaces of first jaw member 3008A and second jaw member 3008B. The opening-closing of jaw members 3008A and 3008B can apply very high compressive forces on tissue using cam mechanisms which may include movable "I-beam" axially moveable member 3016 and the outward facing surfaces 3028A, 3028B of jaw members 3008A, 3008B.

More specifically, referring now to FIGS. 7-9, collectively, the inner cam surfaces 3026A and 3026B of the distal end of axially moveable member 3016 may be adapted to slidably engage the first outward-facing surface 3028A and the second outward-facing surface 3028B of the first jaw member 3008A and the second jaw member 3008B, respectively. The channel 3020A within first jaw member 3008A and the channel 3020B within the second jaw member 3008B may be sized and configured to accommodate the movement of the axially moveable member 3016, which may comprise a tissue-cutting element 3030, for example, comprising a sharp distal edge. FIG. 8, for example, shows the distal end of the axially moveable member 3016 advanced at least partially through channels 3020A and 3020B (FIG. 7). The advancement of the axially moveable member 3016 may close the end effector 3000 from the open configuration shown in FIG. 7. In the closed position shown by FIG. 8, the upper first jaw member 3008A and lower second jaw member 3008B define a gap or dimension D between the first energy delivery surface 3024A and second energy delivery surface 3024B of first jaw member 3008A and second jaw member 3008B, respectively. In various embodiments, dimension D can equal from about 0.0005" to about 0.040", for example, and in some embodiments, between about 0.001" to about 0.010", for example. Also, the edges of the first energy delivery surface 3024A and the second energy delivery surface 3024B may be rounded to prevent the dissection of tissue.

FIG. 10 is a section view of one embodiment of the end effector 3000 of the surgical tool 100. The engagement, or tissue-contacting, surface 3024B of the lower jaw member 3008B is adapted to deliver energy to tissue, at least in part, through a conductive-resistive matrix, such as a variable resistive positive temperature coefficient (PTC) body, as discussed in more detail below. At least one of the upper and lower jaw members 3008A, 3008B may carry at least one electrode 3032 configured to deliver the energy from the generator 3002 to the captured tissue. The engagement, or tissue-contacting, surface 3024A of upper jaw member 3008A may carry a similar conductive-resistive matrix (i.e., a PTC material), or in some embodiments the surface may be a conductive electrode or an insulative layer, for example. Alternatively, the engagement surfaces of the jaw members can carry any of the energy delivery components disclosed in U.S. Pat. No. 6,773,409, filed Oct. 22, 2001, entitled ELECTROSURGICAL JAW STRUCTURE FOR CON-TROLLED ENERGY DELIVERY, the entire disclosure of which is incorporated herein by reference.

The first energy delivery surface 3024A and the second energy delivery surface 3024B may each be in electrical communication with the generator 3002. The first energy delivery surface 3024A and the second energy delivery surface 3024B may be configured to contact tissue and deliver electrosurgical energy to captured tissue which are adapted to seal or weld the tissue. The control unit 3004 regulates the electrical energy delivered by electrical generator 3002 which in turn delivers electrosurgical energy to the first energy delivery surface 3024A and the second energy delivery surface 3024B. The energy delivery may be initiated in any suitable manner (e.g., upon actuation of the robot system 10. In one embodiment, the electrosurgical tool 100 may be energized by the generator 3002 by way of a foot switch 3034 (FIG. 6). When actuated, the foot switch 3034 triggers the generator 3002 to deliver electrical energy to the end effector 3000, for example. The control unit 3004 may regulate the power generated by the generator 3002 during activation. Although the foot switch 3034 may be suitable in many circumstances, other suitable types of switches can be used.

As mentioned above, the electrosurgical energy delivered by electrical generator 3002 and regulated, or otherwise controlled, by the control unit 3004 may comprise radio frequency (RF) energy, or other suitable forms of electrical energy. Further, one or both of the opposing first and second energy delivery surfaces 3024A and 3024B may carry variable resistive positive temperature coefficient (PTC) bodies that are in electrical communication with the generator 3002 and the control unit 3004. Additional details regarding electrosurgical end effectors, jaw closing mechanisms, and electrosurgical energy-delivery surfaces are described in the following U.S. patents and published patent applications: U.S. Pat. Nos. 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,176; and U.S. Patent Application Publication Nos. 2010/0036370 and 2009/0076506, all of which are incorporated herein in their entirety by reference and made a part of this specification.

In one embodiment, the generator 3002 may be implemented as an electrosurgery unit (ESU) capable of supplying power sufficient to perform bipolar electrosurgery using radio frequency (RF) energy. In one embodiment, the ESU can be a bipolar ERBE ICC 350 sold by ERBE USA, Inc. of Marietta, Georgia. In some embodiments, such as for bipolar electrosurgery applications, a surgical tool having an active electrode and a return electrode can be utilized, wherein the active electrode and the return electrode can be positioned against, adjacent to and/or in electrical communication with, the tissue to be treated such that current can flow from the active electrode, through the positive temperature coefficient (PTC) bodies and to the return electrode through the tissue. Thus, in various embodiments, the electrosurgical system 150 may comprise a supply path and a return path, wherein the captured tissue being treated completes, or closes, the circuit. In one embodiment, the generator 3002 may be a monopolar RF ESU and the electrosurgical tool 100 may comprise a monopolar end effector 3000 in which one or more active electrodes are integrated. For such a system, the generator 3002 may require a return pad in intimate contact with the patient at a location remote from the operative site and/or other suitable return path. The return pad may be connected via a cable to the generator 3002.

During operation of electrosurgical tool 100, the clinician generally grasps tissue, supplies energy to the captured tissue to form a weld or a seal (e.g., by actuating button 214 and/or pedal 216), and then drives the tissue-cutting element 3030 at the distal end of the axially moveable member 3016 through the captured tissue. According to various embodiments, the translation of the axial movement of the axially moveable member 3016 may be paced, or otherwise controlled, to aid in driving the axially moveable member 3016 at a suitable rate of travel. By controlling the rate of the travel, the likelihood that the captured tissue has been properly and functionally sealed prior to transection with the cutting element 3030 is increased.

Figure 15:
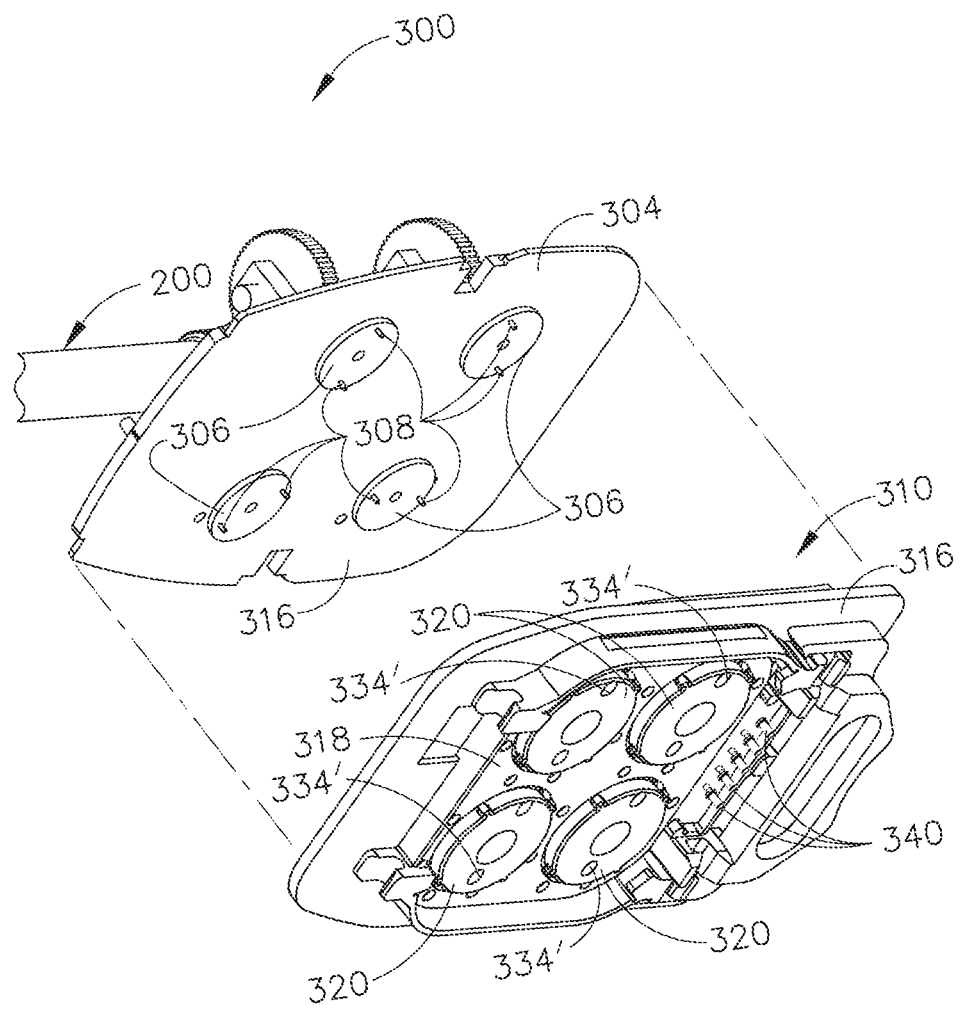
FIG. 15 is a partial bottom perspective view of one embodiment of a surgical tool.

Referring now to the embodiment depicted in FIGS. 11-15, the tool mounting portion 300 includes a tool mounting plate 304 that operably supports a plurality of (four are shown in FIG. 15) rotatable body portions, driven discs or elements 306, that each include a pair of pins 308 that extend from a surface of the driven element 306. One pin 308 is closer to an axis of rotation of each driven elements 306 than the other pin 308 on the same driven element 306, which helps to ensure positive angular alignment of the driven element 306. Interface 302 may include an adaptor portion 310 that is configured to mountingly engage a mounting plate 304 as will be further discussed below. The illustrated adaptor portion 310 includes an array of electrical connecting pins 312 (FIG. 13) which may be coupled to a memory structure by a circuit board within the tool mounting portion 300. While interface 302 is described herein with reference to mechanical, electrical, and magnetic coupling elements, it should be understood that a wide variety of telemetry modalities might be used, including infrared, inductive coupling, or the like in other embodiments.

As can be seen in FIGS. 11-14, the adapter portion 310 generally includes a tool side 314 and a holder side 316. A plurality of rotatable bodies 320 are mounted to a floating plate 318 which has a limited range of movement relative to the surrounding adaptor structure normal to the major surfaces of the adaptor 310. Axial movement of the floating plate 318 helps decouple the rotatable bodies 320 from the tool mounting portion 300 when levers or other latch formations along the sides of the tool mounting portion housing (not shown) are actuated. Other embodiments may employ other mechanisms/arrangements for releasably coupling the tool mounting portion 300 to the adaptor 310. In the embodiment of FIGS. 11-15, rotatable bodies 320 are resiliently mounted to floating plate 318 by resilient radial members which extend into a circumferential indentation about the rotatable bodies 320. The rotatable bodies 320 can move axially relative to plate 318 by deflection of these resilient structures. When disposed in a first axial position (toward tool side 314) the rotatable bodies 320 are free to rotate without angular limitation. However, as the rotatable bodies 320 move axially toward tool side 314, tabs 322 (extending radially from the rotatable bodies 320) laterally engage detents on the floating plates so as to limit angular rotation of the rotatable bodies 320 about their axes. This limited rotation can be used to help drivingly engage the rotatable bodies 320 with drive pins 332 of a corresponding tool holder portion 330 of the robotic system 10, as the drive pins 332 will push the rotatable bodies 320 into the limited rotation position until the pins 332 are aligned with (and slide into) openings 334'. Openings 334 on the tool side 314 and openings 334' on the holder side 316 of rotatable bodies 320 are configured to accurately align the driven elements 306 (FIG. 15) of the tool mounting portion 300 with the drive elements 336 of the tool holder 330. As described above regarding inner and outer pins 308 of driven elements 306, the openings 304, 304' are at differing distances from the axis of rotation on their respective rotatable bodies 306 so as to ensure that the alignment is not 180 degrees from its intended position. Additionally, each of the openings 304 may be slightly radially elongate so as to fittingly receive the pins 308 in the circumferential orientation. This allows the pins 308 to slide radially within the openings 334, 334' and accommodate some axial misalignment between the tool 100 and tool holder 330, while minimizing any angular misalignment and backlash between the drive and driven elements. Openings 334 on the tool side 314 may be offset by about 90 degrees from the openings 334' (shown in broken lines) on the holder side 316, as can be seen most clearly in FIG. 14.

In the embodiment of FIGS. 11-15, an array of electrical connector pins 340 are located on holder side 316 of adaptor 310 and the tool side 314 of the adaptor 310 includes slots 342 (FIG. 14) for receiving a pin array (not shown) from the tool mounting portion 300. In addition to transmitting electrical signals between the surgical tool 100 and the tool holder 330, at least some of these electrical connections may be coupled to an adaptor memory device 344 (FIG. 13) by a circuit board of the adaptor 310.

Figure 11:
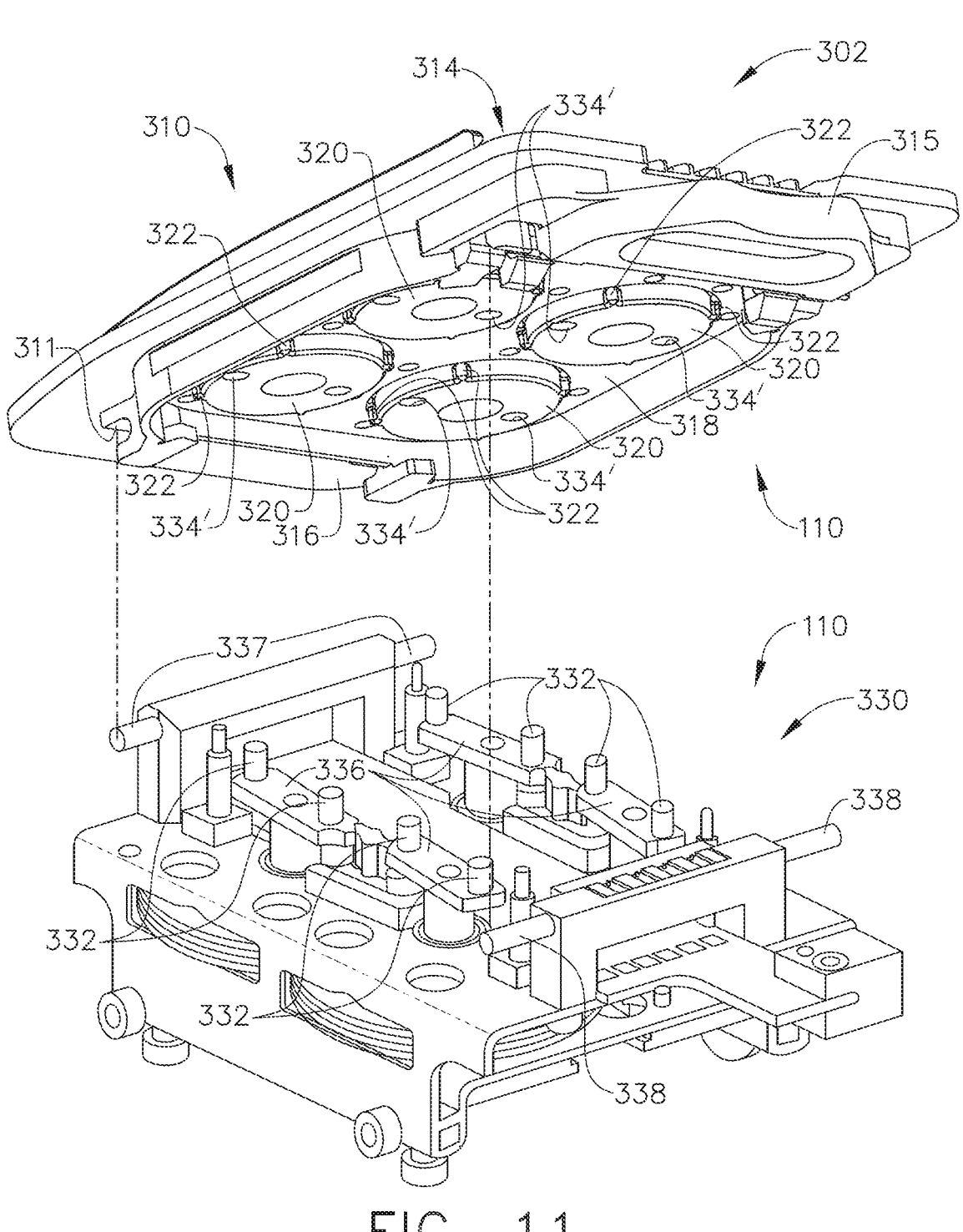
FIG. 11 is an exploded assembly view of one embodiment of an adapter and tool holder arrangement for attaching various surgical tool embodiments to a robotic system.
Figure 12:
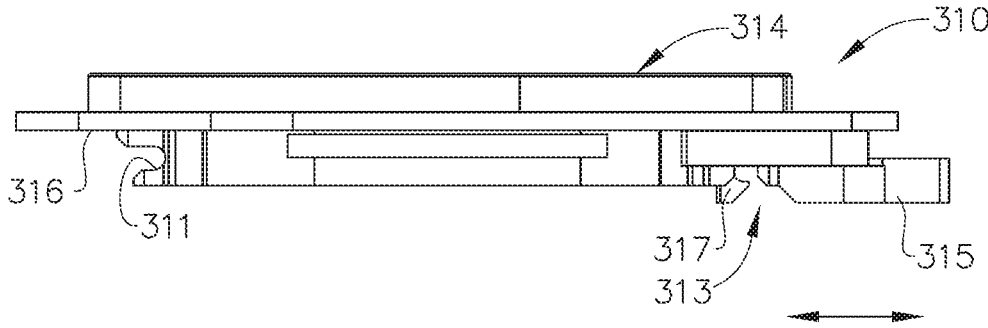
FIG. 12 is a side view of one embodiment of the adapter shown in FIG. 11.
Figure 13:
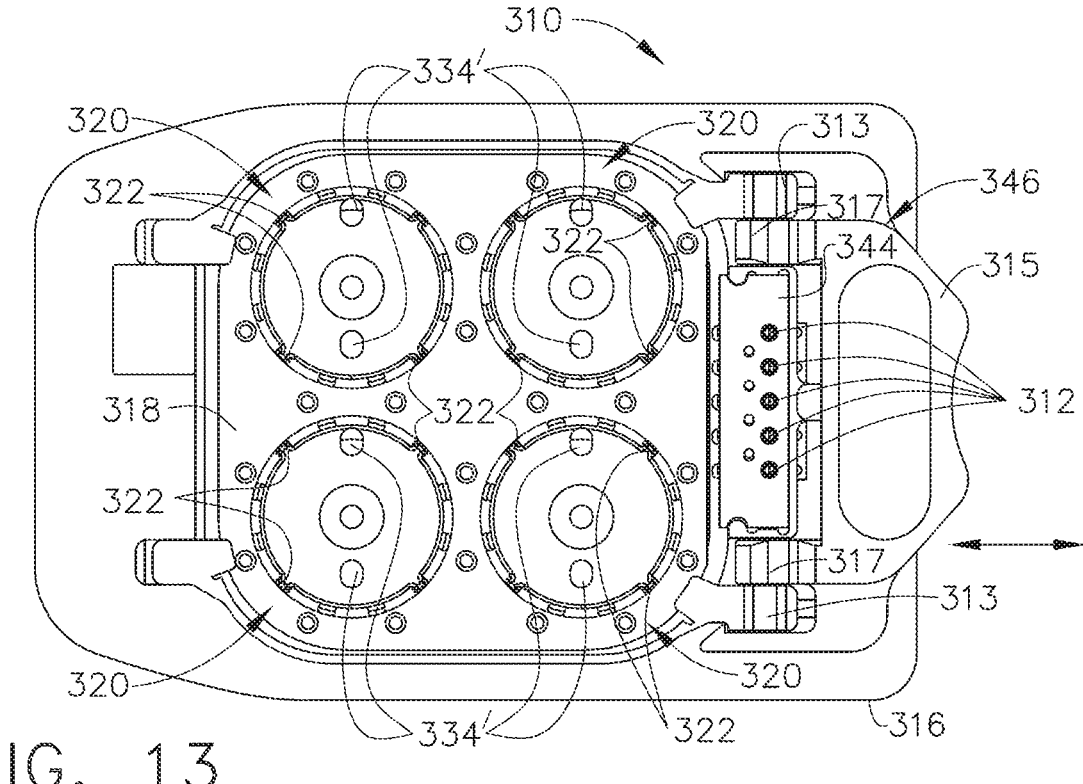
FIG. 13 is a bottom view of one embodiment of the adapter shown in FIG. 11.
Figure 14:
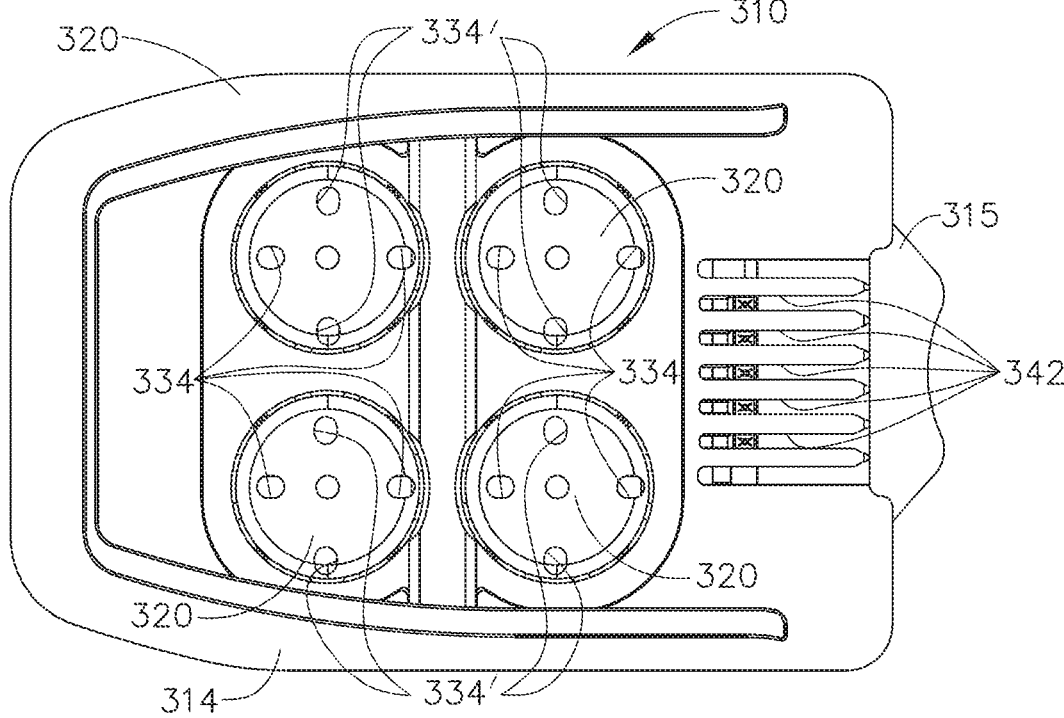
FIG. 14 is a top view of one embodiment of the adapter of FIGS. 11 and 12.

In the embodiment of FIGS. 11-15, a detachable latch arrangement 346 is employed to releasably affix the adaptor 310 to the tool holder 330. As used herein, the term "tool drive assembly" when used in the context of the robotic system 10, at least encompasses the adapter 310 and tool holder 330 and which have been collectively generally designated as 110 in FIG. 11. As can be seen in FIG. 11, the tool holder 330 includes a first latch pin arrangement 337 that is sized to be received in corresponding clevis slots 311 provided in the adaptor 310. In addition, the tool holder 330 further has second latch pins 338 that are sized to be retained in corresponding latch clevises 313 in the adaptor 310. See FIG. 11. A latch assembly 315 is movably supported on the adapter 310 and has a pair of latch devises 317 formed therein that is biasable from a first latched position wherein the latch pins 338 are retained within their respective latch clevis 313 and an unlatched position wherein the devises 317 are aligned with devises 313 to enable the second latch pins 338 may be inserted into or removed from the latch devises 313. A spring or springs (not shown) are employed to bias the latch assembly into the latched position. A lip on the tool side 314 of adaptor 310 slidably receives laterally extending tabs of the tool mounting housing (not shown).

Referring now to FIGS. 5 and 16-21, the tool mounting portion 300 operably supports a plurality of drive systems for generating various forms of control motions necessary to operate a particular type of end effector that is coupled to the distal end of the elongate shaft assembly 200. As shown in FIGS. 5 and 16-21, the tool mounting portion 300 includes a first drive system generally designated as 350 that is configured to receive a corresponding "first" rotary output motion from the tool drive assembly 110 of the robotic system 10 and convert that first rotary output motion to a first rotary control motion to be applied to the surgical end effector. In the illustrated embodiment, the first rotary control motion is employed to rotate the elongate shaft assembly 200 (and surgical end effector 3000) about a longitudinal tool axis LT-LT.

Figure 16:
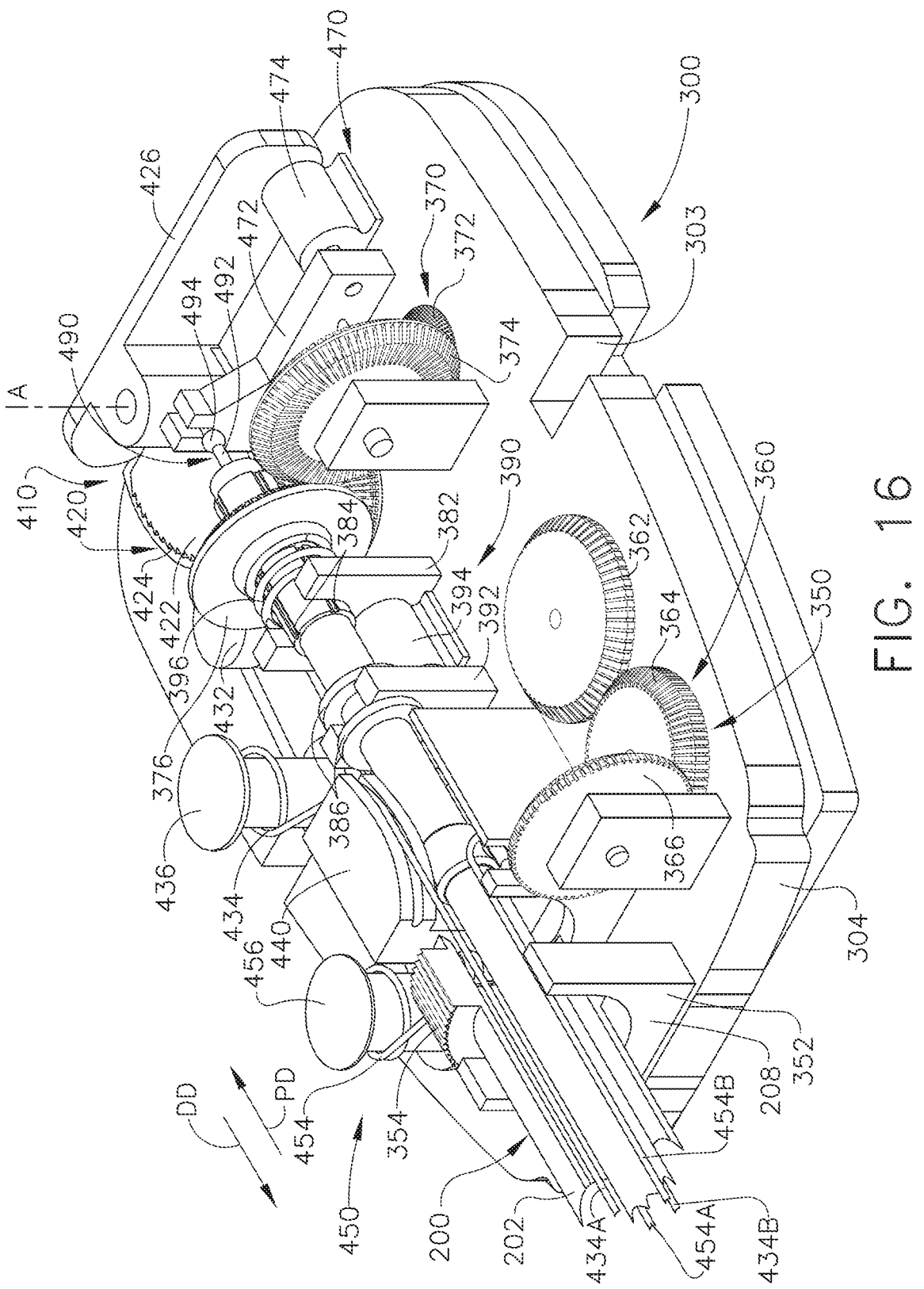
FIG. 16 is a front perspective view of one embodiment of a portion of a surgical tool with some elements thereof omitted for clarity.

In the embodiment of FIGS. 5 and 16-18, the first drive system 350 includes a tube gear segment 354 that is formed on (or attached to) the proximal end 208 of a proximal tube segment 202 of the elongate shaft assembly 200. The proximal end 208 of the proximal tube segment 202 is rotatably supported on the tool mounting plate 304 of the tool mounting portion 300 by a forward support cradle 352 that is mounted on the tool mounting plate 304. See FIG. 16. The tube gear segment 354 is supported in meshing engagement with a first rotational gear assembly 360 that is operably supported on the tool mounting plate 304. As can be seen in FIG. 16, the rotational gear assembly 360 comprises a first rotation drive gear 362 that is coupled to a corresponding first one of the driven discs or elements 306 on the holder side 316 of the tool mounting plate 304 when the tool mounting portion 300 is coupled to the tool drive assembly 110. See FIG. 15. The rotational gear assembly 360 further comprises a first rotary driven gear 364 that is rotatably supported on the tool mounting plate 304. The first rotary driven gear 364 is in meshing engagement with a second rotary driven gear 366 which, in turn, is in meshing engagement with the tube gear segment 354. Application of a first rotary output motion from the tool drive assembly 110 of the robotic system 10 to the corresponding driven element 306 will thereby cause rotation of the rotation drive gear 362. Rotation of the rotation drive gear 362 ultimately results in the rotation of the elongate shaft assembly 200 (and the surgical end effector 3000) about the longitudinal tool axis LT-LT (represented by arrow "R" in FIG. 5). It will be appreciated that the application of a rotary output motion from the tool drive assembly 110 in one direction will result in the rotation of the elongate shaft assembly 200 and surgical end effector 3000 about the longitudinal tool axis LT-LT in a first rotary direction and an application of the rotary output motion in an opposite direction will result in the rotation of the elongate shaft assembly 200 and surgical end effector 3000 in a second rotary direction that is opposite to the first rotary direction.

In embodiment of FIGS. 5 and 16-21, the tool mounting portion 300 further includes a second drive system generally designated as 370 that is configured to receive a corresponding "second" rotary output motion from the tool drive assembly 110 of the robotic system 10 and convert that second rotary output motion to a second rotary control motion for application to the surgical end effector. The second drive system 370 includes a second rotation drive gear 372 that is coupled to a corresponding second one of the driven discs or elements 306 on the holder side 316 of the tool mounting plate 304 when the tool mounting portion 300 is coupled to the tool drive assembly 110. See FIG. 15. The second drive system 370 further comprises a first rotary driven gear 374 that is rotatably supported on the tool mounting plate 304. The first rotary driven gear 374 is in meshing engagement with a shaft gear 376 that is movably and non-rotatably mounted onto a proximal drive shaft segment 380. In this illustrated embodiment, the shaft gear 376 is non-rotatably mounted onto the proximal drive shaft segment 380 by a series of axial keyways 384 that enable the shaft gear 376 to axially move on the proximal drive shaft segment 380 while being non-rotatably affixed thereto. Rotation of the proximal drive shaft segment 380 results in the transmission of a second rotary control motion to the surgical end effector 3000.

Figure 17:
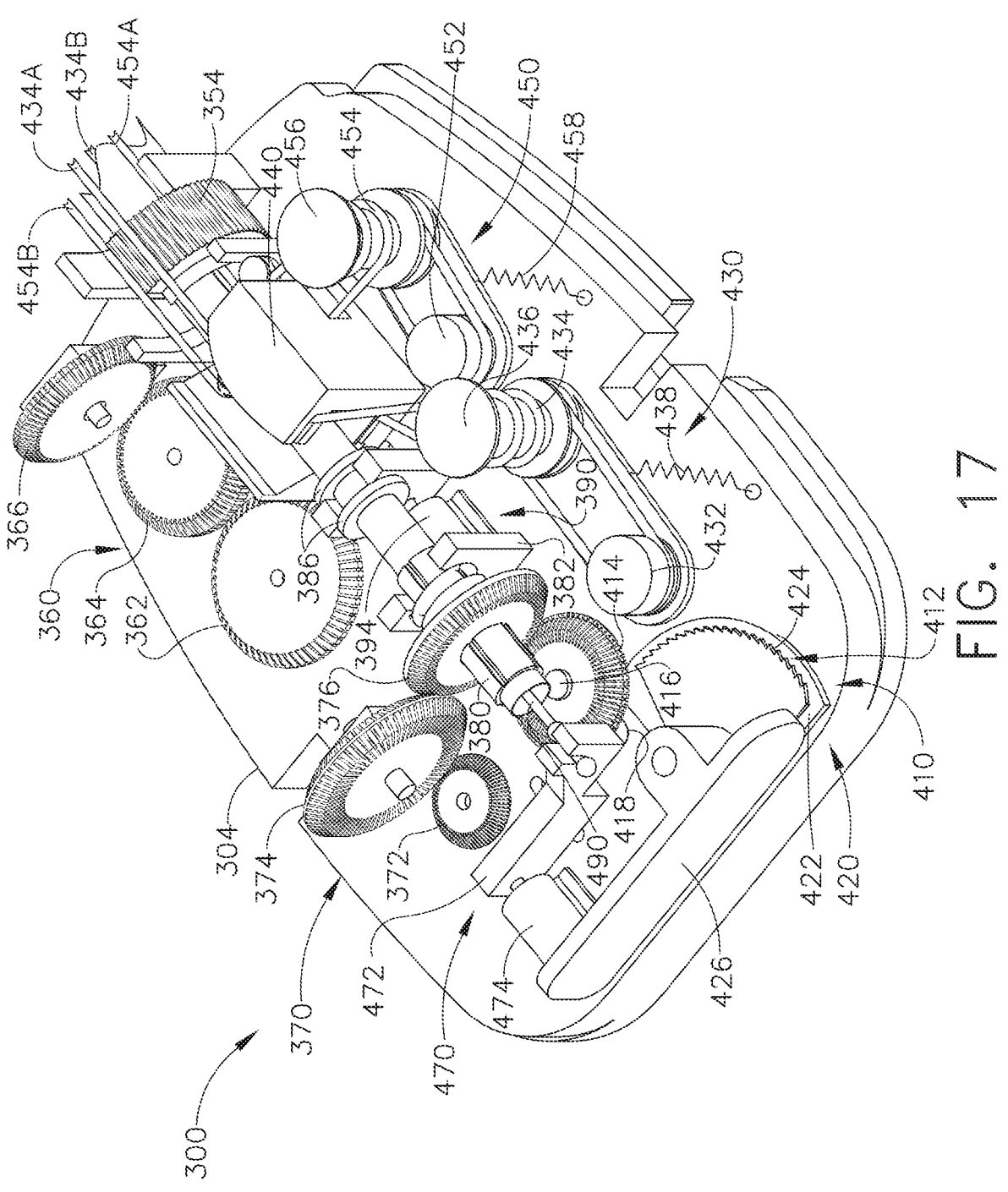
FIG. 17 is a rear perspective view of one embodiment of the surgical tool of FIG. 16.
Figure 18:
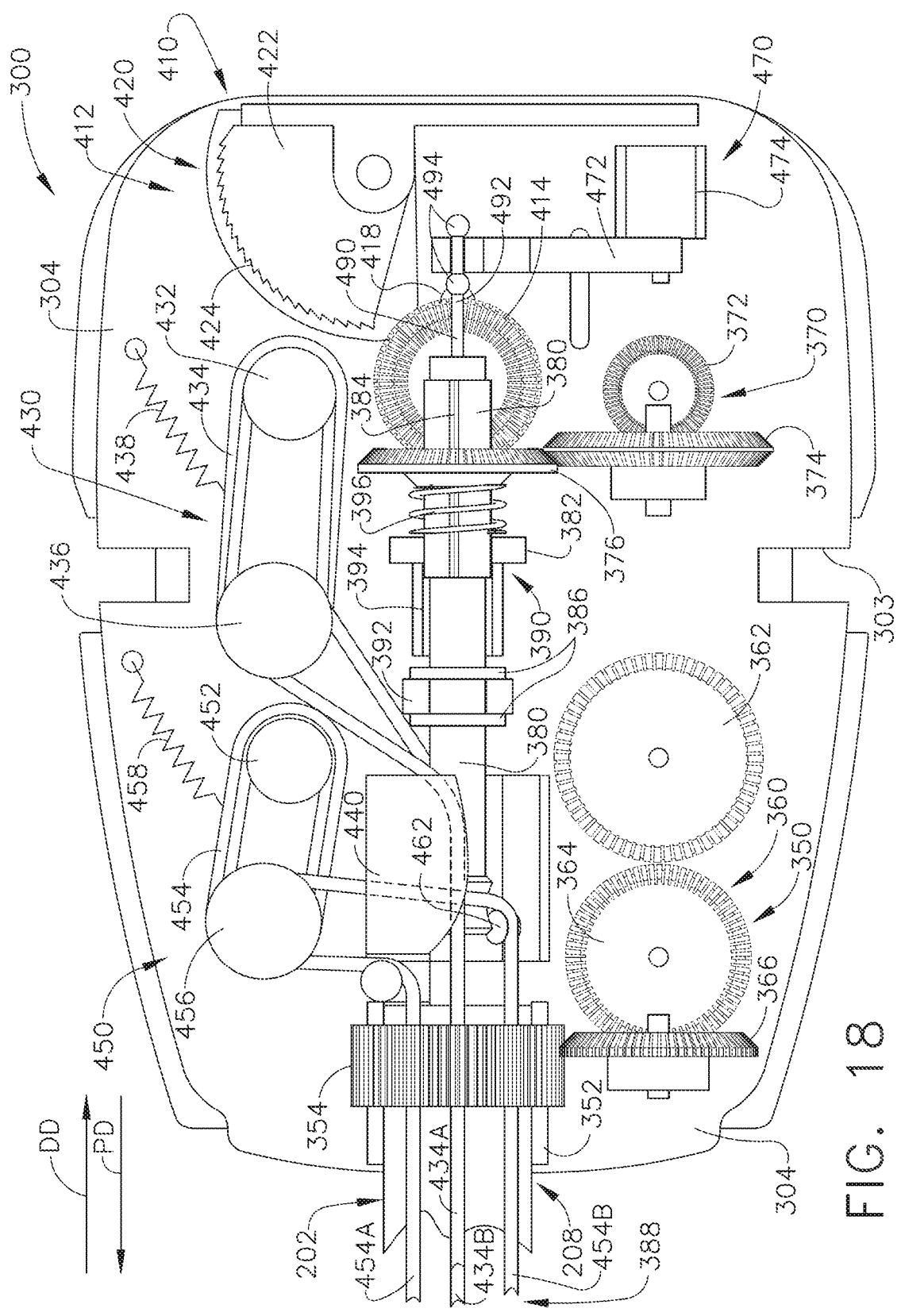
FIG. 18 is a top view of one embodiment of the surgical tool of FIGS. 16 and 17.
Figures 19, 20:
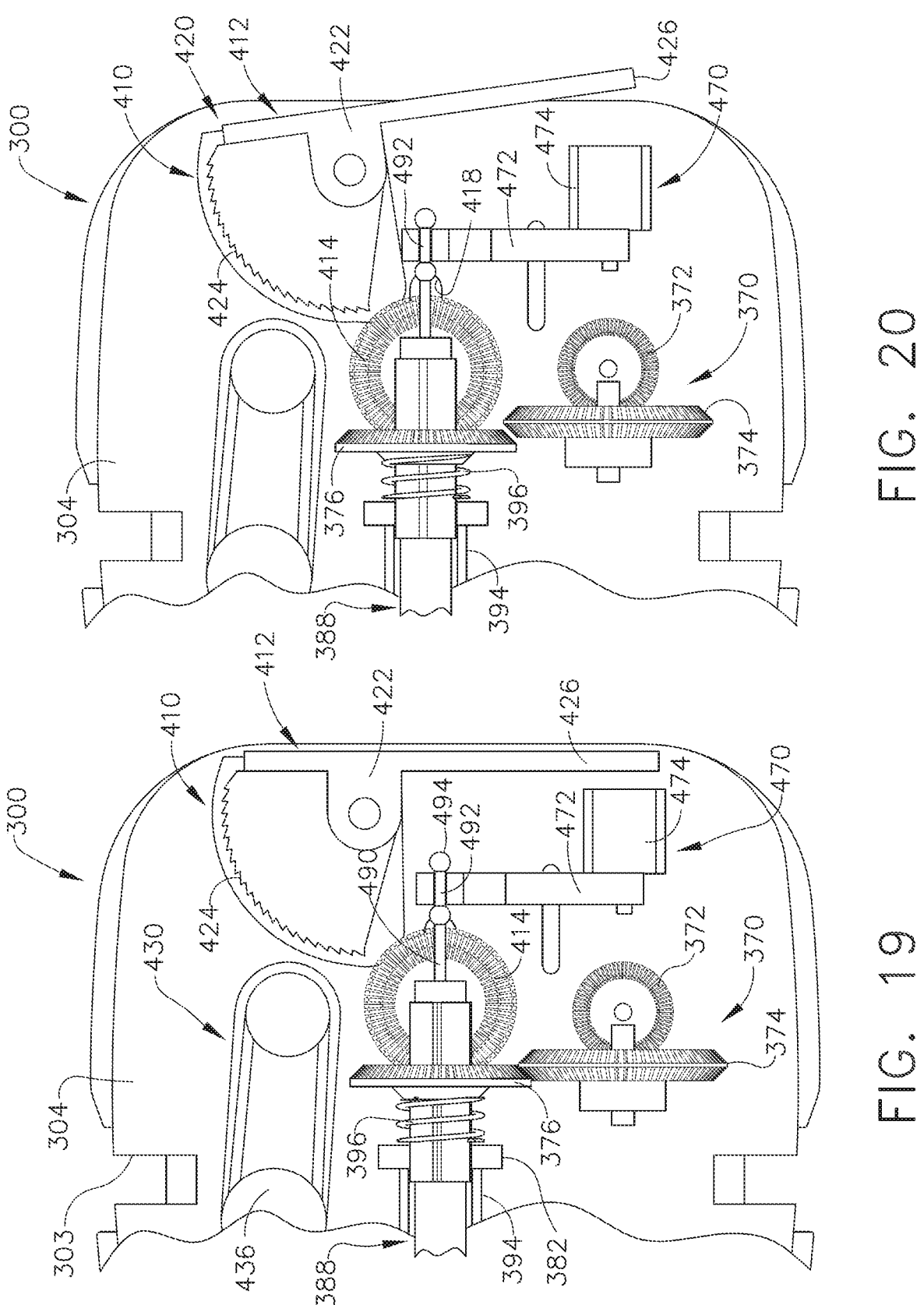
FIG. 19 is a partial top view of one embodiment of the surgical tool of FIGS. 16-18 with the manually actuatable drive gear in an unactuated position.
FIG. 20 is another partial top view of one embodiment of the surgical tool of FIGS. 16-19 with the manually actuatable drive gear in an initially actuated position.
Figure 21:
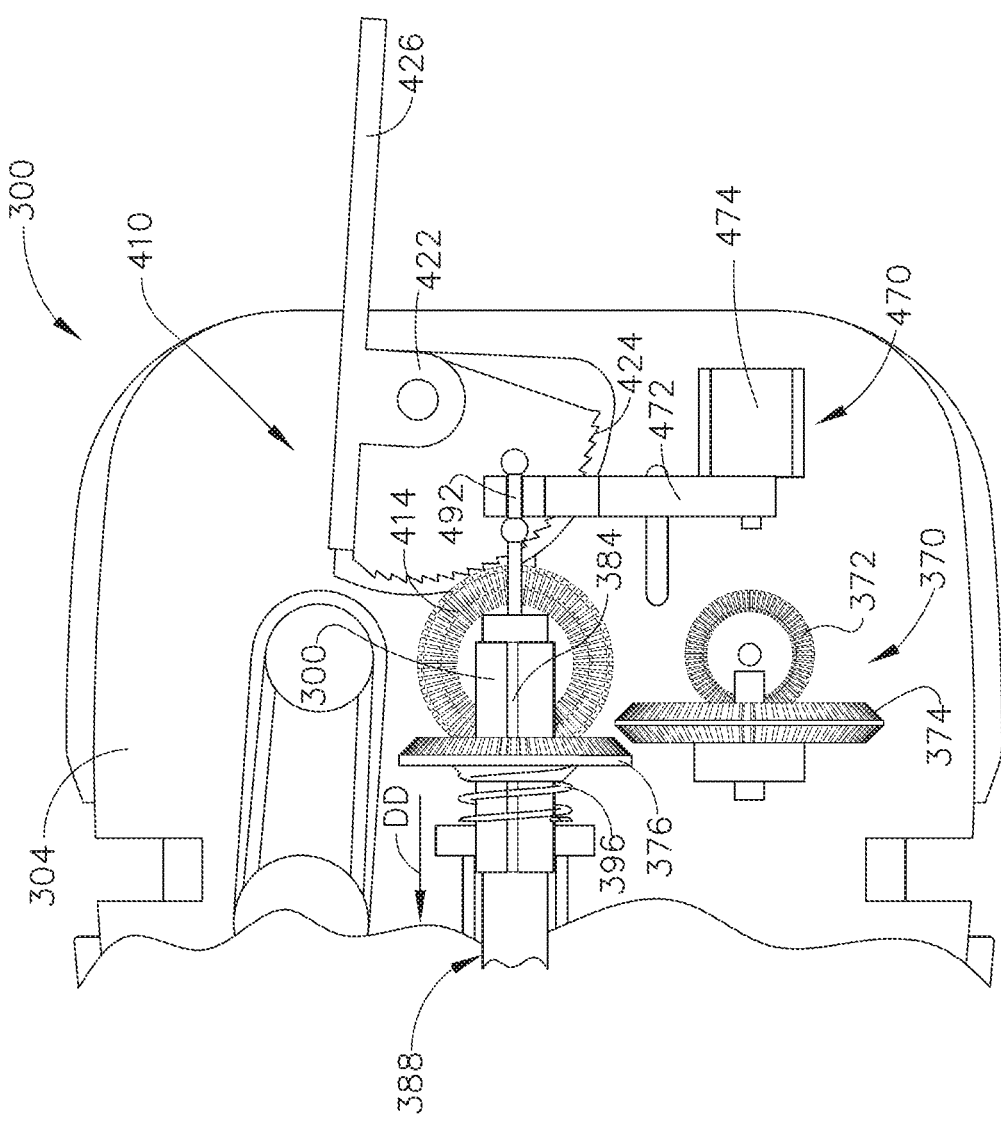
FIG. 21 is another partial top view of one embodiment of the surgical tool of FIGS. 16-20 with the manually actuatable drive gear in an actuated position.

The second drive system 370 in the embodiment of FIGS. 5 and 16-21 includes a shifting system 390 for selectively axially shifting the proximal drive shaft segment 380 which moves the shaft gear 376 into and out of meshing engagement with the first rotary driven gear 374. For example, as can be seen in FIGS. 16-18, the proximal drive shaft segment 380 is supported within a second support cradle 382 that is attached to the tool mounting plate 304 such that the proximal drive shaft segment 380 may move axially and rotate relative to the second support cradle 382. In at least one form, the shifting system 390 further includes a shifter yoke 392 that is slidably supported on the tool mounting plate 304. The proximal drive shaft segment 380 is supported in the shifter yoke 392 and has a pair of collars 386 thereon such that shifting of the shifter yoke 392 on the tool mounting plate 304 results in the axial movement of the proximal drive shaft segment 380. In at least one form, the shifting system 390 further includes a shifter solenoid 394 that operably interfaces with the shifter yoke 392. The shifter solenoid 394 receives control power from the robotic controller 12 such that when the shifter solenoid 394 is activated, the shifter yoke 392 is moved in the distal direction "DD".

In this illustrated embodiment, a shaft spring 396 is journaled on the proximal drive shaft segment 380 between the shaft gear 376 and the second support cradle 382 to bias the shaft gear 376 in the proximal direction "PD" and into meshing engagement with the first rotary driven gear 374. See FIGS. 16, 18 and 19. Rotation of the second rotation drive gear 372 in response to rotary output motions generated by the robotic system 10 ultimately results in the rotation of the proximal drive shaft segment 380 and other drive shaft components coupled thereto (drive shaft assembly 388) about the longitudinal tool axis LT-LT. It will be appreciated that the application of a rotary output motion from the tool drive assembly 110 in one direction will result in the rotation of the proximal drive shaft segment 380 and ultimately of the other drive shaft components attached thereto in a first direction and an application of the rotary output motion in an opposite direction will result in the rotation of the proximal drive shaft segment 380 in a second direction that is opposite to the first direction. When it is desirable to shift the proximal drive shaft segment 380 in the distal direction "DD" as will be discussed in further detail below, the robotic controller 12 activates the shifter solenoid 390 to shift the shifter yoke 392 in the distal direction "DD". IN some embodiments, the shifter solenoid 390 may be capable of shifting the proximal drive shaft segment 380 between more than two longitudinal positions. For example, some embodiments, such as those described herein with respect to FIGS. 83-96, may utilize the rotary drive shaft (e.g., coupled to the proximal drive shaft segment 380) in more than two longitudinal positions.

Figure 22:
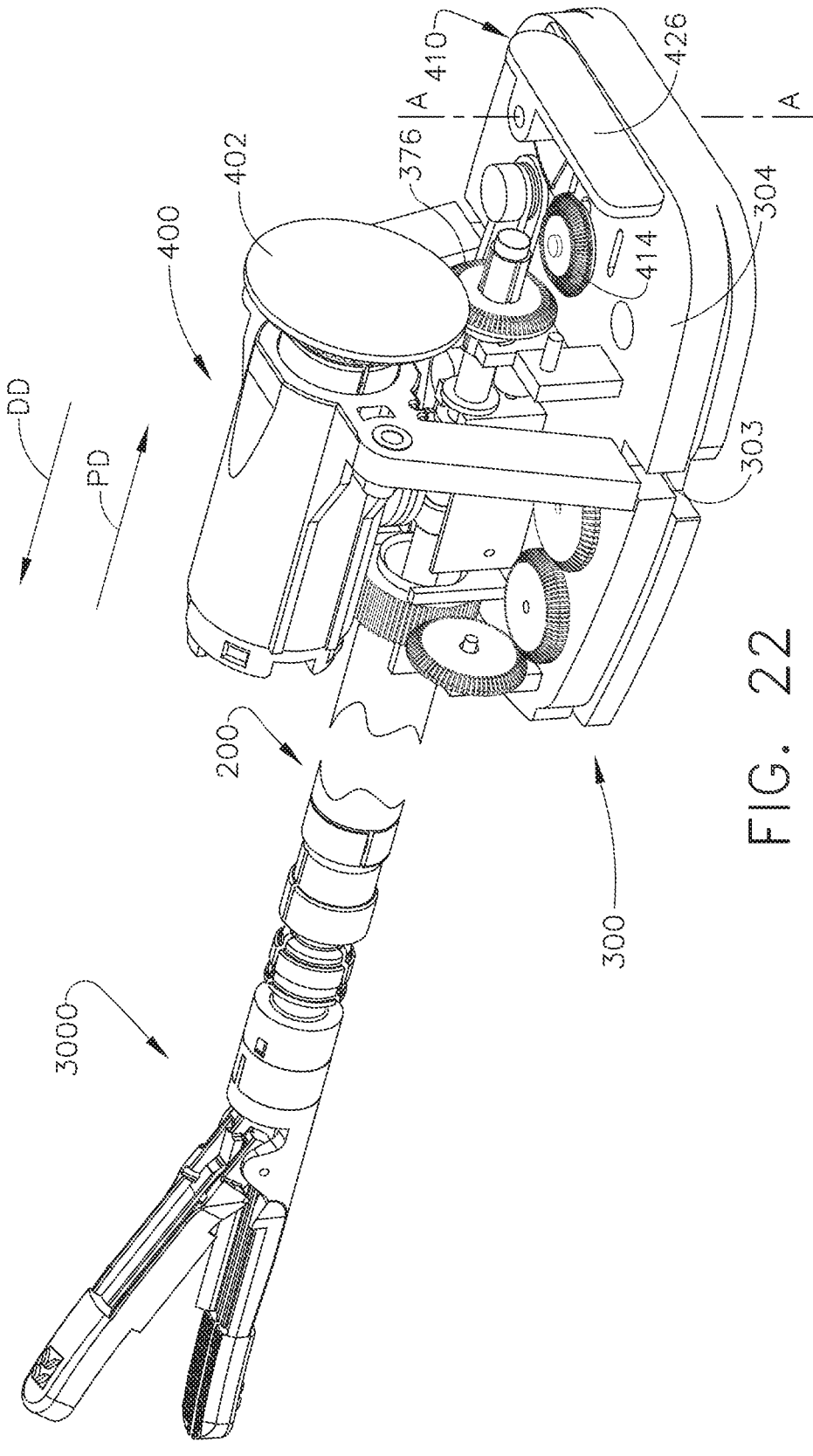
FIG. 22 is a rear perspective view of another surgical tool embodiment.
Figure 23:
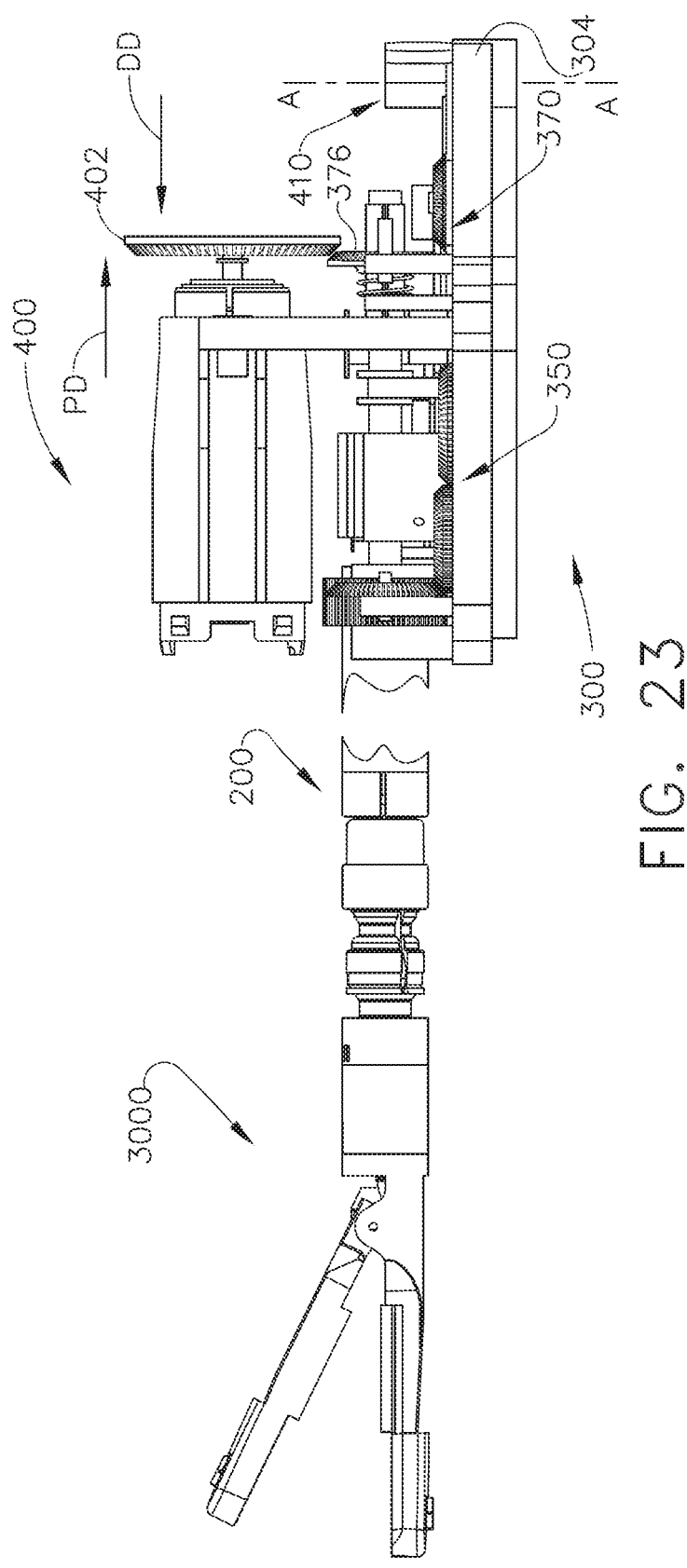
FIG. 23 is a side elevational view of one embodiment of the surgical tool of FIG. 22.

FIGS. 22-23 illustrate another embodiment that employs the same components of the embodiment depicted in FIGS. 5 and 16-21 except that this embodiment employs a battery-powered drive motor 400 for supplying rotary drive motions to the proximal drive shaft segment 380. Such arrangement enables the tool mounting portion to generate higher rotary output motions and torque which may be advantageous when different forms of end effectors are employed. As can be seen in those Figures, the motor 400 is attached to the tool mounting plate 304 by a support structure 402 such that a driver gear 404 that is coupled to the motor 400 is retained in meshing engagement with the shaft gear 376. In the embodiment of FIGS. 22-23, the support structure 402 is configured to removably engage latch notches 303 formed in the tool mounting plate 304 that are designed to facilitate attachment of a housing member (not shown) to the mounting plate 304 when the motor 400 is not employed. Thus, to employ the motor 400, the clinician removes the housing from the tool mounting plate 304 and then inserts the legs 403 of the support structure into the latch notches 303 in the tool mounting plate 304. The proximal drive shaft segment 380 and the other drive shaft components attached thereto are rotated about the longitudinal tool axis LT-LT by powering the motor 400. As illustrated, the motor 400 is battery powered. In such arrangement, however, the motor 400 interface with the robotic controller 12 such that the robotic system 10 controls the activation of the motor 400. In alternative embodiments, the motor 400 is manually actuatable by an on/off switch (not shown) mounted on the motor 400 itself or on the tool mounting portion 300. In still other embodiments, the motor 400 may receive power and control signals from the robotic system.

The embodiment illustrated in FIGS. 5 and 16-21 includes a manually-actuatable reversing system, generally designated as 410, for manually applying a reverse rotary motion to the proximal drive shaft segment 380 in the event that the motor fails or power to the robotic system is lost or interrupted. Such manually-actuatable reversing system 410 may also be particularly useful, for example, when the drive shaft assembly 388 becomes jammed or otherwise bound in such a way that would prevent reverse rotation of the drive shaft components under the motor power alone. In the illustrated embodiment, the mechanically-actuatable reversing system 410 includes a drive gear assembly 412 that is selectively engageable with the second rotary driven gear 376 and is manually actuatable to apply a reversing rotary motion to the proximal drive shaft segment 380. The drive gear assembly 412 includes a reversing gear 414 that is movably mounted to the tool mounting plate 304. The reversing gear 414 is rotatably journaled on a pivot shaft 416 that is movably mounted to the tool mounting plate 304 through a slot 418. See FIG. 17. In the embodiment of FIGS. 5 and 16-21, the manually-actuatable reversing system 410 further includes a manually actuatable drive gear 420 that includes a body portion 422 that has an arcuate gear segment 424 formed thereon. The body portion 422 is pivotally coupled to the tool mounting plate 304 for selective pivotal travel about an actuator axis A-A (FIG. 16) that is substantially normal to the tool mounting plate 304.

FIGS. 16-19 depict the manually-actuatable reversing system 410 in a first unactuated position. In one example form, an actuator handle portion 426 is formed on or otherwise attached to the body portion 422. The actuator handle portion 426 is sized relative to the tool mounting plate 304 such that a small amount of interference is established between the handle portion 426 and the tool mounting plate 304 to retain the handle portion 426 in the first unactuated position. However, when the clinician desires to manually actuate the drive gear assembly 412, the clinician can easily overcome the interference fit by applying a pivoting motion to the handle portion 426. As can also be seen in FIGS. 16-19, when the drive gear assembly 412 is in the first unactuated position, the arcuate gear segment 424 is out of meshing engagement with the reversing gear 414. When the clinician desires to apply a reverse rotary drive motion to the proximal drive shaft segment 380, the clinician begins to apply a pivotal ratcheting motion to drive gear 420. As the drive gear 420 begins to pivot about the actuation axis A-A, a portion of the body 422 contacts a portion of the reversing gear 414 and axially moves the reversing gear 414 in the distal direction DD taking the drive shaft gear 376 out of meshing engagement with the first rotary driven gear 374 of the second drive system 370. See FIG. 20. As the drive gear 420 is pivoted, the arcuate gear segment 424 is brought into meshing engagement with the reversing gear 414. Continued ratcheting of the drive gear 420 results in the application of a reverse rotary drive motion to the drive shaft gear 376 and ultimately to the proximal drive shaft segment 380. The clinician may continue to ratchet the drive gear assembly 412 for as many times as are necessary to fully release or reverse the associated end effector component(s). Once a desired amount of reverse rotary motion has been applied to the proximal drive shaft segment 380, the clinician returns the drive gear 420 to the starting or unactuated position wherein the arcuate gear segment 416 is out of meshing engagement with the drive shaft gear 376. When in that position, the shaft spring 396 once again biases the shaft gear 376 into meshing engagement with first rotary driven gear 374 of the second drive system 370.

In use, the clinician may input control commands to the controller or control unit of the robotic system 10 which "robotically-generates" output motions that are ultimately transferred to the various components of the second drive system 370. As used herein, the terms "robotically-generates" or "robotically-generated" refer to motions that are created by powering and controlling the robotic system motors and other powered drive components. These terms are distinguishable from the terms "manually-actuatable" or "manually generated" which refer to actions taken by the clinician which result in control motions that are generated independent from those motions that are generated by powering the robotic system motors. Application of robotically-generated control motions to the second drive system in a first direction results in the application of a first rotary drive motion to the drive shaft assembly 388. When the drive shaft assembly 388 is rotated in a first rotary direction, the axially movable member 3016 is driven in the distal direction "DD" from its starting position toward its ending position in the end effector 3000, for example, as described herein with respect to FIGS. 64-96. Application of robotically-generated control motions to the second drive system in a second direction results in the application of a second rotary drive motion to the drive shaft assembly 388. When the drive shaft assembly 388 is rotated in a second rotary direction, the axially movable member 3016 is driven in the proximal direction "PD" from its ending position toward its starting position in the end effector 3000. When the clinician desires to manually-apply rotary control motion to the drive shaft assembly 388, the drive shaft assembly 388 is rotated in the second rotary direction which causes a firing member (e.g., axially translatable member 3016) to move in the proximal direction "PD" in the end effector. Other embodiments containing the same components are configured such that the manual-application of a rotary control motion to the drive shaft assembly could cause the drive shaft assembly to rotate in the first rotary direction which could be used to assist the robotically-generated control motions to drive the axially movable member 3016 in the distal direction.

The drive shaft assembly that is used to fire, close and rotate the end effector can be actuated and shifted manually allowing the end effector to release and be extracted from the surgical site as well as the abdomen even in the event that the motor(s) fail, the robotic system loses power or other electronic failure occurs. Actuation of the handle portion 426 results in the manual generation of actuation or control forces that are applied to the drive shaft assembly 388' by the various components of the manually-actuatable reversing system 410. If the handle portion 426 is in its unactuated state, it is biased out of actuatable engagement with the reversing gear 414. The beginning of the actuation of the handle portion 426 shifts the bias. The handle 426 is configured for repeated actuation for as many times as are necessary to fully release the axially movable member 3016 and the end effector 3000.

As illustrated in FIGS. 5 and 16-21, the tool mounting portion 300 includes a third drive system 430 that is configured to receive a corresponding "third" rotary output motion from the tool drive assembly 110 of the robotic system 10 and convert that third rotary output motion to a third rotary control motion. The third drive system 430 includes a third drive pulley 432 that is coupled to a corresponding third one of the driven discs or elements 306 on the holder side 316 of the tool mounting plate 304 when the tool mounting portion 300 is coupled to the tool drive assembly 110. See FIG. 15. The third drive pulley 432 is configured to apply a third rotary control motion (in response to corresponding rotary output motions applied thereto by the robotic system 10) to a corresponding third drive cable 434 that may be used to apply various control or manipulation motions to the end effector that is operably coupled to the shaft assembly 200. As can be most particularly seen in FIGS. 16-17, the third drive cable 434 extends around a third drive spindle assembly 436. The third drive spindle assembly 436 is pivotally mounted to the tool mounting plate 304 and a third tension spring 438 is attached between the third drive spindle assembly 436 and the tool mounting plate 304 to maintain a desired amount of tension in the third drive cable 434. As can be seen in the Figures, cable end portion 434A of the third drive cable 434 extends around an upper portion of a pulley block 440 that is attached to the tool mounting plate 304 and cable end portion 434B extends around a sheave pulley or standoff on the pulley block 440. It will be appreciated that the application of a third rotary output motion from the tool drive assembly 110 in one direction will result in the rotation of the third drive pulley 432 in a first direction and cause the cable end portions 434A and 434B to move in opposite directions to apply control motions to the end effector 3000 or elongate shaft assembly 200 as will be discussed in further detail below. That is, when the third drive pulley 432 is rotated in a first rotary direction, the cable end portion 434A moves in a distal direction "DD" and cable end portion 434B moves in a proximal direction "PD". Rotation of the third drive pulley 432 in an opposite rotary direction result in the cable end portion 434A moving in a proximal direction "PD" and cable end portion 434B moving in a distal direction "DD".

The tool mounting portion 300 illustrated in FIGS. 5 and 16-21 includes a fourth drive system 450 that is configured to receive a corresponding "fourth" rotary output motion from the tool drive assembly 110 of the robotic system 10 and convert that fourth rotary output motion to a fourth rotary control motion. The fourth drive system 450 includes a fourth drive pulley 452 that is coupled to a corresponding fourth one of the driven discs or elements 306 on the holder side 316 of the tool mounting plate 304 when the tool mounting portion 300 is coupled to the tool drive assembly 110. See FIG. 15. The fourth drive pulley 452 is configured to apply a fourth rotary control motion (in response to corresponding rotary output motions applied thereto by the robotic system 10) to a corresponding fourth drive cable 454 that may be used to apply various control or manipulation motions to the end effector that is operably coupled to the shaft assembly 200. As can be most particularly seen in FIGS. 16-17, the fourth drive cable 454 extends around a fourth drive spindle assembly 456. The fourth drive spindle assembly 456 is pivotally mounted to the tool mounting plate 304 and a fourth tension spring 458 is attached between the fourth drive spindle assembly 456 and the tool mounting plate 304 to maintain a desired amount of tension in the fourth drive cable 454. Cable end portion 454A of the fourth drive cable 454 extends around a bottom portion of the pulley block 440 that is attached to the tool mounting plate 304 and cable end portion 454B extends around a sheave pulley or fourth standoff 462 on the pulley block 440. It will be appreciated that the application of a rotary output motion from the tool drive assembly 110 in one direction will result in the rotation of the fourth drive pulley 452 in a first direction and cause the cable end portions 454A and 454B to move in opposite directions to apply control motions to the end effector or elongate shaft assembly 200 as will be discussed in further detail below. That is, when the fourth drive pulley 434 is rotated in a first rotary direction, the cable end portion 454A moves in a distal direction "DD" and cable end portion 454B moves in a proximal direction "PD". Rotation of the fourth drive pulley 452 in an opposite rotary direction result in the cable end portion 454A moving in a proximal direction "PD" and cable end portion 454B to move in a distal direction "DD".

The surgical tool 100 as depicted in FIGS. 5-6 includes an articulation joint 3500. In such embodiment, the third drive system 430 may also be referred to as a "first articulation drive system" and the fourth drive system 450 may be referred to herein as a "second articulation drive system". Likewise, the third drive cable 434 may be referred to as a "first proximal articulation cable" and the fourth drive cable 454 may be referred to herein as a "second proximal articulation cable".

The tool mounting portion 300 of the embodiment illustrated in FIGS. 5 and 16-21 includes a fifth drive system generally designated as 470 that is configured to axially displace a drive rod assembly 490. The drive rod assembly 490 includes a proximal drive rod segment 492 that extends through the proximal drive shaft segment 380 and the drive shaft assembly 388. See FIG. 18. The fifth drive system 470 includes a movable drive yoke 472 that is slidably supported on the tool mounting plate 304. The proximal drive rod segment 492 is supported in the drive yoke 372 and has a pair of retainer balls 394 thereon such that shifting of the drive yoke 372 on the tool mounting plate 304 results in the axial movement of the proximal drive rod segment 492. In at least one example form, the fifth drive system 370 further includes a drive solenoid 474 that operably interfaces with the drive yoke 472. The drive solenoid 474 receives control power from the robotic controller 12. Actuation of the drive solenoid 474 in a first direction will cause the drive rod assembly 490 to move in the distal direction "DD" and actuation of the drive solenoid 474 in a second direction will cause the drive rod assembly 490 to move in the proximal direction "PD". As can be seen in FIG. 5, the end effector 3000 includes a jaw members that are movable between open and closed positions upon application of axial closure motions to a closure system. In the illustrated embodiment of FIGS. 5 and 16-21, the fifth drive system 470 is employed to generate such closure motions. Thus, the fifth drive system 470 may also be referred to as a "closure drive".

Figure 24:
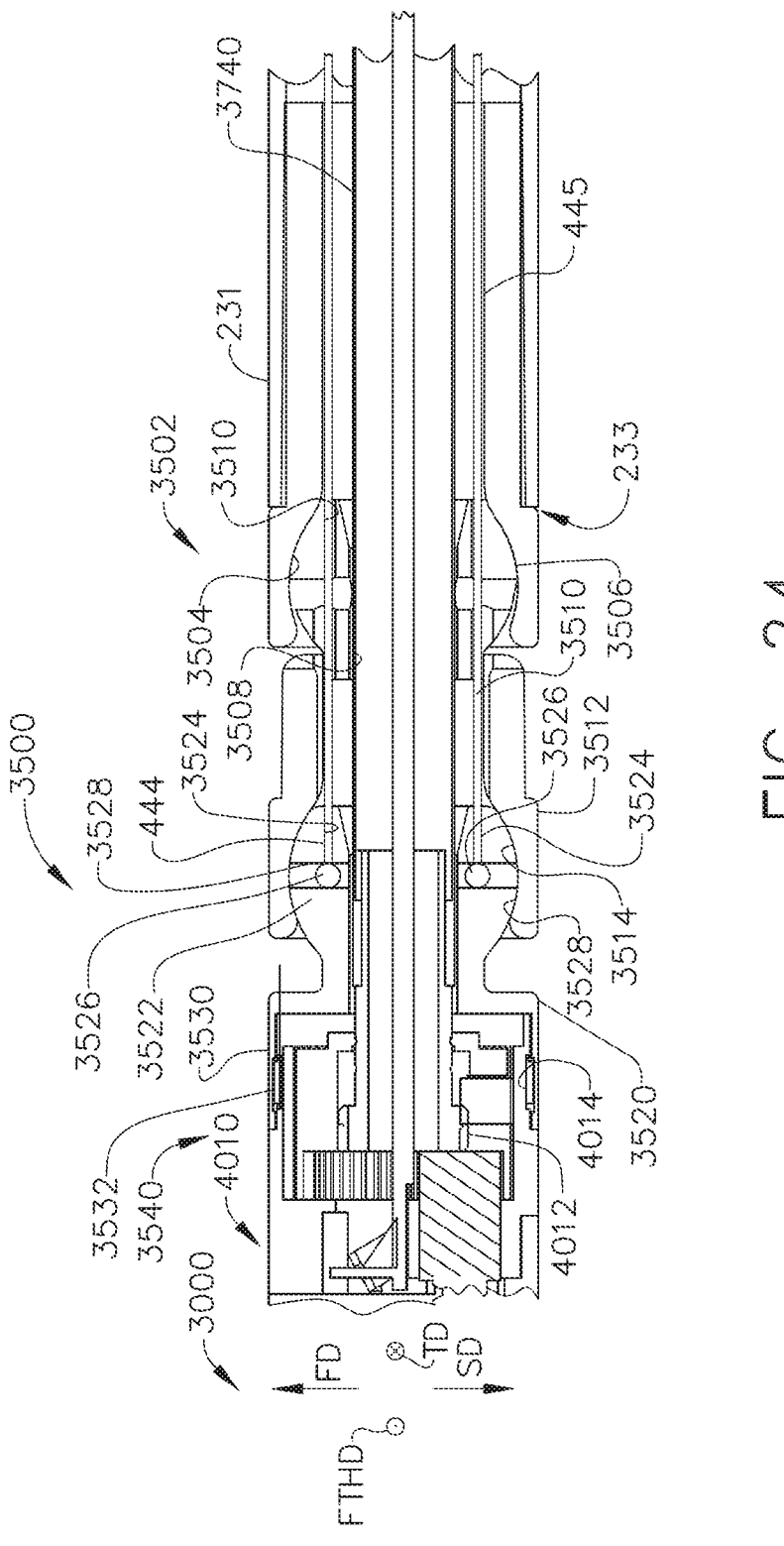
FIG. 24 is a cross-sectional view of one embodiment of a portion of an articulation joint and end effector.
Figure 24A:
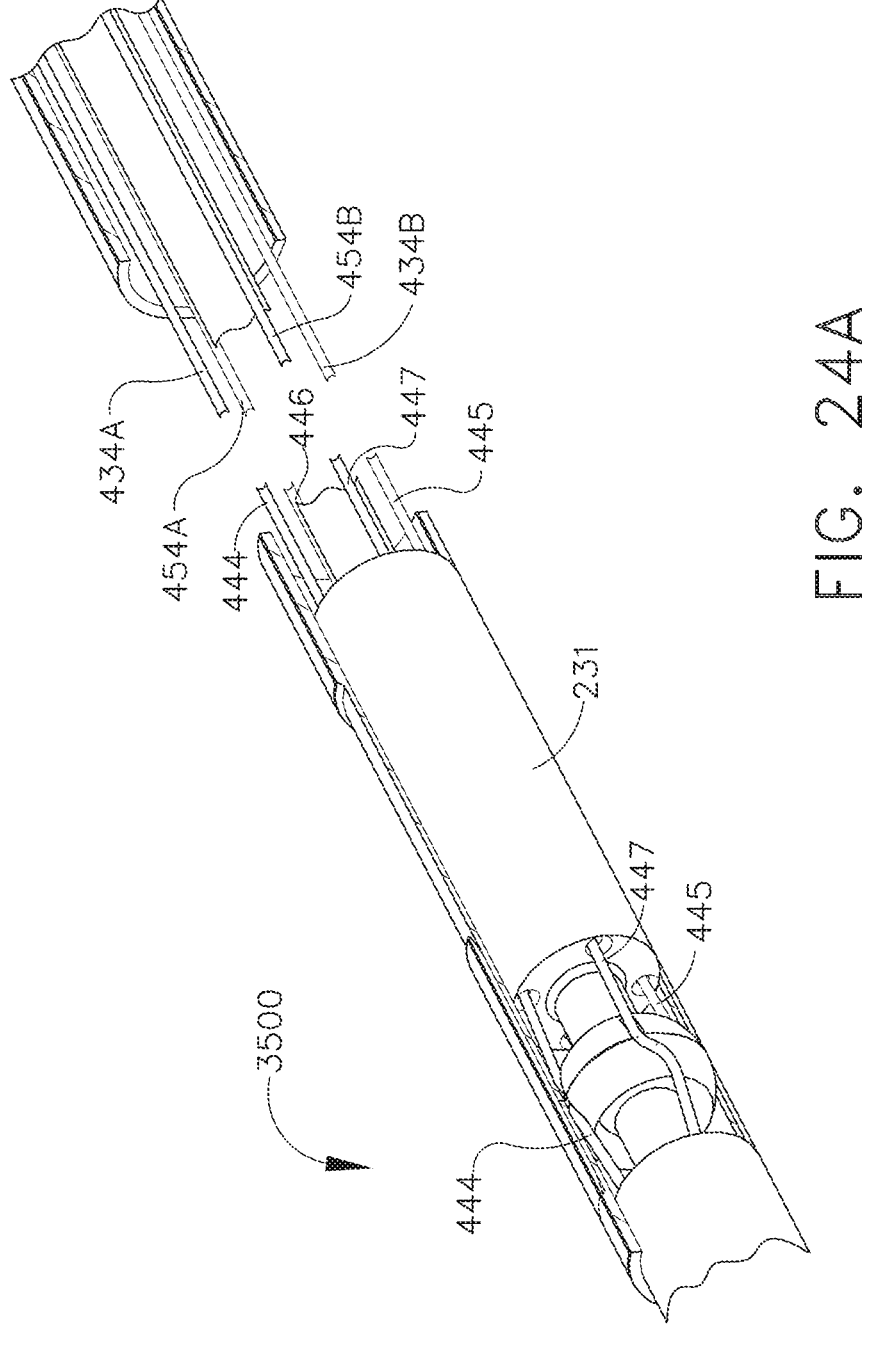
FIG. 24A illustrates one embodiment of the shaft assembly and articulation joint of FIG. 24 showing connections between distal cable sections and proximal cable portions.

The surgical tool 100 depicted in FIGS. 5 and 16-21 includes an articulation joint 3500 that cooperates with the third and fourth drive systems 430, 450, respectively for articulating the end effector 3000 about the longitudinal tool axis "LT". The articulation joint 3500 includes a proximal socket tube 3502 that is attached to the distal end 233 of the distal outer tube portion 231 and defines a proximal ball socket 3504 therein. See FIG. 24. A proximal ball member 3506 is movably seated within the proximal ball socket 3504. As can be seen in FIG. 24, the proximal ball member 3506 has a central drive passage 3508 that enables the distal drive shaft segment 3740 to extend therethrough. In addition, the proximal ball member 3506 has four articulation passages 3510 therein which facilitate the passage of distal cable segments 444, 445, 446, 447 therethrough. In various embodiments, distal cable segments 444, 445, 446, 447 may be directly or indirectly coupled to proximal cable end portions 434A, 434B, 454A, 454B, respectively, for example, as illustrated by FIG. 24A. As can be further seen in FIG. 24, the articulation joint 3500 further includes an intermediate articulation tube segment 3512 that has an intermediate ball socket 3514 formed therein. The intermediate ball socket 3514 is configured to movably support therein an end effector ball 3522 formed on an end effector connector tube 3520. The distal cable segments 444, 445, 446, 447 extend through cable passages 3524 formed in the end effector ball 3522 and are attached thereto by lugs 3526 received within corresponding passages 3528 in the end effector ball 3522. Other attachment arrangements may be employed for attaching distal cable segments 444, 445, 446, 447 to the end effector ball 3522.

Figures 25, 26:
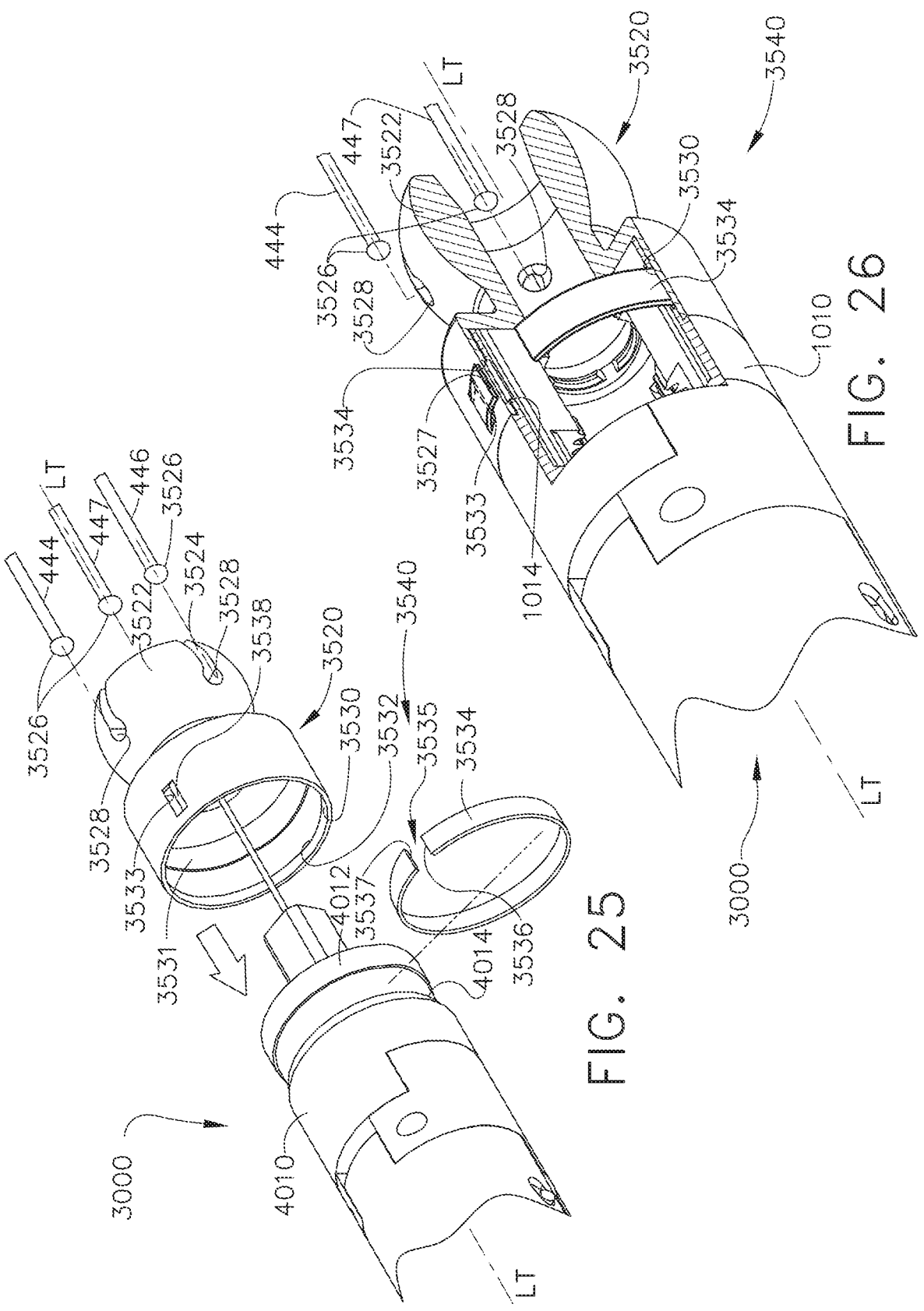
FIG. 25 is an exploded assembly view of one embodiment of a portion of the articulation joint and end effector of FIG. 24.
FIG. 26 is a partial cross-sectional perspective view of one embodiment of the articulation joint and end effector portions depicted in FIG. 25.

A unique and novel rotary support joint assembly, generally designated as 3540, is depicted in FIGS. 25 and 26. The illustrated rotary support joint assembly 3540 includes a connector portion 4012 of the end effector drive housing 4010 that is substantially cylindrical in shape. A first annular race 4014 is formed in the perimeter of the cylindrically-shaped connector portion 4012. The rotary support joint assembly 3540 further comprises a distal socket portion 3530 that is formed in the end effector connector tube 3520 as shown in FIGS. 25 and 26. The distal socket portion 3530 is sized relative to the cylindrical connector portion 4012 such that the connector portion 4012 can freely rotate within the socket portion 3530. A second annular race 3532 is formed in an inner wall 3531 of the distal socket portion 3530. A window 3533 is provided through the distal socket 3530 that communicates with the second annular race 3532 therein. As can also be seen in FIGS. 25 and 26, the rotary support joint assembly 3540 further includes a ring-like bearing 3534. In various example embodiments, the ring-like bearing 3534 comprises a plastic deformable substantially-circular ring that has a cut 3535 therein. The cut forms free ends 3536, 3537 in the ring-like bearing 3534. As can be seen in FIG. 25, the ring-like bearing 3534 has a substantially annular shape in its natural unbiased state.

To couple a surgical end effector 3000 (e.g., a first portion of a surgical tool) to the articulation joint 3500 (e.g., a second portion of a surgical tool), the cylindrically shaped connector position 4012 is inserted into the distal socket portion 3530 to bring the second annular race 3532 into substantial registry with the first annular race 4014. One of the free ends 3536, 3537 of the ring-like bearing is then inserted into the registered annular races 4014, 3532 through the window 3533 in the distal socket portion 3530 of the end effector connector tube 3520. To facilitate easy insertion, the window or opening 3533 has a tapered surface 3538 formed thereon. See FIG. 25. The ring-like bearing 3534 is essentially rotated into place and, because it tends to form a circle or ring, it does not tend to back out through the window 3533 once installed. Once the ring-like bearing 3534 has been inserted into the registered annular races 4014, 3532, the end effector connector tube 3520 will be rotatably affixed to the connector portion 4012 of the end effector drive housing 4010. Such arrangement enables the end effector drive housing 4010 to rotate about the longitudinal tool axis LT-LT relative to the end effector connector tube 3520. The ring-like bearing 3534 becomes the bearing surface that the end effector drive housing 4010 then rotates on. Any side loading tries to deform the ring-like bearing 3534 which is supported and contained by the two interlocking races 4014, 3532 preventing damage to the ring-like bearing 3534. It will be understood that such simple and effective joint assembly employing the ring-like bearing 3534 forms a highly lubricious interface between the rotatable portions 4010, 3530. If during assembly, one of the free ends 3536, 3537 is permitted to protrude out through the window 3533 (see e.g., FIG. 26), the rotary support joint assembly 3540 may be disassembled by withdrawing the ring-like bearing member 3532 out through the window 3533. The rotary support joint assembly 3540 allows for easy assembly and manufacturing while also providing for good end effector support while facilitating rotary manipulation thereof.

The articulation joint 3500 facilitates articulation of the end effector 3000 about the longitudinal tool axis LT. For example, when it is desirable to articulate the end effector 3000 in a first direction "FD" as shown in FIG. 5, the robotic system 10 may power the third drive system 430 such that the third drive spindle assembly 436 (FIGS. 16-18) is rotated in a first direction thereby drawing the proximal cable end portion 434A and ultimately distal cable segment 444 in the proximal direction "PD" and releasing the proximal cable end portion 434B and distal cable segment 445 to thereby cause the end effector ball 3522 to rotate within the socket 3514. Likewise, to articulate the end effector 3000 in a second direction "SD" opposite to the first direction FD, the robotic system 10 may power the third drive system 430 such that the third drive spindle assembly 436 is rotated in a second direction thereby drawing the proximal cable end portion 434B and ultimately distal cable segment 445 in the proximal direction "PD" and releasing the proximal cable end portion 434A and distal cable segment 444 to thereby cause the end effector ball 3522 to rotate within the socket 3514. When it is desirable to articulate the end effector 3000 in a third direction "TD" as shown in FIG. 5, the robotic system 10 may power the fourth drive system 450 such that the fourth drive spindle assembly 456 is rotated in a third direction thereby drawing the proximal cable end portion 454A and ultimately distal cable segment 446 in the proximal direction "PD" and releasing the proximal cable end portion 454B and distal cable segment 447 to thereby cause the end effector ball 3522 to rotate within the socket 3514. Likewise, to articulate the end effector 3000 in a fourth direction "FTH" opposite to the third direction TD, the robotic system 10 may power the fourth drive system 450 such that the fourth drive spindle assembly 456 is rotated in a fourth direction thereby drawing the proximal cable end portion 454B and ultimately distal cable segment 447 in the proximal direction "PD" and releasing the proximal cable end portion 454A and distal cable segment 446 to thereby cause the end effector ball 3522 to rotate within the socket 3514.

Figures 27, 28:
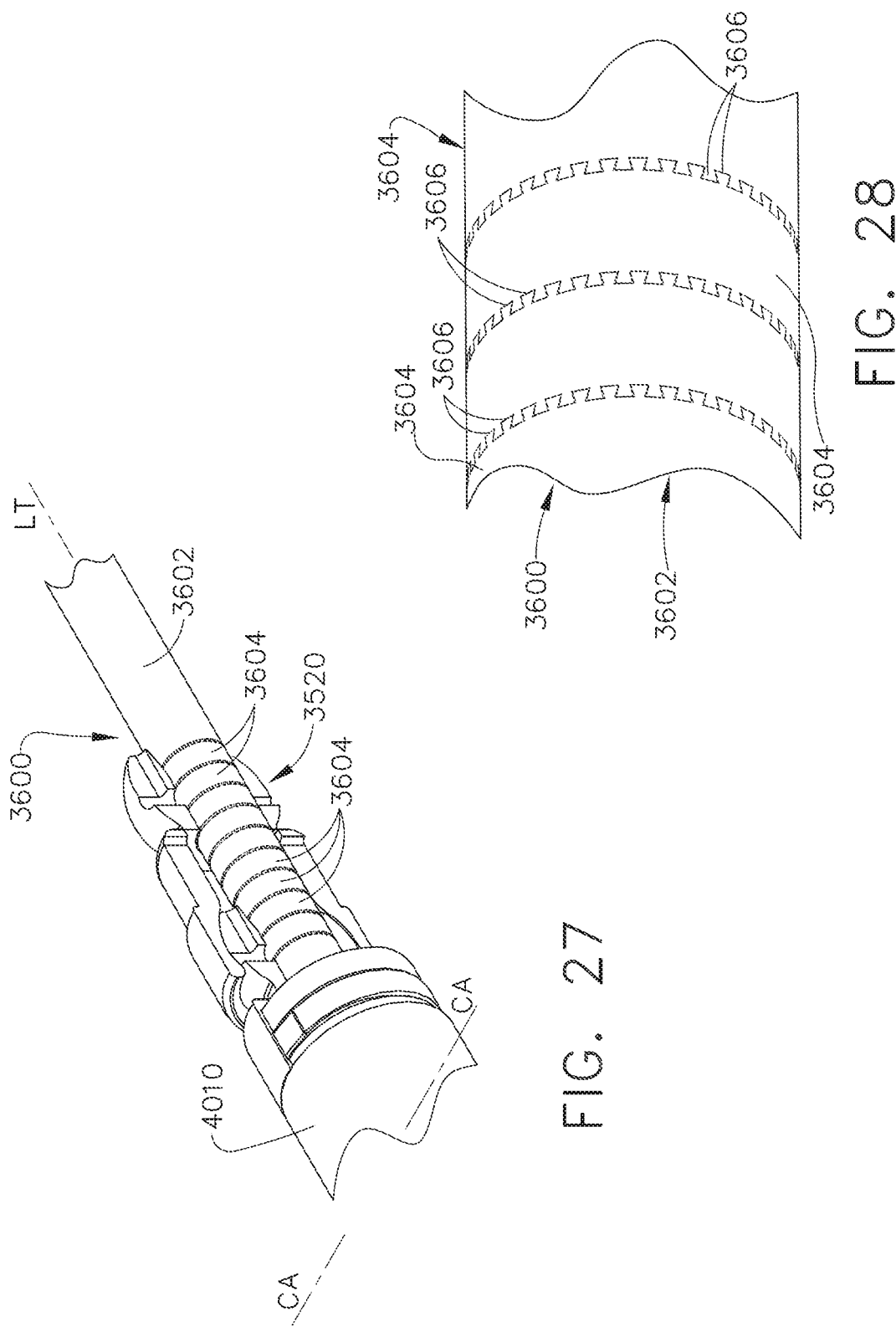
FIG. 27 is a partial perspective view of an end effector and drive shaft assembly embodiment.
FIG. 28 is a partial side view of one embodiment of a drive shaft assembly.

The end effector embodiment depicted in FIGS. 5 and 16-21 employs rotary and longitudinal motions that are transmitted from the tool mounting portion 300 through the elongate shaft assembly for actuation. The drive shaft assembly employed to transmit such rotary and longitudinal motions (e.g., torsion, tension and compression motions) to the end effector is relatively flexible to facilitate articulation of the end effector about the articulation joint. FIGS. 27-28 illustrate an alternative drive shaft assembly 3600 that may be employed in connection with the embodiment illustrated in FIGS. 5 and 16-21 or in other embodiments. In the embodiment depicted in FIG. 5 the proximal drive shaft segment 380 comprises a segment of drive shaft assembly 3600 and the distal drive shaft segment 3740 similarly comprises another segment of drive shaft assembly 3600. The drive shaft assembly 3600 includes a drive tube 3602 that has a series of annular joint segments 3604 cut therein. In that illustrated embodiment, the drive tube 3602 comprises a distal portion of the proximal drive shaft segment 380. For example, the shaft assembly 3600, as well as the shaft assemblies 3600', 3600" described herein with respect to FIGS. 27-45 may be components of and/or mechanically coupled to various rotary drive shafts described herein including, for example, rotary drive shafts 680, 1270, 1382, etc.

The drive tube 3602 comprises a hollow metal tube (stainless steel, titanium, etc.) that has a series of annular joint segments 3604 formed therein. The annular joint segments 3604 comprise a plurality of loosely interlocking dovetail shapes 3606 that are, for example, cut into the drive tube 3602 by a laser and serve to facilitate flexible movement between the adjoining joint segments 3604. See FIG. 28. Such laser cutting of a tube stock creates a flexible hollow drive tube that can be used in compression, tension and torsion. Such arrangement employs a full diametric cut that is interlocked with the adjacent part via a "puzzle piece" configuration. These cuts are then duplicated along the length of the hollow drive tube in an array and are sometimes "clocked" or rotated to change the tension or torsion performance.

Figures 29, 30:
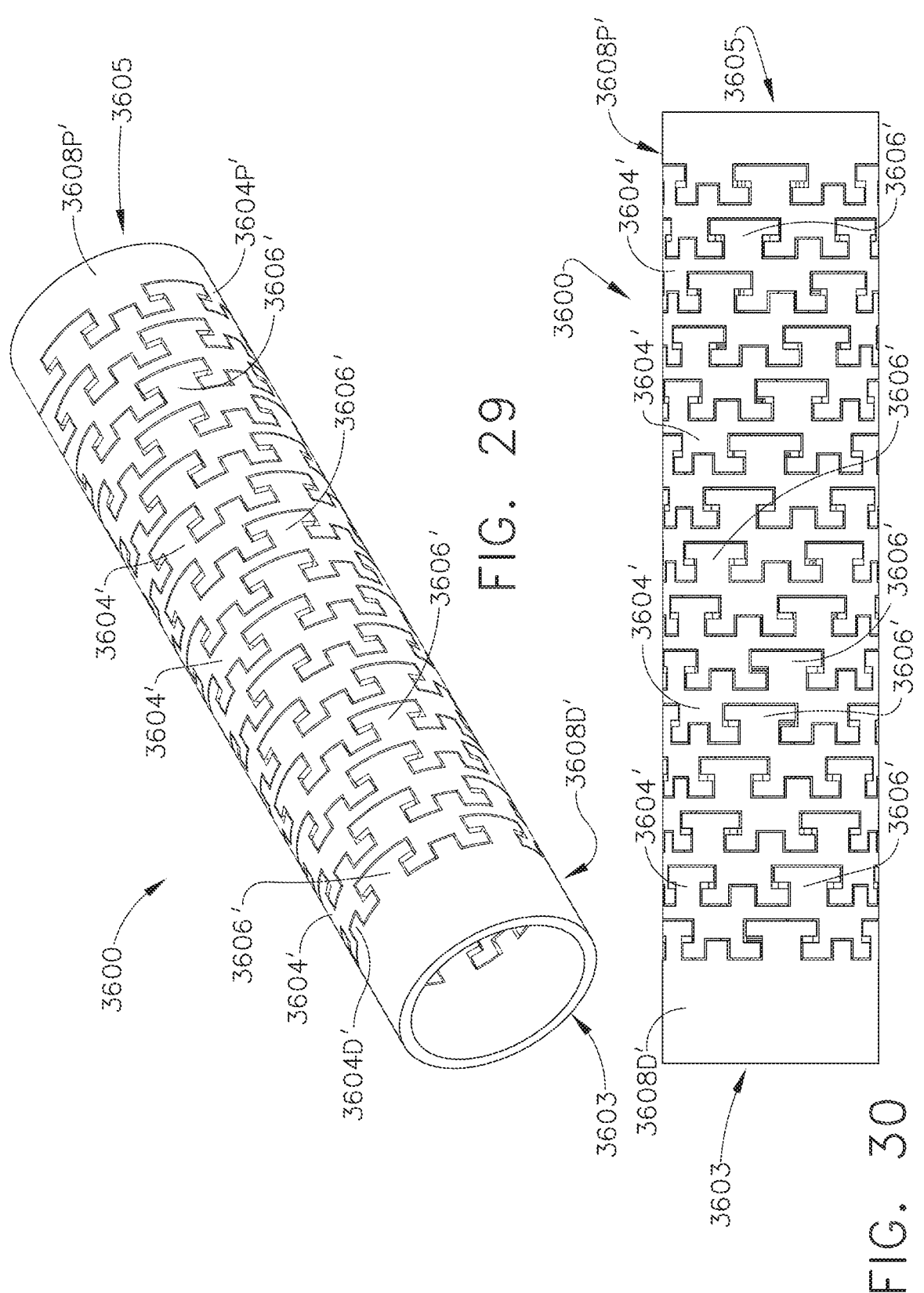
FIG. 29 is a perspective view of one embodiment of a drive shaft assembly.
FIG. 30 is a side view of one embodiment of the drive shaft assembly of FIG. 29.
Figures 31, 32:
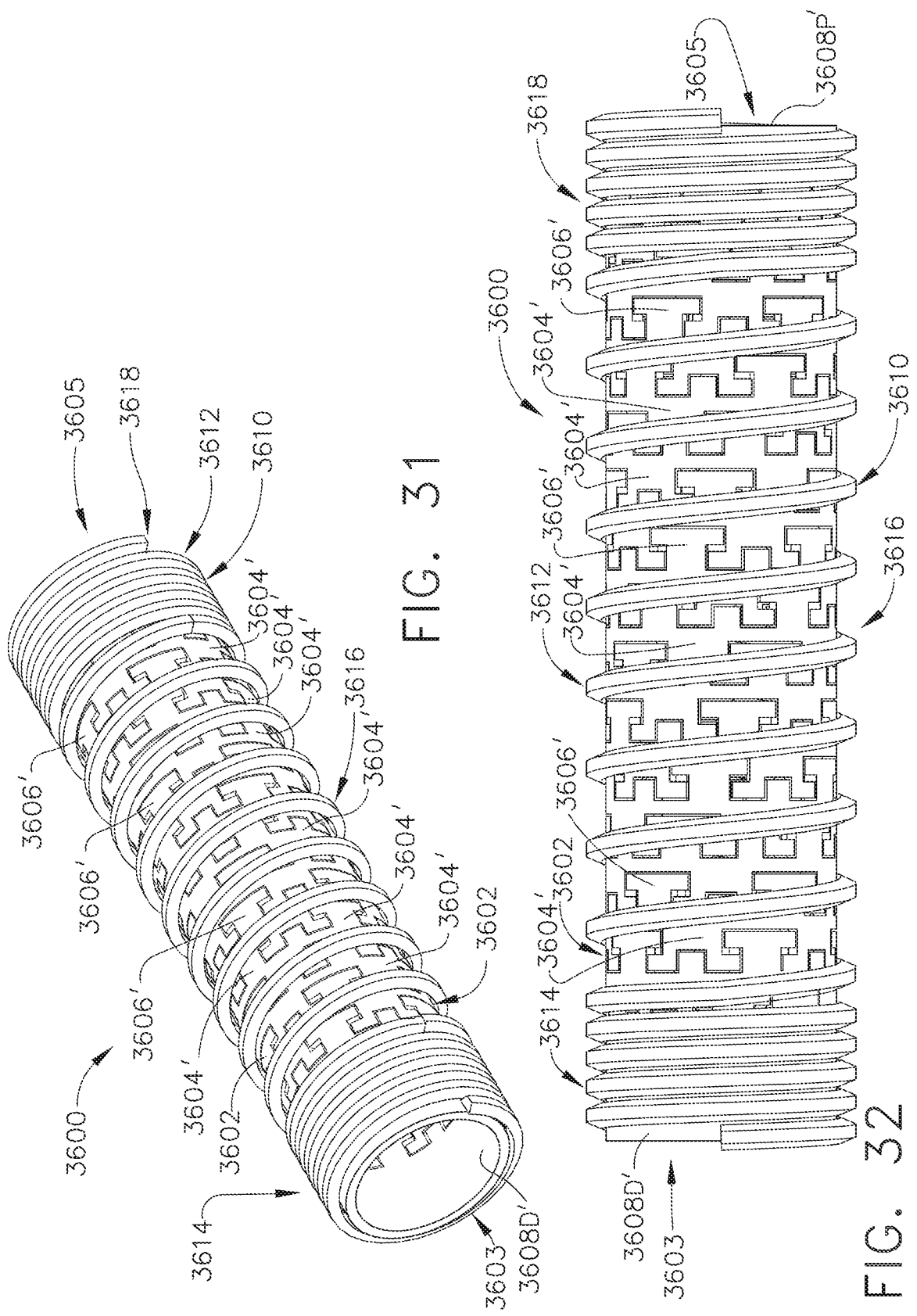
FIG. 31 is a perspective view of one embodiment of a composite drive shaft assembly.
FIG. 32 is a side view of one embodiment of the composite drive shaft assembly of FIG. 31.

FIGS. 29-33 illustrate alternative example micro-annular joint segments 3604' that comprise plurality of laser cut shapes 3606' that roughly resemble loosely interlocking, opposed "T" shapes and T-shapes with a notched portion therein. The annular joint segments 3604, 3604' essentially comprise multiple micro-articulating torsion joints. That is, each joint segment 3604, 3604' can transmit torque while facilitating relative articulation between each annular joint segment. As shown in FIGS. 29-30, the joint segment 3604D' on the distal end 3603 of the drive tube 3602 has a distal mounting collar portion 3608D' that facilitates attachment to other drive components for actuating the end effector or portions of the quick disconnect joint, etc. and the joint segment 3604P' on the proximal end 3605 of the drive tube 3602 has a proximal mounting collar portion 3608P' that facilitates attachment to other proximal drive components or portions of the quick disconnect joint.

Figure 33:
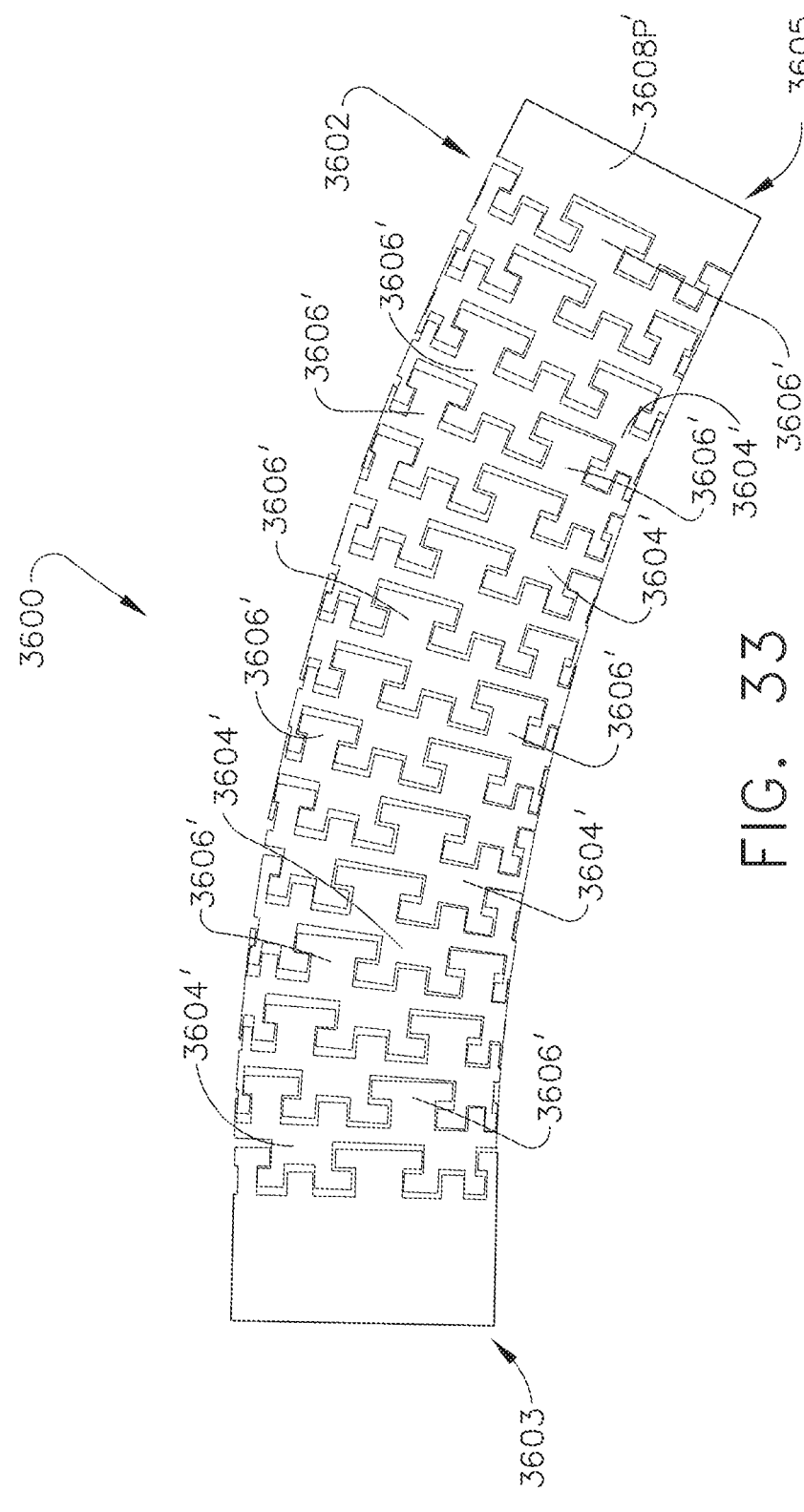
FIG. 33 is another view of one embodiment of the drive shaft assembly of FIGS. 29 and 30 assuming an arcuate or "flexed" configuration.
Figure 33A:
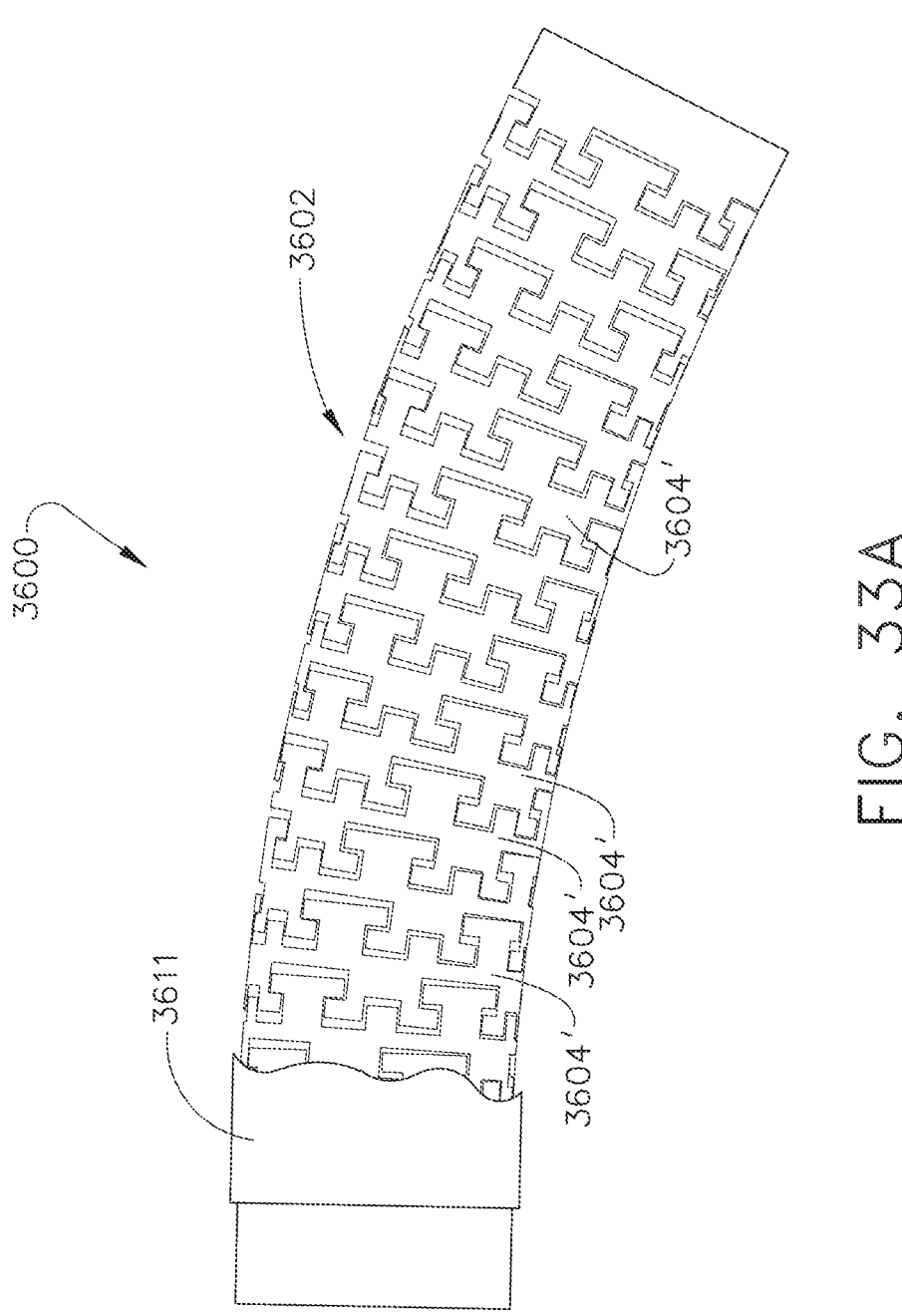
FIG. 33A is a side view of one embodiment of a drive shaft assembly assuming an arcuate or "flexed" configuration.
Figure 33B:
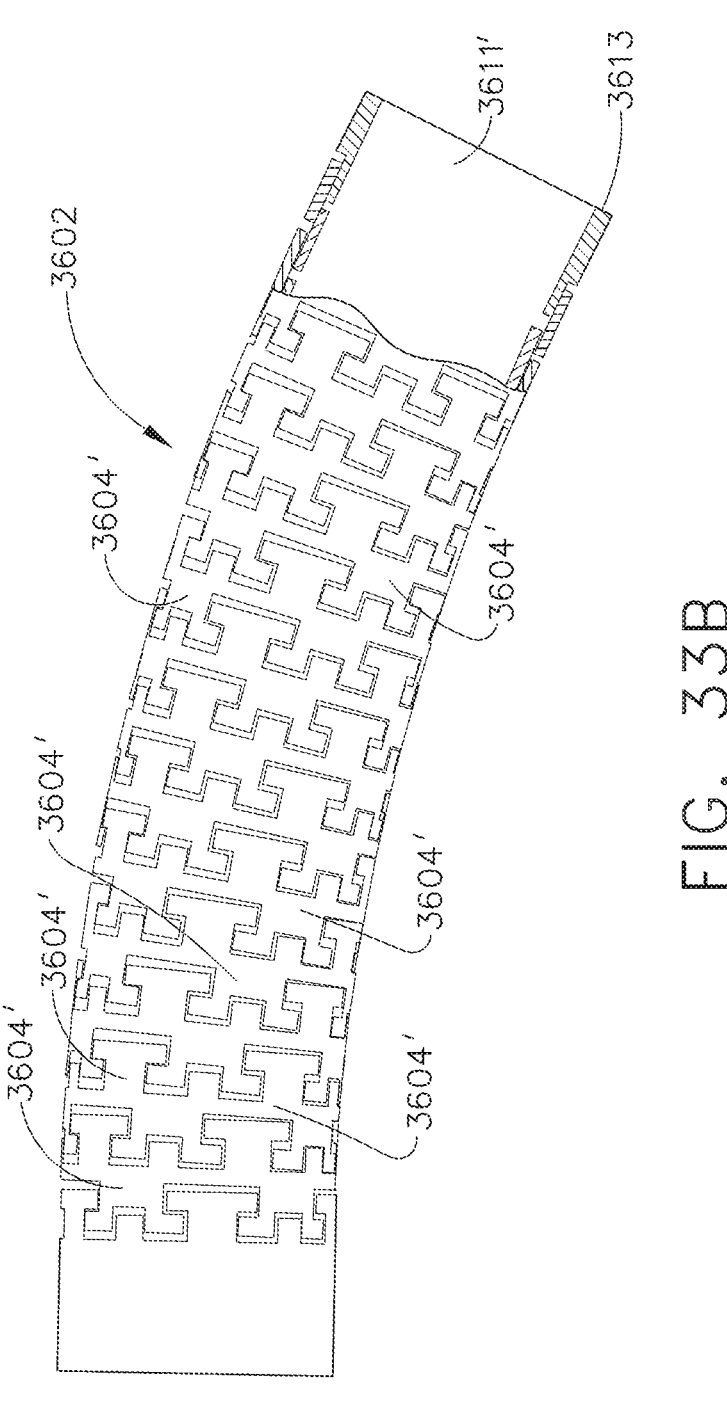
FIG. 33B is a side view of one embodiment of another drive shaft assembly assuming an arcuate or "flexed" configuration.

The joint-to-joint range of motion for each particular drive shaft assembly 3600 can be increased by increasing the spacing in the laser cuts. For example, to ensure that the joint segments 3604' remain coupled together without significantly diminishing the drive tube's ability to articulate through desired ranges of motion, a secondary constraining member 3610 is employed. In the embodiment depicted in FIGS. 31-32, the secondary constraining member 3610 comprises a spring 3612 or other helically-wound member. In various example embodiments, the distal end 3614 of the spring 3612 corresponds to the distal mounting collar portion 3608D' and is wound tighter than the central portion 3616 of the spring 3612. Similarly, the proximal end 3618 of the spring 3612 is wound tighter than the central portion 3616 of the spring 3612. In other embodiments, the constraining member 3610 is installed on the drive tube 3602 with a desired pitch such that the constraining member also functions, for example, as a flexible drive thread for threadably engaging other threaded control components on the end effector and/or the control system. It will also be appreciated that the constraining member may be installed in such a manner as to have a variable pitch to accomplish the transmission of the desired rotary control motions as the drive shaft assembly is rotated. For example, the variable pitch arrangement of the constraining member may be used to enhance open/close and firing motions which would benefit from differing linear strokes from the same rotation motion. In other embodiments, for example, the drive shaft assembly comprises a variable pitch thread on a hollow flexible drive shaft that can be pushed and pulled around a ninety degree bend. In still other embodiments, the secondary constraining member comprises an elastomeric tube or coating 3611 applied around the exterior or perimeter of the drive tube 3602 as illustrated in FIG. 33A. In still another embodiment, for example, the elastomeric tube or coating 3611' is installed in the hollow passageway 3613 formed within the drive tube 3602 as shown in FIG. 33B.

Such drive shaft arrangements comprise a composite torsional drive axle which allows superior load transmission while facilitating a desirable axial range of articulation. See, e.g., FIGS. 33 and 33A-33B. That is, these composite drive shaft assemblies allow a large range of motion while maintaining the ability to transmit torsion in both directions as well as facilitating the transmission of tension and compression control motions therethrough. In addition, the hollow nature of such drive shaft arrangements facilitate passage of other control components therethrough while affording improved tension loading. For example, some other embodiments include a flexible internal cable that extends through the drive shaft assembly which can assist in the alignment of the joint segments while facilitating the ability to apply tension motions through the drive shaft assembly. Moreover, such drive shaft arrangements are relatively easily to manufacture and assemble.

FIGS. 34-37 depict a segment 3620 of a drive shaft assembly 3600'. This embodiment includes joint segments 3622, 3624 that are laser cut out of tube stock material (e.g., stainless steel, titanium, polymer, etc.). The joint segments 3622, 3624 remain loosely attached together because the cuts 3626 are radial and are somewhat tapered. For example, each of the lug portions 3628 has a tapered outer perimeter portion 3629 that is received within a socket 3630 that has a tapered inner wall portion. See, e.g., FIGS. 35 and 37. Thus, there is no assembly required to attach the joint segments 3622, 3624 together. As can be seen in the Figures, joint segment 3622 has opposing pivot lug portions 3628 cut on each end thereof that are pivotally received in corresponding sockets 3630 formed in adjacent joint segments 3624.

Figures 36, 37:
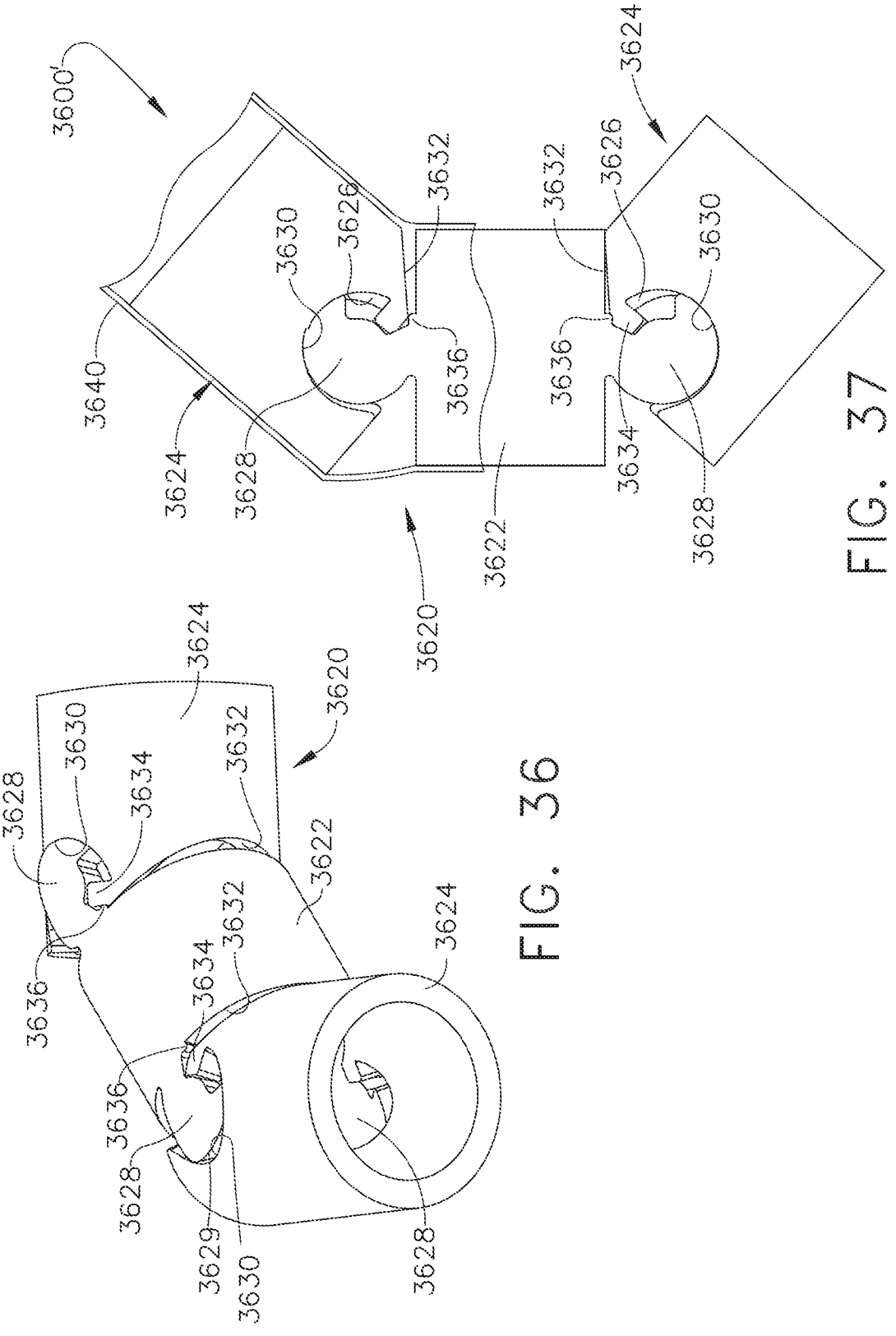
FIG. 36 is another perspective view of the drive shaft assembly embodiment of FIGS. 34 and 35 in an arcuate configuration.
FIG. 37 is a top view of the drive shaft assembly embodiment depicted in FIG. 36.
Figures 38, 39:
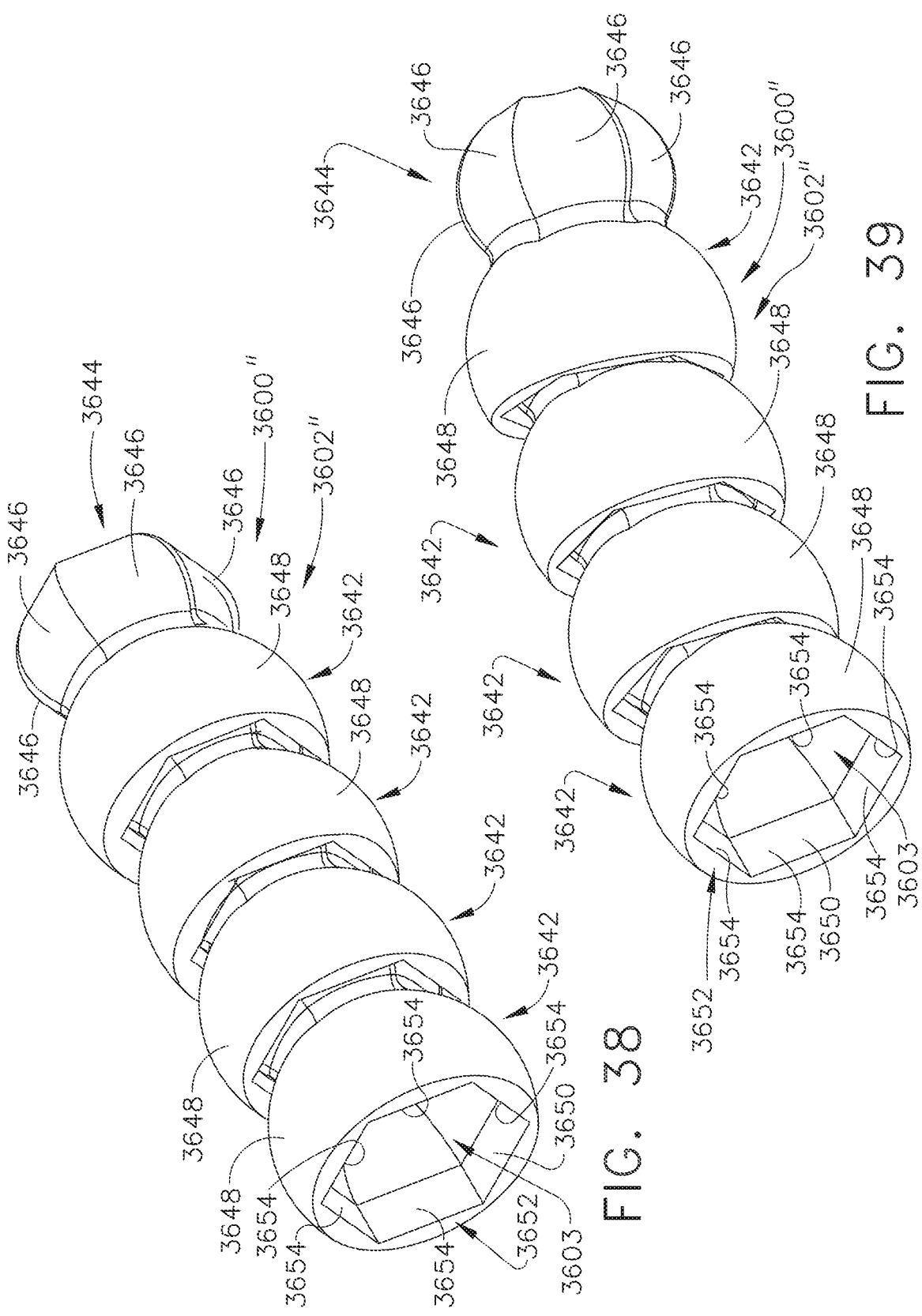
FIG. 38 is a perspective view of another drive shaft assembly embodiment.
FIG. 39 is another perspective view of the drive shaft assembly embodiment of FIG. 38 in an arcuate configuration.

FIGS. 34-37 illustrate a small segment of the drive shaft assembly 3600'. Those of ordinary skill in the art will appreciate that the lugs/sockets may be cut throughout the entire length of the drive shaft assembly. That is, the joint segments 3624 may have opposing sockets 3630 cut therein to facilitate linkage with adjoining joint segments 3622 to complete the length of the drive shaft assembly 3600'. In addition, the joint segments 3624 have an angled end portion 3632 cut therein to facilitate articulation of the joint segments 3624 relative to the joint segments 3622 as illustrated in FIGS. 36-37. In the illustrated embodiment, each lug 3628 has an articulation stop portion 3634 that is adapted to contact a corresponding articulation stop 3636 formed in the joint segment 3622. See FIGS. 36-37. Other embodiments, which may otherwise be identical to the segment 3620, are not provided with the articulation stop portions 3634 and stops 3636.

Figures 34, 35:
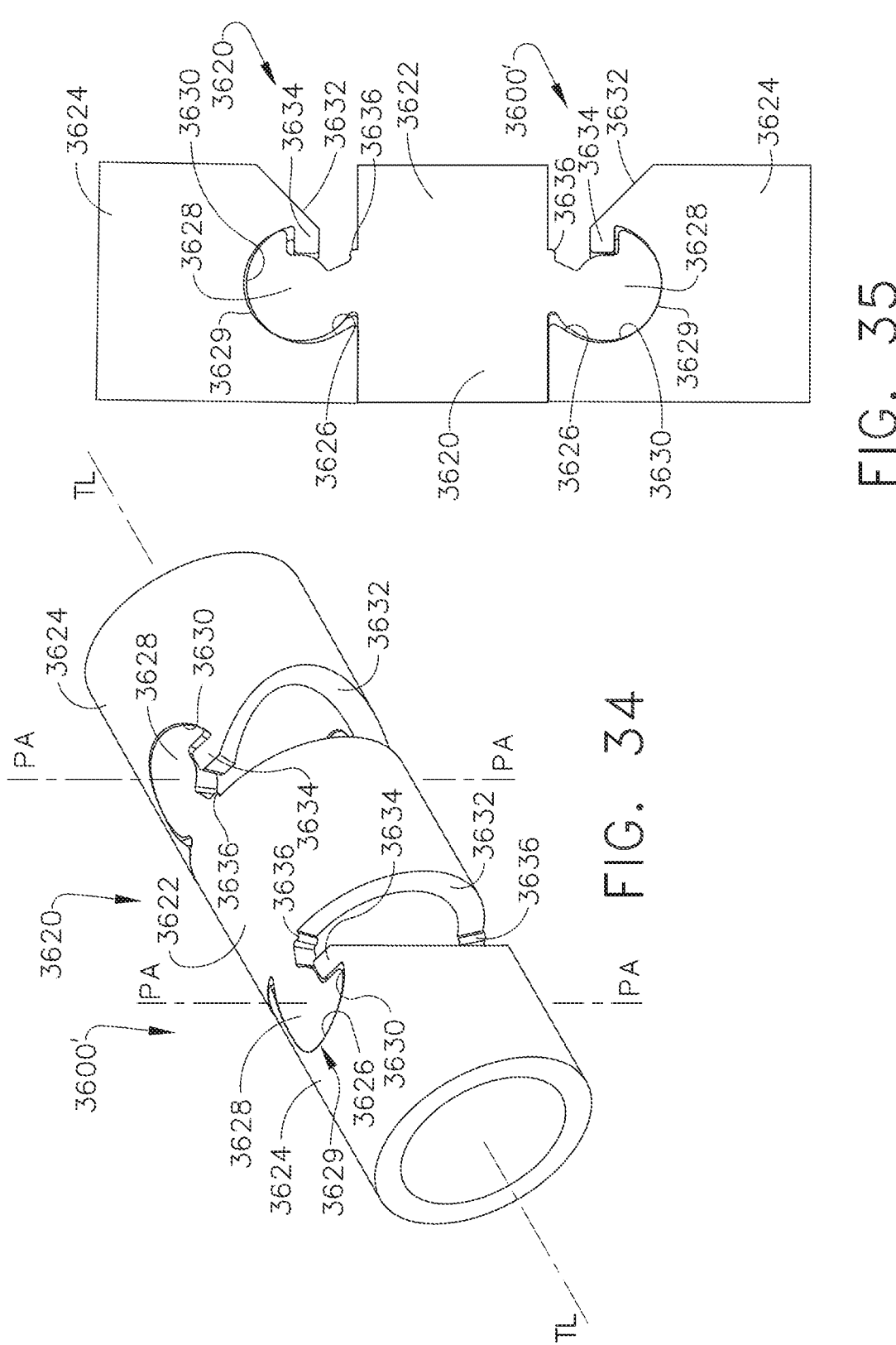
FIG. 34 is a perspective view of a portion of another drive shaft assembly embodiment.
FIG. 35 is a top view of the drive shaft assembly embodiment of FIG. 34.

As indicated above, the joint-to-joint range of motion for each particular drive shaft assembly can be increased by increasing the spacing in the laser cuts. In such embodiments, to ensure that the joint segments 3622, 3624 remain coupled together without significantly diminishing the drive tube's ability to articulate through desired ranges of motion, a secondary constraining member in the form of an elastomeric sleeve or coating 3640 is employed. Other embodiments employ other forms of constraining members disclosed herein and their equivalent structures. As can be seen in FIG. 34, the joint segments 3622, 3624 are capable of pivoting about pivot axes "PA-PA" defined by the pivot lugs 3628 and corresponding sockets 3630. To obtain an expanded range of articulation, the drive shaft assembly 3600' may be rotated about the tool axis TL-TL while pivoting about the pivot axes PA-PA.

FIGS. 38-43 depict a segment 3640 of another drive shaft assembly 3600". The drive shaft assembly 3600" comprises a multi-segment drive system that includes a plurality of interconnected joint segments 3642 that form a flexible hollow drive tube 3602". A joint segment 3642 includes a ball connector portion 3644 and a socket portion 3648. Each joint segment 3642 may be fabricated by, for example, metal injection molding "MIM" and be fabricated from 17-4, 17-7, 420 stainless steel. Other embodiments may be machined from 300 or 400 series stainless steel, 6065 or 7071 aluminum or titanium. Still other embodiments could be molded out of plastic infilled or unfilled Nylon, Ultem, ABS, Polycarbonate or Polyethylene, for example. As can be seen in the Figures, the ball connector 3644 is hexagonal in shape. That is, the ball connector 3644 has six arcuate surfaces 3646 formed thereon and is adapted to be rotatably received in like-shaped sockets 3650. Each socket 3650 has a hexagonally-shaped outer portion 3652 formed from six flat surfaces 3654 and a radially-shaped inner portion 3656. See FIG. 41. Each joint segment 3642 is identical in construction, except that the socket portions of the last joint segments forming the distal and proximal ends of the drive shaft assembly 3600 may be configured to operably mate with corresponding control components. Each ball connector 3644 has a hollow passage 3645 therein that cooperate to form a hollow passageway 3603 through the hollow flexible drive tube 3602".

Figures 40, 41, 42, 43:
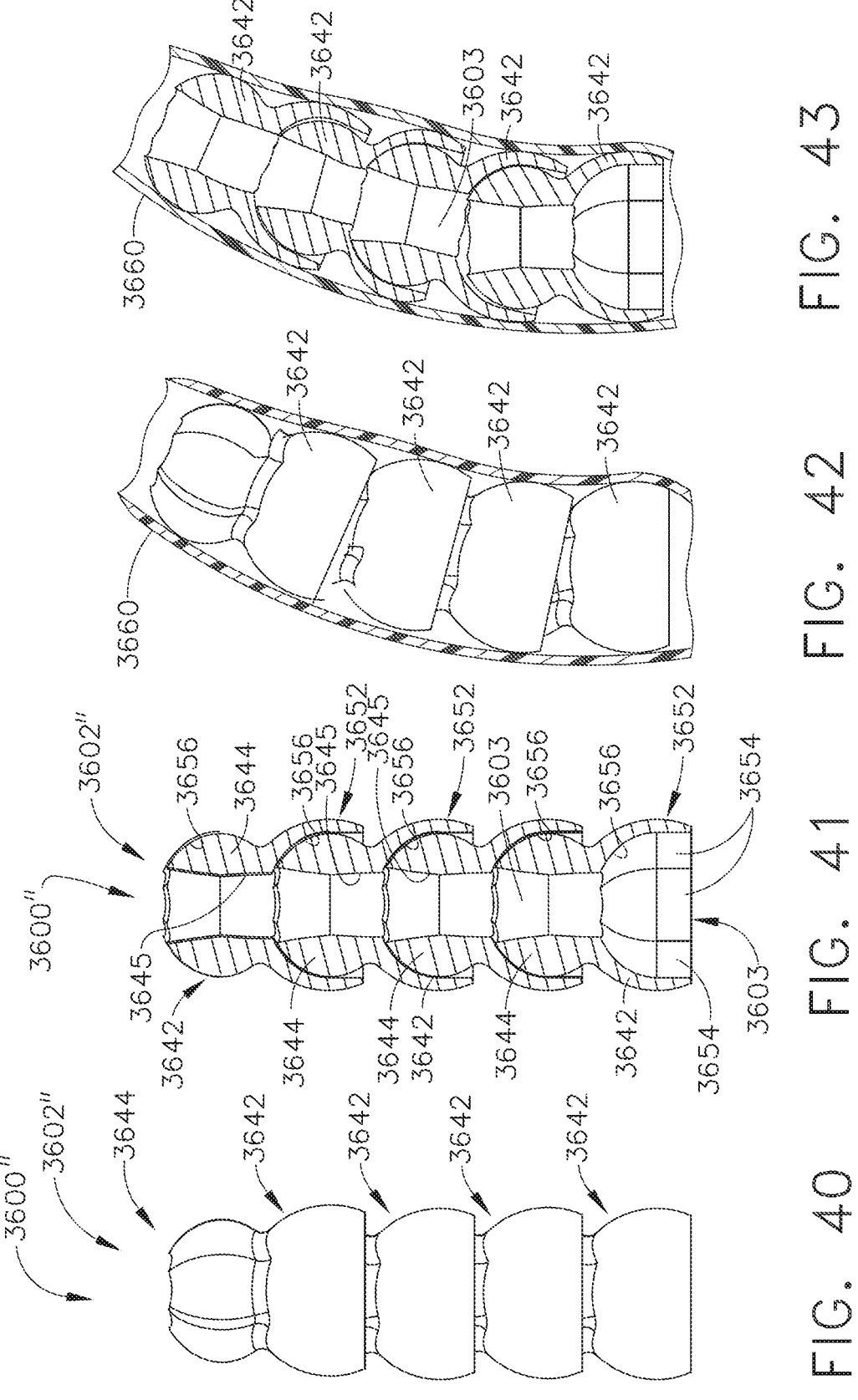
FIG. 40 is a top view of the drive shaft assembly embodiment of FIGS. 38 and 39.
FIG. 41 is a cross-sectional view of the drive shaft assembly embodiment of FIG. 40.
FIG. 42 is a partial cross-sectional view of another drive shaft assembly embodiment.
FIG. 43 is another cross-sectional view of the drive shaft assembly embodiment of FIG. 42.
Figures 44, 45:
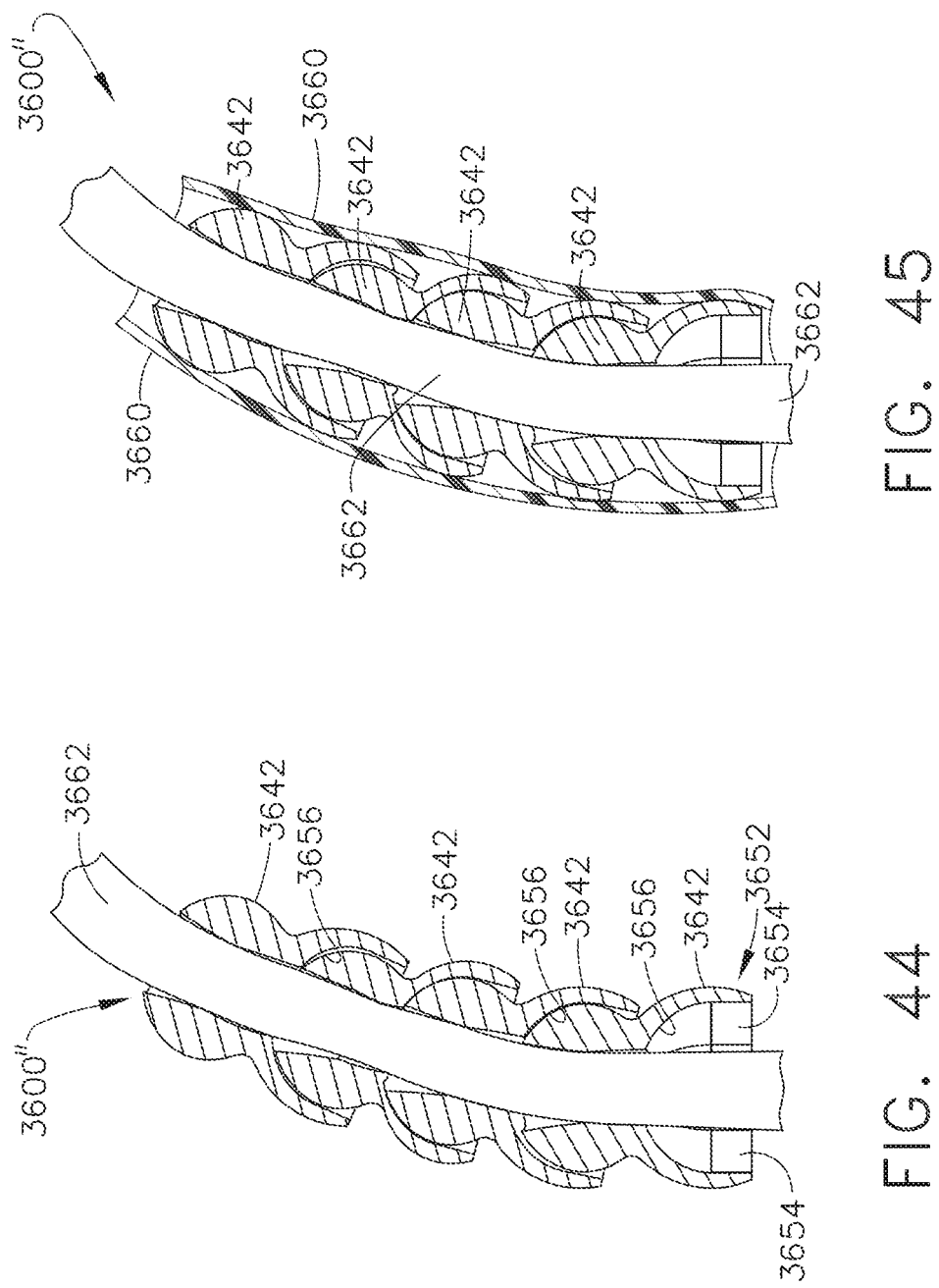
FIG. 44 is another cross-sectional view of a portion of another drive shaft assembly embodiment.
FIG. 45 is another cross-sectional view of one embodiment of the drive shaft assembly of FIG. 44.

As can be seen in FIGS. 42 and 43, the interconnected joint segments 3642 are contained within a constraining member 3660 which comprises a tube or sleeve fabricated from a flexible polymer material, for example. FIG. 44 illustrates a flexible inner core member 3662 extending through the interconnected joint segments 3642. The inner core member 3662 comprises a solid member fabricated from a polymer material or a hollow tube or sleeve fabricated from a flexible polymer material. FIG. 45 illustrates another embodiment wherein a constraining member 3660 and an inner core member 3662 are both employed.

Drive shaft assembly 3600" facilitates transmission of rotational and translational motion through a variable radius articulation joint. The hollow nature of the drive shaft assembly 3600" provides room for additional control components or a tensile element (e.g., a flexible cable) to facilitate tensile and compressive load transmission. In other embodiments, however, the joint segments 3624 do not afford a hollow passage through the drive shaft assembly. In such embodiments, for example, the ball connector portion is solid. Rotary motion is translated via the edges of the hexagonal surfaces. Tighter tolerances may allow greater load capacity. Using a cable or other tensile element through the centerline of the drive shaft assembly 3600", the entire drive shaft assembly 3600" can be rotated bent, pushed and pulled without limiting range of motion. For example, the drive shaft assembly 3600" may form an arcuate drive path, a straight drive path, a serpentine drive path, etc.

Figure 46:
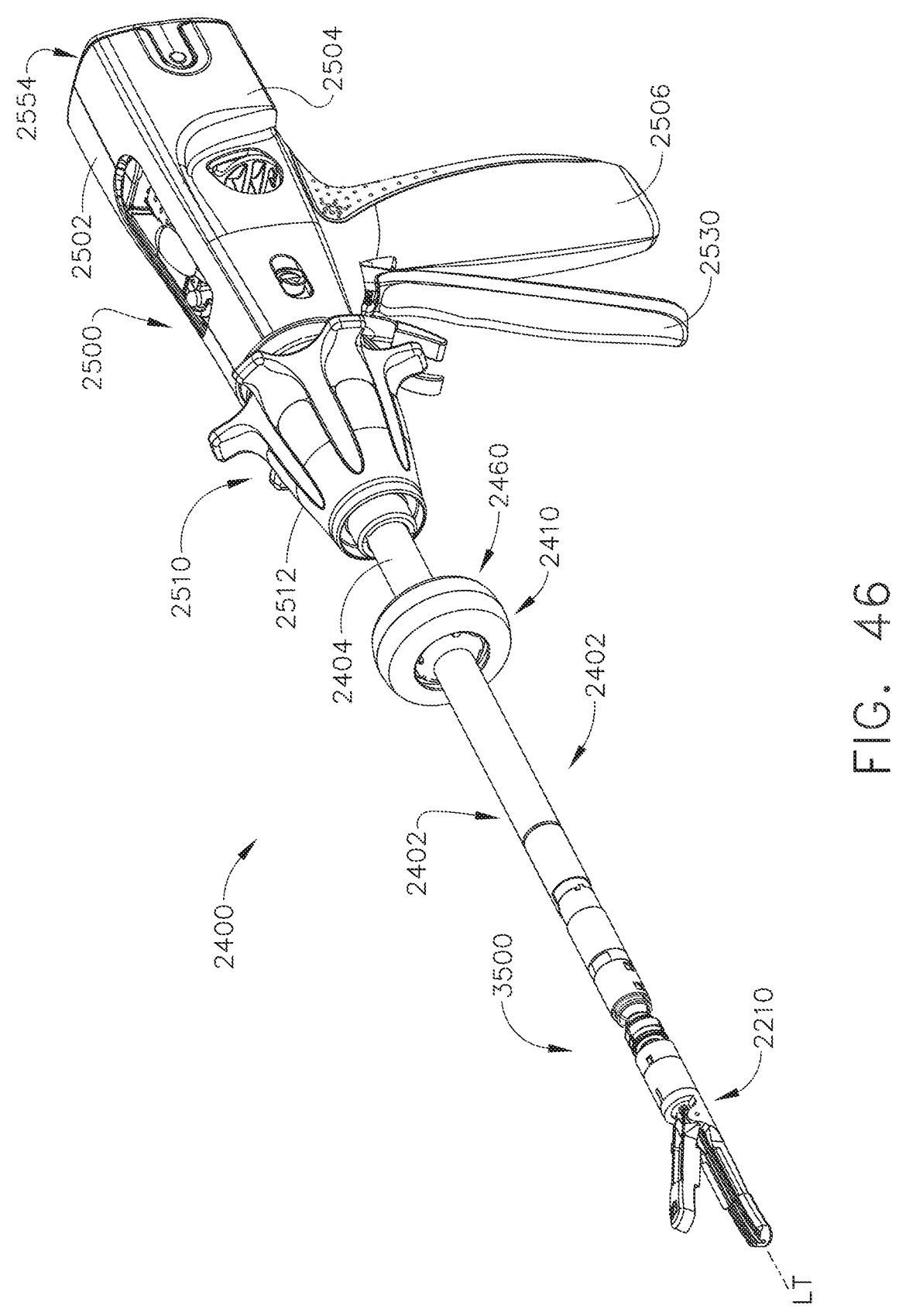
FIG. 46 is a perspective view of another surgical tool embodiment.
Figure 47:
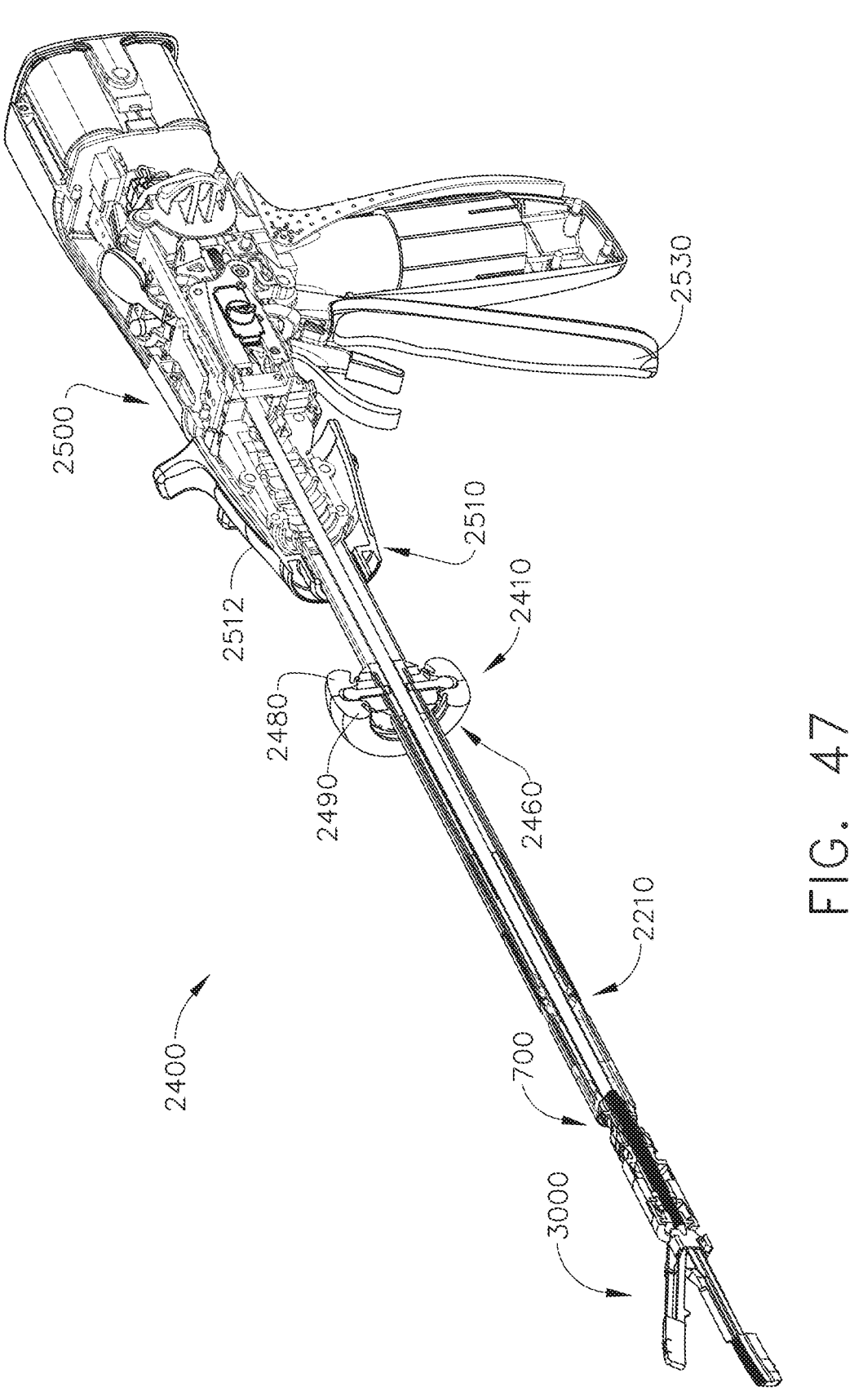
FIG. 47 is a cross-sectional perspective view of the surgical tool embodiment of FIG.

While the various example embodiments described herein are configured to operably interface with and be at least partially actuated by a robotic system, the various end effector and elongate shaft components described herein, may be effectively employed in connection with handheld tools. For example, FIGS. 46-47 depict a handheld surgical tool 2400 that may employ various components and systems described above to operably actuate an electrosurgical end effector 3000 coupled thereto. It will be appreciated that the handheld surgical tool 2400 may contain and/or be electrically connected to a generator, such as the generator 3002, for generating an electrosurgical drive signal to drive the end effector 3000. In the example embodiment depicted in FIGS. 46-47, a quick disconnect joint 2210 is employed to couple the end effector 3000 to an elongate shaft assembly 2402. For example, the quick disconnect joint 2210 may operate to remove the end effector 3000 in the manner described herein with reference to FIGS. 106-115. To facilitate articulation of the end effector 3000 about the articulation joint 3500, the proximal portion of the elongate shaft assembly 2402 includes an example manually actuatable articulation drive 2410.

Figure 48:
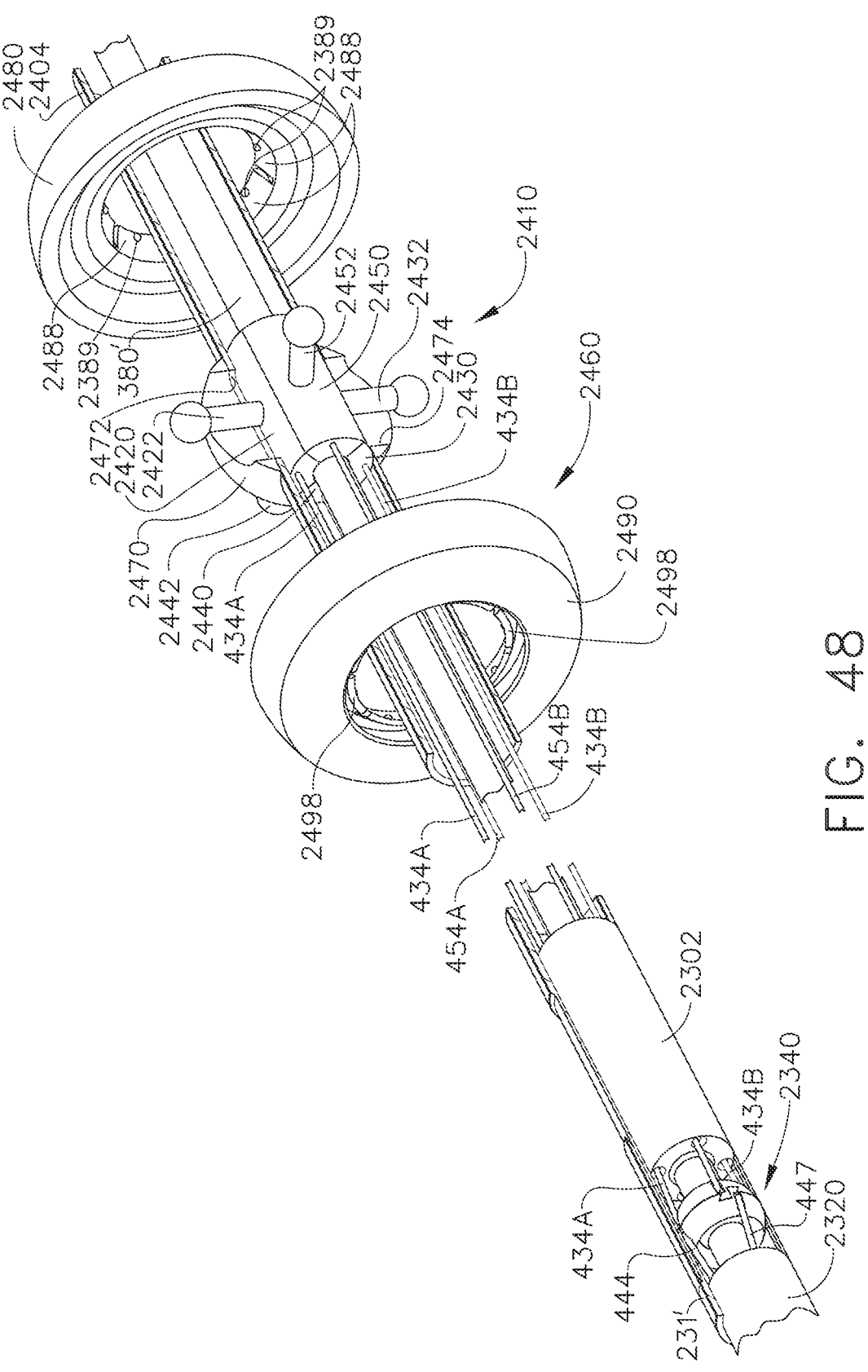
FIG. 48 is a cross-sectional perspective view of a portion of one embodiment of an articulation system.
Figure 49:
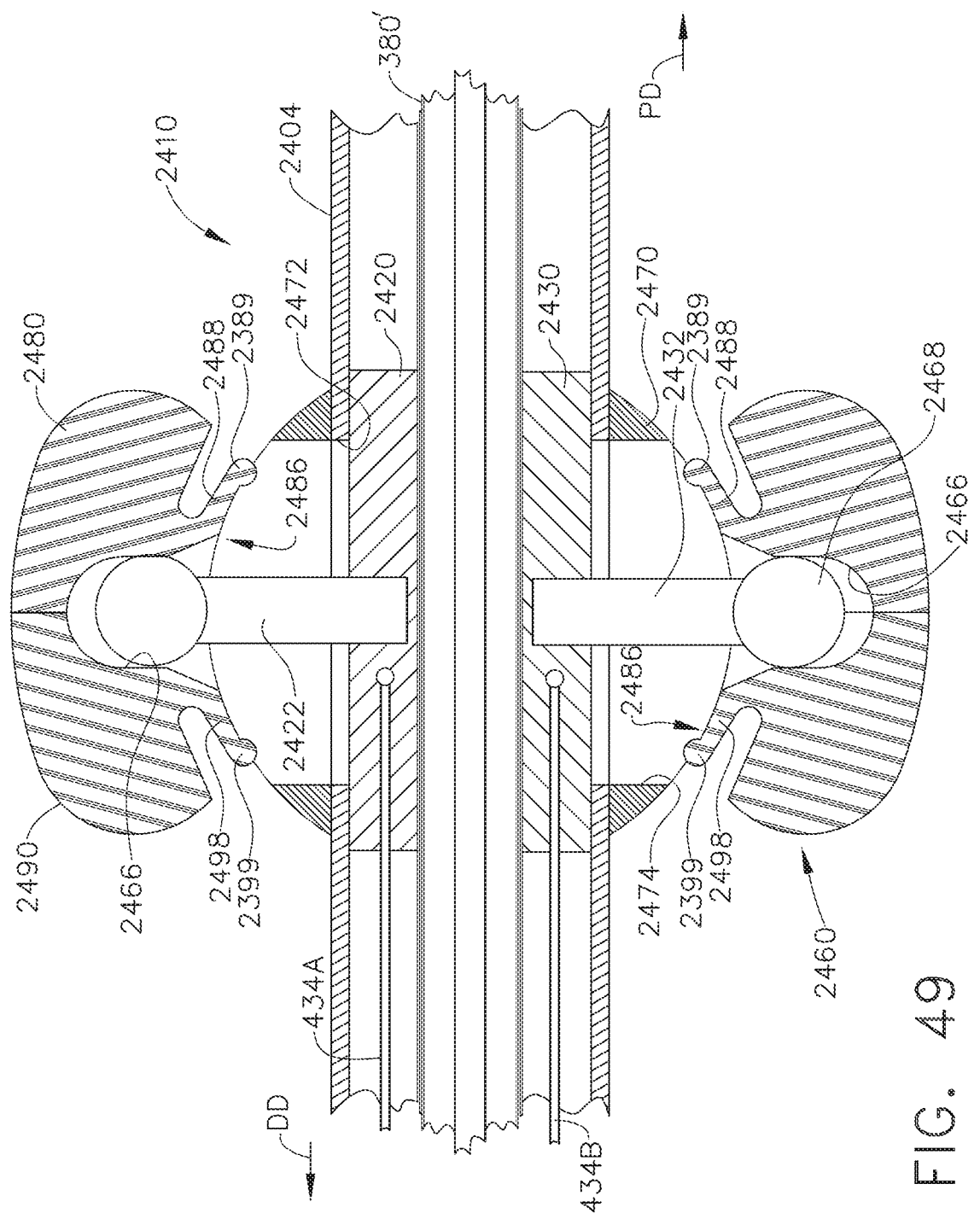
FIG. 49 is a cross-sectional view of one embodiment of the articulation system of FIG. 48 in a neutral position.
Figure 50:
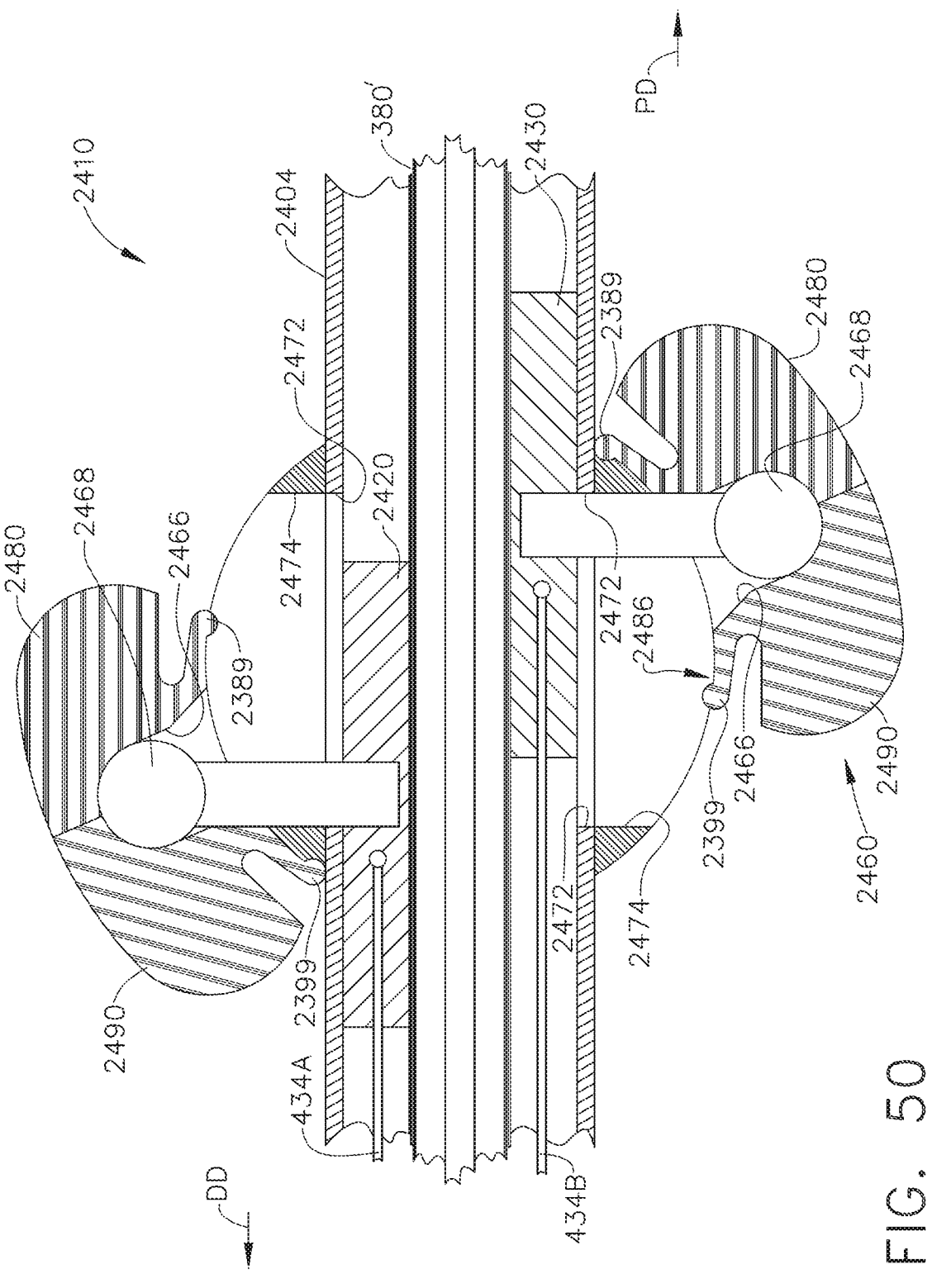
FIG. 50 is another cross-sectional view of one embodiment of the articulation system of FIGS. 48 and 49 in an articulated position.

Referring now to FIGS. 48-50, in at least one example form, the articulation drive 2410 includes four axially movable articulation slides that are movably journaled on the proximal drive shaft segment 380' between the proximal outer tube segment 2214 and the proximal drive shaft segment 380'. For example, the articulation cable segment 434A' is attached to a first articulation slide 2420 that has a first articulation actuator rod 2422 protruding therefrom. Articulation cable segment 434B' is attached to a second articulation slide 2430 that is diametrically opposite from the first articulation slide 2420. The second articulation slide 2430 has a second articulation actuator rod 2432 protruding therefrom. Articulation cable segment 454A' is attached to a third articulation slide 2440 that has a third articulation actuator rod 2442 protruding therefrom. Articulation cable segment 454B' is attached to a fourth articulation slide 2450 that is diametrically opposite to the third articulation slide 2440. A fourth articulation actuator rod 2452 protrudes from the fourth articulation slide 2450. Articulation actuator rods 2422, 2432, 2442, 2452 facilitate the application of articulation control motions to the articulation slides 2420, 2430, 2440, 2450, respectively by an articulation ring assembly 2460.

As can be seen in FIG. 48, the articulation actuator rods 2422, 2432, 2442, 2452 movably pass through a mounting ball 2470 that is journaled on a proximal outer tube segment 2404. In at least one embodiment, the mounting ball 2470 may be manufactured in segments that are attached together by appropriate fastener arrangements (e.g., welding, adhesive, screws, etc.). As shown in FIG. 50, the articulation actuator rods 2422 and 2432 extend through slots 2472 in the proximal outer tube segment 2404 and slots 2474 in the mounting ball 2470 to enable the articulation slides 2420, 2430 to axially move relative thereto. Although not shown, the articulation actuator rods 2442, 2452 extend through similar slots 2472, 2474 in the proximal outer tube segment 2404 and the mounting ball 2470. Each of the articulation actuator rods 2422, 2432, 2442, 2452 protrude out of the corresponding slots 2474 in the mounting ball 2470 to be operably received within corresponding mounting sockets 2466 in the articulation ring assembly 2460. See FIG. 49.

In at least one example form, the articulation ring assembly 2460 is fabricated from a pair of ring segments 2480, 2490 that are joined together by, for example, welding, adhesive, snap features, screws, etc. to form the articulation ring assembly 2460. The ring segments 2480, 2490 cooperate to form the mounting sockets 2466. Each of the articulation actuator rods has a mounting ball 2468 formed thereon that are each adapted to be movably received within a corresponding mounting socket 2466 in the articulation ring assembly 2460.

Various example embodiments of the articulation drive 2410 may further include an example locking system 2486 configured to retain the articulation ring assembly 2460 in an actuated position. In at least one example form, the locking system 2486 comprises a plurality of locking flaps formed on the articulation ring assembly 2460. For example, the ring segments 2480, 2490 may be fabricated from a somewhat flexible polymer or rubber material. Ring segment 2480 has a series of flexible proximal locking flaps 2488 formed therein and ring segment 2490 has a series of flexible distal locking flaps 2498 formed therein. Each locking flap 2488 has at least one locking detent 2389 formed thereon and each locking flap 2498 has at least one locking detent 2399 thereon. Locking detents 2389, 2399 may serve to establish a desired amount of locking friction with the articulation ball so as to retain the articulation ball in position. In other example embodiments, the locking detents 2389, 2399 are configured to matingly engage various locking dimples formed in the outer perimeter of the mounting ball 2470.

Operation of the articulation drive 2410 can be understood from reference to FIGS. 49 and 50. FIG. 49 illustrates the articulation drive 2410 in an unarticulated position. In FIG. 50, the clinician has manually tilted the articulation ring assembly 2460 to cause the articulation slide 2420 to move axially in the distal direction "DD" thereby advancing the articulation cable segment 434A' distally. Such movement of the articulation ring assembly 2460 also results in the axial movement of the articulation slide 2430 in the proximal direction which ultimately pulls the articulation cable 434B in the proximal direction. Such pushing and pulling of the articulation cable segments 434A', 434B' will result in articulation of the end effector 3000 relative to the longitudinal tool axis "LT-LT" in the manner described above. To reverse the direction of articulation, the clinician simply reverses the orientation of the articulation ring assembly 2460 to thereby cause the articulation slide 2430 to move in the distal direction "DD" and the articulation slide 2420 to move in the proximal direction "PD". The articulation ring assembly 2460 may be similarly actuated to apply desired pushing and pulling motions to the articulation cable segments 454A', 454B'. The friction created between the locking detents 2389, 2399 and the outer perimeter of the mounting ball serves to retain the articulation drive 2410 in position after the end effector 3000 has been articulated to the desired position. In alternative example embodiments, when the locking detents 2389, 2399 are positioned so as to be received in corresponding locking dimples in the mounting ball, the mounting ball will be retained in position.

In the illustrated example embodiments and others, the elongate shaft assembly 2402 operably interfaces with a handle assembly 2500. An example embodiment of handle assembly 2500 comprises a pair of handle housing segments 2502, 2504 that are coupled together to form a housing for various drive components and systems as will be discussed in further detail below. See, e.g., FIG. 46. The handle housing segments 2502, 2504 may be coupled together by screws, snap features, adhesive, etc. When coupled together, the handle segments 2502, 2504 may form a handle assembly 2500 that includes a pistol grip portion 2506.

To facilitate selective rotation of the end effector 3000 about the longitudinal tool axis "LT=LT", the elongate shaft assembly 2402 may interface with a first drive system, generally designated as 2510. The drive system 2510 includes a manually-actuatable rotation nozzle 2512 that is rotatably supported on the handle assembly 2500 such that it can be rotated relative thereto as well as be axially moved between a locked position and an unlocked position.

Figure 51:
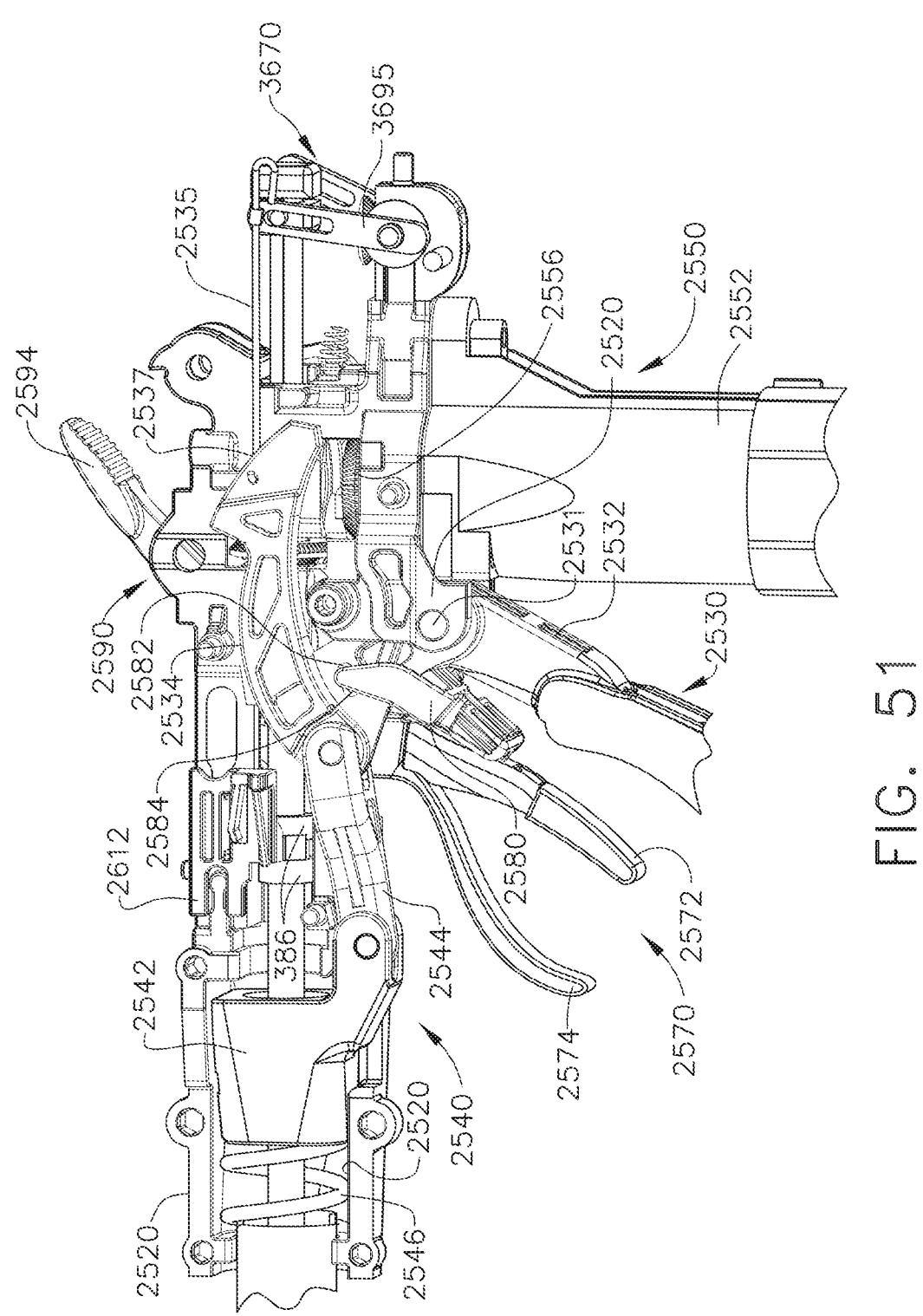
FIG. 51 is a side elevational view of a portion of one embodiment of the surgical tool of FIGS. 46-47 with portions thereof omitted for clarity.

The surgical tool 2400 may include a closure system 3670. The closure system 3670 may be used in some embodiments to bring about distal and proximal motion in the elongate shaft assembly 2402 and end effector 3000. For example, in some embodiments, the closure system 3670 may drive an axially movable member such as 3016. For example, the closure system 3670 may be used to translate the axially movable member 3016 instead of the various rotary drive shafts described herein with respect to FIGS. 64-82, 83-91 and 92-96. In this example embodiment, the closure system 3670 is actuated by a closure trigger 2530 that is pivotally mounted to the handle frame assembly 2520 that is supported within the handle housing segments 2502, 2504. The closure trigger 2530 includes an actuation portion 2532 that is pivotally mounted on a pivot pin 2531 that is supported within the handle frame assembly 2520. See FIG. 51. Such example arrangement facilitates pivotal travel toward and away from the pistol grip portion 2506 of the handle assembly 2500. As can be seen in FIG. 51, the closure trigger 2530 includes a closure link 2534 that is linked to the first pivot link and gear assembly 3695 by a closure wire 2535. Thus, by pivoting the closure trigger 2530 toward the pistol grip portion 2506 of the handle assembly 2500 into an actuated position, the closure link 2534 and closure wire 2535 causes the first pivot link and gear assembly 3695 to move in the distal direction "DD" to cause distal motion through the shaft and, in some embodiments, to the end effector.

Figure 52:
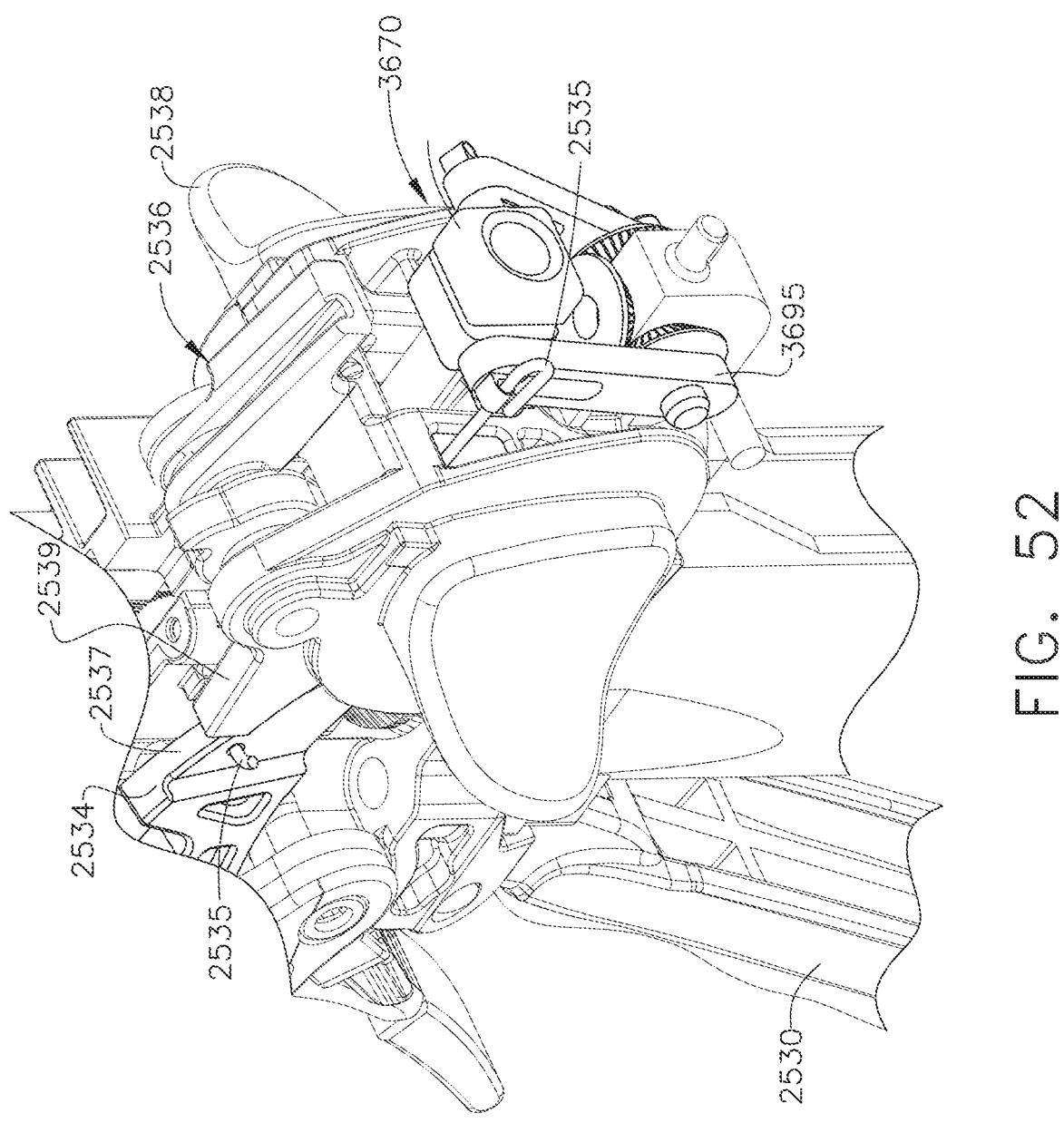
FIG. 52 is a rear perspective view of a portion of one embodiment of the surgical tool of FIGS. 46-47 with portions thereof omitted for clarity.
Figure 53:
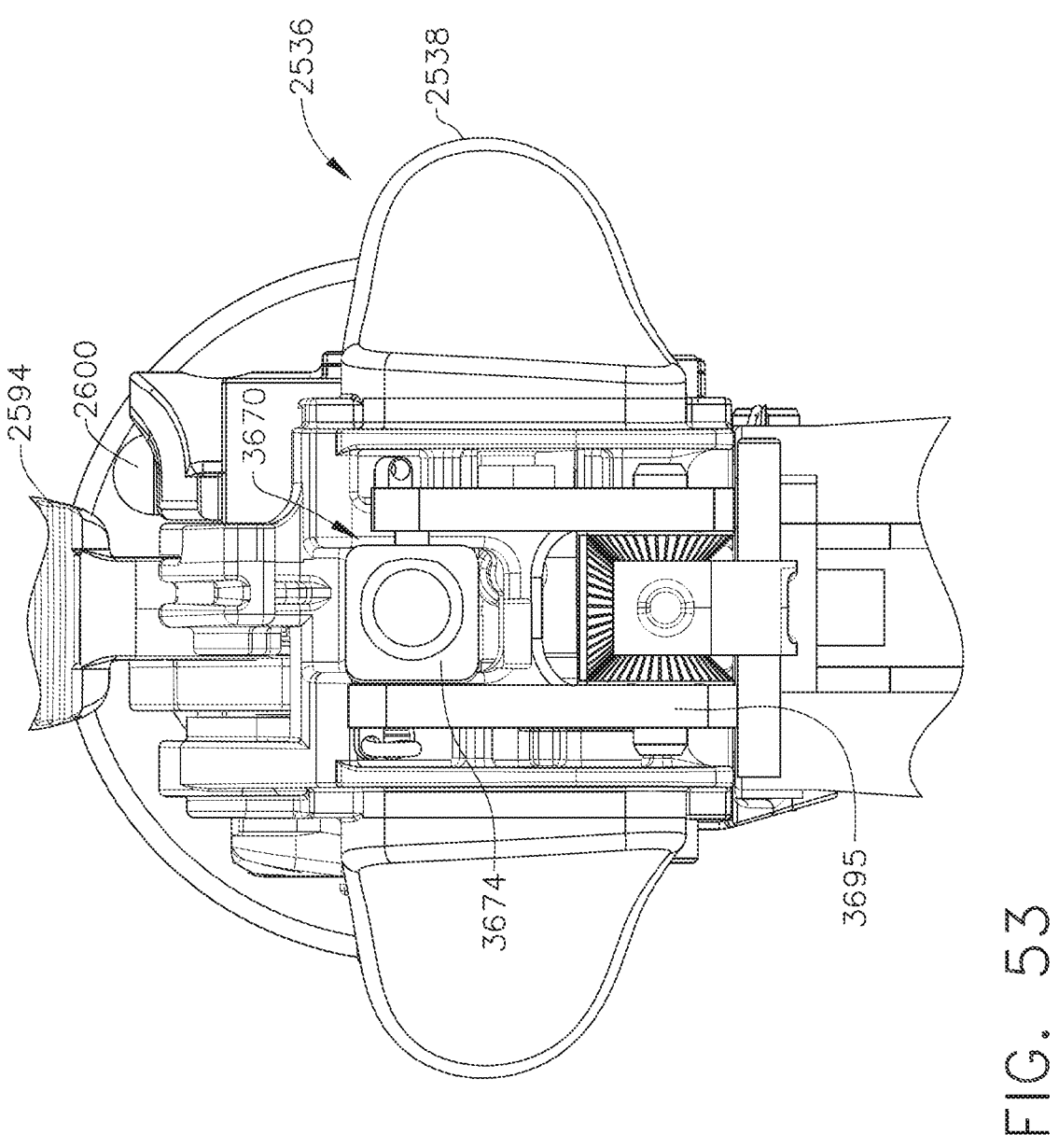
FIG. 53 is a rear elevational view of a portion of one embodiment of the surgical tool of FIGS. 46-47 with portions thereof omitted for clarity.

The surgical tool 2400 may further include a closure trigger locking system 2536 to retain the closure trigger in the actuated position. In at least one example form, the closure trigger locking system 2536 includes a closure lock member 2538 that is pivotally coupled to the handle frame assembly 2520. As can be seen in FIGS. 52 and 53, the closure lock member 2538 has a lock arm 2539 formed thereon that is configured to ride upon an arcuate portion 2537 of the closure link 2534 as the closure trigger 2530 is actuated toward the pistol grip portion 2506. When the closure trigger 2530 has been pivoted to the fully actuated position, the lock arm 2539 drops behind the end of the closure link 2534 and prevents the closure trigger 2530 from returning to its unactuated position. Thus, the distal motion translated through the shaft assembly to the end effector may be locked. To enable the closure trigger 2530 to return to its unactuated position, the clinician simply pivots the closure lock member 2538 until the lock arm 2539 thereof disengages the end of the closure link 2534 to thereby permit the closure link 2534 to move to the unactuated position.

The closure trigger 2530 is returned to the unactuated position by a closure return system 2540. For example, as can be seen in FIG. 51, one example form of the closure trigger return system 2540 includes a closure trigger slide member 2542 that is linked to the closure link 2534 by a closure trigger yoke 2544. The closure trigger slide member 2542 is slidably supported within a slide cavity 2522 in the handle frame assembly 2520. A closure trigger return spring 2546 is positioned within the slide cavity 2520 to apply a biasing force to the closure trigger slide member 2542. Thus, when the clinician actuates the closure trigger 2530, the closure trigger yoke 2544 moves the closure trigger slide member 2542 in the distal direction "DD" compressing the closure trigger return spring 2546. When the closure trigger locking system 2536 is disengaged and the closure trigger 2530 is released, the closure trigger return spring 2546 moves the closure trigger slide member 2542 in the proximal direction "PD" to thereby pivot the closure trigger 2530 into the starting unactuated position.

Figure 55:
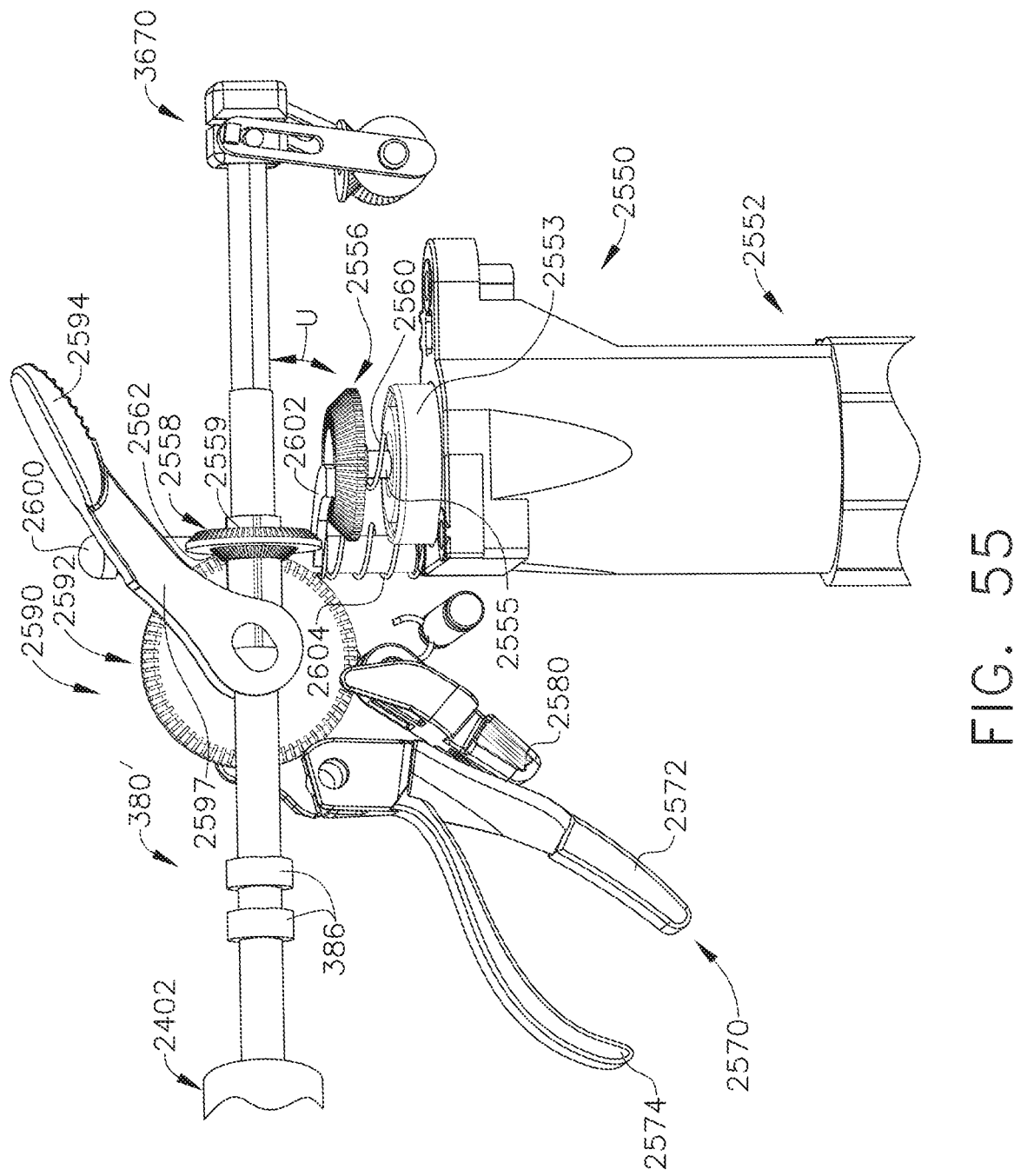
FIG. 55 is a side elevational view of a portion of the surgical tool embodiment of FIGS. 46-47 with portions thereof omitted for clarity.

The surgical tool 2400 can also employ any of the various example drive shaft assemblies described above. In at least one example form, the surgical tool 2400 employs a second drive system 2550 for applying rotary control motions to a proximal drive shaft assembly 380'. See FIG. 55. The second drive system 2550 may include a motor assembly 2552 that is operably supported in the pistol grip portion 2506. The motor assembly 2552 may be powered by a battery pack 2554 that is removably attached to the handle assembly 2500 or it may be powered by a source of alternating current. A second drive gear 2556 is operably coupled to the drive shaft 2555 of the motor assembly 2552. The second drive gear 2556 is supported for meshing engagement with a second rotary driven gear 2558 that is attached to the proximal drive shaft segment 380' of the drive shaft assembly. In at least one form, for example, the second drive gear 2556 is also axially movable on the motor drive shaft 2555 relative to the motor assembly 2552 in the directions represented by arrow "U" in FIG. 55. A biasing member, e.g., a coil spring 2560 or similar member, is positioned between the second drive gear 2556 and the motor housing 2553 and serves to bias the second drive gear 2556 on the motor drive shaft 2555 into meshing engagement with a first gear segment 2559 on the second driven gear 2558.

The second drive system 2550 may further include a firing trigger assembly 2570 that is movably, e.g., pivotally attached to the handle frame assembly 2520. In at least one example form, for example, the firing trigger assembly 2570 includes a first rotary drive trigger 2572 that cooperates with a corresponding switch/contact (not shown) that electrically communicates with the motor assembly 2552 and which, upon activation, causes the motor assembly 2552 to apply a first rotary drive motion to the second driven gear 2558. In addition, the firing trigger assembly 2570 further includes a retraction drive trigger 2574 that is pivotal relative to the first rotary drive trigger. The retraction drive trigger 2574 operably interfaces with a switch/contact (not shown) that is in electrical communication with the motor assembly 2552 and which, upon activation, causes the motor assembly 2552 to apply a second rotary drive motion to the second driven gear 2558. The first rotary drive motion results in the rotation of the drive shaft assembly and the implement drive shaft in the end effector to cause the firing member to move distally in the end effector 3000. Conversely, the second rotary drive motion is opposite to the first rotary drive motion and will ultimately result in rotation of the drive shaft assembly and the implement drive shaft in a rotary direction which results in the proximal movement or retraction of the firing member in the end effector 3000.

The illustrated embodiment also includes a manually actuatable safety member 2580 that is pivotally attached to the closure trigger actuation portion 2532 and is selectively pivotable between a first "safe" position wherein the safety member 2580 physically prevents pivotal travel of the firing trigger assembly 2570 and a second "off" position, wherein the clinician can freely pivot the firing trigger assembly 2570. As can be seen in FIG. 51, a first dimple 2582 is provided in the closure trigger actuation portion 2532 that corresponds to the first position of the safety member 2580. When the safety member 2580 is in the first position, a detent (not shown) on the safety member 2580 is received within the first dimple 2582. A second dimple 2584 is also provided in the closure trigger actuation portion 2532 that corresponds to the second position of the safety member 2580. When the safety member 2580 is in the second position, the detent on the safety member 2580 is received within the second dimple 2582.

In at least some example forms, the surgical tool 2400 may include a mechanically actuatable reversing system, generally designated as 2590, for mechanically applying a reverse rotary motion to the proximal drive shaft segment 380' in the event that the motor assembly 2552 fails or battery power is lost or interrupted. Such mechanical reversing system 2590 may also be particularly useful, for example, when the drive shaft system components operably coupled to the proximal drive shaft segment 380' become jammed or otherwise bound in such a way that would prevent reverse rotation of the drive shaft components under the motor power alone. In at least one example form, the mechanically actuatable reversing system 2590 includes a reversing gear 2592 that is rotatably mounted on a shaft 2524A formed on the handle frame assembly 2520 in meshing engagement with a second gear segment 2562 on the second driven gear 2558. See FIG. 53. Thus, the reversing gear 2592 freely rotates on shaft 2524A when the second driven gear 2558 rotates the proximal drive shaft segment 380' of the drive shaft assembly.

Figure 56:
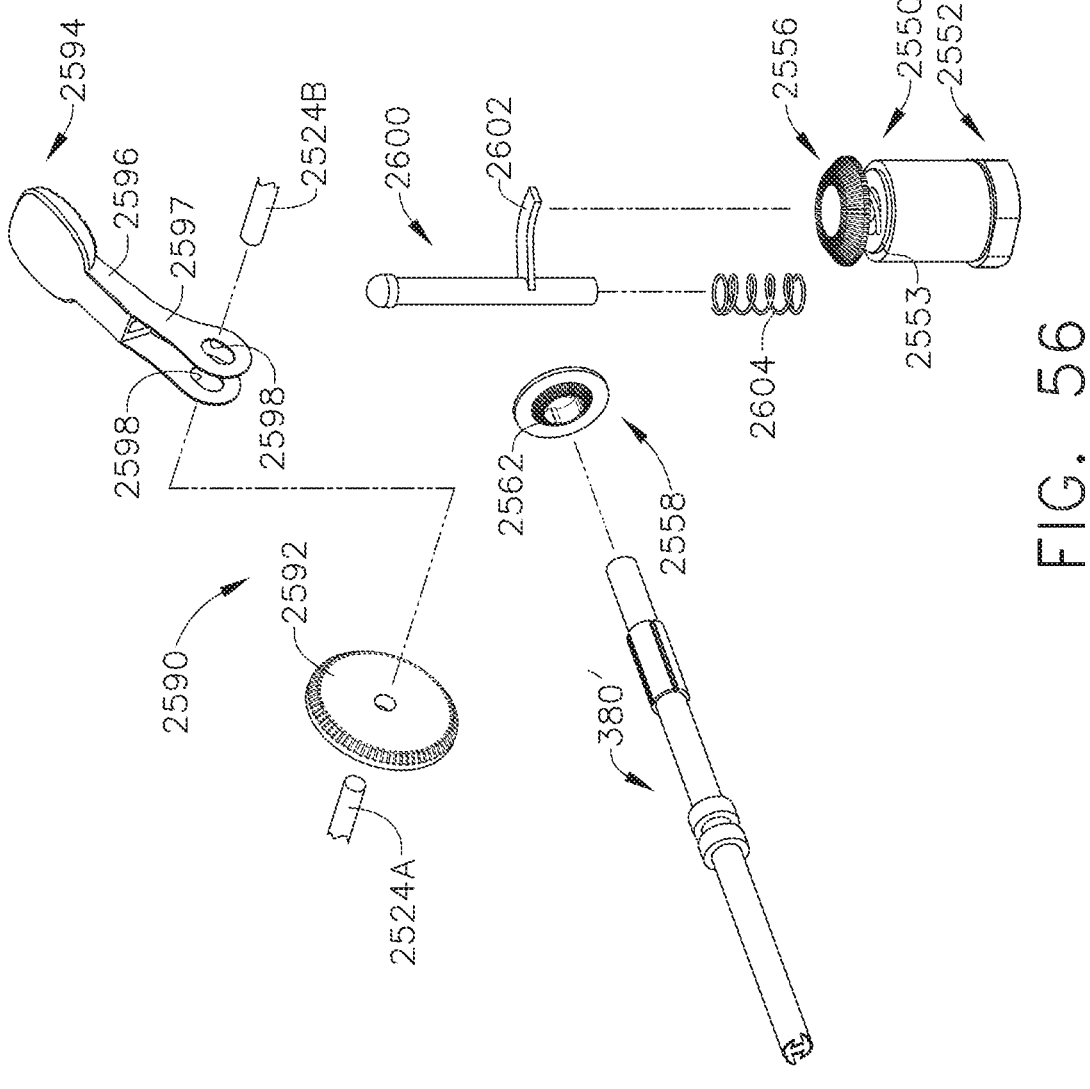
FIG. 56 is an exploded assembly view of an example reversing system embodiment of the surgical tool of FIGS. 46-47.
Figure 58:
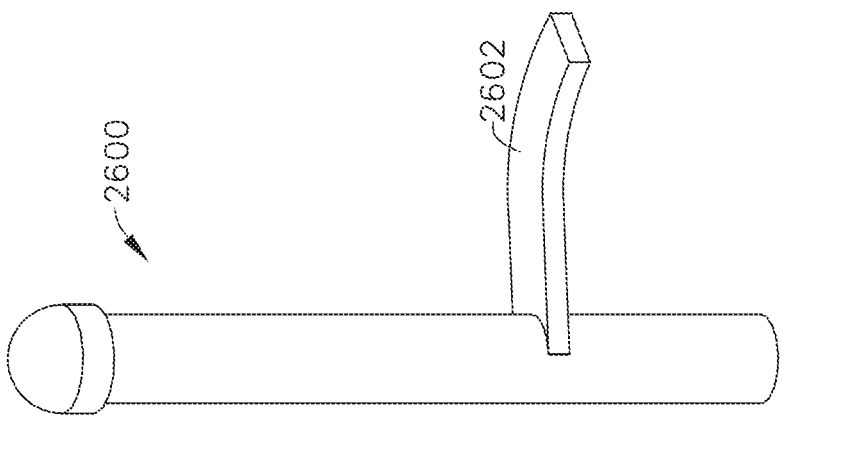
FIG. 58 is a perspective view of a knife retractor button of one embodiment of the reversing system of FIG. 56.
Figure 57:
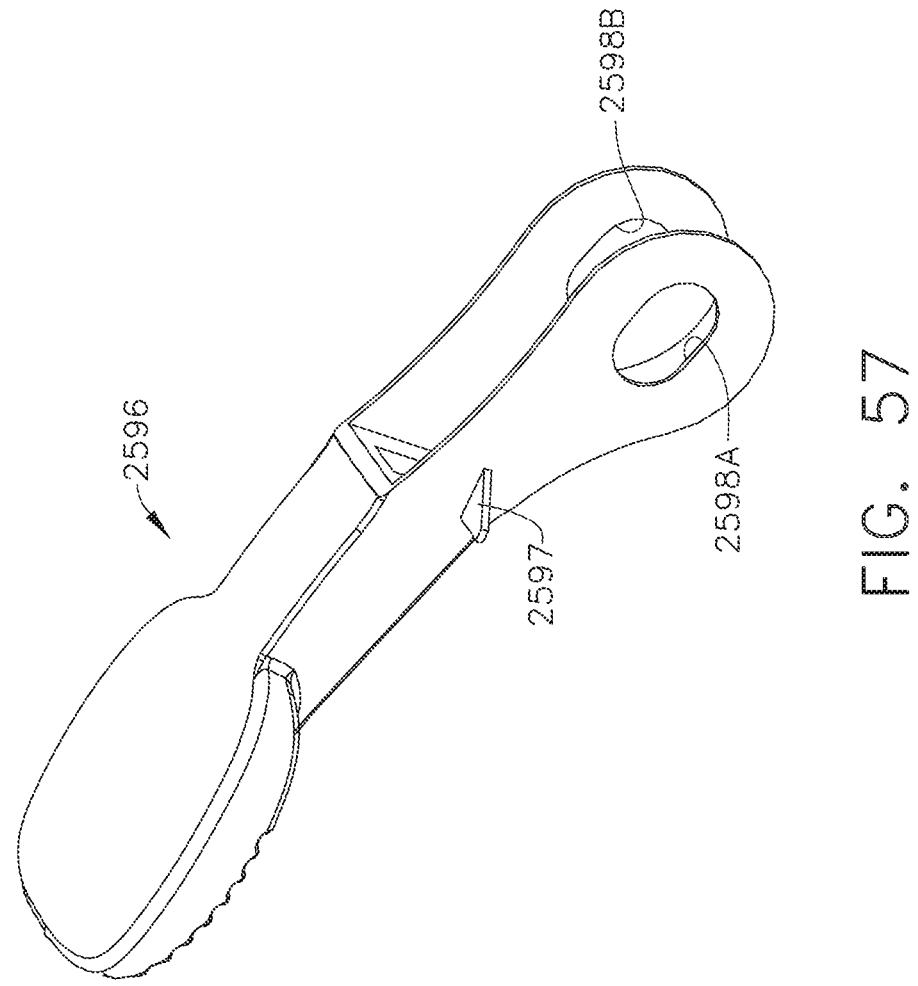
FIG. 57 is a perspective view of a lever arm embodiment of the reversing system of FIG. 56.
Figure 59:
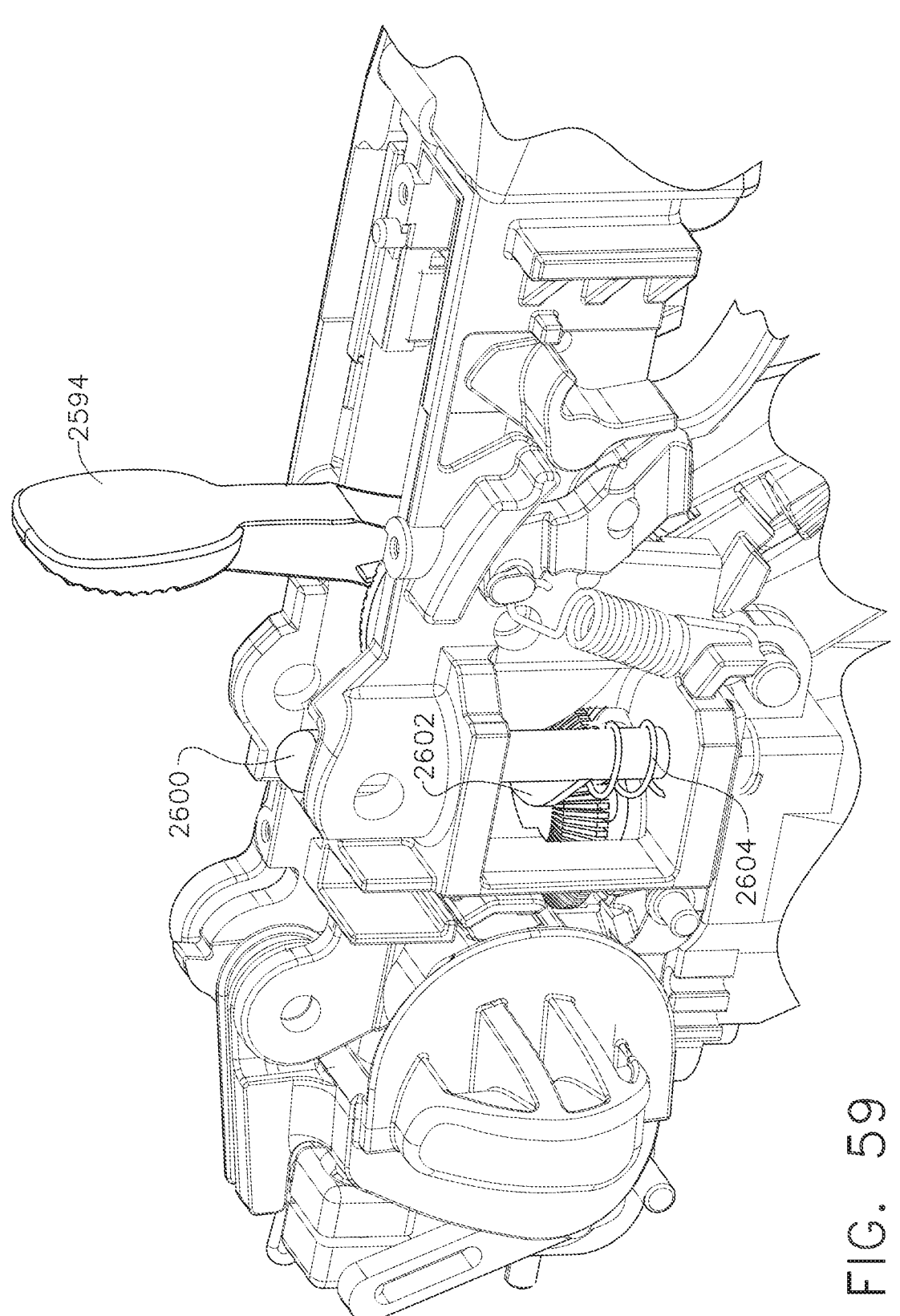
FIG. 59 is a perspective view of a portion of the surgical tool embodiment of FIGS. 46-47 with portions thereof omitted for clarity and with the lever arm in actuatable engagement with the reversing gear.
Figure 60:
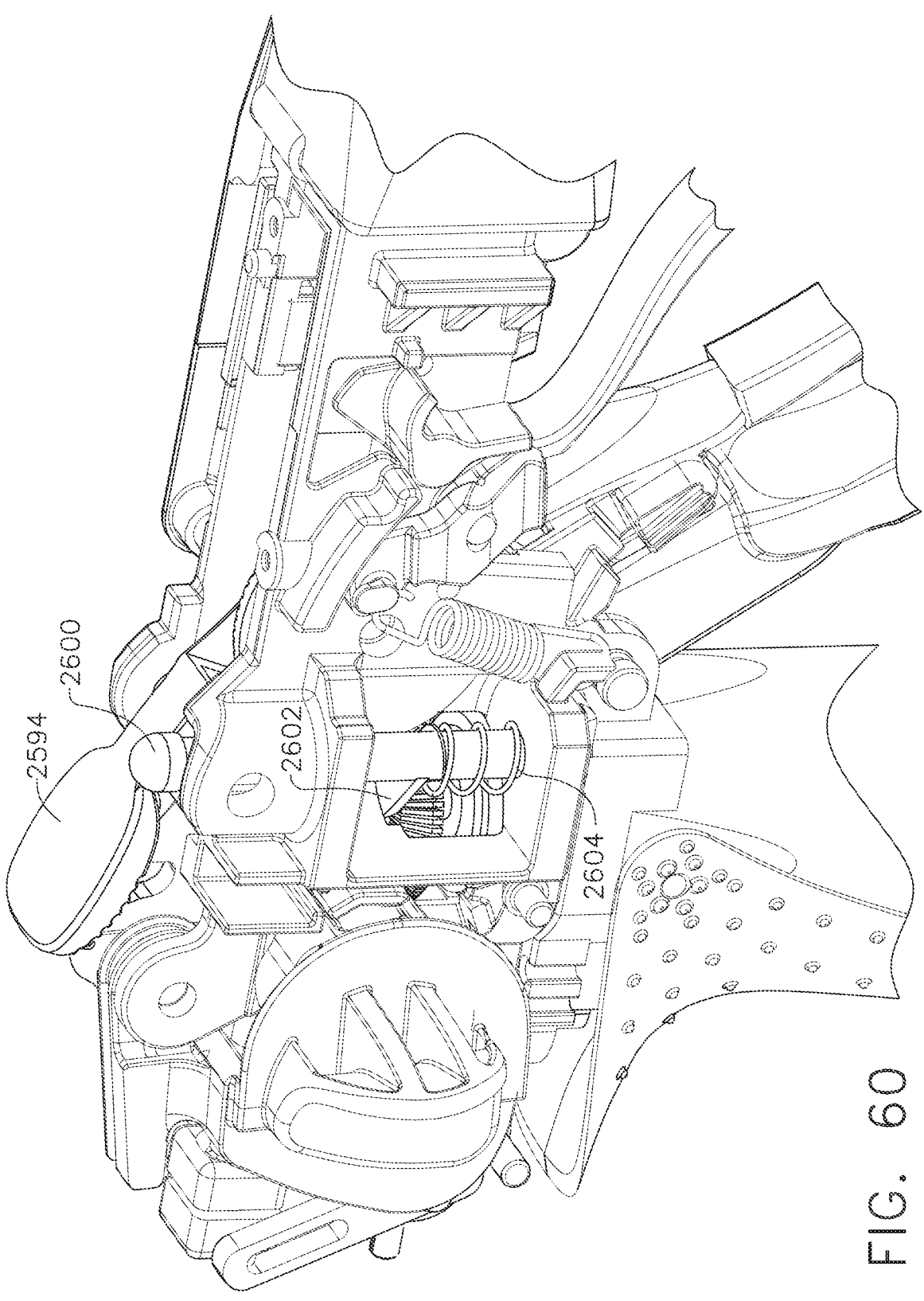
FIG. 60 is a perspective view of a portion of the surgical tool embodiment of FIGS. 46-47 with portions thereof omitted for clarity and with the lever arm in an unactuated position.

In various example forms, the mechanical reversing system 2590 further includes a manually actuatable driver 2594 in the form of a lever arm 2596. As can be seen in FIGS. 56 and 57, the lever arm 2596 includes a yoke portion 2597 that has elongate slots 2598 therethrough. The shaft 2524A extends through slot 2598A and a second opposing shaft 2598B formed on the handle housing assembly 2520 extends through the other elongate slot to movably affix the lever arm 2596 thereto. In addition, the lever arm 2596 has an actuator fin 2597 formed thereon that can meshingly engage the reversing gear 2592. There is a detent or interference that keeps the lever arm 2596 in the unactuated state until the clinician exerts a substantial force to actuate it. This keeps it from accidentally initiating if inverted. Other embodiments may employ a spring to bias the lever arm into the unactuated state. Various example embodiments of the mechanical reversing system 2590 further includes a knife retractor button 2600 that is movably journaled in the handle frame assembly 2520. As can be seen in FIGS. 56 and 57, the knife retractor button 2600 includes a disengagement flap 2602 that is configured to engage the top of the second drive gear 2556. The knife retractor button 2600 is biased to a disengaged position by a knife retractor spring 2604. When in the disengaged position, the disengagement flap 2602 is biased out of engagement with the second drive gear 2556. Thus, until the clinician desires to activate the mechanical reversing system 2590 by depressing the knife retractor button 2600, the second drive gear 2556 is in meshing engagement with the first gear segment 2559 of the second driven gear 2558.

When the clinician desires to apply a reverse rotary drive motion to the proximal drive shaft segment 380', the clinician depresses the knife retractor button 2600 to disengage the first gear segment 2559 on the second driven gear 2558 from the second drive gear 2556. Thereafter, the clinician begins to apply a pivotal ratcheting motion to the manually actuatable driver 2594 which causes the gear fin 2597 thereon to drive the reversing gear 2592. The reversing gear 2592 is in meshing engagement with the second gear segment 2562 on the second driven gear 2558. Continued ratcheting of the manually actuatable driver 2594 results in the application of a reverse rotary drive motion to the second gear segment 2562 and ultimately to the proximal drive shaft segment 380'. The clinician may continue to ratchet the driver 2594 for as many times as are necessary to fully release or reverse the associated end effector component(s). Once a desired amount of reverse rotary motion has been applied to the proximal drive shaft segment 380', the clinician releases the knife retractor button 2600 and the driver 2594 to their respective starting or unactuated positions wherein the fin 2597 is out of engagement with the reversing gear 2592 and the second drive gear 2556 is once again in meshing engagement with the first gear segment 2559 on the second driven gear 2558.

Figure 54:
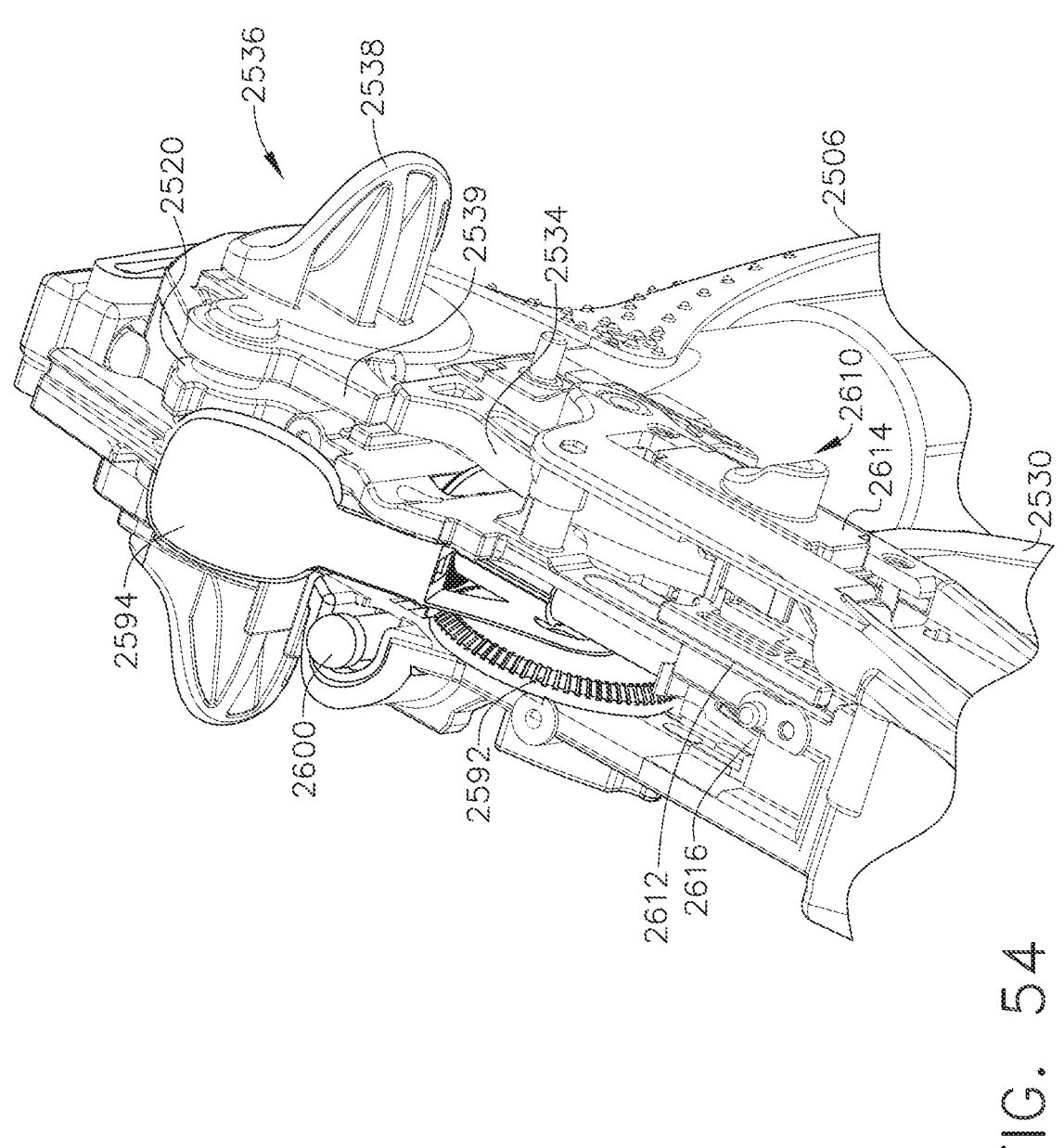
FIG. 54 is a front perspective view of a portion of one embodiment of the surgical tool of FIGS. 46-47 with portions thereof omitted for clarity.
Figure 61:
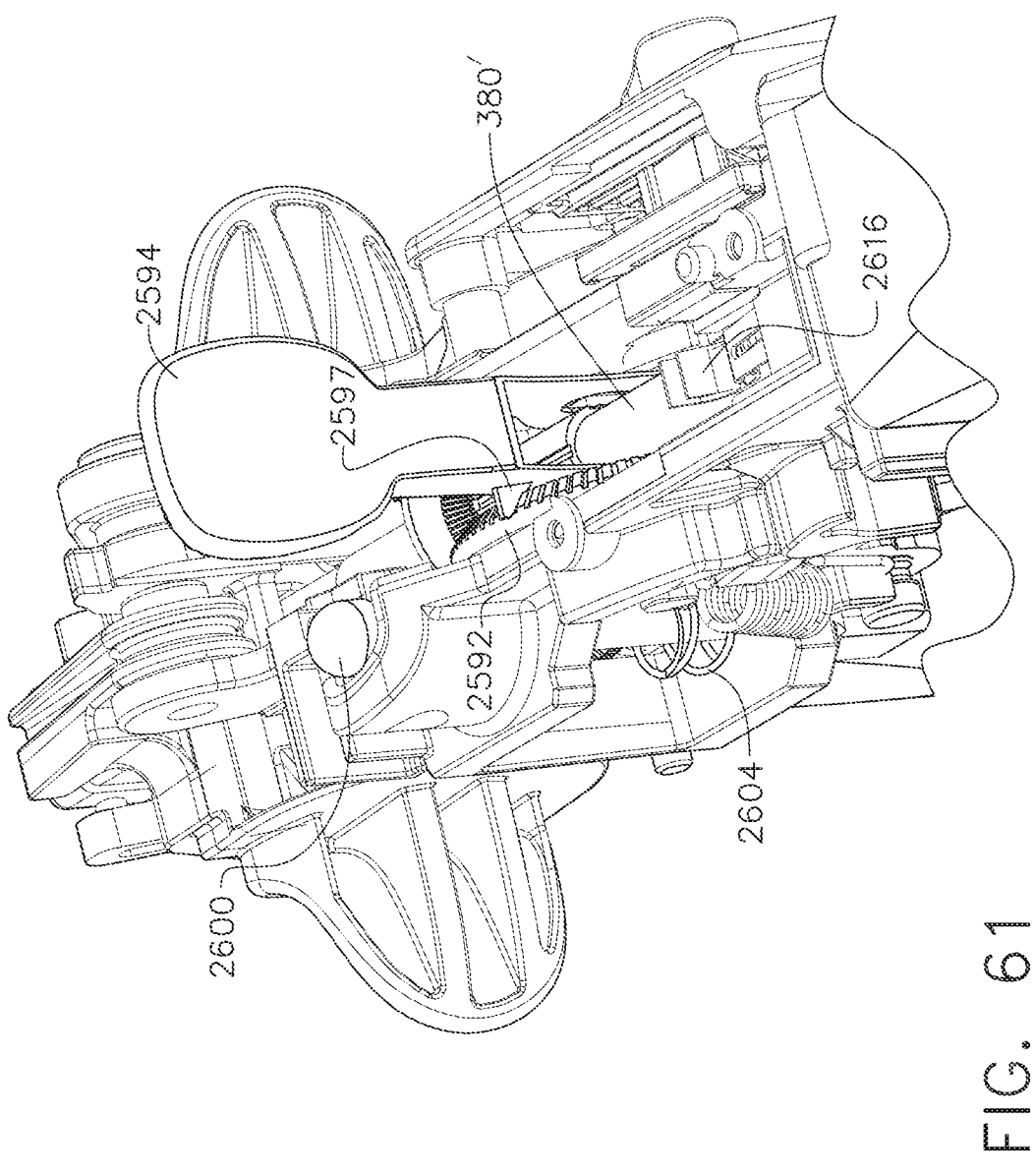
FIG. 61 is another perspective view of a portion of the surgical tool embodiment of FIGS. 46-47 with portions thereof omitted for clarity and with the lever arm in actuatable engagement with the reversing gear.
Figure 63:
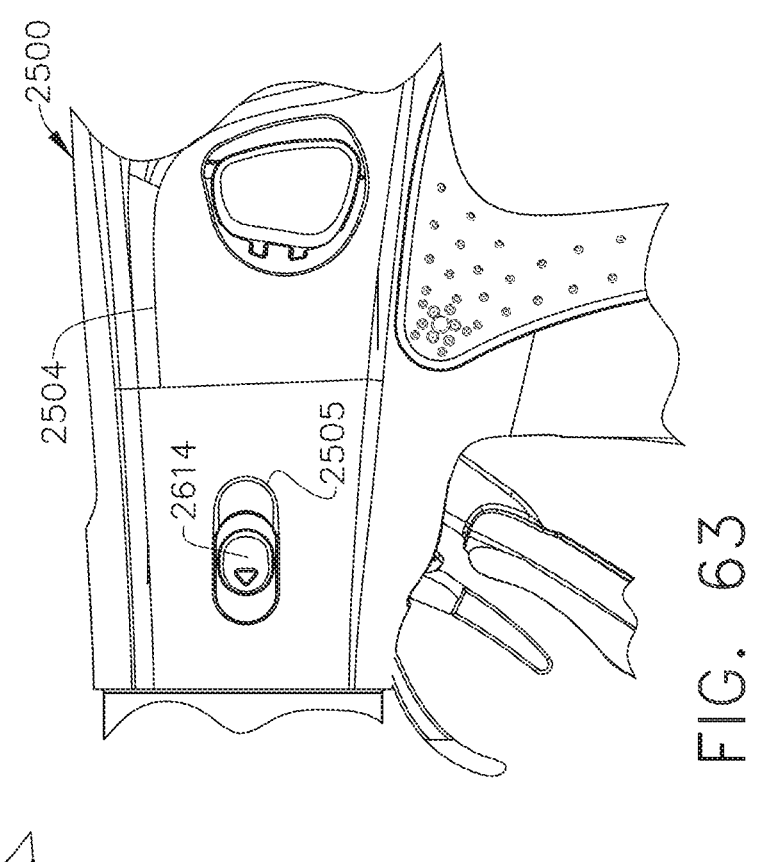
FIG. 63 is another side elevational view of a portion of a handle assembly portion of one embodiment of the surgical tool of FIGS. 46-47 with the a shifter button assembly moved into another position which will result in the firing of the firing member in the end effector when the drive shaft assembly is actuated.
Figure 62:
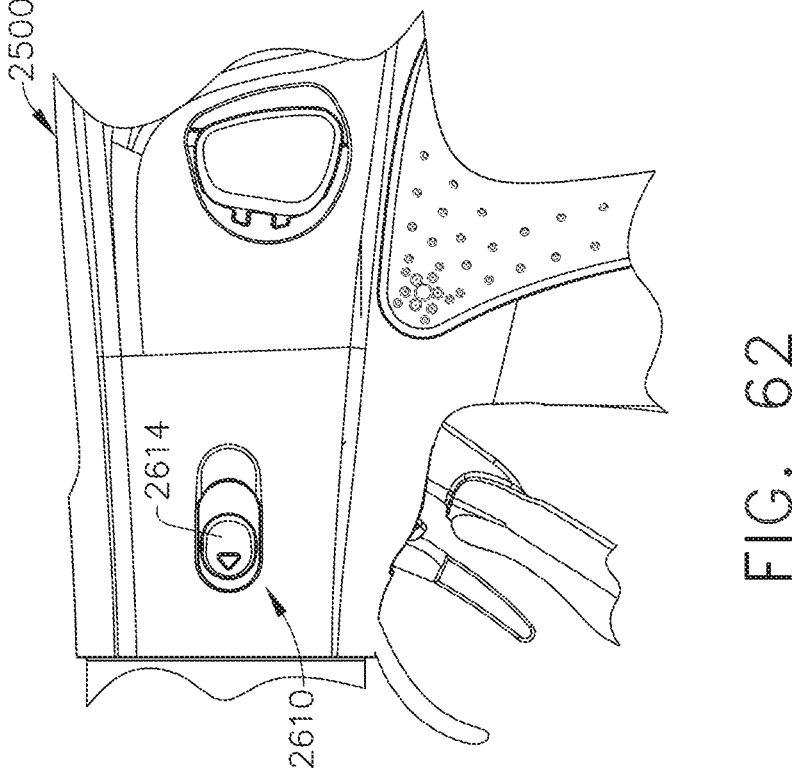
FIG. 62 is a side elevational view of a portion of a handle assembly portion of the surgical tool embodiment of FIGS. 46-47 with a shifter button assembly moved into a position which will result in the rotation of the end effector when the drive shaft assembly is actuated.
Figure 64:
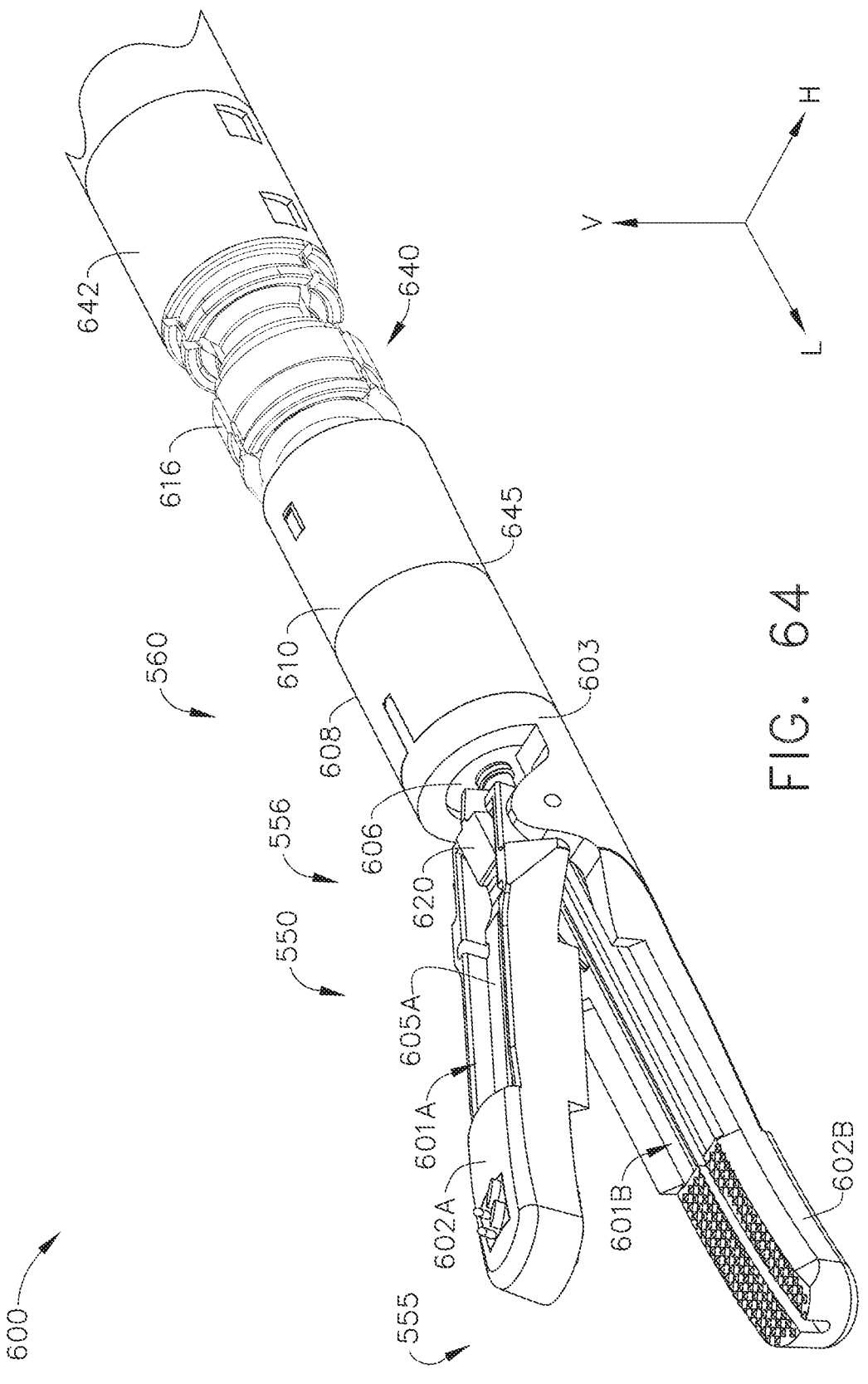
FIG. 64 is a perspective view of an embodiment of a multi-axis articulating and rotating surgical tool.

The surgical tool 2400 can also be employed with an electrosurgical end effector comprising various rotary drive components that are driven differently with a rotary drive shaft at different axial positions. Examples of such end effectors and drive mechanisms are described herein with respect to FIGS. 64-82, 83-91 and 92-96. The surgical tool 2400 may employ a shifting system 2610 for selectively axially shifting the proximal drive shaft segment 380' which moves the shaft gear 376 into and out of meshing engagement with the first rotary driven gear 374. For example, the proximal drive shaft segment 380' is movably supported within the handle frame assembly 2520 such that the proximal drive shaft segment 380' may move axially and rotate therein. In at least one example form, the shifting system 2610 further includes a shifter yoke 2612 that is slidably supported by the handle frame assembly 2520. See FIGS. 51 and 54. The proximal drive shaft segment 380' has a pair of collars 386 (shown in FIGS. 51 and 55) thereon such that shifting of the shifter yoke 2612 on the handle frame assembly 2520 results in the axial movement of the proximal drive shaft segment 380'. In at least one form, the shifting system 2610 further includes a shifter button assembly 2614 operably interfaces with the shifter yoke 2612 and extends through a slot 2505 in the handle housing segment 2504 of the handle assembly 2500. See FIGS. 62 and 63. A shifter spring 2616 is mounted with the handle frame assembly 2520 such that it engages the proximal drive shaft segment 380'. See FIGS. 54 and 61. The spring 2616 serves to provide the clinician with an audible click and tactile feedback as the shifter button assembly 2614 is slidably positioned between the first axial position depicted in FIG. 62 wherein rotation of the drive shaft assembly results in rotation of the end effector 3000 about the longitudinal tool axis "LT-LT" relative to the articulation joint 3500 (illustrated in FIG. 67) and the second axial position depicted in FIG. 63 wherein rotation of the drive shaft assembly results in the axial movement of the firing member in the end effector (illustrated in FIG. 66). Thus, such arrangement enables the clinician to easily slidably position the shifter button assembly 2614 while holding the handle assembly 2500. In some embodiments, the shifter button assembly 2500 may have more than two axial positions, corresponding to more than two desired axial positions of the rotary drive shaft. Examples of such surgical tools are provided herein in conjunction with FIGS. 83-91 and 92-96.

Referring to FIGS. 64-72, a multi-axis articulating and rotating surgical tool 600 comprises an end effector 550 comprising a first jaw member 602A and a second jaw member 602B. The first jaw member 602A is movable relative to the second jaw member 602B between an open position (FIGS. 64, 66-69, 71) and a closed position (FIGS. 70 and 72) to clamp tissue between the first jaw member 602A and the second jaw member 602B. The surgical tool 600 is configured to independently articulate about an articulation joint 640 in a vertical direction (labeled direction V in FIGS. 64 and 66-72) and a horizontal direction (labeled direction H in FIGS. 64 and 65-68). Actuation of the articulation joint 640 may be brought about in a manner similar to that described above with respect to FIGS. 24-26. The surgical tool 600 is configured to independently rotate about a head rotation joint 645 in a longitudinal direction (labeled direction H in FIGS. 64 and 66-72). The end effector 550 comprises an I-beam member 620 and a jaw assembly 555 comprising the first jaw member 602A, the second jaw member 602B, a proximal portion 603 of the second jaw member 602B, and a rotary drive nut 606 seated in the proximal portion 603. The I-beam member 620 and jaw assembly 555 may operate in a manner described herein and similar to that described above with respect to the axially movable member 3016 and jaw members 3008A, 3008B described herein above.

The end effector 550 is coupled to a shaft assembly 560 comprising an end effector drive housing 608, an end effector connector tube 610, an intermediate articulation tube segment 616, and a distal outer tube portion 642. The end effector 550 and the shaft assembly 560 together comprise the surgical tool 600. The end effector 550 may be removably coupled to the end effector drive housing 608 using a mechanism as described, for example, in connection with FIGS. 106-115. The end effector connector tube 610 comprises a cylindrical portion 612 and a ball member 614. The end effector drive housing 608 is coupled to the cylindrical portion 612 of the end effector connector tube 610 through the head rotation joint 645. The end effector 550 and the end effector drive housing 608 together comprise a head portion 556 of the surgical tool 600. The head portion 556 of the surgical tool 600 is independently rotatable about the head rotation joint 645, as described in greater detail below.

The intermediate articulation tube segment 616 comprises a ball member 618 and a ball socket 619. The end effector connector tube 610 is coupled to the intermediate articulation tube segment 616 through a ball-and-socket joint formed by the mutual engagement of the ball member 614 of the end effector connector tube 610 and the ball socket 619 of the intermediate articulation tube segment 616. The intermediate articulation tube segment 616 is coupled to the distal outer tube portion 642 through a ball-and-socket joint formed by the mutual engagement of the ball member 618 of the intermediate articulation tube segment 616 and a ball socket of the distal outer tube portion 642. The articulation joint 640 comprises the end effector connector tube 610, the intermediate articulation tube segment 616, and the distal outer tube portion 642. The independent vertical articulation and/or horizontal articulation of the surgical tool 600 about the articulation joint 640 may be actuated, for example, using independently actuatable cable segments, such as 444, 445, 446, 447 described herein above, connected to the ball member 614 of the end effector connector tube 610. This independent articulation functionality is described, for example, in connection with FIGS. 24, 24A and 25. Robotic and hand-held apparatuses for allowing a clinician to initiate articulation functionality are described, for example, in connection with FIGS. 6, 16-21 and 46-50.

Figures 73, 74:
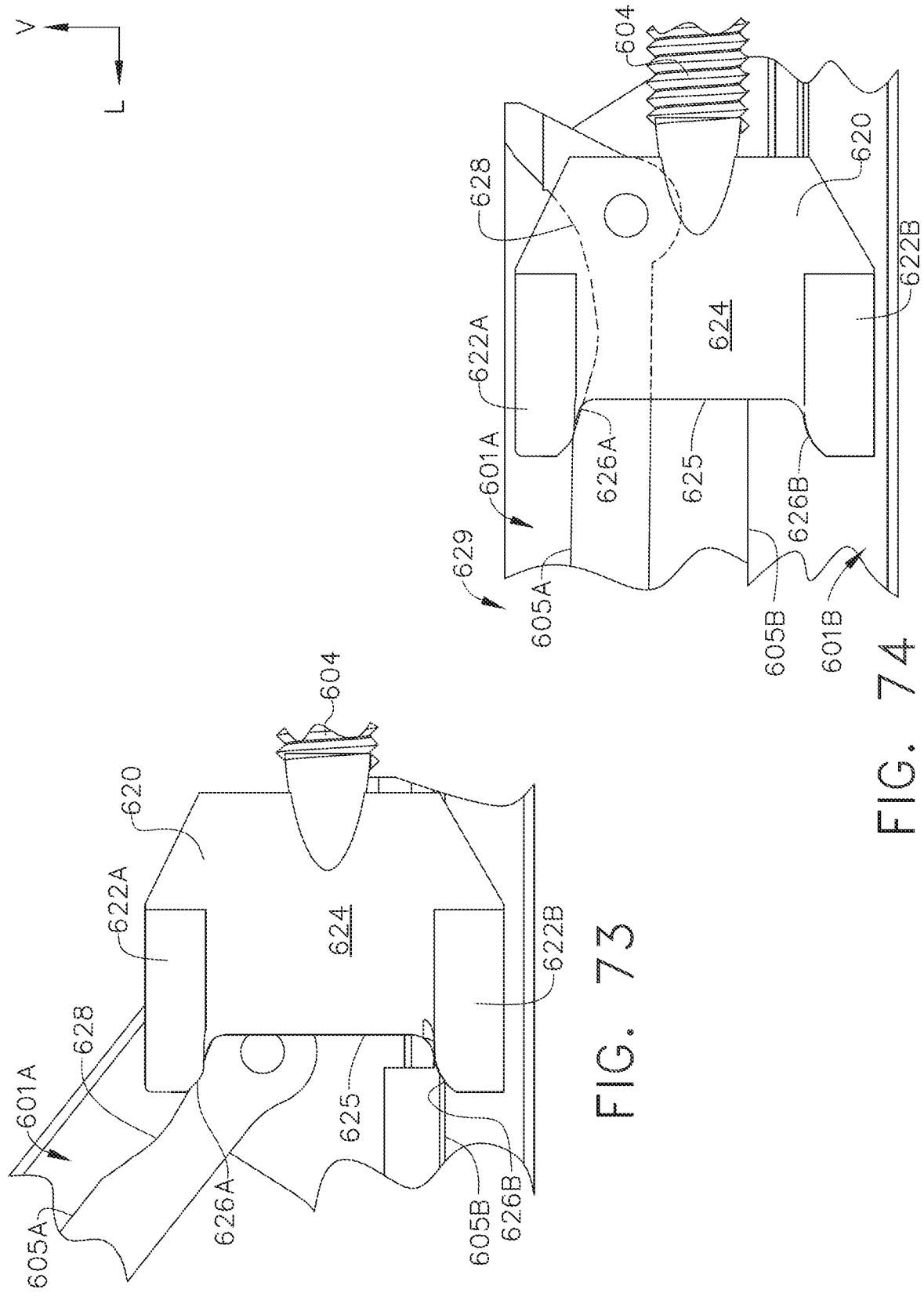
FIGS. 73 and 74 are side cross-sectional detail views of one embodiment of the surgical tool shown in FIG. 64, illustrating the engagement of cam surfaces of an I-beam member with anvil surfaces of a first jaw member to move the first jaw member relative to a second jaw member between an open position and a closed position.

The movement of the first jaw member 602A relative to the second jaw member 602B between an open position (FIGS. 64, 66-69, and 71) and a closed position (FIGS. 70 and 72) may be actuated with a suitable closure actuation mechanism. Referring to FIGS. 73 and 74, closure of the jaw assembly 555 may be actuated by translation of the I-beam member 620. The I-beam member 620 comprises a first I-beam flange 622A and a second I-beam flange 622B. The first I-beam flange 622A and the second I-beam flange 622B are connected with an intermediate portion 624. The intermediate portion 624 of the I-beam member 620 comprises a cutting member 625, which is configured to transect tissue clamped between the first jaw member 602A and the second jaw member 602B when the jaw assembly 555 is in a closed position. The I-beam member 620 is configured to translate within a first channel 601A in the first jaw member 602A and within a second channel 601B in the second jaw member 602B. The first channel 601A comprises a first channel flange 605A, and the second channel 601B comprises a second channel flange 605B. The first I-beam flange 622A can define a first cam surface 626A, and the second I-beam flange 622B can define a second cam surface 626B. The first and second cam surfaces 626A and 626B can slidably engage outwardly-facing opposed surfaces of the first and second channel flanges 605A and 605B, respectively. More particularly, the first cam surface 626A can comprise a suitable profile configured to slidably engage the opposed surface of the first channel flange 605A of the first jaw member 602A and, similarly, the second cam surface 626B can comprise a suitable profile configured to slidably engage the opposed surface of the second channel flange 605B of the second jaw member 602B, such that, as the I-beam member 620 is advanced distally, the cam surfaces 626A and 626B can co-operate to cam first jaw member 602A toward second jaw member 602B and move the jaw assembly 555 from an open position to a closed position as indicated by arrow 629 in FIG. 74.

Figures 71, 72:
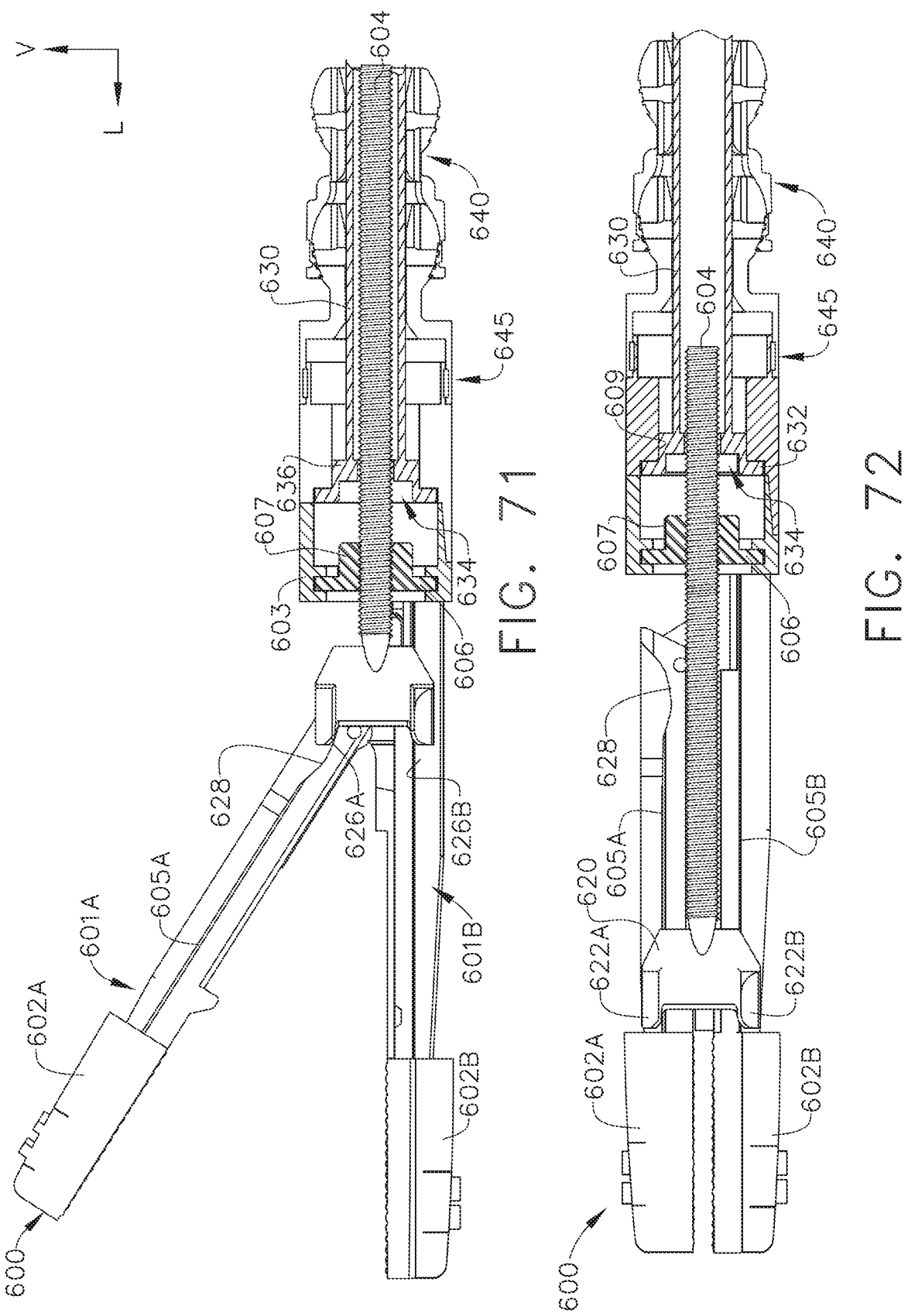
FIG. 71 is a side cross-sectional view of one embodiment of the surgical tool shown in FIG. 64, illustrating the jaw assembly of an end effector in an open position, an I-beam member in a proximally retracted position, and a rotary drive shaft engaging a shaft coupling for actuating rotation of the end effector.
FIG. 72 is a side cross-sectional view of one embodiment of the surgical tool shown in FIG. 64, illustrating the jaw assembly of an end effector in a closed position, an I-beam member in a distally advanced position, and a rotary drive shaft engaging a shaft coupling for actuating rotation of the end effector.

FIG. 73 shows the I-beam member 620 in a fully proximal position and the jaw assembly 555 in an open position. In the position shown in FIG. 73, the first cam surface 626A is engaging a proximal portion of an arcuate-shaped anvil surface 628, which mechanically holds the first jaw member 602A open relative to the second jaw member 602B (FIGS. 69 and 71). Translation of the I-beam member 620 distally in a longitudinal direction (labeled direction L in FIGS. 64 and 66-74) results in sliding engagement of the first cam surface 626A with the length of the arcuate-shaped anvil surface 628, which cams first jaw member 602A toward second jaw member 602B until the first cam surface 626A is engaging a distal portion of the arcuate-shaped anvil surface 628. After the distal translation of the I-beam member 620 for a predetermined distance, the first cam surface 626A engages a distal portion of the arcuate-shaped anvil surface 628 and the jaw assembly is in the closed position (FIG. 74). Thereafter, the I-beam member 620 can be further translated distally in order to transect tissue clamped between the first jaw member 602A and the second jaw member 602B when in the closed position.

During distal translation of the I-beam member 620 after closure of the jaw assembly, the first and second cam surfaces 626A and 626B of the first and second I-beam flanges 622A and 622B slidably engage the opposed surfaces of the first and second channel flanges 605A and 605B, respectively. In this manner, the I-beam member is advanced distally through the first and second channels 601A and 601B of the first and second jaw members 602A and 602B.

The distal, or leading, end of the I-beam member 620 comprises a cutting member 625, which may be a sharp edge or blade configured to cut through clamped tissue during a distal translation stroke of the I-beam member, thereby transecting the tissue. FIGS. 72 and 70 show the I-beam member 620 in a fully distal position after a distal translation stroke. After a distal translation stroke, the I-beam member 620 may be proximally retracted back to the longitudinal position shown in FIG. 74 in which the jaw assembly remains closed, clamping any transected tissue between the first jaw member 602A and the second jaw member 602B. Further retraction of the I-beam member to the fully proximal position (FIGS. 69, 71, and 73) will result in engagement of the first cam surface 626A and the proximal portion of the anvil surface 628, which cams the first jaw member 602A away from the second jaw member 602B, opening the jaw assembly 555.

Before, during, and/or after the I-beam member 620 is advanced through tissue clamped between the first jaw member 602A and the second jaw member 602B, electrical current can be supplied to electrodes located in the first and/or second jaw members 602A and 602B in order to weld/fuse the tissue, as described in greater detail in this specification. For example, electrodes may be configured to deliver RF energy to tissue clamped between the first jaw member 602A and the second jaw member 602B when in a closed position to weld/fuse the tissue.

Distal and proximal translation of the I-beam member 620 between a proximally retracted position (FIGS. 64, 66-69, 71, and 73), an intermediate position (FIG. 74), and a distally advanced position (FIGS. 70 and 72) may be accomplished with a suitable translation actuation mechanism. Referring to FIGS. 65-72, the I-beam member 620 is connected to a threaded rotary drive member 604. A threaded rotary drive nut 606 is threaded onto the threaded rotary drive member 604. The threaded rotary drive nut 606 is seated in the proximal portion 603 of the second jaw member 602B. The threaded rotary drive nut 606 is mechanically constrained from translation in any direction, but the threaded rotary drive nut 606 is rotatable within the proximal portion 603 of the second jaw member 602B. Therefore, given the threaded engagement of the rotary drive nut 606 and the threaded rotary drive member 604, rotational motion of the rotary drive nut 606 is transformed into translational motion of the threaded rotary drive member 604 in the longitudinal direction and, in turn, into translational motion of the I-beam member 620 in the longitudinal direction.

The threaded rotary drive member 604 is threaded through the rotary drive nut 606 and is located inside a lumen of a rotary drive shaft 630. The threaded rotary drive member 604 is not attached or connected to the rotary drive shaft 630. The threaded rotary drive member 604 is freely movable within the lumen of the rotary drive shaft 630 and will translate within the lumen of the rotary drive shaft 630 when driven by rotation of the rotary drive nut 606. The rotary drive shaft 630 comprising the threaded rotary drive member 604 located within the lumen of the rotary drive shaft 630 forms a concentric rotary drive shaft/screw assembly that is located in the lumen of the shaft assembly 560.

Figure 65:
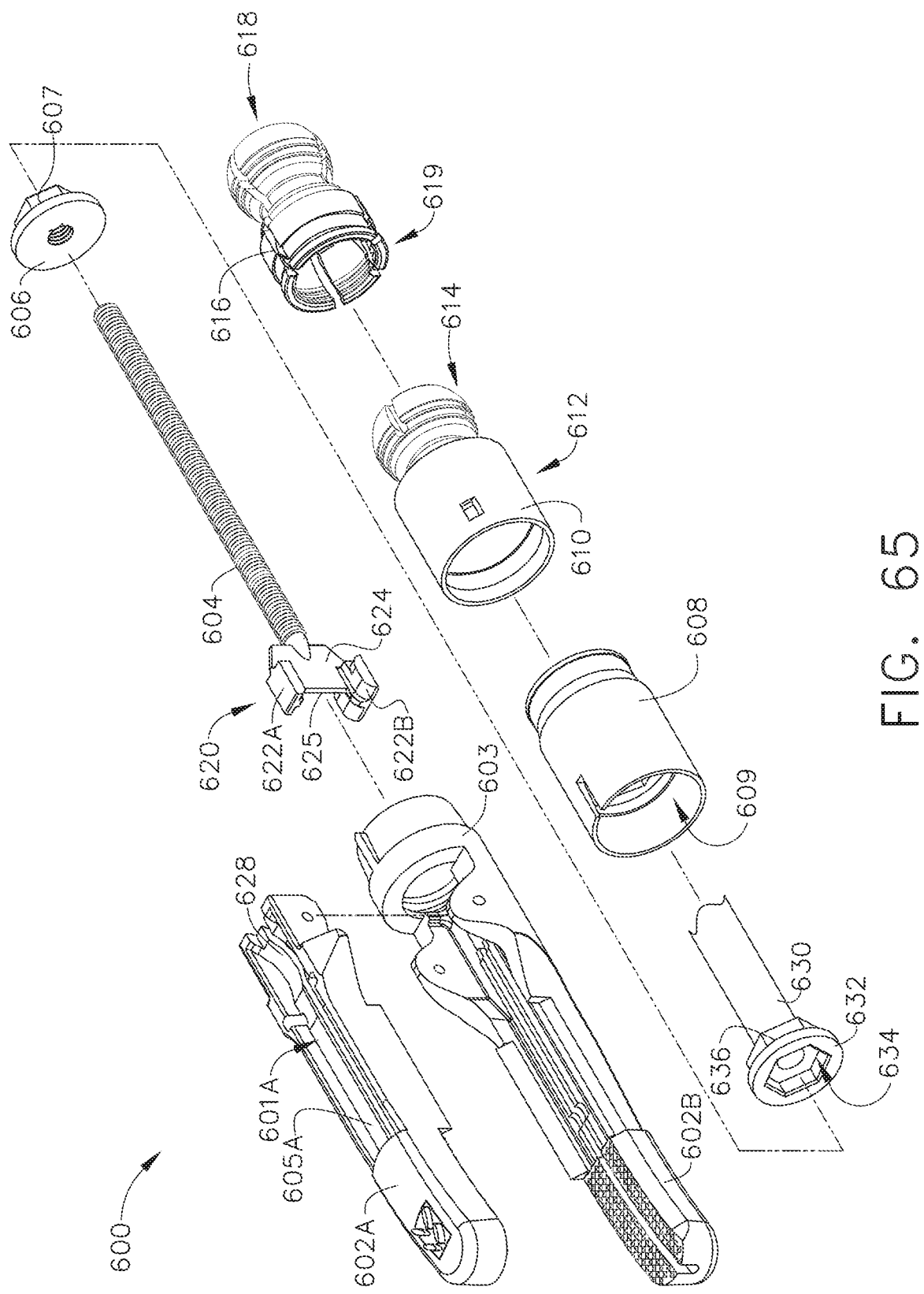
FIG. 65 is an exploded perspective view of various components of one embodiment of the surgical tool shown in FIG. 64.
Figure 66:
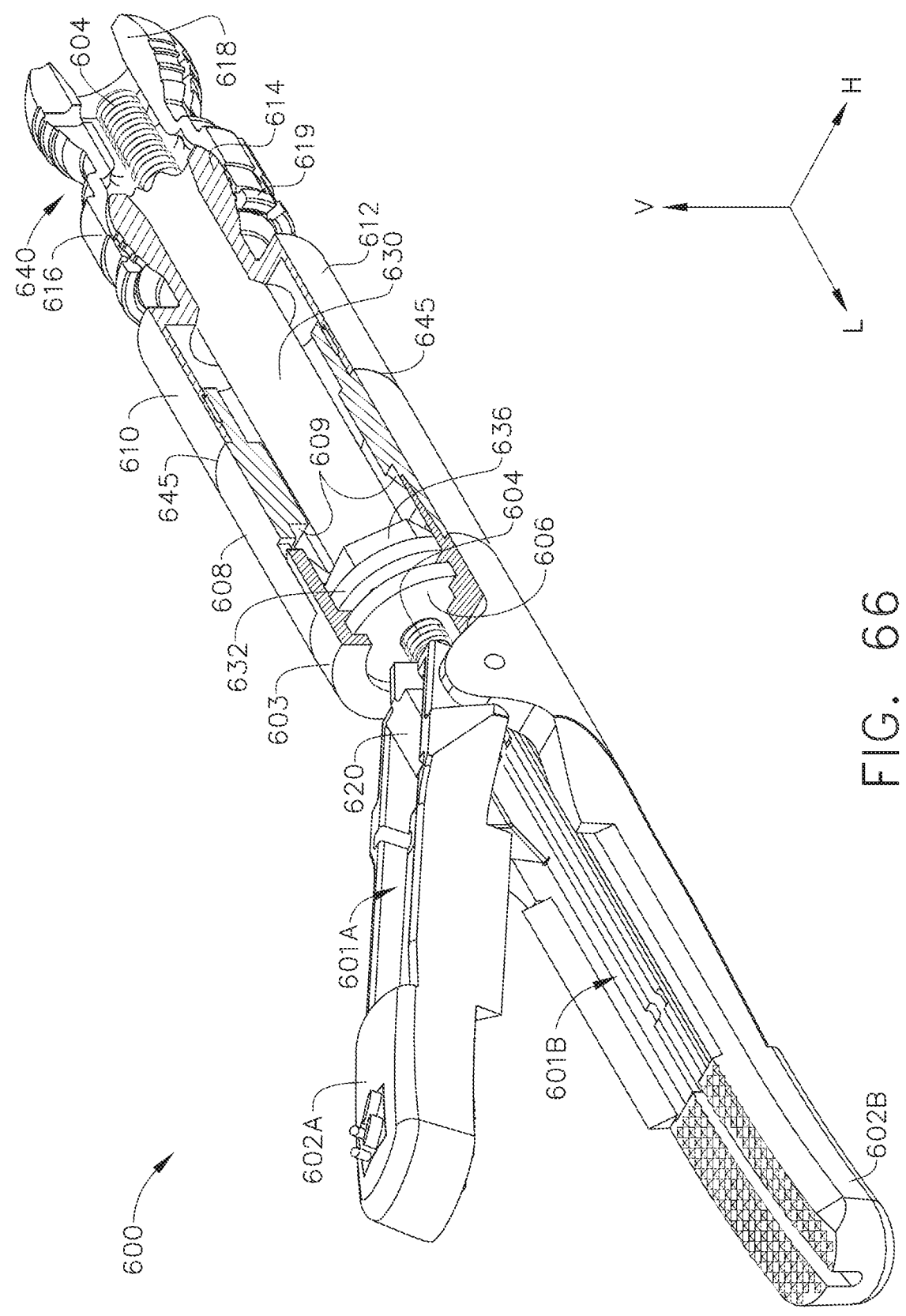
FIG. 66 is a partial cross-sectional perspective view of one embodiment of the surgical tool shown in FIG. 64, illustrating a rotary drive shaft engaging a rotary drive nut for actuating translation of an I-beam member and closure of a jaw assembly of an end effector.
Figure 67:
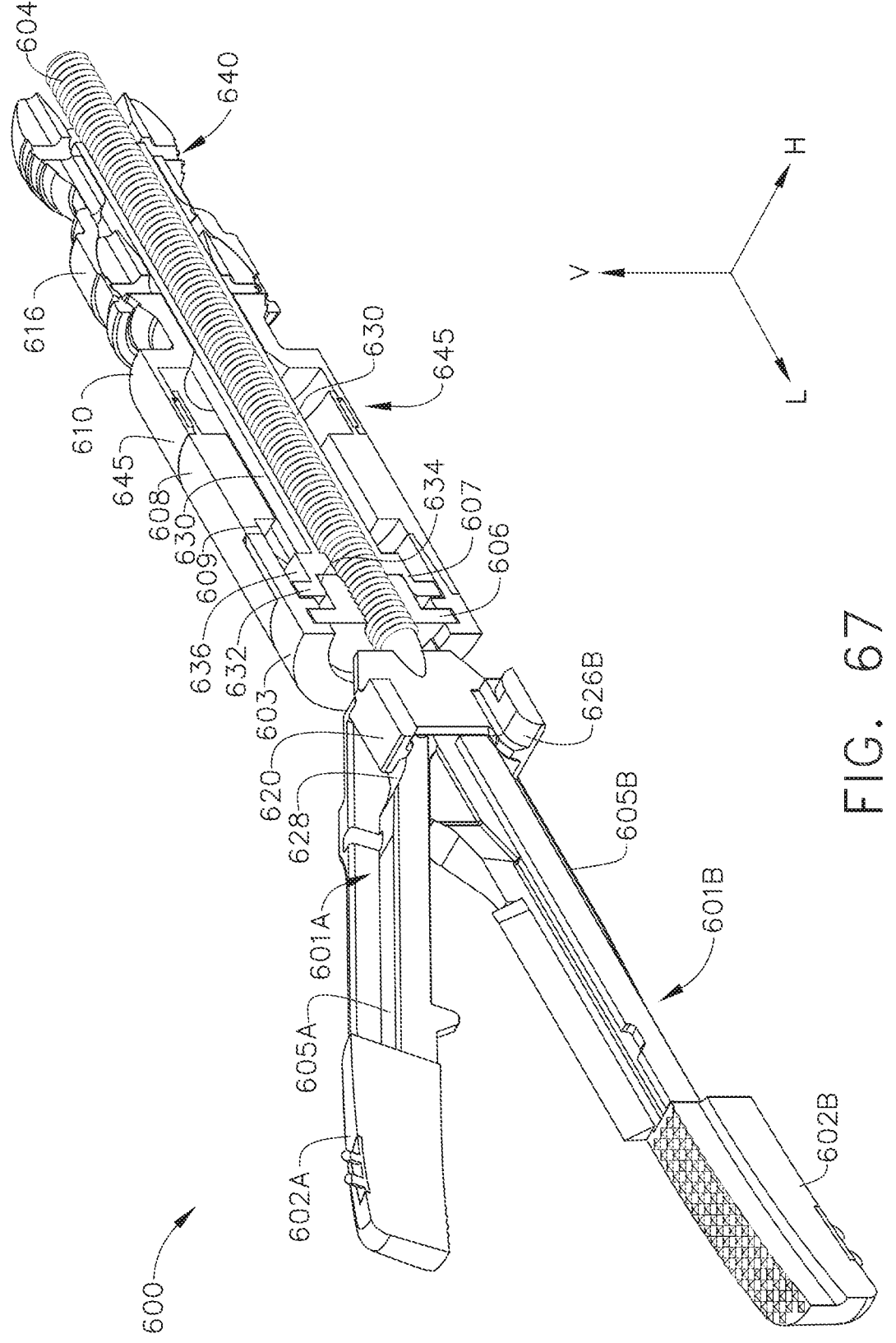
FIG. 67 is a cross-sectional perspective view of one embodiment of the surgical tool shown in FIG. 64, illustrating a rotary drive shaft engaging a rotary drive nut for actuating translation of an I-beam member and closure of a jaw assembly of an end effector.
Figure 68:
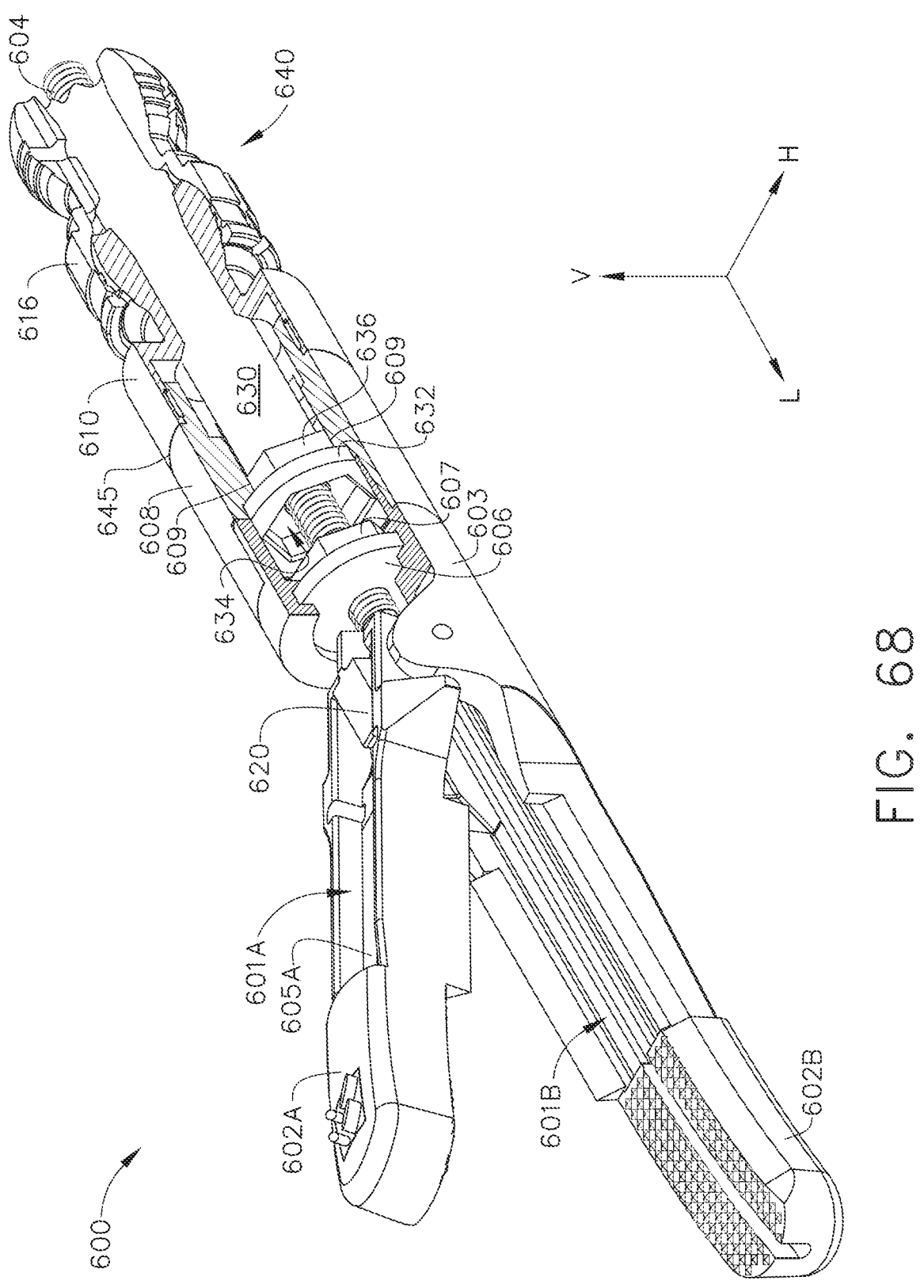
FIG. 68 is a partial cross-sectional perspective view of one embodiment of the surgical tool shown in FIG. 64, illustrating a rotary drive shaft engaging a shaft coupling for actuating rotation of an end effector.
Figures 69, 70:
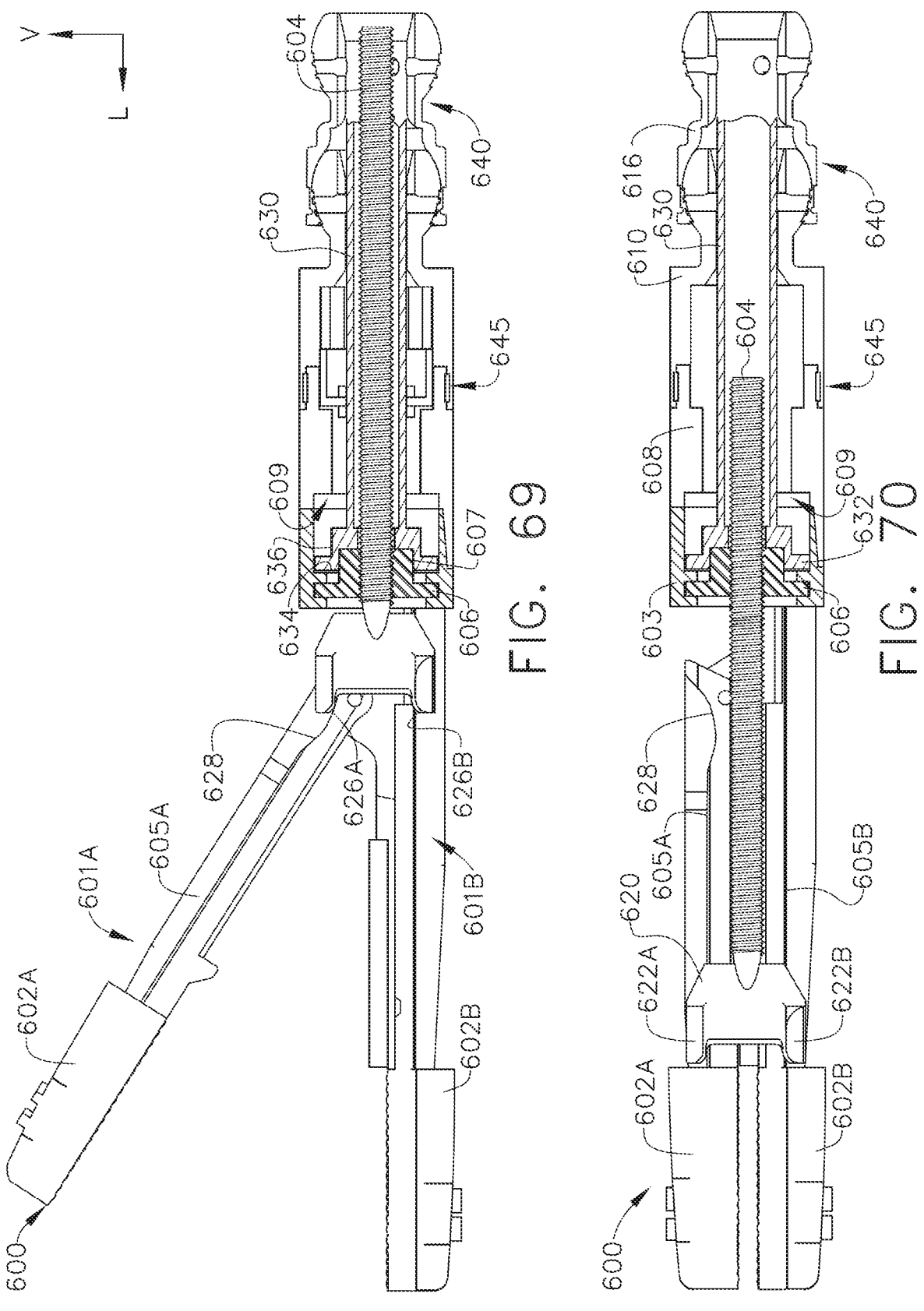
FIG. 69 is a side cross-sectional view of one embodiment of the surgical tool shown in FIG. 64, illustrating the jaw assembly of an end effector in an open position, an I-beam member in a proximally retracted position, and a rotary drive shaft engaging a rotary drive nut for actuating translation of the I-beam member and closure of the jaw assembly of the end effector.
FIG. 70 is a side cross-sectional view of one embodiment of the surgical tool shown in FIG. 64, illustrating the jaw assembly of an end effector in a closed position, an I-beam member in a distally advanced position, and a rotary drive shaft engaging a rotary drive nut for actuating translation of the I-beam member and opening of the jaw assembly of the end effector.

As shown in FIG. 65, the end effector drive housing 608, the end effector connector tube 610, and the intermediate articulation tube segment 616, which together comprise the shaft assembly 560, have open lumens and, therefore, the shaft assembly has a lumen, as shown in FIGS. 66-68. Referring again to FIGS. 66-68, the concentric rotary drive shaft/threaded rotary drive member assembly is located within the lumen of the shaft assembly 560 and passes through the end effector drive housing 608, the end effector connector tube 610, and the intermediate articulation tube segment 616. Although not shown in FIGS. 66-68, at least the rotary drive shaft 630 passes through a lumen of the distal outer tube portion 642 and is operably coupled to a driving mechanism that provides rotational and axial translational motion to the rotary drive shaft 630. For example, in some embodiments, the surgical tool 600 may be operably coupled through the shaft assembly 560 to a robotic surgical system that provides rotational motion and axial translational motion to the rotary drive shaft 630, such as, for example, the robotic surgical systems described in connection with FIGS. 5 and 16-21. For example, the rotary drive shaft 630 may be operably coupled, through the shaft assembly 560, to the proximal drive shaft segment 380 described herein above. Also, in some embodiments, the surgical tool 600 may be utilized in conjunction with a hand-held surgical device, such as the device described herein above with respect to FIGS. 46-63. For example, the rotary drive shaft 630 may be operably coupled, though the shaft assembly 560, to the proximal drive shaft segment 380' described herein above.

The rotary drive shaft 630 comprises a rotary drive head 632. The rotary drive head 632 comprises a female hex coupling portion 634 on the distal side of the rotary drive head 632, and the rotary drive head 632 comprises a male hex coupling portion 636 on the proximal side of the rotary drive head 632. The distal female hex coupling portion 634 of the rotary drive head 632 is configured to mechanically engage with a male hex coupling portion 607 of the rotary drive nut 606 located on the proximal side of the rotary drive nut 606. The proximal male hex coupling portion 636 of the rotary drive head 632 is configured to mechanically engage with a female hex shaft coupling portion 609 of the end effector drive housing 608.

Referring to FIGS. 66, 67, 69, and 70, the rotary drive shaft 630 is shown in a fully distal axial position in which the female hex coupling portion 634 of the rotary drive head 632 is mechanically engaged with the male hex coupling portion 607 of the rotary drive nut 606. In this configuration, rotation of the rotary drive shaft 630 actuates rotation of the rotary drive nut 606, which actuates translation of the threaded rotary drive member 604, which actuates translation of the I-beam member 620. The orientation of the threading of the threaded rotary drive member 604 and the rotary drive nut 606 may be established so that either clockwise or counterclockwise rotation of the rotary drive shaft 630 will actuate distal or proximal translation of the threaded rotary drive member 604 and I-beam member 620. In this manner, the direction, speed, and duration of rotation of the rotary drive shaft 630 can be controlled in order to control the direction, speed, and magnitude of the longitudinal translation of the I-beam member 620 and, therefore, the closing and opening of the jaw assembly and the transection stroke of the I-beam member along the first and second channels 601A and 601B, as described above.

Referring to FIG. 69, for example, rotation of the rotary drive shaft 630 in a clockwise direction (as viewed from a proximal-to-distal vantage point) actuates clockwise rotation of the rotary drive nut 606, which actuates distal translation of the threaded rotary drive member 604, which actuates distal translation of the I-beam member 620, which actuates closure of the jaw assembly and a distal transection stroke of the I-beam member 620/cutting member 625. Referring to FIG. 70, for example, rotation of the rotary drive shaft 630 in a counterclockwise direction (as viewed from a proximal-to-distal vantage point) actuates counterclockwise rotation of the rotary drive nut 606, which actuates proximal translation of the threaded rotary drive member 604, which actuates proximal translation of the I-beam member 620, which actuates a proximal return stroke of the I-beam member 620/cutting member 625 and opening of the jaw assembly. In this manner, the rotary drive shaft 630 may be used to independently actuate the opening and closing of the jaw assembly and the proximal-distal transection stroke of the I-beam 620/cutting member 625.

Referring to FIGS. 68, 71, and 72, the rotary drive shaft 630 is shown in a fully proximal axial position in which the male hex coupling portion 636 of the rotary drive head 632 is mechanically engaged with the female hex shaft coupling portion 609 of the end effector drive housing 608. In this configuration, rotation of the rotary drive shaft 630 actuates rotation of the head portion 556 of the surgical tool 600 about rotation joint 645, including rotation of the end effector 550 and the end effector drive housing 608. In this configuration, the portion of the surgical tool 600 that is distal to the head rotation joint 645 (i.e., the head portion 556 of the surgical tool 600, comprising the end effector 550 and the end effector drive housing 608) rotates with rotation of the rotary drive shaft 630, and the portion of the surgical tool that is proximal to the head rotation joint 645 (e.g., the end effector connector tube 610, the intermediate articulation tube segment 616, and the distal outer tube portion 642) does not rotate with rotation of the rotary drive shaft 630. It will be appreciated that a desired rotation speed of the rotary drive shaft 630 to drive the rotary drive nut 606 may be greater than a desired rotational speed for rotating the head portion 556. For example, the rotary drive shaft 630 may be driven by a motor (not shown) that is operable at different rotary speeds.

Referring to FIG. 71, for example, rotation of the rotary drive shaft 630 in a clockwise direction (as viewed from a proximal-to-distal vantage point) actuates clockwise rotation of the end effector 550 and the end effector drive housing 608 (i.e., the head portion 556 of the surgical tool 600) with the jaw assembly 555 in an open position. Rotation of the rotary drive shaft 630 in a counterclockwise direction (as viewed from a proximal-to-distal vantage point) actuates counterclockwise rotation of the end effector 550 and the end effector drive housing 608 with the jaw assembly 555 in an open position. Referring to FIG. 72, for example, rotation of the rotary drive shaft 630 in a clockwise direction (as viewed from a proximal-to-distal vantage point) actuates clockwise rotation of the end effector 550 and the end effector drive housing 608 with the jaw assembly 555 in a closed position. Rotation of the rotary drive shaft 630 in a counterclockwise direction (as viewed from a proximal-to-distal vantage point) actuates counterclockwise rotation of the end effector 550 and the end effector drive housing 608 with the jaw assembly 555 in a closed position. Although not shown, it is understood that the I-beam member 620 may be located in an intermediate position where the jaw assembly is closed but the I-beam is not fully distally advanced (see, e.g., FIG. 74) when the rotary drive shaft 630 is in a fully proximal axial position and the male hex coupling portion 636 of the rotary drive head 632 is mechanically engaged with the female hex shaft coupling portion 609 of the end effector drive housing 608 to actuate rotation of the head portion of the surgical tool.

Thus, the rotary drive shaft 630 may be used to independently actuate the opening and closing of the jaw assembly, the proximal-distal transection stroke of the I-beam 620/cutting member 625, and the rotation of the head portion 556 of the surgical tool 600d.

In various embodiments, a surgical tool may comprise an end effector, a first actuation mechanism, and a second actuation mechanism. The surgical tool may also comprise a clutch member configured to selectively engage and transmit rotary motion to either the first actuation mechanism or the second actuation mechanism. For example, in various embodiments, a clutch member may comprise a rotary drive shaft comprising a rotary drive head as described, for example, in connection with FIGS. 64-72. In various embodiments, a first actuation mechanism may comprise an I-beam member connected to a threaded rotary drive member threaded through a rotary drive nut, as described, for example, in connection with FIGS. 64-74, wherein the I-beam, the threaded rotary drive member, and the rotary drive nut are configured to actuate the closing and opening of a jaw assembly and/or the translation of a cutting member. In various embodiments, a second actuation mechanism may comprise a shaft coupling portion, as described, for example, in connection with FIGS. 64-72, wherein the shaft coupling portion is configured to actuate rotation of a head portion of a surgical tool.

In various embodiments, a surgical tool may comprise an end effector comprising a first jaw member, a second jaw member, and a first actuation mechanism configured to move the first jaw member relative to the second jaw member between an open position and a closed position. The surgical tool may also comprise a shaft assembly proximal to the surgical end effector. The surgical tool may also comprise a rotary drive shaft. The rotary drive shaft may be configured to transmit rotary motions and may also be selectively moveable between a first position and a second position relative to the shaft assembly. The rotary drive shaft may be configured to engage and selectively transmit the rotary motions to the first actuation mechanism when in the first position and the rotary drive shaft may be configured to disengage from the actuation mechanism when in the second position. For example, in various embodiments, the first actuation mechanism may comprise an I-beam member connected to a threaded rotary drive member threaded through a rotary drive nut, as described, for example, in connection with FIGS. 64-74, wherein the I-beam, the threaded rotary drive member, and the rotary drive nut are configured to actuate the closing and opening of a jaw assembly when the rotary drive shaft engages and selectively transmits rotary motion to the drive nut.

In various embodiments, a surgical tool may comprise a surgical end effector comprising a first jaw member, a second jaw member, and a closure mechanism configured to move the first jaw member relative to the second jaw member between an open position and a closed position. The surgical tool may also comprise a shaft assembly proximal to the surgical end effector, wherein the surgical end effector is configured to rotate relative to the shaft assembly. The surgical tool may also comprise a rotary drive shaft configured to transmit rotary motions, the rotary drive shaft selectively movable axially between a first position and a second position relative to the shaft assembly, wherein the rotary drive shaft is configured to apply the rotary motions to the closure mechanism when in the first axial position, and wherein the rotary drive shaft is configured to apply the rotary motions to the surgical end effector when in the second axial position. For example, in various embodiments, the first axial position may correspond to the rotary drive shaft being in a fully distal axial position in which a rotary drive head is mechanically engaged with a rotary drive nut as described, for example, in connection with FIGS. 64-72. In various embodiments, the second axial position may correspond to the rotary drive shaft being in a fully proximal axial position in which a rotary drive head is mechanically engaged with a shaft coupling portion of a shaft member as described, for example, in connection with FIGS. 64-72.

In various embodiments, a surgical tool comprising an end effector, a first actuation mechanism, and a second actuation mechanism, may further comprise a head locking mechanism. For example, referring to FIGS. 75-82, a multi-axis articulating and rotating surgical tool 650 comprises an end effector 570, a shaft assembly 580, and a head locking mechanism 590. The end effector 570 comprises a first jaw member 652A and a second jaw member 652B. The first jaw member 602A is movable relative to the second jaw member 602B between an open position (FIGS. 77 and 79) and a closed position (FIGS. 78 and 80) to clamp tissue between the first jaw member 652A and the second jaw member 652B. The surgical tool 650 is configured to independently articulate about an articulation joint in a vertical direction and a horizontal direction like the surgical tool 600 shown in FIGS. 64-72. The surgical tool 650 is also configured to independently rotate about a head rotation joint like the surgical tool 600 shown in FIGS. 64-72. The end effector 570 comprises an I-beam member 670 and a jaw assembly 575 comprising the first jaw member 652A, the second jaw member 652B, a proximal portion 653 of the second jaw member 652B, and a rotary drive nut 656 seated in the proximal portion 653.

The end effector 570 is coupled to a shaft assembly 580 comprising an end effector drive housing 658, an end effector connector tube 660, an intermediate articulation tube segment 666, and a surgical tool shaft member (not shown). The end effector 570 and the shaft assembly 580 together comprise the surgical tool 650. The end effector 570 may be removably coupled to the end effector drive housing 658 using a mechanism as described, for example, in connection with FIGS. 106-115. The end effector drive housing 608 is coupled to the end effector connector tube 660 through the head rotation joint. The end effector 570 and the end effector drive housing 658 together comprise a head portion 578 of the surgical tool 650. The head portion 578 of the surgical tool 650 is independently rotatable about the head rotation joint, as described in greater detail above in connection FIGS. 64-72 showing the surgical tool 600.

The end effector connector tube 660 is coupled to the intermediate articulation tube segment 666 through a ball-and-socket joint formed by the mutual engagement of the ball member of the end effector connector tube 660 and the ball socket of the intermediate articulation tube segment 666. The intermediate articulation tube segment 666 is coupled to a surgical tool shaft member through a ball-and-socket joint formed by the mutual engagement of the ball member of the intermediate articulation tube segment 616 and a ball socket of the surgical tool shaft member. The articulation joint comprises the end effector connector tube 660, the intermediate articulation tube segment 666, and the surgical tool shaft member. The independent vertical articulation and/or horizontal articulation of the surgical tool 650 about the articulation joint may be actuated, for example, using independently actuatable drive cables connected to the ball member of the end effector connector tube 660. This independent articulation functionality is described, for example, in connection with FIGS. 24-25. Robotic and hand-held apparatuses for allowing a clinician to initiate articulation functionality are described, for example, in connection with FIGS. 6, 16-21 and 46-50.

The movement of the first jaw member 652A relative to the second jaw member 652B is actuated using the same actuation mechanism described above in connection with FIGS. 73 and 74. Distal and proximal translation of the I-beam member 670 between a proximally retracted position (FIGS. 77 and 79), an intermediate position (see FIG. 74), and a distally advanced position (FIGS. 78 and 80) may be accomplished with a suitable translation actuation mechanism. Referring to FIGS. 75-80, the I-beam member 670 is connected to a threaded rotary drive member 654. A threaded rotary drive nut 656 is threaded onto the threaded rotary drive member 654. The threaded rotary drive nut 656 is seated in the proximal portion 653 of the second jaw member 652B. The threaded rotary drive nut 656 is mechanically constrained from translation in any direction, but is rotatable within the proximal portion 653 of the second jaw member 652B. Therefore, given the threaded engagement of the rotary drive nut 656 and the threaded rotary drive member 654, rotational motion of the rotary drive nut 656 is transformed into translational motion of the threaded rotary drive member 654 in the longitudinal direction and, in turn, into translational motion of the I-beam member 670 in the longitudinal direction.

The threaded rotary drive member 654 is threaded through the rotary drive nut 656 and is located inside a lumen of a rotary drive shaft 680. The threaded rotary drive member 654 is not attached or connected to the rotary drive shaft 680. The threaded rotary drive member 654 is freely movable within the lumen of the rotary drive shaft 680 and will translate within the lumen of the rotary drive shaft 680 when driven by rotation of the rotary drive nut 656. The rotary drive shaft 680 comprising the threaded rotary drive member 654 located within the lumen of the rotary drive shaft 680 forms a concentric rotary drive shaft/screw assembly that is located in the lumen of the shaft assembly 580.

Referring to FIGS. 77-80, the concentric rotary drive shaft/screw assembly is located within the lumen of the shaft assembly 560 and passes through the end effector drive housing 658, the end effector connector tube 660, and the intermediate articulation tube segment 666. Although not shown in FIGS. 77-80, at least the rotary drive shaft 680 passes through a lumen of the surgical tool shaft member and is operably coupled to a driving mechanism that provides rotary motion and axial translational motion to the rotary drive shaft 680. For example, in some embodiments, the surgical tool 650 may be operably coupled through the shaft assembly 580 to a robotic surgical system that provides rotary motion and axial translational motion to the rotary drive shaft 680, such as, for example, the robotic surgical systems described in connection with FIGS. 5 and 16-21. In some embodiments, for example, the surgical tool 650 may be operably coupled through the shaft assembly 580 to a hand-held surgical device that provides rotary motion and axial translational motion to the rotary drive shaft 680, such as, for example, the hand-held surgical devices described in connection with FIGS. 46-63. In some embodiments, the threaded rotary drive member 654 has a length that is less than the length of the rotary drive shaft 680 and, therefore, lies within only a distal portion of the rotary drive shaft 680.

The threaded rotary drive member 654 and the rotary drive shaft 680 are flexible so that the portions of the threaded rotary drive member 654 and the rotary drive shaft 680 that are located in the articulation joint can bend without damage or loss of operability during independent articulation of the surgical tool 650 about the articulation joint. Example configurations of the rotary drive shaft 680 are provided herein with reference to FIGS. 28-45.

The rotary drive shaft 680 comprises a rotary drive head 682. The rotary drive head 682 comprises a female hex coupling portion 684 on the distal side of the rotary drive head 682, and the rotary drive head 682 comprises a male hex coupling portion 686 on the proximal side of the rotary drive head 682. The distal female hex coupling portion 684 of the rotary drive head 682 is configured to mechanically engage with a male hex coupling portion 657 of the rotary drive nut 656 located on the proximal side of the rotary drive nut 656. The proximal male hex coupling portion 686 of the rotary drive head 682 is configured to mechanically engage with a female hex shaft coupling portion 659 of the end effector drive housing 658.

Figures 77, 78:
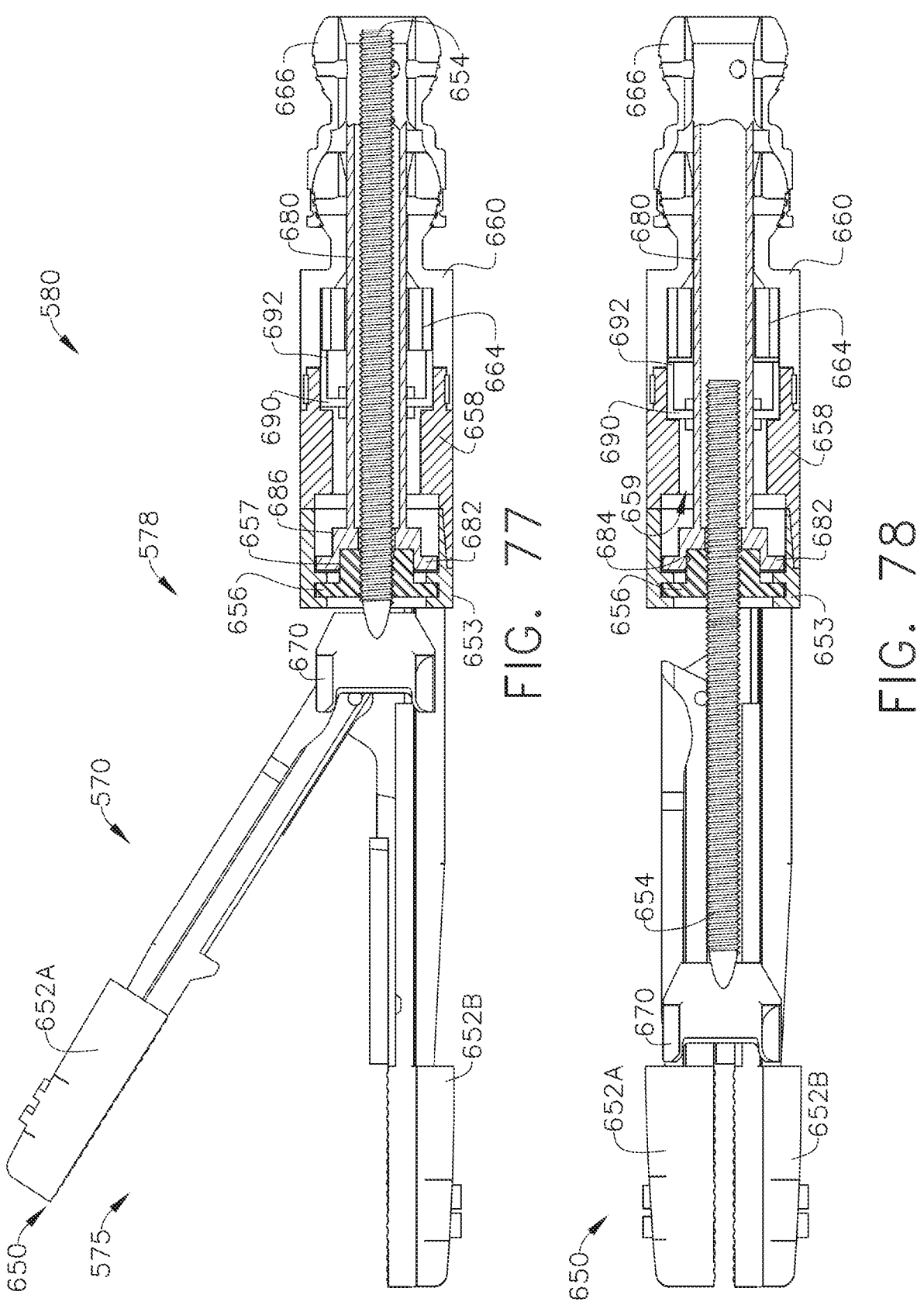
FIG. 77 is a side cross-sectional view of one embodiment of the surgical tool shown in FIG. 75, illustrating the jaw assembly of an end effector in an open position, an I-beam member in a proximally retracted position, a rotary drive shaft engaging a rotary drive nut for actuating translation of the I-beam member and closure of the jaw assembly of the end effector, and an engaged spline lock preventing rotation of the end effector.
FIG. 78 is a side cross-sectional view of one embodiment of the surgical tool shown in FIG. 75, illustrating the jaw assembly of an end effector in a closed position, an I-beam member in a distally advanced position, a rotary drive shaft engaging a rotary drive nut for actuating translation of the I-beam member and opening of the jaw assembly of the end effector, and an engaged spline lock preventing rotation of the end effector.
Figures 79, 80:
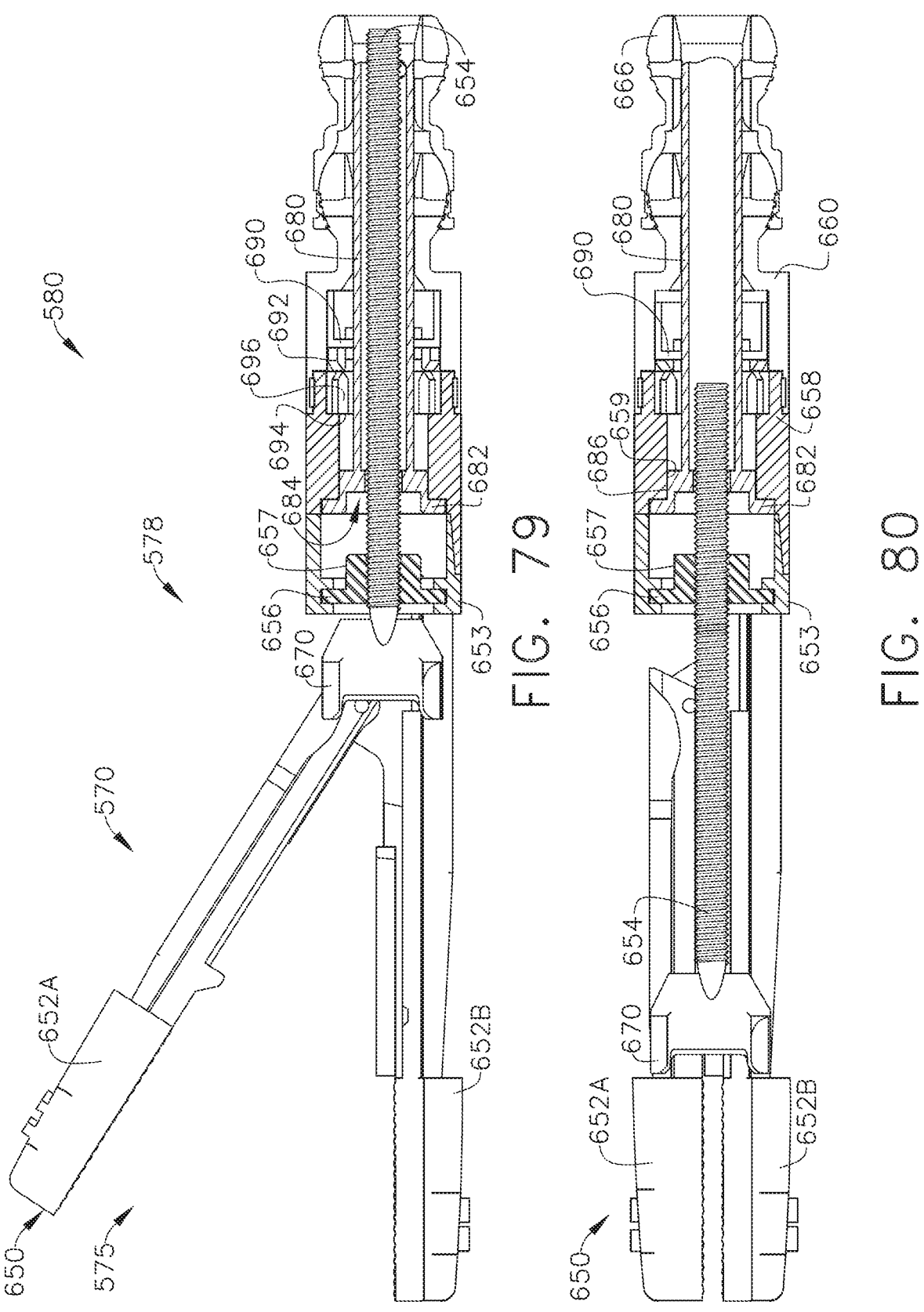
FIG. 79 is a side cross-sectional view of one embodiment of the surgical tool shown in FIG. 75, illustrating the jaw assembly of an end effector in an open position, an I-beam member in a proximally retracted position, a rotary drive shaft engaging a shaft coupling for actuating rotation of the end effector, and a disengaged spline lock allowing rotation of the end effector.
FIG. 80 is a side cross-sectional view of one embodiment of the surgical tool shown in FIG. 64, illustrating the jaw assembly of an end effector in a closed position, an I-beam member in a distally advanced position, a rotary drive shaft engaging a shaft coupling for actuating rotation of the end effector, and a disengaged spline lock allowing rotation of the end effector.

Referring to FIGS. 77 and 78, the rotary drive shaft 680 is shown in a fully distal axial position in which the female hex coupling portion 684 of the rotary drive head 682 is mechanically engaged with the male hex coupling portion 657 of the rotary drive nut 656. In this configuration, rotation of the rotary drive shaft 680 actuates rotation of the rotary drive nut 656, which actuates translation of the threaded rotary drive member 654, which actuates translation of the I-beam member 670. Referring to FIGS. 79 and 80, the rotary drive shaft 680 is shown in a fully proximal axial position in which the male hex coupling portion 686 of the rotary drive head 682 is mechanically engaged with the female hex shaft coupling portion 659 of the end effector drive housing 658. In this configuration, rotation of the rotary drive shaft 680 actuates rotation of the head portion 578 of the surgical tool 650 about rotation joint, including rotation of the end effector 570 and the end effector drive housing 658.

Figure 75:
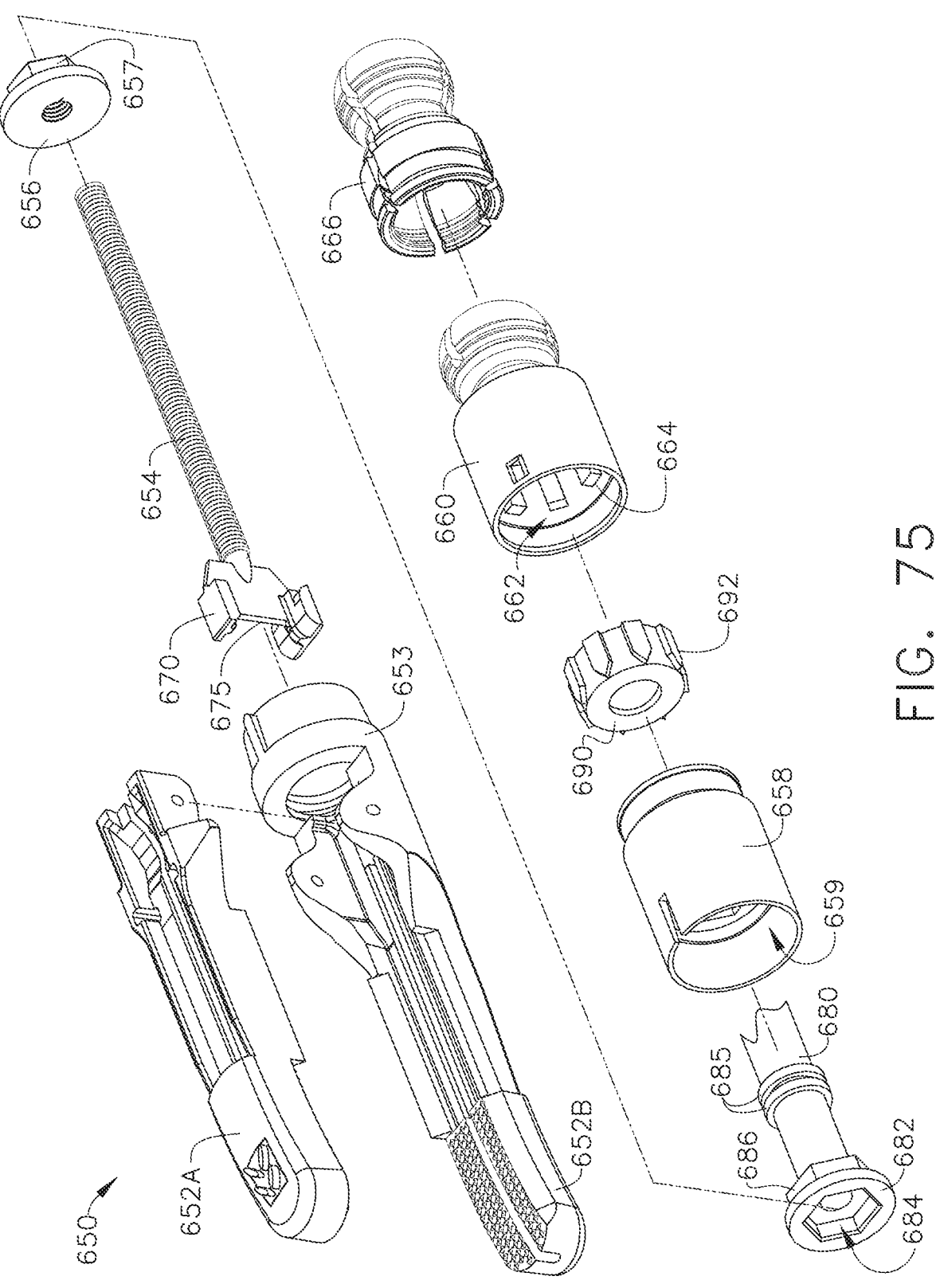
FIG. 75 is an exploded view of the components comprising an embodiment of a multi-axis articulating and rotating surgical tool comprising a head locking mechanism.
Figure 76:
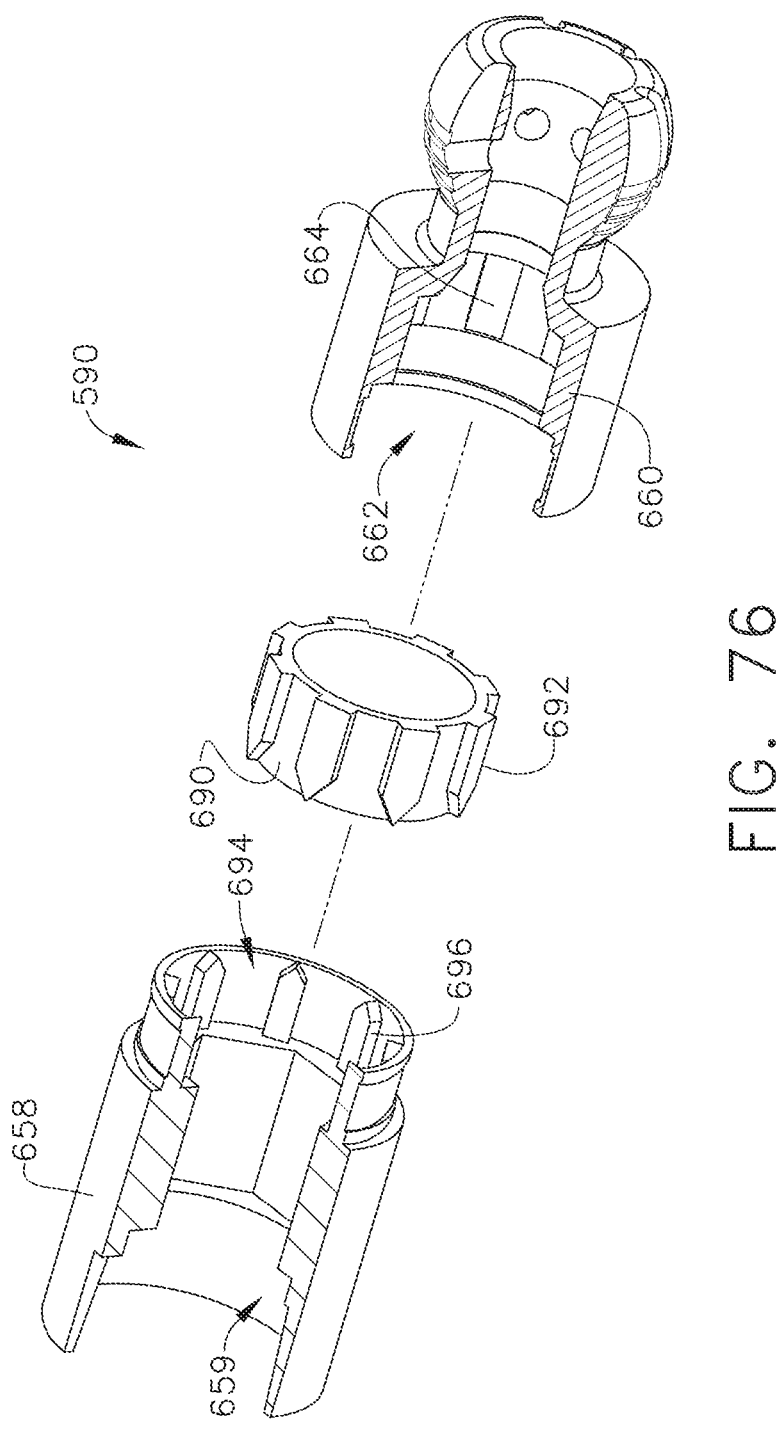
FIG. 76 is an exploded view of spline lock components of one embodiment of the head locking mechanism of the surgical tool illustrated in FIG. 75.

The rotary drive shaft 680 also comprises a spline lock 690. The spline lock 690 is coupled to the rotary drive shaft 680 using shaft flanges 685. The spline lock 690 is mechanically constrained from translation in any direction by the rotary drive shaft 680 and the shaft flanges 685, but the spline lock 690 is freely rotatable about the rotary drive shaft 680. The spline lock 690 comprises spline members 692 disposed circumferentially around the external surface of the spline lock 690 and oriented co-axially with the shaft assembly 580. As shown in FIGS. 75 and 76, the spline lock 690 is located at the rotational joint formed by the coupling of the end effector drive housing 658 and the end effector connector tube 660. The end effector drive housing 658 comprises a spline coupling portion 694 comprising spline members 696 disposed circumferentially around the internal surface of the end effector drive housing 658 and oriented co-axially with the shaft assembly 580. The end effector connector tube 660 comprises a spline coupling portion 662 comprising spline members 664 disposed circumferentially around the internal surface of the end effector connector tube 660 and oriented co-axially with the shaft assembly 580.

Figures 81, 82:
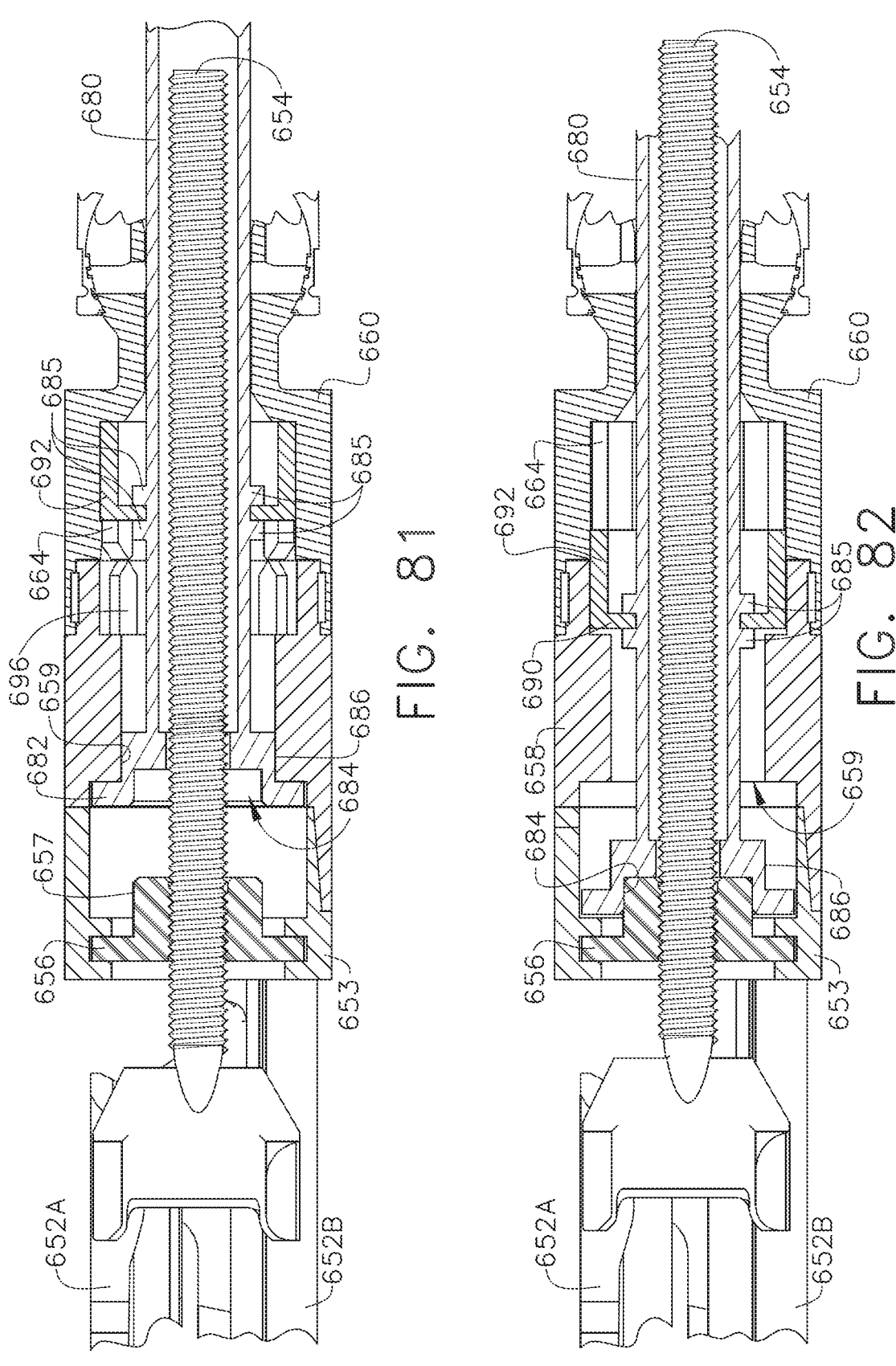
FIG. 81 is a side cross-sectional detail view of one embodiment of the surgical tool shown in FIG. 80.
FIG. 82 is a side cross-sectional detail view of one embodiment of the surgical tool shown in FIG. 78.

The spline members 692, 696, and 664 of the spline lock 690, the end effector drive housing 658, and the end effector connector tube 660, respectively, are configured to mechanically engage with each other when the rotary drive shaft 680 is in a fully distal axial position in which the female hex coupling portion 684 of the rotary drive head 682 is mechanically engaged with the male hex coupling portion 657 of the rotary drive nut 656 to drive rotation of the rotary drive nut 656 and translation of the threaded rotary drive member 654 and the I-beam member 670 (FIGS. 77, 78, and 82). The mechanical engagement of the respective spline members 692, 696, and 664 locks the end effector drive housing 658 into position with the end effector connector tube 660, thereby locking the rotational joint and preventing rotation of the head portion 578 of the surgical tool 650. Because the spline lock 690 is freely rotatable about the rotary drive shaft 680, the mechanical engagement of the respective spline members 692, 696, and 664 does not prevent the rotary drive shaft 680 from actuating the rotary drive nut 656, the threaded rotary drive member 654, and the I-beam member 670.

When the rotary drive shaft 680 is in a fully proximal axial position in which the male hex coupling portion 686 of the rotary drive head 682 is mechanically engaged with the female hex shaft coupling portion 659 of the end effector drive housing 658 to drive rotation of the head portion 578 of the surgical tool 650, the spline lock 690 is completely retracted into the lumen of the end effector connector tube 660 and the spline lock 690 is completely disengaged from the spline coupling portion 694 of the end effector drive housing 658. (FIGS. 79, 80, and 81). In this configuration, the spline members 692 of the spline lock 690 and the spline members 664 of the end effector connector tube 660 are completely engaged, and the spline members 692 of the spline lock 690 and the spline members 696 of the end effector drive housing 658 are completely disengaged. The mechanical disengagement of the spline members 692 of the spline lock 690 and the spline members 696 of the end effector drive housing 658 when the rotary drive shaft 680 is in a fully proximal axial position unlocks the end effector drive housing 658 from the end effector connector tube 660, thereby unlocking the rotational joint and permitting rotation of the head portion 578 of the surgical tool 650. Because the spline lock 690 is freely rotatable about the rotary drive shaft 680, the mechanical engagement of spline members 692 of the spline lock 690 and the spline members 664 of the end effector connector tube 660 does not prevent the rotary drive shaft 680 from actuating the rotation of the head portion 578 of the surgical tool 650.

The head locking mechanism 590 ensures that the head portion 578 of the surgical tool 650 does not rotate when the rotary drive shaft 680 is in a fully distal axial position engaging the rotary drive nut 656 to drive actuation of the jaw closure mechanism and/or the I-beam translation mechanism as described above (FIGS. 77, 78, and 82). The head locking mechanism 590 ensures that the head portion 578 of the surgical tool 650 is freely rotatable when the rotary drive shaft 680 is in a fully proximal axial position engaging the shaft coupling portion 659 of the end effector drive housing 658 to drive actuation of head rotation as described above (FIGS. 79, 80, and 81).

Referring to FIGS. 77 and 78, for example, rotation of the rotary drive shaft 680 actuates rotation of the rotary drive nut 656, which actuates distal or proximal translation of the threaded rotary drive member 654 (depending on the direction of rotary motion of the rotary drive shaft 680), which actuates distal or proximal translation of the I-beam member 670, which actuates the closing and opening of the jaw assembly 575, and distal and proximal transection strokes of the I-beam member 670/cutting member 675. Simultaneously, the spline lock 690 engages both the end effector drive housing 658 and the end effector connector tube 660 to prevent unintended head rotation.

Referring to FIGS. 79 and 80, for example, rotation of the rotary drive shaft 680 actuates rotation of the end effector drive housing 658, which actuates rotation of the end effector 570. Simultaneously, the spline lock 690 is disengaged both the end effector drive housing 658 and does not prevent head rotation. Thus, the rotary drive shaft 680 may be used to independently actuate the opening and closing of the jaw assembly 575, the proximal-distal transection stroke of the I-beam 670/cutting member 675, and the rotation of the head portion 578 of the surgical tool 650.

In various embodiments, an end effector, such as the end effectors 550 and 570 shown in FIGS. 64-82, may comprise first and second jaw members comprising a first and second distal textured portions, respectively. The first and second distal textured portions of the first and second jaw members of an end effector may be opposed and may allow the end effector to grip, pass, and/or manipulate surgical implements such as needles for suturing tissue, in addition to gripping tissue, for example, during dissection operations. In some embodiments, the distal textured portions may also be electrodes configured, for example, to deliver RF energy to tissue during dissection operations. This gripping, passing, manipulating, and/or dissecting functionality is described, for example, in connection with FIGS. 153-168.

In various embodiments, an end effector, such as the end effectors 550 and 570 shown in FIGS. 64-82, may comprise first and second jaw members comprising first and second gripping portions disposed on outwardly facing surfaces of the first and second jaw members. The first and second gripping portions of the first and second jaw members of an end effector may function to aid in tissue dissection as described, for example, in connection with FIGS. 116-131.

In various embodiments, an end effector, such as the end effectors 550 and 570 shown in FIGS. 64-82, may comprise at least one electrode disposed on at least one tissue-contacting surface of at least one jaw member. The electrodes may be configured, for example, to deliver RF energy to tissue clamped between the jaw members when in a closed position to weld/fuse the tissue, which in some embodiments, may also be transected by translating an I-beam member comprising a cutting member. In some embodiments, a second jaw member may also comprise an offset electrode located at the distal tip of the jaw member, the electrode configured to deliver RF energy to tissue during dissection operations, for example. This electrode functionality is described, for example, in connection with 153-168.

In various embodiments, an end effector, such as the end effectors 550 and 570 shown in FIGS. 64-82, may comprise jaw members comprising angled tissue-contacting surfaces as described, for example, in connection with FIGS. 132-142.

Figures 83, 84:
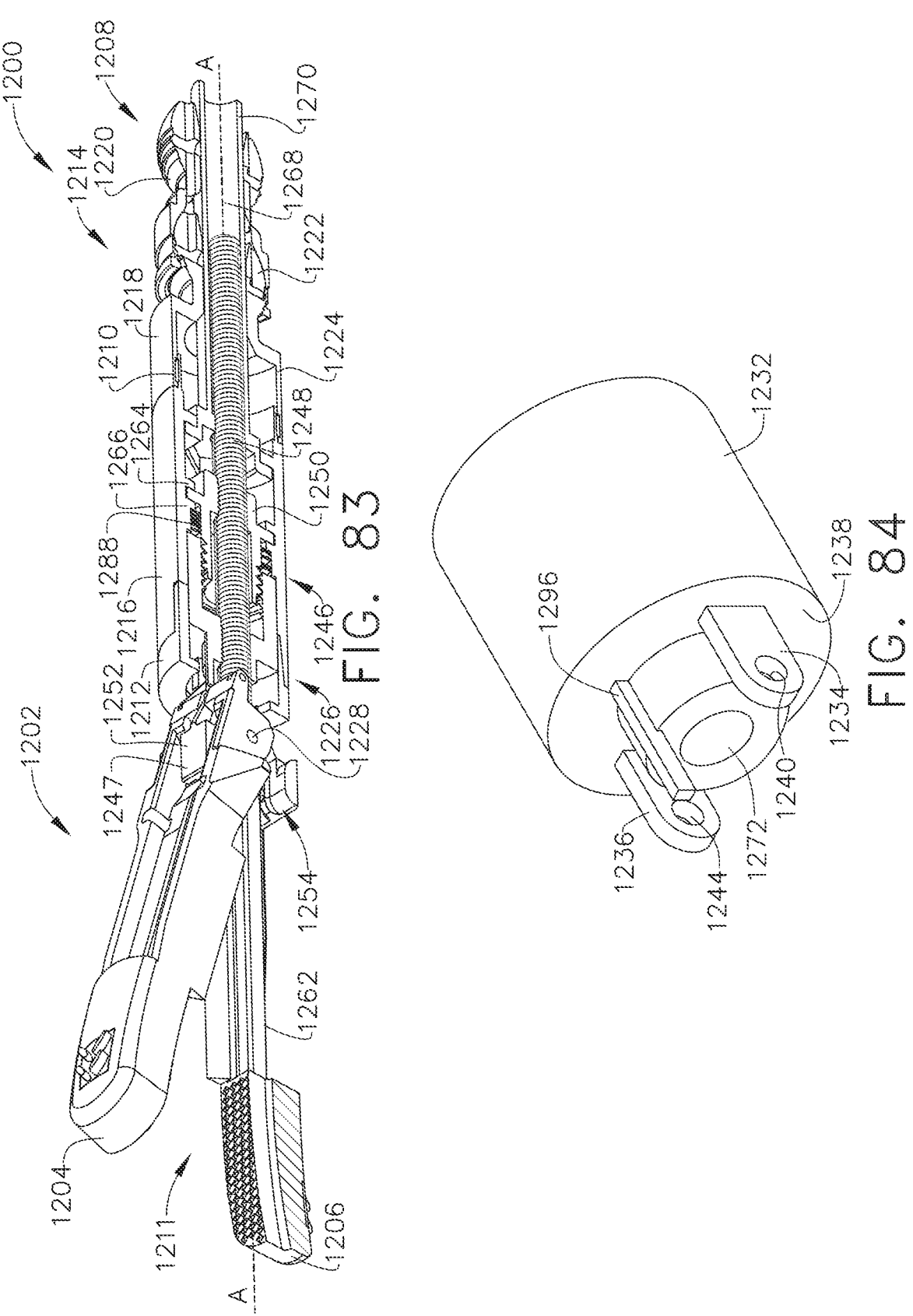
FIG. 83 is a cross sectional perspective view of a surgical tool having first and second jaw members in accordance with certain embodiments described herein.
FIG. 84 is prospective view of a closure nut of one embodiment of the surgical tool of FIG. 83.

Referring to FIGS. 83-91, a multi-axis articulating and rotating surgical tool 1200 comprises an end effector 1202 including a jaw assembly 1211 comprising a first jaw member 1204 and a second jaw member 1206. The first jaw member 1204 is movable relative to the second jaw member 1206 between an open position and a closed position to clamp tissue between the first jaw member 1204 and the second jaw member 1206. The surgical tool 1200 is configured to independently articulate about an articulation joint 1208. As described above, the surgical tool 1200 is also configured to independently rotate about a head rotation joint 1210. Referring primarily to FIG. 83, the end effector 1202 further comprises a proximal shaft portion 1212.

The end effector 1202 is coupled to a shaft assembly 1214 comprising an end effector drive housing 1216, an end effector connector tube 1218, an intermediate articulation tube segment 1220, and a distal outer tube portion (not shown in FIGS. 83-91). The end effector 1202 and the shaft assembly 1214 together can comprise the surgical tool 1200.

The end effector 1202 may be removably coupled to the end effector drive housing 1216 using a mechanism as described, for example, in connection with FIGS. 106-115. The end effector connector tube 1218 comprises a cylindrical portion 1222 and a ball portion 1224. The end effector drive housing 1216 is coupled to the cylindrical portion 1222 of the end effector connector tube 1218 through the head rotation joint 1210. The end effector 1202 and the end effector drive housing 1216 together comprise a head portion of the surgical tool 1200. The head portion of the surgical tool 1200 is independently rotatable about the head rotation joint 1210.

Figures 85, 86:
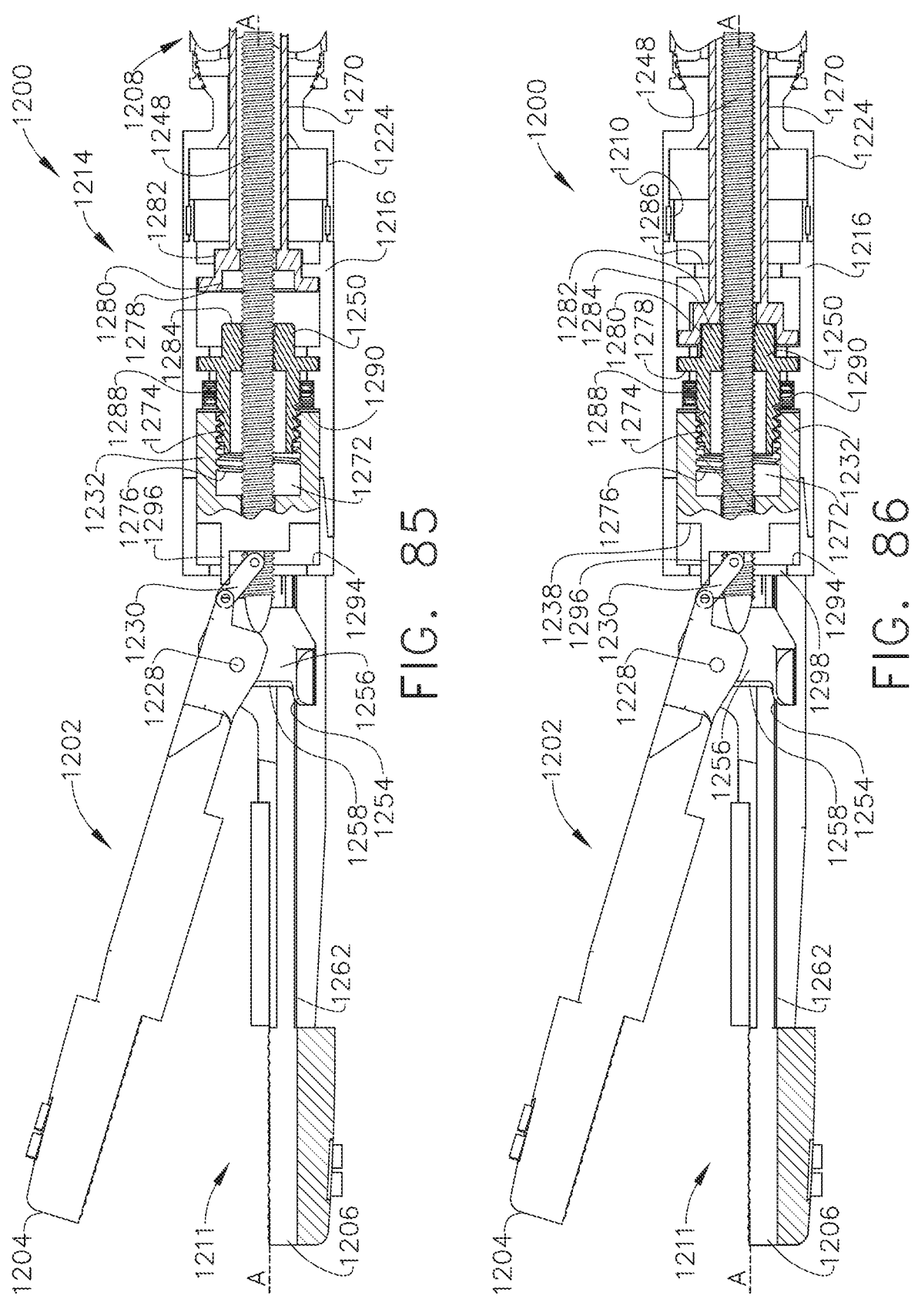
FIG. 85 is a cross sectional elevation view of one embodiment of the surgical tool of FIG. 83 wherein the first jaw member and the second jaw member are in an at least partially open position, and wherein the rotary drive shaft is operably disengaged with the rotary drive nut.
FIG. 86 is a cross sectional elevation view of one embodiment of the surgical tool of FIG. 83 wherein the first jaw member and the second jaw member are in an at least partially open position, and wherein the rotary drive shaft is operably engaged with the rotary drive nut.
Figures 87, 88:
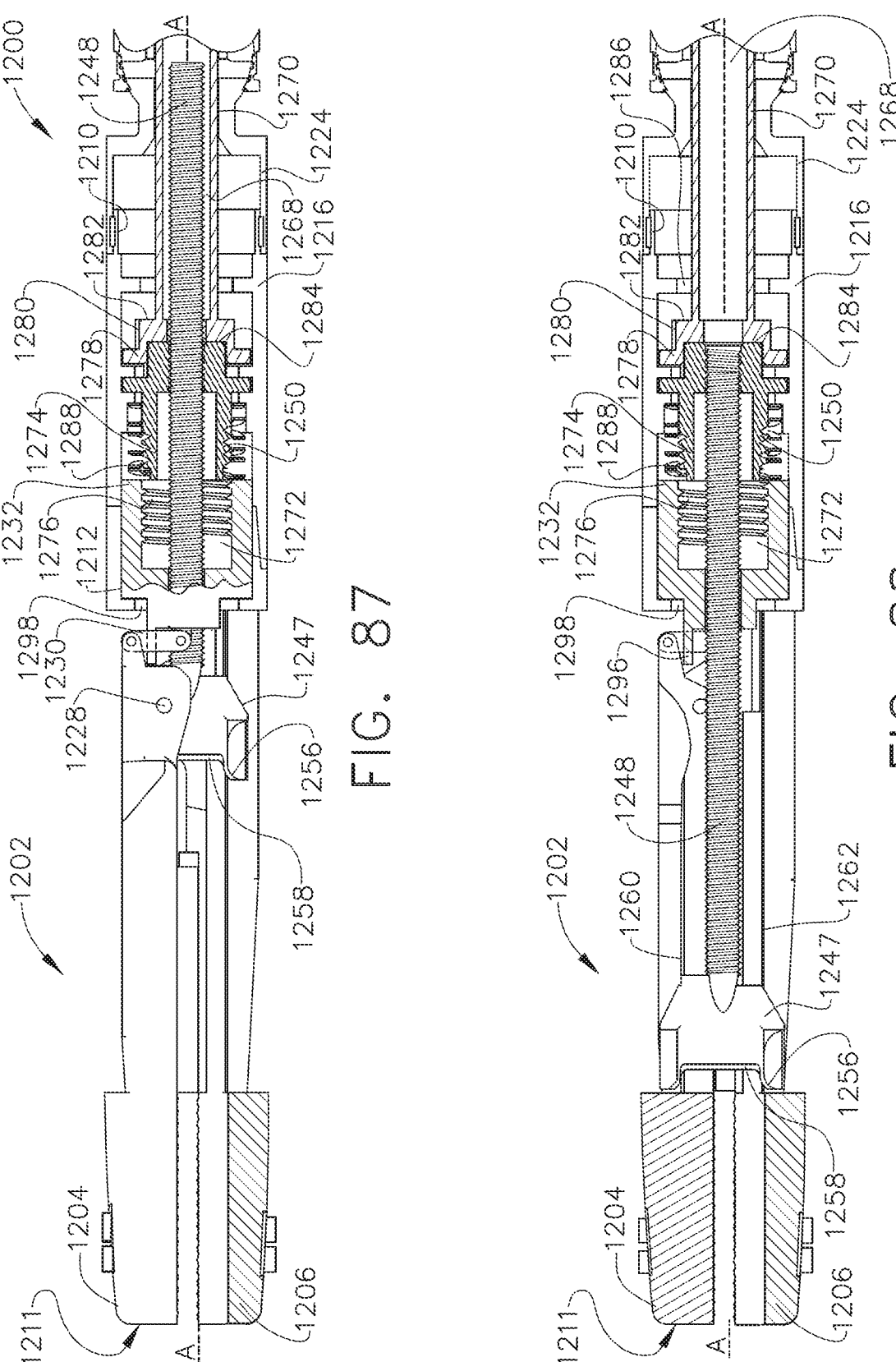
FIG. 87 is a cross sectional elevation view of one embodiment of the surgical tool of FIG. 83 wherein the first jaw member and the second jaw member are in an at least partially closed position, wherein the rotary drive shaft is operably engaged with the rotary drive nut, and wherein the closure nut is operably disengaged from the rotary drive nut.
FIG. 88 is a cross sectional elevation view of one embodiment of the surgical tool of FIG. 83 wherein the first jaw member and the second jaw member are in an at least partially closed position, wherein the rotary drive shaft is operably engaged with the rotary drive nut, and wherein the I-beam member is at least partially extended.

Referring primarily to FIGS. 85-87, the surgical tool 1200 may include a closure mechanism 1226 for moving the first jaw member 1204 relative to the second jaw member 1206 between an open position (FIG. 86) and a closed position (FIG. 87). As illustrated in FIG. 83, the first jaw member 1204 may include first mounting holes 1228, and the second jaw member 1206 may include second mounting holes (not shown in FIGS. 83-91). The first jaw member 1204 can be arranged relative to the second jaw member 1206 such that a pivot or trunnion pin (not shown in FIGS. 83-91) extends through the first mounting holes 1228 of the first jaw member 1204 and the second mounting holes of the second jaw member 1206 to pivotally couple the first jaw member 1204 to the second jaw member 1206. Other suitable means for coupling the first jaw member 1204 and the second jaw member 1206 are within the scope of this disclosure.

Referring to FIGS. 83-91, the closure mechanism 1226 may comprise a linkage arrangement which may comprise a first link 1230 and a second link (not shown in FIGS. 83-91). The closure mechanism 1226 may also comprise a closure driver in the form of a closure nut 1232 for example. The closure nut 1232 (FIG. 84) may be at least partially positioned within the end effector drive housing 1216. In use, the closure nut 1232 may translate axially between a first position (FIG. 86) and a second position (FIG. 87) relative to the end effector drive housing 1216 and may include a first arm 1234 and a second arm 1236. Referring primarily to FIG. 84, the first arm 1234 and the second arm 1236 may extend distally from a distal portion 1238 of the closure nut 1232, wherein the first arm 1234 may comprise a first opening 1240 and the first arm 1234 may be pivotally connected to the first link 1230 by a first pin (not shown in FIGS. 83-91) through the first opening 1240. Similarly, the second arm 1236 may comprise a second opening 1244, wherein the second arm 1236 may be pivotally connected to the second link by a second pin (not shown in FIGS. 83-91) through the second opening 1244. The first link 1230 and the second link (not shown in FIGS. 83-91) are also pivotally connected to the first jaw member 1204 such that when the closure nut 1232 is advanced distally from the first position (FIG. 86) to the second position (FIG. 87), the first jaw member 1204 is pivoted relative to the second jaw member 1206 towards a closed position. Correspondingly, when the closure nut 1232 is retracted proximally from the second position (FIG. 89) to the first position (FIG. 91), the first jaw member 1204 is pivoted relative to the second jaw member 1206 towards the open position. FIG. 85 illustrates the closure nut 1232 in a first position and the jaw assembly 1211 in an open position. FIG. 87 shows the closure nut 1232 in a second position and the jaw assembly 1211 in a closed position. The closure nut 1232, however, may be constrained from rotation relative to the end effector drive housing 1316 by an indexing feature, for example, abutting against the end effector drive housing 11316.

Referring to FIGS. 83-91, the surgical tool 1200 may include a firing mechanism 1246 having a suitable firing driver. The firing mechanism 1246 may include an I-beam member 1247, a threaded drive member 1248, and a threaded rotary drive nut 1250. The I-beam member 1247 may comprise a first I-beam flange 1252 and a second I-beam flange 1254. The I-beam member 1247 may operate in a manner similar to that described above with respect to the axially movable member 3016 described herein above. For example, the first I-beam flange 1252 and the second I-beam flange 1254 are connected with an intermediate portion 1256. The intermediate portion 1256 of the I-beam member 1247 may comprise a cutting member 1258 on a distal or a leading end thereof. The I-beam member 1247 is configured to translate within a first channel 1260 in the first jaw member 1204 and within a second channel 1262 in the second jaw member 1206. FIG. 84 shows the I-beam member 1247 in a fully proximal position and the jaw assembly 1211 in an open position. The I-beam member 1247 may be translated distally in order for the cutting member 1258 to transect tissue clamped between the first jaw member 1204 and the second jaw member 1206 when in the closed position. The cutting member 1258, which may comprise a sharp edge or blade for example, is configured to cut through clamped tissue during a distal translation (firing) stroke of the I-beam member 1247, thereby transecting the tissue. FIG. 88 shows the I-beam member 1247 in a fully distal position after a firing stroke.

Before, during, and/or after the I-beam member 1247 is advanced through tissue clamped between the first jaw member 1204 and the second jaw member 1206, electrical current can be supplied to electrodes located in the first jaw member 1204 and/or second jaw member 1206 in order to weld/fuse the tissue, as described in greater detail in this specification. For example, electrodes may be configured to deliver RF energy to tissue clamped between the first jaw member 1204 and the second jaw member 1206 when in a closed position to weld/fuse the tissue.

Distal and proximal translation of the I-beam member 1247 between a proximally retracted position and a distally advanced position may be accomplished with a suitable firing mechanism 1246. Referring to FIGS. 83-91, the I-beam member 1247 is connected to the threaded drive member 1248, wherein the threaded rotary drive nut 1250 is in a threaded engagement with the threaded drive member 1248. Referring primarily to FIG. 83, the threaded rotary drive nut 1250 is positioned within in the end effector drive housing 1216 proximal to the closure nut 1232 between a proximal annular flange 1264 and a distal annular flange 1266. The threaded rotary drive nut 1250 is mechanically constrained from translation in any direction, but is rotatable within the end effector drive housing 1216 around a central axis A. Therefore, given the threaded engagement of the rotary drive nut 1250 and the threaded drive member 1248, rotational motion of the rotary drive nut 1250 is transformed into translational motion of the threaded drive member 1248 along the central axis A and, in turn, into translational motion of the I-beam member 1247 along the central axis A.

The threaded drive member 1248 is threaded through the rotary drive nut 1250 and is located at least partially inside a lumen 1268 of a rotary drive shaft 1270. The threaded drive member 1248 is not attached or connected to the rotary drive shaft 1270. In use, the threaded drive member 1248 is freely movable within the lumen of the rotary drive shaft 1270 and will translate within the lumen of the rotary drive shaft 1270 when driven by rotation of the rotary drive nut 1250. The rotary drive shaft 1270 and the threaded drive member 1248 form a concentric rotary drive shaft/screw assembly that is located in the shaft assembly 1214. In addition, the threaded drive member 1248 extends distally through a lumen 1272 of the closure nut 1232. Similar to the above, the threaded drive member 1248 is freely movable within the lumen 1272 of the closure nut 1232, and, as a result, the threaded drive member 1248 will translate within the lumen 1272 of the closure nut 1232 when driven by rotation of the rotary drive nut 1250.

Referring to FIGS. 83-91, the rotary drive nut 1250 may comprise a threaded distal portion 1274. The closure nut 1232 may comprise a threaded proximal portion 1276. The threaded distal portion 1274 of the rotary drive nut 1250 and the threaded proximal portion 1276 of the closure nut 1232 are in a threaded engagement. As described above, the threaded rotary drive nut 1250 is mechanically constrained from translation in any direction, but is rotatable within the end effector drive housing 1216 around a central axis A. Therefore, given the threaded engagement of the rotary drive nut 1250 and the closure nut 1232, the rotational motion of the rotary drive nut 1250 is transformed into translational motion of the closure nut 1232 along the central axis A and, in turn, into pivotal motion in the jaw assembly 1211.

As shown in FIG. 83, the end effector drive housing 1216, the end effector connector tube 1218, and the intermediate articulation tube segment 1220, which together comprise the shaft assembly 1214, have open lumens and, therefore, the shaft assembly 1214 comprises a lumen extending longitudinally therethrough, as shown in FIGS. 83 and 85-91. Referring again to FIGS. 83 and 85-91, the concentric rotary drive shaft/threaded drive member assembly is located within the lumen of the shaft assembly 1214 and passes through the end effector drive housing 1216, the end effector connector tube 1218, and the intermediate articulation tube segment 1220. Although not shown in FIGS. 83-91, at least the rotary drive shaft 1270 passes through a lumen of the shaft assembly 1214 and is operably coupled to a driving mechanism that provides rotational motion and axial translational motion to the rotary drive shaft 1270. For example, in some embodiments, the surgical tool 1200 may be operably coupled through the shaft assembly 1214 to a robotic surgical system that provides rotational motion and axial translational motion to the rotary drive shaft 1270, such as, for example, the robotic surgical systems described in connection with FIGS. 5 and 16-21. For example, the rotary drive shaft 1270 may be coupled, through the shaft assembly, to the proximal drive shaft segment 380 described herein above. In some embodiments, for example, the surgical tool 1200 may be operably coupled through the shaft assembly 1214 to a hand-held surgical device, such as the device described herein above with respect to FIGS. 46-63. For example, the rotary drive shaft 1270 may be operably coupled, though the shaft assembly 560, to the proximal drive shaft segment 380' described herein above.

In some embodiments, the threaded drive member 1248 has a length that is less than the length of the rotary drive shaft 1270 and, therefore, lies within only a distal portion of the rotary drive shaft 1270, for example. The threaded drive member 1248 and the rotary drive shaft 1270 may be flexible so that the threaded drive member 1248 and the rotary drive shaft 1270 can bend without damage or loss of operability during articulation of the surgical tool 1200 about the articulation joint 1208.

Described in greater detail elsewhere in the specification, the rotary drive shaft 1270 may comprise a rotary drive head 1278. The rotary drive head 1278 comprises a female hex coupling portion 1280 on the distal side of the rotary drive head 1278 and the rotary drive head 1278 comprises a male hex coupling portion 1282 on the proximal side of the rotary drive head 1278. The distal female hex coupling portion 1280 of the rotary drive head 1278 is configured to mechanically engage with a male hex coupling portion 1284 of the rotary drive nut 1250 located on the proximal side of the rotary drive nut 1250. As described elsewhere, the proximal male hex coupling portion 1282 of the rotary drive head 1278 is configured to mechanically engage with a female hex coupling portion 1286 of the end effector drive housing 1216 in order to rotate the end effector 1202 around the central axis A.

Referring to FIG. 85, the rotary drive shaft 1270 is shown in a fully proximal axial position in which the hex coupling portion 1282 of the rotary drive head 1278 is mechanically engaged with the female hex shaft coupling portion of the end effector drive housing 1216. In this configuration, rotation of the rotary drive shaft 1270 causes rotation of the head portion of the surgical tool 1200 about the head rotation joint 1210, including rotation of the end effector 1202 and the end effector drive housing 1216. In this configuration, the portion of the surgical tool 1200 that is distal to the head rotation joint 1210 (e.g., a head portion) rotates with rotation of the rotary drive shaft 1270, and the portion of the surgical tool 1200 that is proximal to the head rotation joint 1210 does not rotate with rotation of the rotary drive shaft 1270. An example of a head rotation joint 1210 is described in connection with FIGS. 64-82, 83-91 and 92-96. Other suitable techniques and rotation means for rotating the end effector 1202 relative to the shaft assembly 1214 are within the scope of the current disclosure. It will be appreciated that a desired rotation speed of the rotary drive shaft 1270 to drive the rotary drive nut 1250 may be greater than a desired rotational speed for rotating the head portion. For example, the rotary drive shaft 1270 may be driven by a motor (not shown) that is operable at different rotary speeds.

The orientation of the threading of the threaded drive member 1248 and the rotary drive nut 1250 may be established so that either clockwise or counterclockwise rotation of the rotary drive shaft 1270 will cause distal or proximal translation of the threaded drive member 1248 and I-beam member 1247. Stated another way, the rotary drive shaft 1270, and the rotary drive nut 1250 can be rotated in a first direction to advance the threaded drive member 1248 distally and correspondingly, rotated in a second opposite direction to retract the threaded drive member 1248 proximally. The pitch and/or number of starts of the threading of the threaded drive member 1248 and the threading of the rotary drive nut 1250 may be selected to control the speed and/or duration of the rotation of the rotary drive nut 1250 and, in turn, the translation of the threaded drive member 1248. In this manner, the direction, speed, and/or duration of rotation of the rotary drive shaft 1270 can be controlled in order to control the direction, speed, and magnitude of the longitudinal translation of the I-beam member 1247 along the first channel 1260 and second channel 1262, as described above.

Similar to the above, the orientation of the threading of the threaded distal portion 1274 of the rotary drive nut 1250 and the threading of the threaded proximal portion 1276 of the closure nut 1232 may be established so that either clockwise or counterclockwise rotation of the rotary drive shaft 1270 will cause distal or proximal translation of the closure nut 1232 and in turn closure or opening of the jaw assembly 1211. Stated another way, threaded distal portion 1274 can be rotated in a first direction to advance the threaded proximal portion 1276 distally and correspond-ingly, rotated in a second opposite direction to retract the threaded proximal portion 1276 proximally. The pitch and/or number of starts of the threading of the threaded distal portion 1274 of the threaded drive member 1248 and the threading of threaded proximal portion 1276 of the closure nut 1232 may be selected to control speed and/or duration of the rotation of the rotary drive nut 1250 and translation of the closure nut 1232. In this manner, the direction, speed, and/or duration of rotation of the rotary drive shaft 1270 can be controlled in order to control the direction, speed, and magnitude of the pivoting of the of the jaw assembly 1211.

Referring to FIGS. 86-88, the rotary drive shaft 1270 is shown in a fully extended distal axial position in which the female hex coupling portion 1280 of the rotary drive head 1278 is mechanically engaged with the male hex coupling portion 1284 of the rotary drive nut 1250. In this configuration, rotation of the rotary drive shaft 1270 in a first direction (for example a clockwise direction) around the central axis A begins a firing stroke by causing rotation of the rotary drive nut 1250 in the first direction. The rotation of the rotary drive nut advances the threaded drive member 1248, which, in turn, advances the I-beam member 1247 distally. Simultaneously, the rotation of the rotary drive nut 1250 advances the closure nut 1232 distally, which closes the jaw assembly 1211. The closure nut 1232 and the threaded drive member 1248 are advanced distally until the closure nut 1232 is disengaged from threaded engagement with the rotary drive nut 1250 as illustrated in FIG. 88. Stated another way, the closure nut 1232 can be advanced distally until the threads of the threaded distal portion 1274 of the rotary drive nut 1250 are no longer threadedly engaged with the threads of the threaded proximal portion 1276 of the closure nut 1232. Thus, as a result, further rotation of the rotary drive nut 1250 in the first direction will not advance the closure nut 1232 distally. The closure nut 1232 will sit idle during the remainder of a firing stroke. Additional rotation of the rotary drive nut 1250, in the same direction, continues the distal advancement of the threaded drive member 1248, which continues the distal advancement of the I-beam member 1247 for the remainder of the firing stroke.

The surgical tool 1200 may comprise a biasing member 1288, a helical spring, and/or a washer spring for example, situated at least partially around the threaded distal portion 1274 of the rotary drive nut 1250. As illustrated in FIG. 86, the biasing member 1288 may include a proximal end abutted against the distal annular flange 1266 of the end effector drive housing 1216, and a distal end abutted against a proximal end 1290 of the closure nut 1232. Once the closure nut 1232 is released from threaded engagement with the rotary drive nut 1250, the biasing member 1288 can keep the closure nut 1232 from reengaging the rotary drive nut 1250 by pushing the closure nut 1232 axially in a distal direction along the central axis A until the distal portion 1238 of the closure nut 1232 abuts against a terminal wall 1294 of the proximal shaft portion 1212 of the end effector 1202. The biasing member 1288 also ensures that the jaw assembly 1211 remains under positive closure pressure by biasing the closure nut 1232 abutted against the terminal wall 1294 of the proximal shaft portion 1212 of the end effector 1202 as the I-beam member 1247 is being advanced distally through the closed jaw assembly 1211.

Referring primarily to FIG. 84, the closure nut 1232 may comprise a cam member 1296 extending distally from the closure nut 1232. Referring primarily to FIG. 87, the cam member 1296 may extend through an opening 1298 of the terminal wall 1294 of the proximal shaft portion 1212 of the end effector 1202 when the distal portion 1238 of the closure nut 1232 is abutted against the terminal wall 1294 of the proximal shaft portion 1212 of the end effector 1202 under positive pressure from the biasing member 1288.

Referring to FIG. 88, the rotary drive shaft 1270 is shown in a fully extended distal axial position in which the female hex coupling portion 1280 of the rotary drive head 1278 is mechanically engaged with the make hex coupling portion 1284 of the rotary drive nut 1250. In this configuration, rotation of the rotary drive shaft 1270 in a second direction opposite the first direction (for example a counter clockwise direction) begins a reverse stroke by causing an opposite rotation of the rotary drive nut 1250, which retracts the threaded drive member 1248, which in turn retracts the I-beam member 1247. At least during the initial phase of the reverse stroke, the closure nut 1232 remains disengaged from the rotary drive nut 1250. However, when the I-beam member 1247 is being retracted, the I-beam member 1247 can engage the cam member 1296 of the closure nut 1232. Any further retraction of the I-beam member 1247 can simultaneously open the jaw assembly 1211 by pushing the closure nut 1232 axially in a proximal direction along the central axis A toward the rotary drive nut 1250. In order for the I-beam member 1247 to push the closure nut 1232 proximally, the I-beam member 1247 must compress the biasing member 1288. As the I-beam member 1247 is retracted, the I-beam member 1247 can push the closure nut 1232 proximally until the closure nut is returned into threaded engagement with the rotary drive nut 1250. At such point, the rotary drive nut 1250 can pull the closure nut 1232 proximally owing to the threaded engagement therebetween. As the closure nut 1232 is retracted proximally, the first link 1230, and the second link will cause the jaw assembly 1211 to open. The retraction of the I-beam member 1247 and the opening of the jaw assembly 1211 continue simultaneously during the remainder of the reverse stroke.

The sequence of events causing the closure of the jaw assembly 1211, the full extension of the I-beam member 1247, the full retraction of the I-beam member 1247, and the reopening of the jaw assembly 1211 is illustrated in FIGS. 85-91 in a chronological order. FIG. 85 shows the jaw assembly 1211 in a fully open position, the I-beam member 1247 in a fully retracted position, and the rotary drive shaft 1270 in a fully retracted axial position, wherein the female hex coupling portion 1280 of the rotary drive head 1278 is mechanically disengaged from the male hex coupling portion 1284 of the rotary drive nut 1250. In a first phase of operation, returning to FIG. 86, the rotary drive shaft 1270 is advanced axially to mechanically engage the female hex coupling portion 1280 of the rotary drive head 1278 with the male hex coupling portion 1284 of the rotary drive nut 1250. Referring again to FIG. 86, the rotation of the rotary drive shaft 1270 in a first direction (for example a clockwise direction) around the central axis A causes the rotation of the rotary drive nut 1250 in the first direction. The closure nut 1232 and the threaded drive member 1248 are simultaneously advanced distally by rotation of the rotary drive nut 1250 in the first direction. In turn, the closure of the jaw assembly 1211 and the initial advancement of the I-beam member 1247 occur simultaneously during the first phase of operation. In a second phase of operation, referring now to FIG. 87, the closure nut 1232 is disengaged from threaded engagement with the rotary drive nut 1250. During the remainder of the second phase of operation, the rotary drive nut 1250 continues to advance the threaded drive member 1248 independently of the closure nut 1232. As a result, referring primarily to FIG. 88, the jaw assembly 1211 remains closed and the I-beam member 1247 continues to advance until the end of the second phase of operation.

Figure 89:
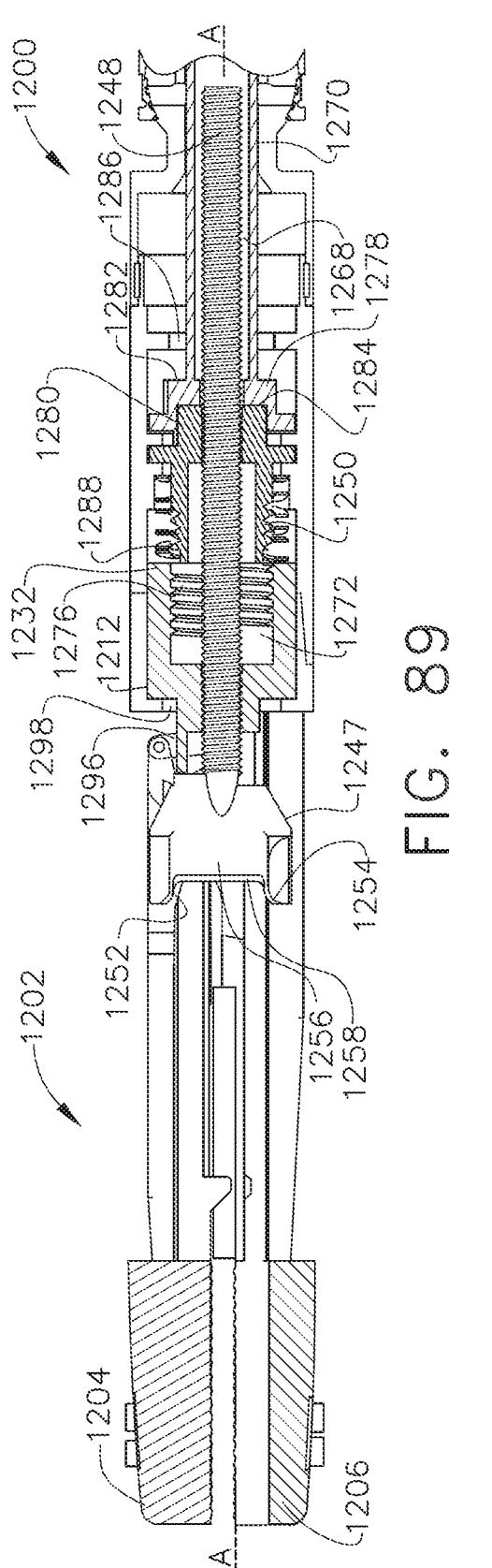
FIG. 89 is a cross sectional elevation view of one embodiment of the surgical tool of FIG. 83 wherein the first jaw member and the second jaw member are in an at least partially closed position, wherein the rotary drive shaft is operably engaged with the rotary drive nut, and wherein the I-beam member is at least partially retracted.
Figure 90:
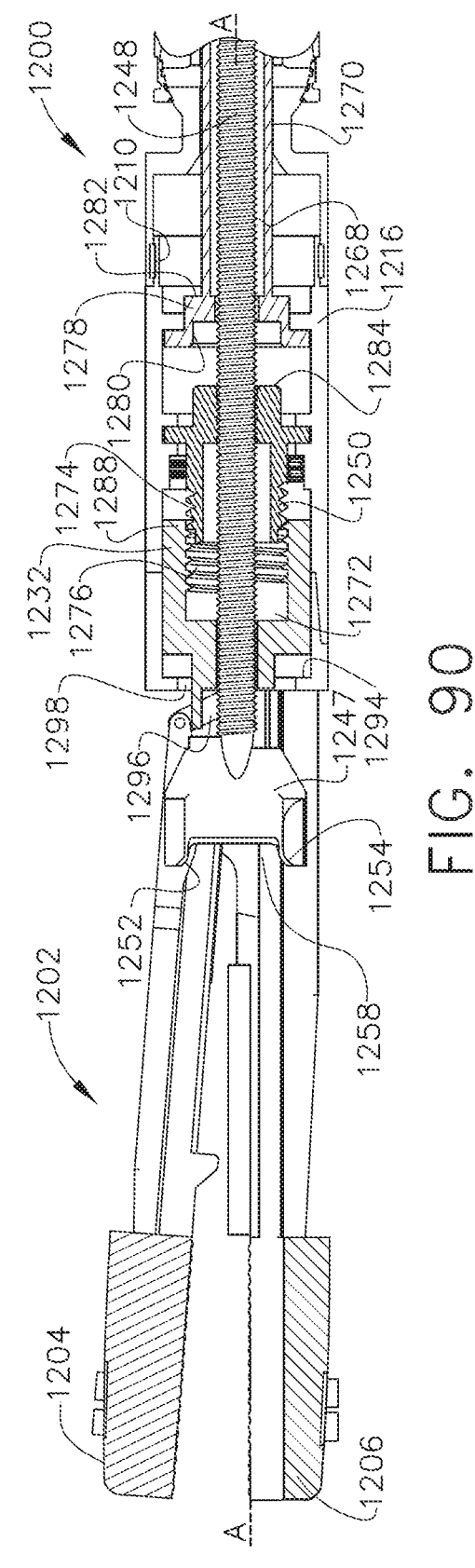
FIG. 90 is a cross sectional elevation view of one embodiment of the surgical tool of FIG. 83 wherein the first jaw member and the second jaw member are in an at least partially closed position, wherein the rotary drive shaft is operably engaged with the rotary drive nut, and wherein the I-beam member is at least partially retracted.
Figure 91:
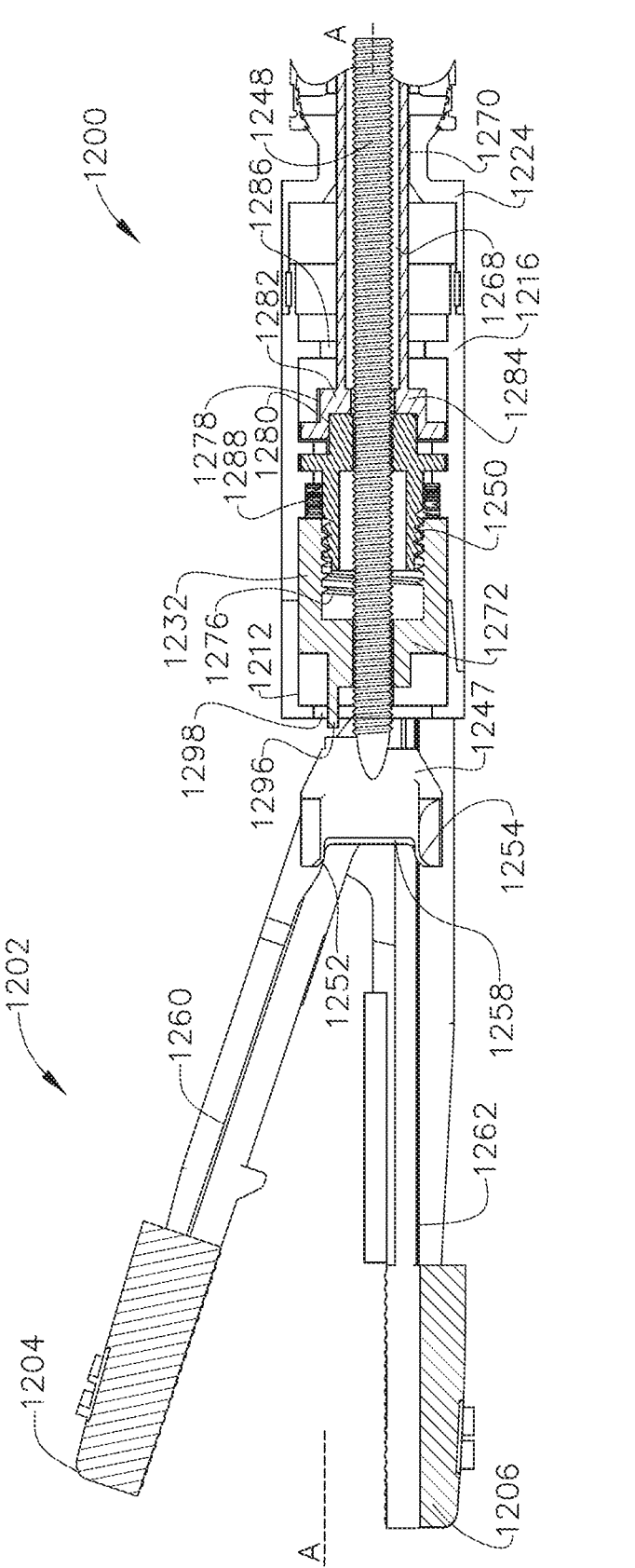
FIG. 91 is a cross sectional elevation view of one embodiment of the surgical tool of FIG. 83 wherein the first jaw member and the second jaw member are in an at least partially open position, wherein the rotary drive shaft is operably engaged with the rotary drive nut, and wherein the closure nut is operably engaged from the rotary drive nut.

In a third phase of operation, as illustrated in FIG. 89, the rotary drive shaft 1270 is rotated in a second direction opposite the first direction, which causes the rotation of the rotary drive nut 1250 in the second direction. In the third phase of operation, the closure nut 1232 remains disengaged from rotary drive nut 1250. The rotation of the rotary drive nut 1250 retracts the threaded drive member 1248 independent of the closure nut 1232. In result, the jaw assembly 1211 remains closed, and the I-beam member 1247 is retracted in response to the rotation of the rotary drive. In a fourth phase of operation, referring primarily to FIG. 90, the rotary drive nut 1250 continues its rotation in the second direction thereby retracting the threaded drive member 1248 which retracts I-beam member 1247 until the I-beam member 1247 engages the cam member 1296 of closure nut 1232. Any further retraction of the I-beam member 1247 simultaneously opens the jaw assembly 1211 by pushing the closure nut 1232 axially in a proximal direction along the central axis A towards the rotary drive nut 1250 compressing the biasing member 1288. Referring primarily to FIG. 91, the I-beam member 1247 can continue to push the closure nut 1232 proximally until it is returned into threaded engagement with the rotary drive nut 1250. The retraction of the I-beam member 1247 and the opening of the jaw assembly 1211 continue simultaneously during the remainder of the fourth phase of operation.

Referring to FIGS. 92-96, a multi-axis articulating and rotating surgical tool 1300 comprises an end effector 1302 including a jaw assembly 1311 comprising a first jaw member 1304 and a second jaw member 1306. The first jaw member 1304 is movable relative to the second jaw member 1306 between an open position and a closed position to clamp tissue between the first jaw member 1304 and the second jaw member 1306. The surgical tool 1300 is configured to independently articulate about an articulation joint 1308. As described above, the surgical tool 1300 is also configured to independently rotate about a head rotation joint 1310.

The end effector 1302 is coupled to a shaft assembly 1314 comprising an end effector drive housing 1316, an end effector connector tube 1318, an intermediate articulation tube segment 1320, and a distal outer tube portion (not shown in FIGS. 92-96). The end effector 1302 and the shaft assembly 1314 together can comprise the surgical tool 1300. The end effector 1302 may be removably coupled to the end effector drive housing 1316 using a mechanism as described, for example, in connection with FIGS. 106-115. The end effector connector tube 1318 comprises a cylindrical portion 1322 and a ball portion 1324. The end effector drive housing 1316 is coupled to the cylindrical portion 1322 of the end effector connector tube 1318 through the head rotation joint 1310. The end effector 1302 and the end effector drive housing 1316 together comprise a head portion of the surgical tool 1300. The head portion of the surgical tool 1300 is independently rotatable about the head rotation joint 1310.

Figures 92, 93:
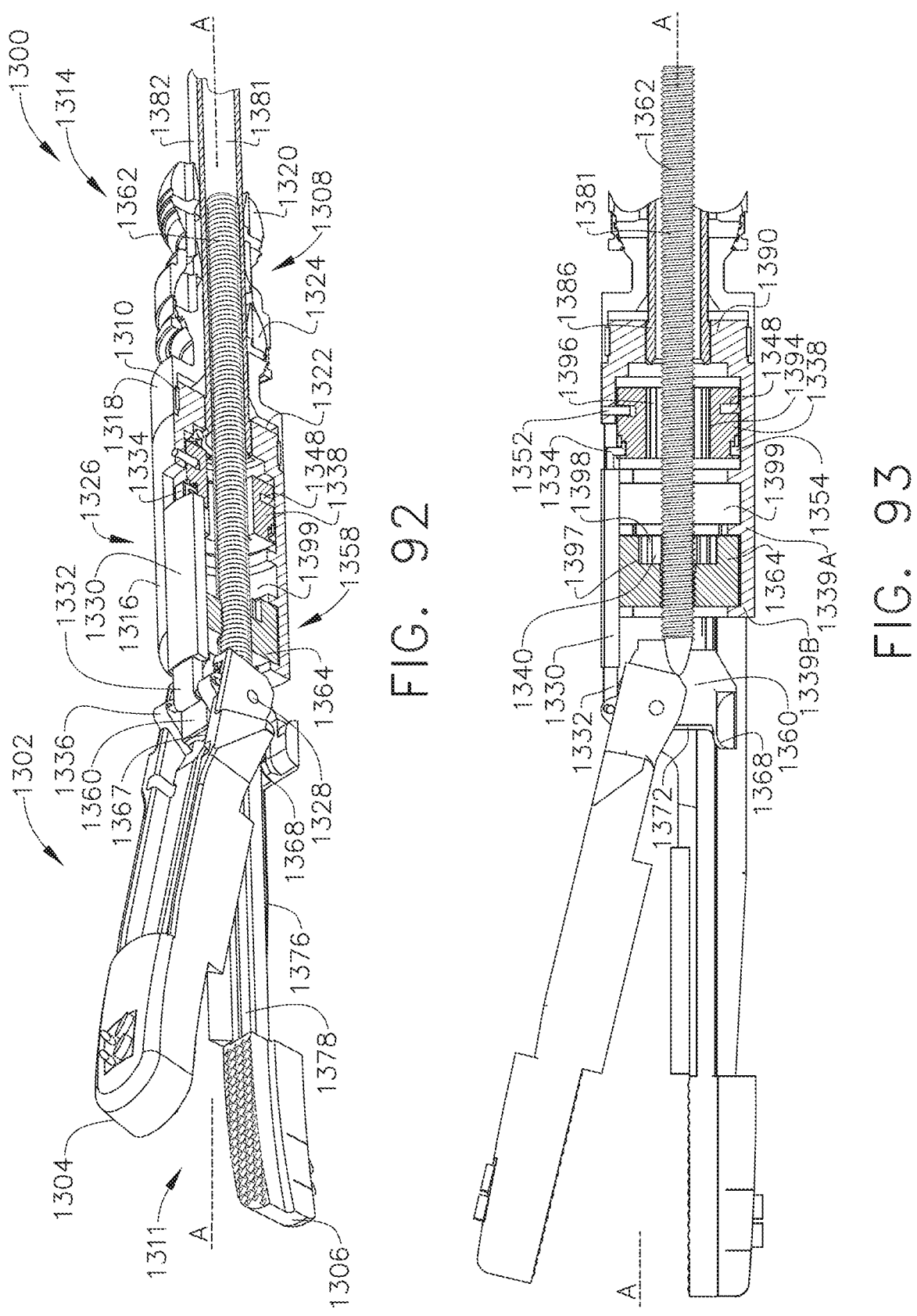
FIG. 92 is a cross sectional perspective view of a surgical tool having first and second jaw members in accordance with certain embodiments described herein.
FIG. 93 is a cross sectional elevation view of one embodiment of the surgical tool of FIG. 92 wherein the first jaw member and the second jaw member are in an at least partially open position, and wherein the rotary drive shaft is operably engaged with spline coupling portion of the end effector drive housing.
Figures 94, 95:
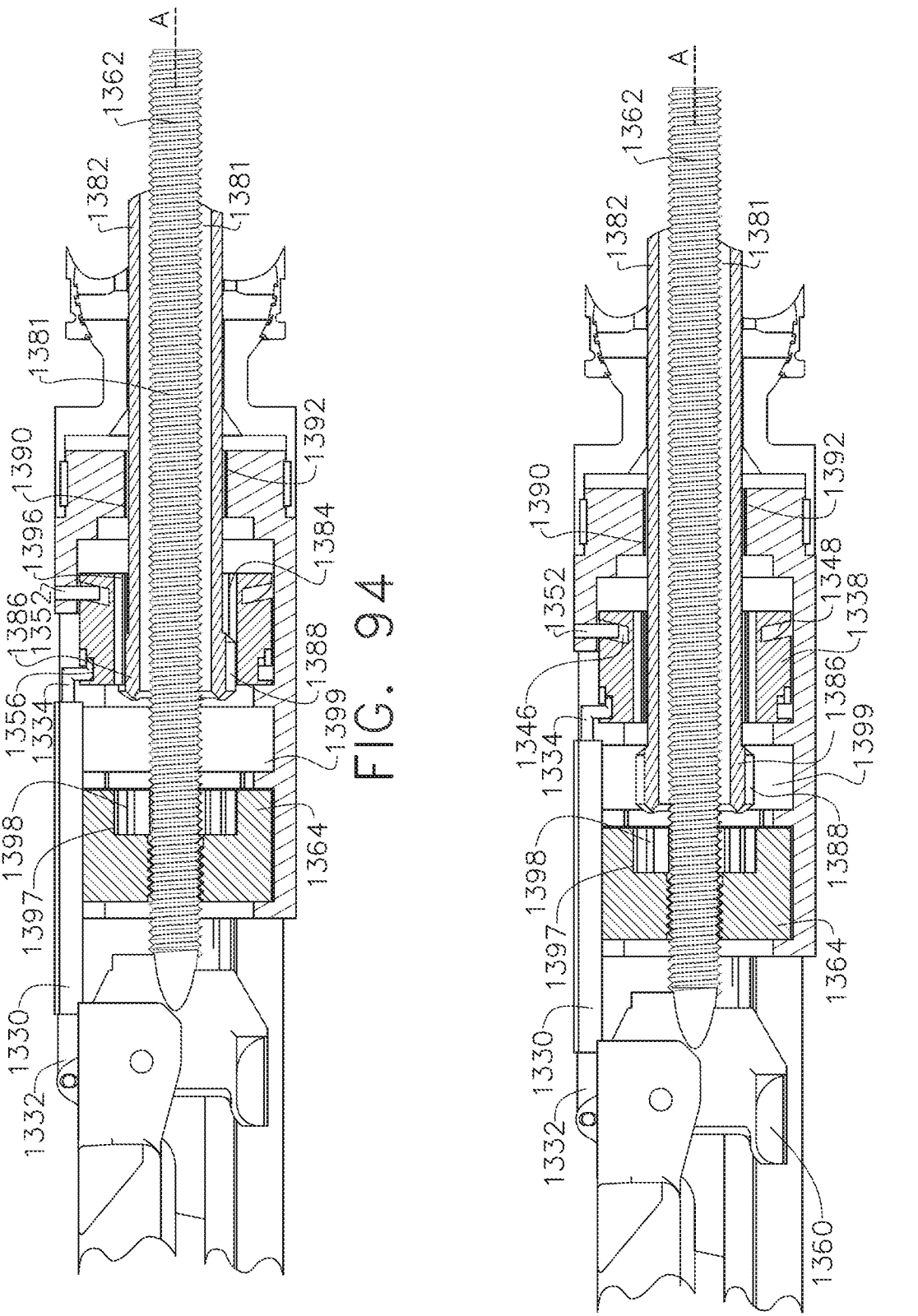
FIG. 94 is a cross sectional elevation view of one embodiment of the surgical tool of FIG. 92 wherein the first jaw member and the second jaw member are in an at least partially closed position, and wherein the rotary drive shaft is operably engaged with spline coupling portion of the barrel cam.
FIG. 95 is a cross sectional elevation view of one embodiment of the surgical tool of FIG. 92 wherein the first jaw member and the second jaw member are in an at least partially closed position, and wherein the rotary drive shaft is not operably engaged with any of the spline coupling portions.

Referring primarily to FIG. 92, the surgical tool 1300 may include a closure mechanism 1326 for moving the first jaw member 1304 relative to the second jaw member 1306 between an open position (FIG. 93) and a closed position (FIG. 94). As illustrated in FIG. 83, the first jaw member 1304 may include first mounting holes 1328, and the second jaw member 1306 may include second mounting holes (not shown in FIGS. 92-96). The first jaw member 1304 can be arranged relative to the second jaw member 1306 such that a pivot or trunnion pin (not shown in FIGS. 92-96) extends through the first mounting holes 1328 of the first jaw member 1304 and the second mounting holes of the second jaw member 1306 to pivotally couple the first jaw member 1304 to the second jaw member 1306. Other suitable means for coupling the first jaw member 1304 and the second jaw member 1306 are within the scope of this disclosure.

Referring to FIGS. 92-96, the closure mechanism may comprise a closure link 1330 which translates axially relative to the end effector drive housing 1316 between a first position and a second position. The closure link 1330 may comprise a distal end 1332 and a proximal end 1334. The distal end 1332 may be pivotally connected to a proximal portion 1336 of the first jaw member 1304 such that when the closure link 1330 is translated between the first position and the second position, the first jaw member 1304 is moved relative to the second jaw member 1306 between an open and a closed position.

Referring to FIGS. 92-96, the closure mechanism 1328 may also comprise a closure driver in the form of a barrel cam 1338 for example. The barrel cam 1338 may be positioned within the end effector drive housing 1316. The barrel cam 1338 may comprise a generally cylindrical shape having a lumen 1340 therethrough. The barrel cam 1338 may include a first arcuate groove 1346, and a second arcuate groove 1348 defined in a peripheral surface thereof. The first arcuate groove 1346 may receive a first pin 1352 extending from the end effector drive housing 1316. The second arcuate groove 1348 may receive a second pin (not shown in FIGS. 92-96) extending from the end effector drive housing 1316. The first pin 1352 and the second pin (not shown in FIGS. 92-96) may extend from circumferentially opposite sides of an inner wall of the end effector drive housing 1316. The barrel cam 1338 may rotate around central axis A, wherein, as the barrel cam 1338 is rotated around central axis A, the first pin 1352 travels along the first arcuate groove 1346, and the second pin travels along the second arcuate groove 1348 thereby translating the barrel cam 1338 axially along central axis A. The result is a conversion of the rotational motion of the barrel cam 1338 into an axial motion of the closure link 1330. Stated another way, the rotation of the barrel cam 1338 in a first direction (for example a clockwise direction) around the central axis A may result in advancing the barrel cam 1338 axially in a distal direction. Correspondingly, the rotation of the barrel cam 1338 in a second direction (for example a counter clockwise direction) opposite the first direction may result in retracting the barrel cam 1338 axially in a proximal direction along the central axis A.

Referring to FIGS. 92-96, the proximal end 1334 of the closure link 1330 may be operatively engaged with the barrel cam 1338 such that the axially advancement of the barrel cam 1338 may cause the closure link 1330 to be advanced axially, and, in turn close the jaw assembly 1311. Similarly, the proximal retraction of the barrel cam 1338 may retract the closure link 1330, which may open the jaw assembly 1311. As illustrated in FIGS. 92-96, the barrel cam 1338 may include a circumferential recess 1354 on the external wall of the barrel cam 1338 at a distal portion thereof. The proximal end of the closure link 1330 may comprise a connector member 1356. The connector member 1356 may be operably engaged with the barrel cam 1338 along the recess 1354. As a result, the barrel cam 1338 may translate axial motions to the closure link 1330 through the connector member 1356.

Referring primarily to FIG. 92, the surgical tool 1300 may include a firing mechanism 1358. The firing mechanism

Figure 96:
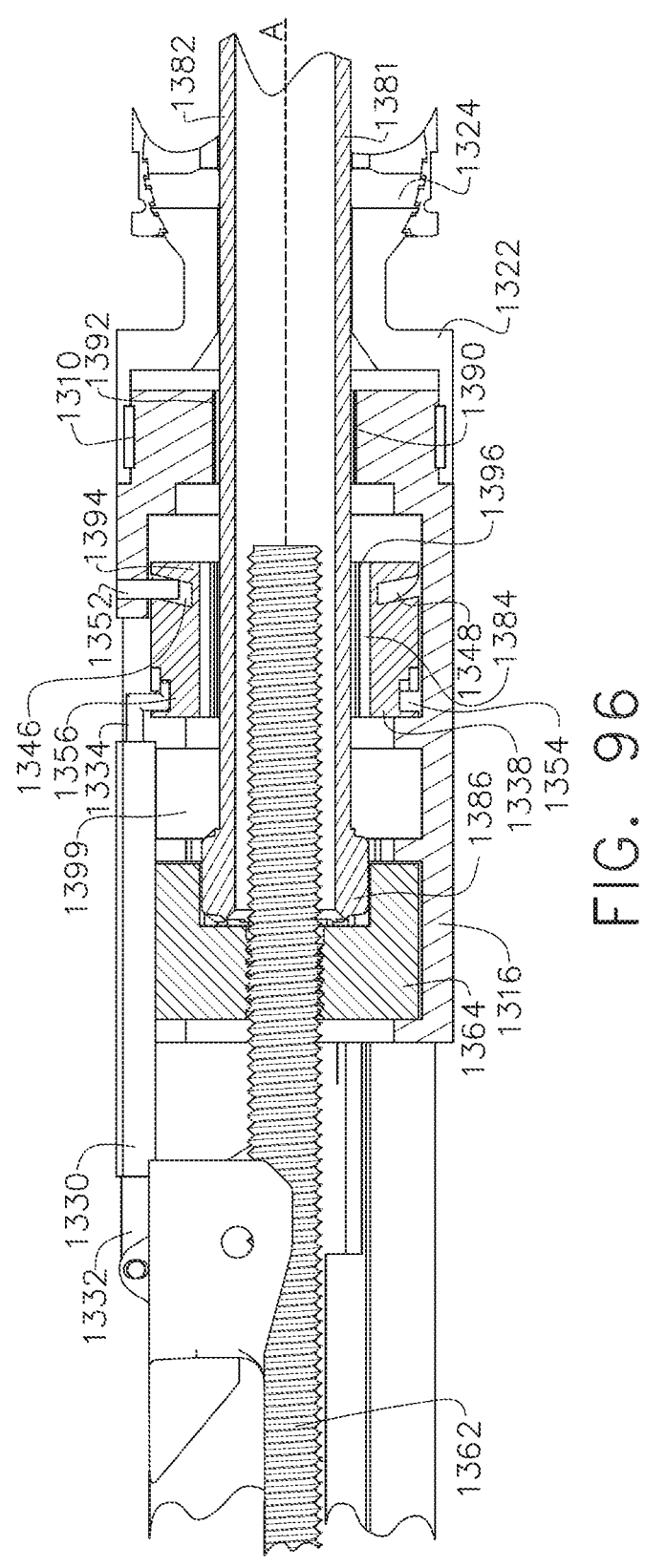
FIG. 96 is a cross sectional elevation view of one embodiment of the surgical tool of FIG. 92 wherein the first jaw member and the second jaw member are in an at least partially closed position, and wherein the rotary drive shaft is operably engaged with spline coupling portion of the rotary drive nut.

1358 may include an I-beam member 1360, a threaded drive member 1362, and a threaded rotary drive nut 1364. The I-beam member 1360 may operate in a manner similar to that of the axially movable member 3016 described herein above and may comprise a first I-beam flange 1367 and a second I-beam flange 1368. The first I-beam flange 1367 and the second I-beam flange 1368 are connected with an intermediate portion 1370. The intermediate portion 1370 of the I-beam member 1360 may comprise a cutting member 1372, which may comprise a sharp edge or blade for example, to transect tissue clamped between the first jaw member 1304 and the second jaw member 1306 when the jaw assembly 1311 is closed. The I-beam member 1360 may translate distally within a first channel (not shown in FIGS. 92-96) defined in the first jaw member 1304 and within a second channel 1376 defined in the second jaw member 1306 to cut through clamped tissue during a distal translation (firing) stroke. FIG. 96 illustrates the I-beam member 1360 after a firing stroke.

Before, during, and/or after the I-beam member 1360 is advanced through tissue clamped between the first jaw member 1304 and the second jaw member 1306, electrical current can be supplied to electrodes 1378 located in the first jaw member 1304 and/or second jaw member 1306 in order to weld/fuse the tissue, as described in greater detail in this specification. For example, electrodes 1378 may be configured to deliver RF energy to tissue clamped between the first jaw member 1304 and the second jaw member 1306 when in a closed position to weld/fuse the tissue.

Distal and proximal translation of the I-beam member 1360 between a proximally retracted position and a distally advanced position may be accomplished with a suitable firing mechanism 1358. Referring to FIGS. 92-96, the I-beam member 1360 is connected to the threaded drive member 1362, wherein the threaded drive member 1362 is threadedly engaged with the rotary drive nut 1364. The threaded rotary drive nut 1364 is positioned within the end effector drive housing 1316 distal to the barrel cam 1338 between a proximal annular flange 1339A and a distal annular flange 1339B. The threaded rotary drive nut 1364 is mechanically constrained from translation in any direction, but is rotatable within the end effector drive housing 1316. Therefore, given the threaded engagement of the rotary drive nut 1364 and the threaded drive member 1362, rotational motion of the rotary drive nut 1364 is transformed into translational motion of the threaded drive member 1362 along the central axis A and, in turn, into translational motion of the I-beam member 1360 along the central axis A.

The threaded drive member 1362 is threaded through the rotary drive nut 1364 and is located at least partially inside a lumen 1381 of a rotary drive shaft 1382. The threaded drive member 1362 is not attached or connected to the rotary drive shaft 1382. The threaded drive member 1362 is freely movable within the lumen 1381 of the rotary drive shaft 1382 and will translate within the lumen 1381 of the rotary drive shaft 1382 when driven by rotation of the rotary drive nut 1364. The rotary drive shaft 1382 and the threaded drive member 1362 form a concentric rotary drive shaft/threaded drive member assembly that is located in the shaft assembly 1314. In addition, the threaded drive member 1362 extends distally through a lumen 1384 of the barrel cam 1338 wherein the threaded drive member 1362 is freely movable within the lumen 1384 of the barrel cam 1338 and will translate within the lumen 1384 of the barrel cam 1338 when the threaded drive member is driven by rotation of the rotary drive nut 1364.

As shown in FIG. 92, the end effector drive housing 1316, the end effector connector tube 1318, and the intermediate articulation tube segment 1320, which together comprise the shaft assembly 1314, have lumens extending therethrough. As a result, the shaft assembly 1314 can comprise a lumen extending therethrough, as illustrated in FIGS. 92-96. Referring again to FIGS. 92-96, the concentric rotary drive shaft/threaded drive member assembly is located within the lumen of the shaft assembly 1314 and passes through the end effector drive housing 1316, the end effector connector tube 1318, and the intermediate articulation tube segment 1320. Although not shown in FIGS. 92-96, at least the rotary drive shaft 1382 passes through a lumen of the shaft assembly 1314 and is operably coupled to a driving mechanism that provides rotational and/or axial translational motion to the rotary drive shaft 1382. For example, in some embodiments, the surgical tool 1300 may be operably coupled through the shaft assembly 1314 to a robotic surgical system that provides rotational motion and/or axial translational motion to the rotary drive shaft 1382, such as, for example, the robotic surgical systems described in connection with FIGS. 5 and 16-21. For example, the rotary drive shaft 1382 may be operably coupled, though the shaft assembly 1314, to the proximal drive shaft segment 380 described herein above. Also, in some embodiments, the surgical tool 1300 may be utilized in conjunction with a hand-held surgical device, such as the device described herein above with respect to FIGS. 46-63. For example, the rotary drive shaft 1382 may be operably coupled, through the shaft assembly 1314, to the proximal drive shaft segment 380' described herein above.

In some embodiments, the threaded drive member 1362 has a length that is less than the length of the rotary drive shaft 1382 and, therefore, lies within only a distal portion of the rotary drive shaft 1382, for example. The threaded drive member 1362 and the rotary drive shaft 1382 may be flexible so that the threaded drive member 1362 and the rotary drive shaft 1382 can bend without damage or loss of operability during articulation of the surgical tool 1300 about the articulation joint 1308.

The rotary drive shaft 1382 may comprise a rotary drive head 1386. The rotary drive head 1386 may comprise spline members 1388 disposed circumferentially around an external surface of the rotary drive head 1386 and oriented co-axially with the shaft assembly 1314. The end effector drive housing 1316 may comprise a spline coupling portion 1390 comprising spline members 1392 disposed circumferentially around an internal wall of the end effector drive housing 1316 and oriented co-axially with the shaft assembly 1314. The barrel cam 1338 may comprise a spline coupling portion 1394 comprising spline members 1396 disposed circumferentially around an internal wall of barrel cam 1338 and oriented co-axially with the shaft assembly 1314. The rotary drive nut 1364 may also comprise a spline coupling portion 1397 comprising spline members 1398 disposed circumferentially around an internal wall of rotary drive nut 1364 and oriented co-axially with the shaft assembly 1314. As illustrated in FIG. 93, the rotary drive shaft 1382 may be selectively retracted proximally to bring the rotary drive head 1386 into operable engagement with the spline coupling portion 1390 of the end effector drive housing 1316. In this configuration, rotation of the rotary drive shaft 1382 causes rotation of the head portion of the surgical tool 1300 about the head rotation joint 1310, including rotation of the end effector 1302 and the end effector drive housing 1316. In this configuration, the portion of the surgical tool 1300 that is distal to the head rotation joint 1310 rotates with rotation of the rotary drive shaft 1382, and the portion of the surgical tool 1300 that is proximal to the head rotation joint 1310 does not rotate with rotation of the rotary drive shaft 1382. An example of a head rotation joint 1310 is described in connection with FIGS. 64-82, 83-91 and 92-96. Other suitable techniques and rotation means for rotating the end effector 1302 relative to the shaft assembly 1314 are within the scope of the current disclosure. It will be appreciated that a desired rotation speed of the rotary drive shaft 1382 to drive the rotary drive nut 1364 may be greater than a desired rotational speed for rotating the head portion. For example, the rotary drive shaft 1270 may be driven by a motor (not shown) that is operable at different rotary speeds.

As illustrated in FIG. 94, the rotary drive shaft 1382 may be selectively advanced distally to bring the rotary drive head 1386 into operable engagement with the spline coupling portion 1394 of the barrel cam 1338. In this configuration, rotation of the rotary drive shaft 1382 causes rotation of the barrel cam 1338. As described above, the rotation of the barrel cam 1338 causes axial motions in the closure link 1330. In result, the rotation of the rotary drive shaft 1382 in a first direction (for example a clockwise direction) around the central axis A may cause the closure link 1330 to be advanced distally along the central axis A, which may close the jaw assembly 1311. Alternatively, the rotation of the rotary drive shaft 1382 in a second direction (for example a clockwise direction) opposite the first direction may cause the closure link 1330 to be retracted proximally along the central axis A, which in turn may open the jaw assembly 1311.

As illustrated in FIG. 95, the rotary drive shaft 1382 may be selectively advanced distally to pass the rotary drive head 1386 through the lumen of the barrel cam 1338 into a space 1399 in the end effector drive housing 1316 between the barrel cam 1338 and the rotary drive nut 1364 wherein the rotary drive head 1386 is not in operable engagement with any of the spline coupling portions. The rotary drive shaft 1382 may then be further advanced distally to bring rotary drive head 1386 into operable engagement with the spline coupling portion 1397 of the rotary drive nut 1364 as illustrated in FIG. 96. In this configuration, rotation of the rotary drive shaft 1382 causes rotation of the rotary drive nut 1364. As described above, the rotation of the rotary drive nut 1364 causes axial motions in the threaded drive member 1362. In result, rotation of the rotary drive shaft 1382 in a first direction (for example a clockwise direction) around the central axis A, may cause the threaded drive member 1362 to be advanced distally, which in turn may advance the I-beam member 1360 distally. Alternatively, rotation of the rotary drive shaft 1382 in a second direction (for example a clockwise direction) opposite the first direction may cause the threaded drive member 1362 to be retracted proximally, which may retract the I-beam member 1360 proximally.

The sequence of events causing the closure of the jaw assembly 1311, the full extension of the I-beam member 1360, the full retraction of the I-beam member 1360, and the reopening of the jaw assembly 1311 is illustrated in FIGS. 93-96 in a chronological order. FIG. 93 shows the jaw assembly 1311 in a fully open position, the I-beam member 1360 in a fully retracted position, and the rotary drive shaft 1382 in a retracted axial position, wherein the rotary drive head 1386 is operably engaged with the spline coupling portion 1390 of the end effector drive housing 1316. In a first phase of operation, the rotary drive shaft 1382 is rotated to rotate the end effector 1302 into an appropriate orientation, for example relative to a blood vessel. In a second phase of operation, the rotary drive shaft 1382 is advanced axially to bring the rotary drive head 1386 into operable engagement with the spline coupling portion 1394 of the barrel cam 1338. In this configuration, the rotary drive shaft 1382 may be rotated in a first direction (for example a clockwise direction) around the central axis A to close the jaw assembly 1311 around the blood vessel. The electrodes 1378 in the first jaw member 1304 and the second jaw member 1306 may be activated to seal the blood vessel. In a third phase of operation, the rotary drive shaft 1382 may then be advanced axially to bring the rotary drive head 1386 into operable engagement with the spline coupling portion 1397 of the rotary drive nut 1364. In this configuration, the rotary drive shaft 1382 may be rotated in a first direction around the central axis A (for example a clockwise direction) to advance the I-beam member 1360 thereby transecting the sealed blood vessel. In a fourth phase of operation, the rotary drive shaft 1382 may be rotated in a second direction (for example a counter clockwise direction) opposite the first direction to retract the I-beam member 1360.

In a fifth phase of operation, the rotary drive shaft 1382 is retracted axially to bring the rotary drive head 1386 into operable engagement with the spline coupling portion 1394 of the barrel cam 1338. In this configuration, the rotary drive shaft 1382 may be rotated in a second direction (for example a counter clockwise direction) opposite the first direction to reopen the jaw assembly 1311 thereby releasing the sealed cut blood vessel.

Figures 97, 98:
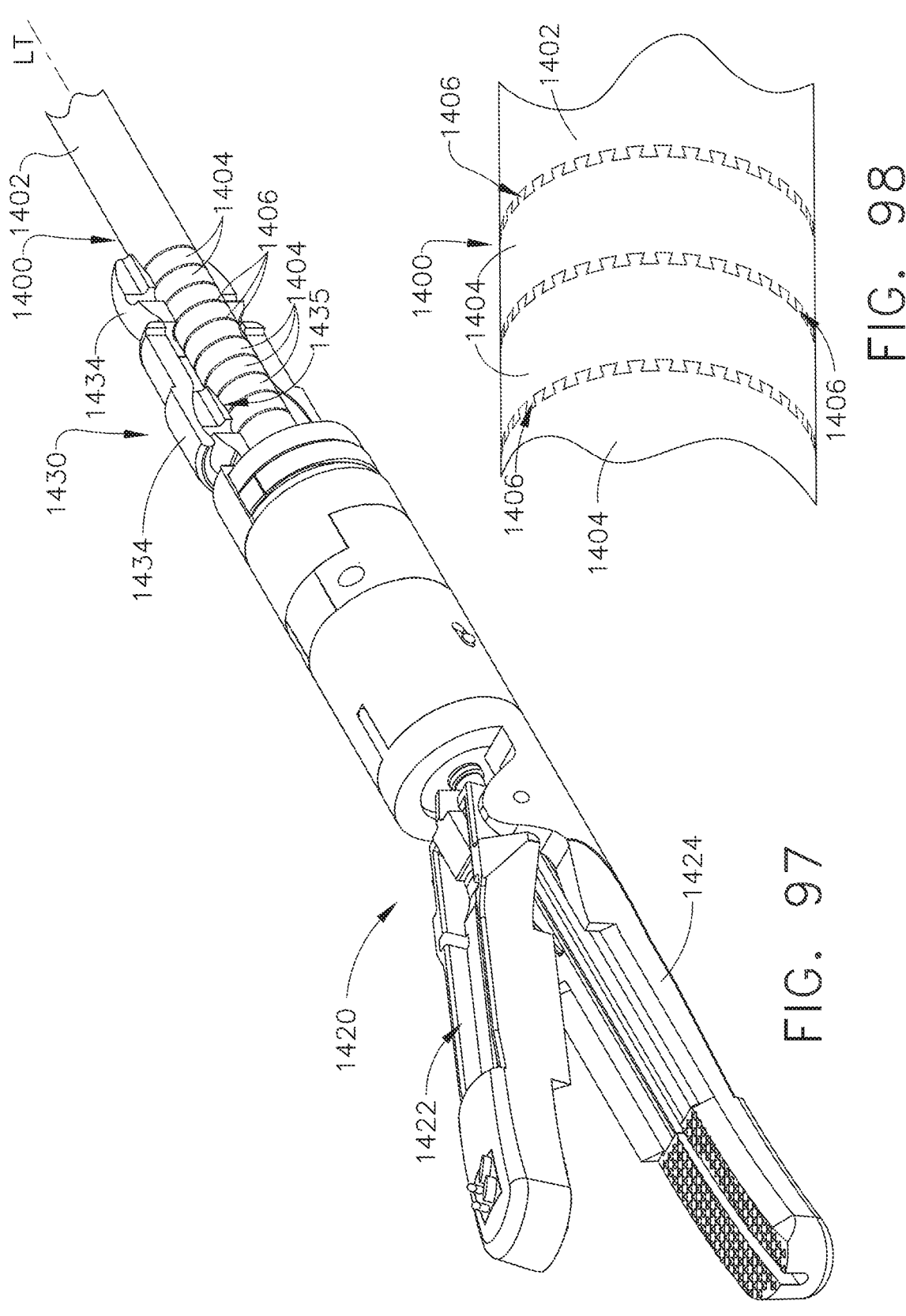
FIG. 97 illustrates a perspective view of an end effector and an articulation joint of a surgical instrument in accordance with at least one embodiment illustrated with portions removed for the purposes of illustration.
FIG. 98 illustrates a detail view of a drive shaft in accordance with at least one embodiment configured to be translated within the end effector and the articulation joint of FIG. 97.

As described above, a surgical tool can utilize a drive system for translating a drive member distally within an end effector of the surgical tool, to advance a cutting member within the end effector, for example, and for translating the drive tube proximally to retract the drive tube and/or cutting member. FIGS. 97 and 98 illustrate an example drive shaft assembly 1400 that may be employed in connection with an end effector 1420 and/or any of the end effectors described herein. For example, the drive shaft assembly 1400 (as well as the assembly 1400') may correspond to various threaded rotary drive members described herein including, for example, the threaded rotary drive members 604, 654, 1040, 1248, 1364, etc. Further to the above, the drive shaft assembly 1400 can be advanced distally in order to rotate a jaw member 1422 of the end effector 1420 between a closed position and an open position, as illustrated in FIG. 97, and advance a cutting member between the jaw member 1422 and a jaw member 1424 positioned opposite the jaw member 1422. In one example form, the drive shaft assembly 1400 includes a drive member, or tube, 1402 that can comprise a series of annular joint segments 1404 cut therein.

In various example embodiments, the drive member 1402 can comprise a hollow metal tube comprised of stainless steel, titanium, and/or any other suitable material, for example, that has a series of annular joint segments 1404 formed therein. In at least one embodiment, the annular joint segments 1404 can comprise a plurality of loosely interlocking dovetail shapes 1406 that are, for example, cut into the drive member 1402 by a laser and serve to facilitate flexible movement between the adjoining joint segments 1404. Such laser cutting of a tube stock can create a flexible hollow drive tube that can be used in compression, tension and/or torsion. Such an arrangement can employ a full diametric cut that is interlocked with the adjacent part via a "puzzle piece" configuration. These cuts are then duplicated along the length of the hollow drive tube in an array and are sometimes "clocked" or rotated to change the tension or torsion performance. Further to the above, the interlocking dovetails shapes 1406 are but one example embodiment and, in various circumstances, the drive member 1402 can comprise any suitable array of articulation joints comprising interlocking drive projections and drive recesses. In various circumstances, the drive member 1402 can comprise an articulation joint lattice comprising operably engaged projections and recesses which can be interlocked to transmit linear and/or rotary motions therebetween. In a sense, in various embodiments, the drive member 1402 can comprise a plurality or a multitude of articulation joints defined within the body of the drive member 1402. The drive member 1402 can include a plurality of articulation joints which are intrinsic to the body of the drive member 1402.

Figures 99, 100:
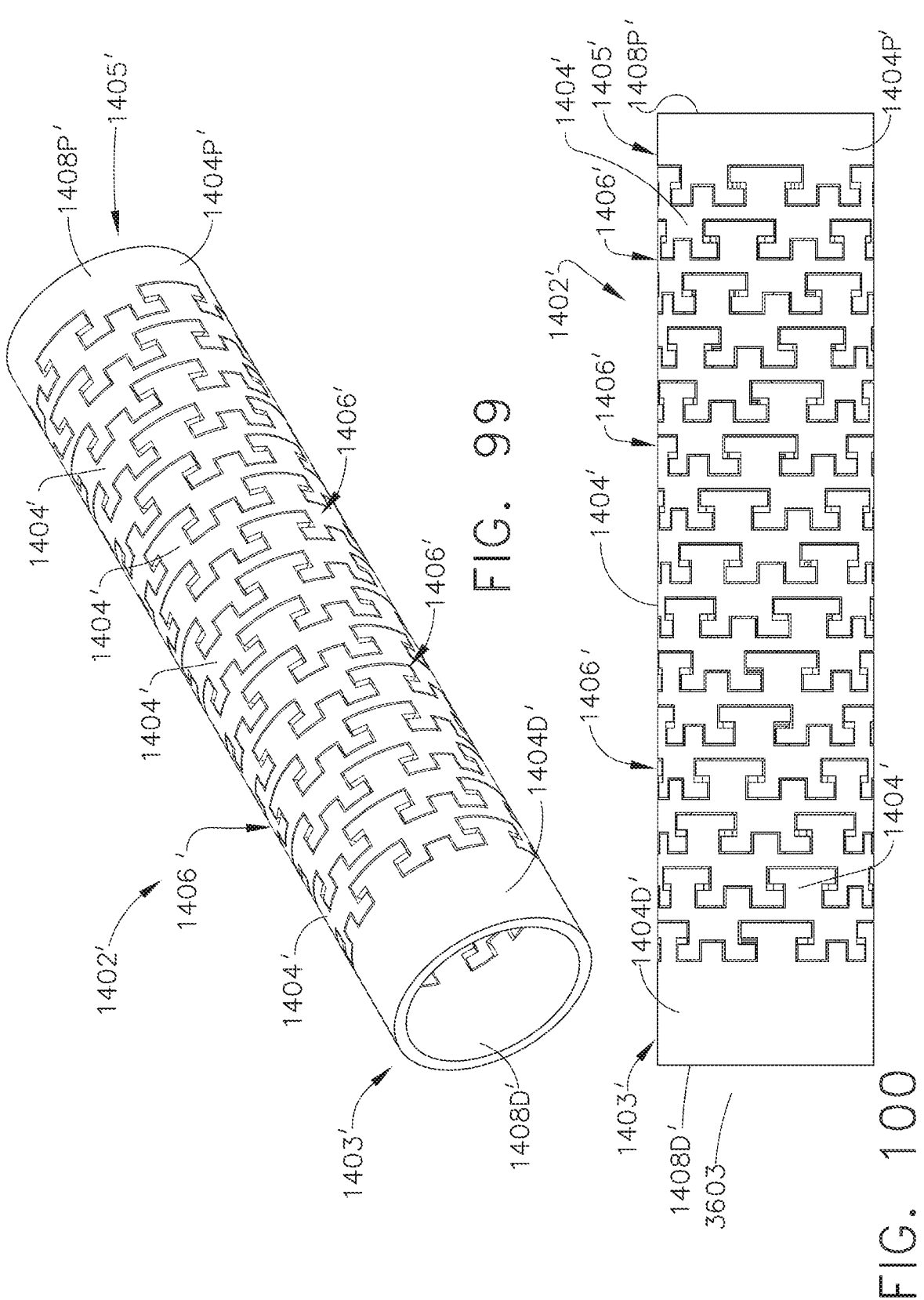
FIG. 99 illustrates a perspective view of a drive shaft in accordance with at least one alternative embodiment.
FIG. 100 illustrates an elevational view of one embodiment of the drive shaft of FIG. 99.
Figure 101:
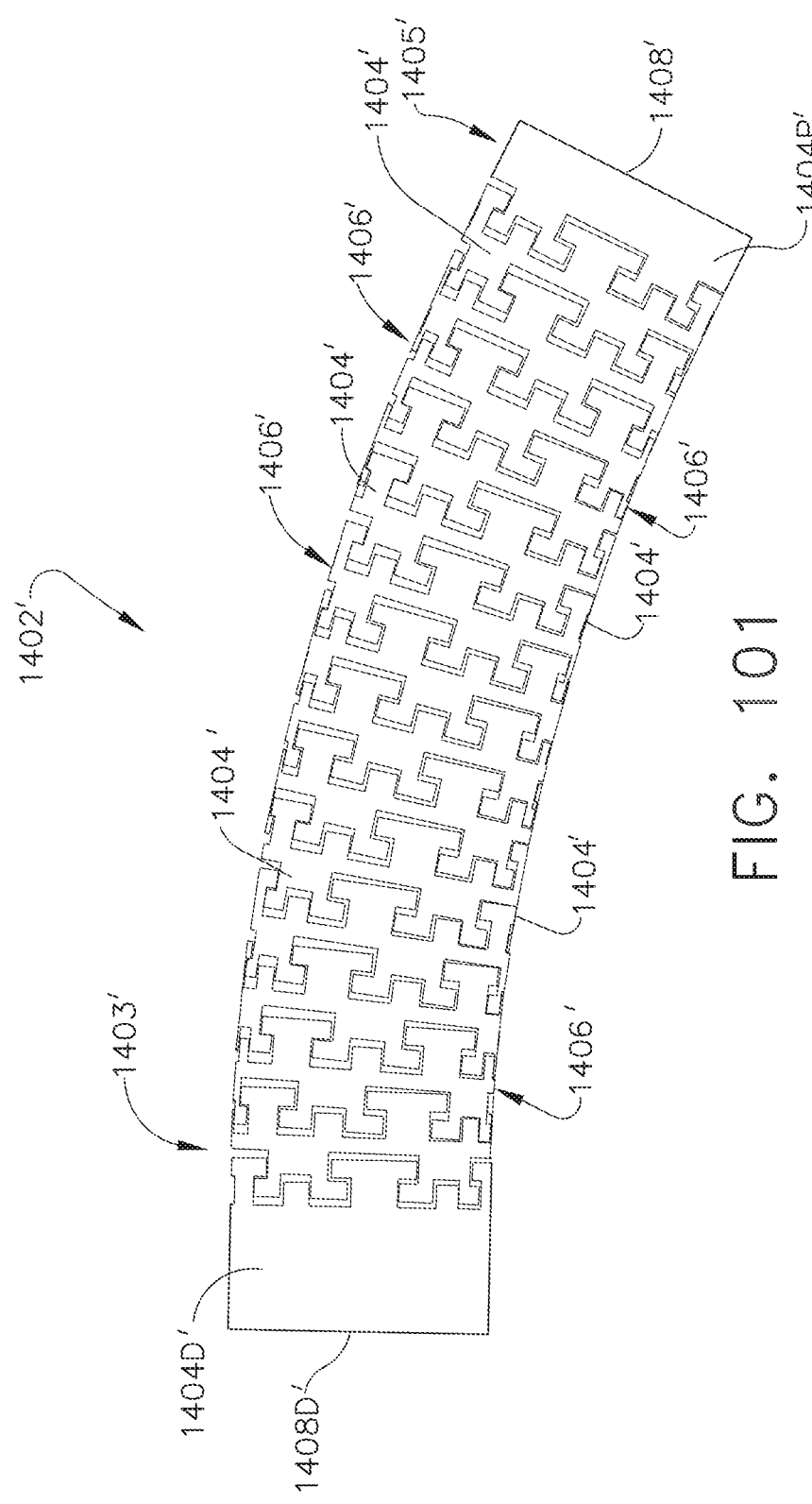
FIG. 101 illustrates an elevational view of one embodiment of the drive shaft of FIG. 99 illustrated in an articulated condition.

Further to the above, the drive member 1402 can be pushed distally such that a longitudinal force is transmitted through the drive member 1402 and to a cutting member, for example, operably coupled with a distal end of the drive member 1402. Correspondingly, the drive member 1402 can be pulled proximally such that a longitudinal force is transmitted through the drive member 1402 and to the cutting member. The interlocking dovetail shapes 1406 can be configured to transmit the longitudinal pushing and pulling forces between the joint segments 1404 regardless of whether the joint segments 1404 are longitudinally aligned, as illustrated in FIG. 98, and/or articulated relative to each other to accommodate the articulation of the articulation joint 1430 which rotatably connects the end effector 1420 to the shaft of the surgical instrument. More particularly, further to the above, the articulation joint 1430 can comprise one or more articulation segments 1434 which can move relative to one another to permit the end effector 1420 to rotate wherein, in order to accommodate the relative movement of the articulation joint segments 1434, the joint segments 1404 of the drive member 1402 can rotate or shift relative to each other. In at least the illustrated embodiment of FIG. 97, the articulation joint segments 1434 can define a passage 1435 extending therethrough which can be configured to closely receive the drive tube 1402 and constrain large transverse movements between the joint segments 1404 while concurrently permitting sufficient relative movement between the joint segments 1404 when the articulation joint 1430 has been articulated. FIGS. 99-101 illustrate alternative example micro-annular joint segments 1404' of a drive member 1402' that can comprise a plurality of laser cut shapes 1406' that roughly resemble loosely interlocking, opposed "T" shapes and T-shapes with a notched portion therein, for example. The laser cut shapes 1406' can also roughly resemble loosely interlocking, opposed "L" shapes and L-shapes defining a notched portion, for example. The annular joint segments 1404, 1404' can essentially comprise multiple micro-articulating torsion joints. That is, each joint segment 1404, 1404' can transmit torque while facilitating at least some relative articulation between each annular joint segment. As shown in FIGS. 99 and 100, the joint segment 1404D' on the distal end 1403' of the drive member 1402' has a distal mounting collar portion 1408D' that facilitates attachment to other drive components for actuating the end effector. Similarly, the joint segment 1404P' on the proximal end 1405' of the drive member 1402' has a proximal mounting collar portion 1408P' that facilitates attachment to other proximal drive components or portions of a quick disconnect joint, for example.

Figures 102, 103:
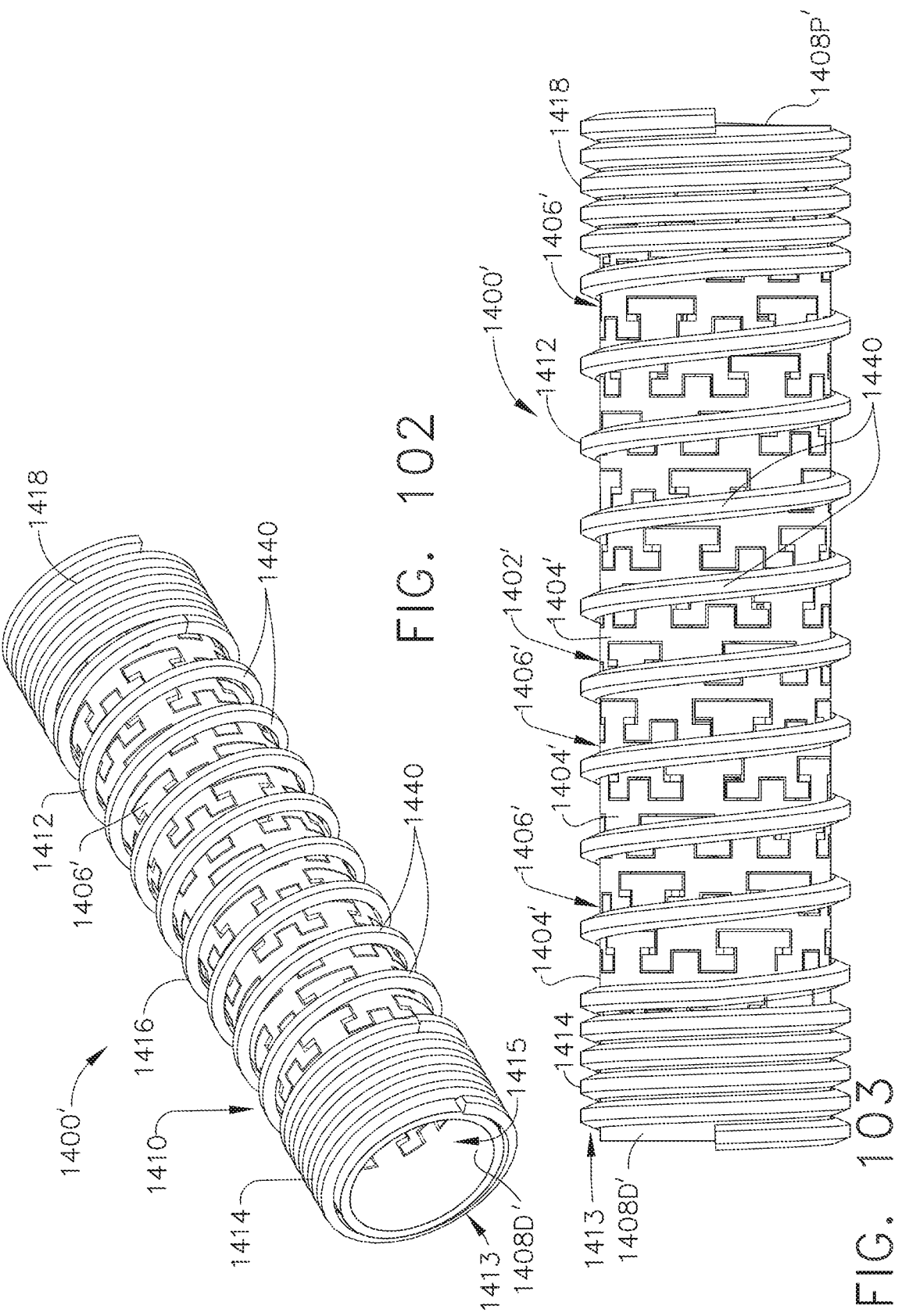
FIG. 102 illustrates a perspective view of a drive shaft assembly comprising a drive tube and a thread extending around the drive tube in accordance with at least one alternative embodiment.
FIG. 103 illustrates an elevational view of one embodiment of the drive shaft assembly of FIG. 102.

The joint-to-joint range of motion for each particular joint segment 1404' can be increased by increasing the spacing in the laser cuts. In various circumstances, however, the number and/or density of the laser cuts within any particular region of the drive member 1402' can cause the drive member 1402' to be particularly flexible in that region. To ensure that the joint segments 1404' remain coupled together without significantly diminishing the drive tube's ability to articulate through desired ranges of motion, a secondary constraining member can be employed to limit or prevent the outward expansion of the joint segments 1404'. In the example embodiment depicted in FIGS. 102 and 103, a secondary constraining member 1410 comprises a spring 1412 or an otherwise helically-wound member. In various example embodiments, the distal end 1414 of the spring 1412 can correspond to and can be attached to the distal mounting collar portion 1408D' and can be wound tighter than the central portion 1416 of the spring 1412. Similarly, the proximal end 1418 of the spring 1412 can correspond to and can be attached to the proximal collar portion 1408P' and can be wound tighter than the central portion 1416 of the spring 1412. As a result of the tighter winding, the distal end 1414 and/or the proximal end 1418 can comprise coils which are positioned closer together than the coils of the central portion 1416. Stated another way, the coils per unit distance of the distal end 1414 and/or the proximal end 1418 can be greater than the coils per unit distance of the central portion 1416. In any event, the spring 1412 can define a longitudinal aperture 1413 within which the drive member 1402', and/or the drive member 1402, for example, can be positioned. The longitudinal aperture 1413 and the drive member 1402' can be sized and configured such that the drive member 1402' is closely received within the longitudinal aperture 1413 wherein, in various circumstances, the coils of the spring 1412 can limit the outward movement of the joint segments 1404' such that the joint segments 1404' do not become disconnected from one another when they are articulated relative to one other. As outlined above, the distal end 1414 of the spring 1412 can be fixedly mounted to the distal end 1403' of the drive member 1402' and the proximal end 1418 of the spring 1412 can be fixedly mounted to the proximal end 1405' of the drive member 1402' wherein the movement of the distal tube end 1403' can move the distal spring end 1414 and, correspondingly, the movement of the proximal tube end 1405' can move the proximal spring end 1418. In various circumstances, the spring ends 1414 and 1418 can be welded, for example, to the tube ends 1403' and 1405', respectively. In at least the illustrated embodiment, the coils of the central portion 1416 may not be fixedly mounted to the drive member 1402'. In at least one such embodiment, the drive member 1402' can be configured to at least partially articulate within the coils of the central portion 1416 until the drive member 1402' contacts the coils wherein, at such point, the coils can be configured to at least partially expand or shift to accommodate the lateral movement of the drive member 1402'. In various other embodiments, at least portions of the coils of the central portion 1416 can be fixedly mounted, such as by welding, for example, to the drive member 1402'.

Further to the above, the constraining member 1410 may be installed on the drive member 1402' with a desired pitch such that the constraining member 1410 also functions, for example, as a flexible drive thread 1440 which can be threadably engaged with other threaded drive components on the end effector and/or the drive system, as described above. The drive member 1402' can be constrained from being revolved around its longitudinal axis wherein, when a threaded drive input is engaged with the thread 1440 and is rotated in a first direction by a motor, for example, the drive member 1402' can be advanced distally within the end effector 1420. Correspondingly, when the threaded drive input engaged with the thread 1440 is rotated in a second, or opposite, direction, the drive member 1402' can be retracted proximally. It will be appreciated that the constraining member 1410 may be installed in such a manner that the thread 1440 includes a constant, or at least substantially constant, pitch along the length thereof. In such embodiments, the drive member 1402' can be advanced and/or retracted at a constant, or an at least substantially constant, rate for a given rate in which the threaded drive input is rotated. It will also be appreciated that the constraining member 1410 can be installed in such a manner that the thread 1440 includes a variable pitch, or a pitch which changes along the length of the drive member 1402'. For example, the variable pitch arrangement of the constraining member 1410 may be used to slow the drive assembly 1400' down or speed the drive assembly 1400' up during certain portions of the firing stroke of the drive assembly 1400'. For instance a first portion of the thread 1440 can include a first pitch which is smaller than the pitch of a second portion of the thread 1440 wherein the first pitch can drive a closing member at a first rate and the second portion can drive a firing member at a second rate, for example. In at least some forms, for example, the drive shaft assembly comprises a variable pitch thread on a hollow flexible drive shaft that can be pushed and pulled around a ninety degree bend or greater, for example.

As discussed above, the drive member 1402' can be constrained from revolving about its longitudinal axis. Moreover, the entire drive shaft assembly 1400' can be constrained from rotating about its longitudinal axis. In various embodiments, the drive member 1402' can comprise a longitudinal slot defined therein which can be engaged with one or more projections which can extend inwardly from the end effector 1420 and/or the articulation joint members 1434 into the longitudinal slot, for example. Such an arrangement of the longitudinal slot and the projections can be configured to prevent or at least limit the rotation of the drive shaft assembly 1400' about its own longitudinal axis. As used herein, the longitudinal axis of the drive shaft assembly 1400', and/or the drive member 1402', can extend along the center of the drive shaft assembly 1400' regardless of whether the drive shaft assembly 1400' is in a straight configuration or a bent configuration. As a result, the path and direction of the longitudinal axis of the drive shaft assembly 1400' may change when the end effector 1420 is articulated and the drive shaft assembly 1400' articulates to accommodate the articulation of the end effector 1420. Further to the above, the drive member 1402' can be fixedly mounted to and extend proximally from a cutting member positioned within the end effector 1420. As described herein, the cutting member can be closely received within various slots and/or channels defined in the end effector which can prevent the cutting member, and the drive shaft assembly 1400' extending therefrom, from being rotated, or at least substantially rotated about its longitudinal axis. While the longitudinal axis of the drive shaft assembly 1400' can be defined by the drive member 1402', the longitudinal axis can be defined by the spring 1412. In at least one such embodiment, the center path of the spring coils can define the longitudinal axis of the drive shaft assembly 1400'. In any event, the drive shaft assembly 1400' can be constrained from revolving around its longitudinal axis.

Figures 104, 105:
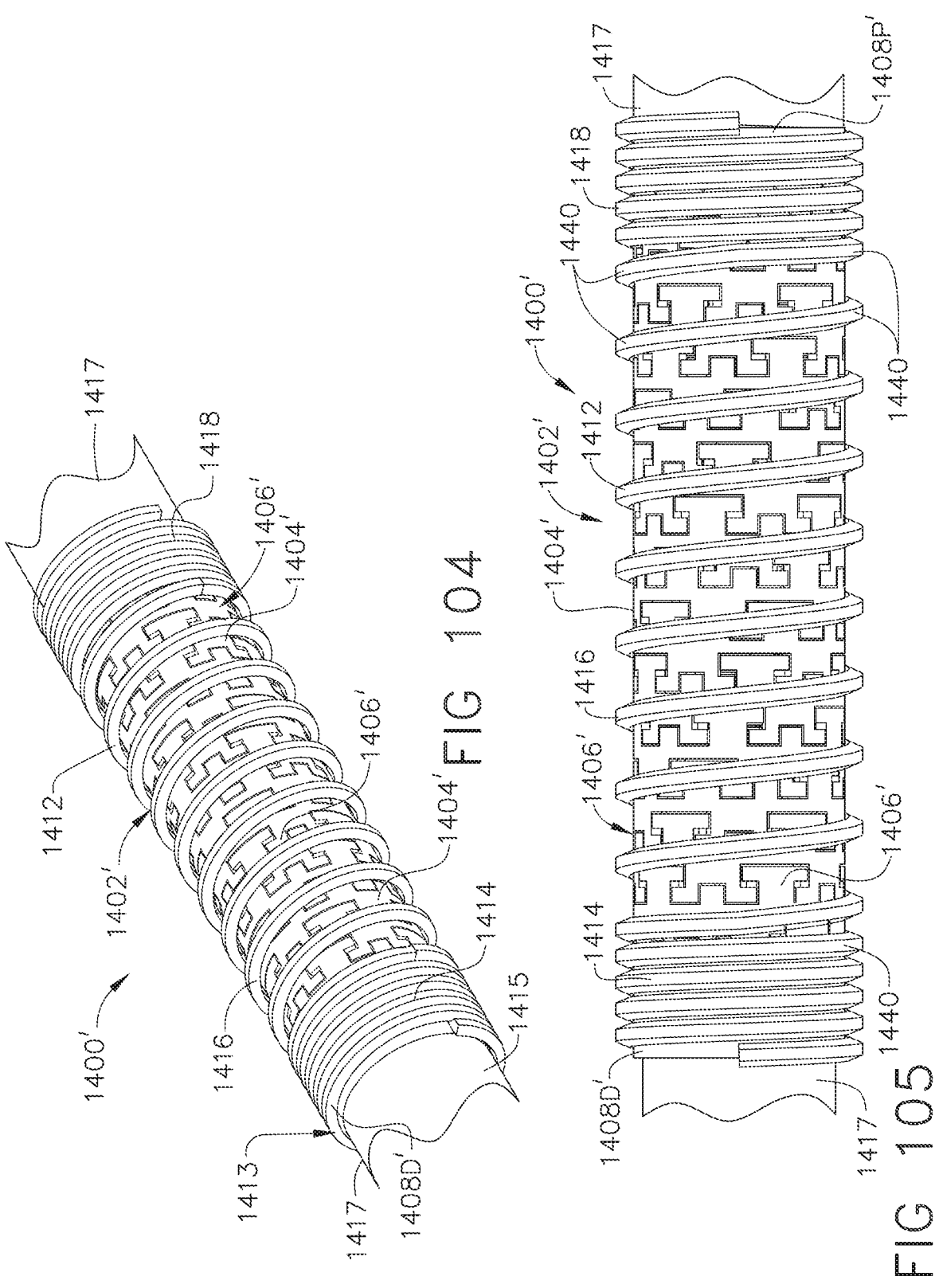
FIG. 104 illustrates a perspective view of a drive shaft assembly comprising a drive tube, a thread extending around the drive tube, and an inner core extending through the drive tube in accordance with at least one embodiment.
FIG. 105 illustrates an elevational view of one embodiment of the drive shaft assembly of FIG. 104.

Turning now to FIGS. 104 and 105, the drive shaft assembly 1400' can comprise an internal constraining member, such as a flexible core 1417, for example, which can be configured to limit or prevent the inward movement or collapse of the joint segments 1404' of the drive member 1402'. The drive member 1402' can define an internal longitudinal cavity 1415 which can be configured to closely receive the flexible core 1417. In at least one such embodiment, the internal cavity 1415 defined in the drive member 1402' can comprise a diameter or width which is equal to, or at least substantially equal to, the diameter or width of the flexible core 1417. In various circumstances during the articulation of the end effector 1420, for example, portions of the joint segments 1404' can deflect or be displaced inwardly toward the flexible core 1417 wherein, when the joint segments 1404' contact the flexible core 1417, the core 1417 can inhibit the inward movement of the joint segments 1404' and prevent the drive member 1402' from collapsing inwardly. The flexible core 1417 can be mounted to at least portions of the drive member 1402' such as the distal end 1408D' and/or the proximal end 1408P' thereof, for example. In certain embodiments, the flexible core 1417 may not be fixedly mounted to the drive member 1402' wherein, in such embodiments, the flexible core 1417 can be held in place by the drive member 1402'. In any event, the flexible core 1417 can be sufficiently flexible so as to permit the drive shaft assembly 1400' to bend or articulate as necessary to transmit the pushing and pulling motions applied thereto, as described above.

As outlined above, the shaft assembly 1400', for example, can be configured to bend or flex to accommodate the articulation of the end effector 1420 about the articulation joint 1430. The drive member 1402', the flexible core 1417, and/or the spring 1412 can be resilient such that the shaft assembly 1400' can return to its original longitudinal configuration, for example. In various circumstances, the end effector 1420 can be rotated from its articulated position back to its longitudinal, or straight, position and, as such, the shaft assembly 1400' can be configured to bend or flex in order to accommodate the return of the end effector 1420.

Figure 106:
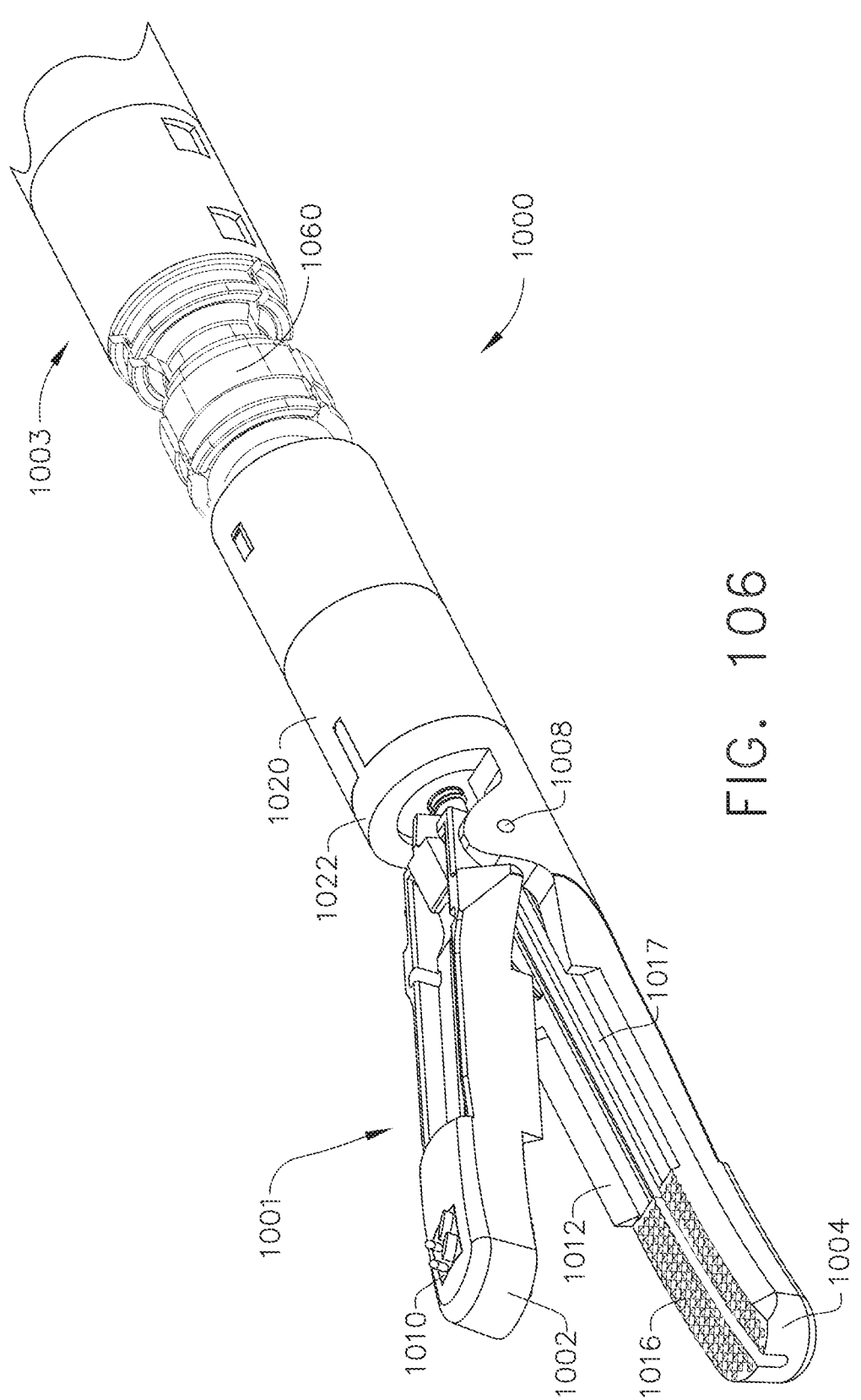
FIG. 106 is a perspective view of a surgical tool having first and second jaw members in accordance with certain embodiments described herein.
Figure 107:
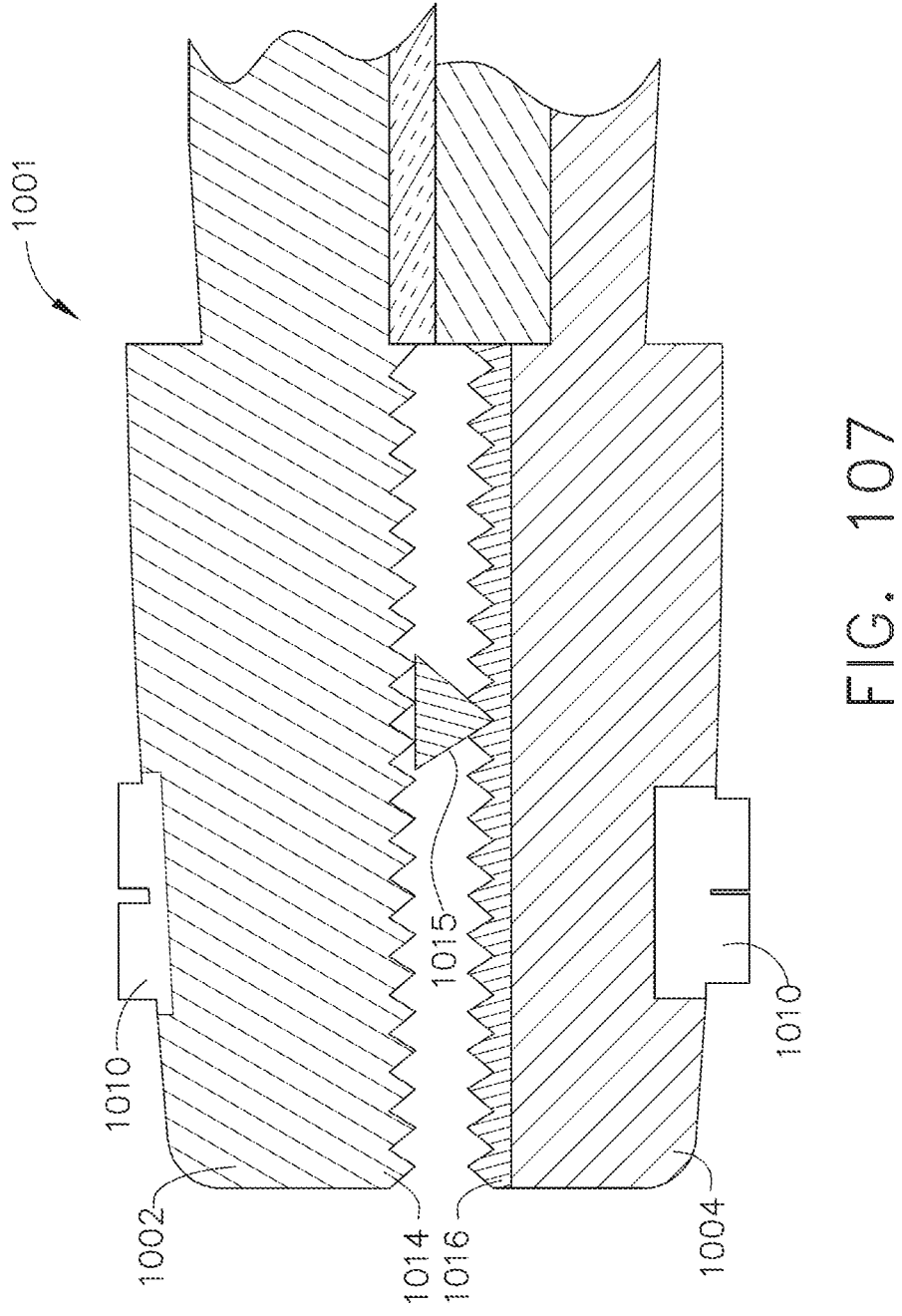
FIG. 107 is cross sectional view of distal portions of one embodiment of the first and second jaw members of the surgical end tool shown in FIG. 106.
Figures 108, 109:
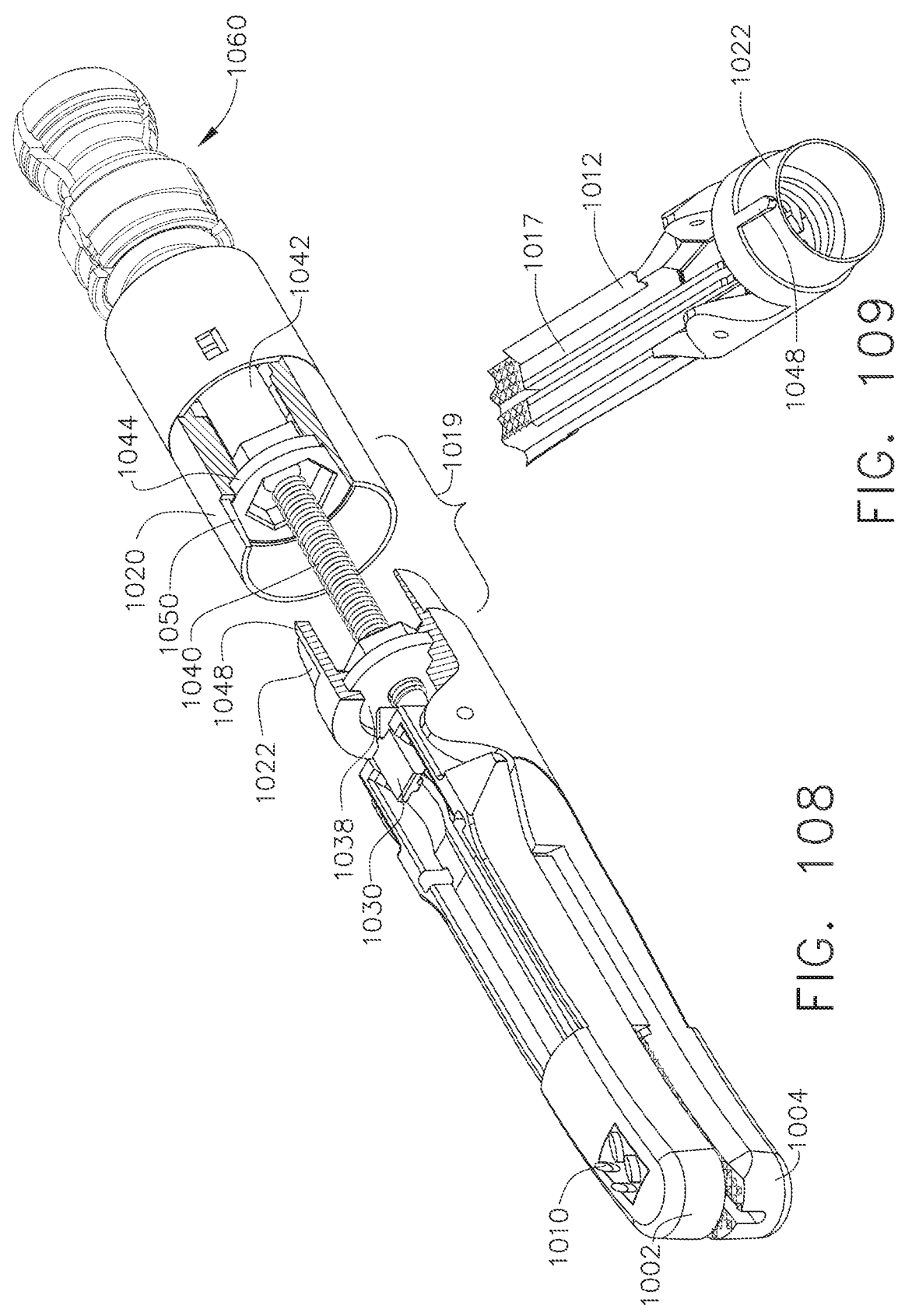
FIG. 108 is a perspective view of a surgical end effector and a shaft assembly in accordance with certain embodiments described herein.
FIG. 109 is a prospective view of a jaw member of a surgical end effector in accordance with certain embodiments described herein.

Referring to FIGS. 106-108, a surgical tool 1000 may include a surgical end effector 1001 and a shaft assembly 1003. Surgical end effector 1001 may be configured to perform surgical activities in response to drive motions applied thereto. Shaft assembly 1003 may be configured to transmit such drive motions to surgical end effector 1001. The surgical end effector 1001 may include a first jaw member 1002, and a second jaw member 1004. The first jaw member 1002 may be movable relative to the second jaw member 1004 between a first position and a second position. Alternatively, the first jaw member 1002 and second jaw member 1004 may be moveable relative to each other between a first position and a second position. The first position may be an open position and the second position may be a closed position.

Referring to FIGS. 106-108, the first jaw member 1002 may be pivotally movable relative to the second jaw member 1004 between a first position and a second position. As illustrated in FIG. 108, the first jaw member 1002 may include mounting holes (not shown), and the second jaw member 1004 may include mounting holes 1008. The first jaw member 1002 can be arranged relative to the second jaw member 1004 such that a pivot or trunnion pin (not shown) is inserted through the mounting holes of the first jaw member 1002 and the mounting holes 1008 of the second jaw member 1004 to pivotally couple the first jaw member 1002 to the second jaw member 1004. Other suitable means for coupling the first jaw member 1002 and the second jaw member 1004 are contemplated within the scope of this disclosure.

Referring to FIGS. 106-108, surgical end effector 1001 may be adapted to perform multiple functions. For example, surgical end effector 1001 may include gripping portions 1010 disposed on exterior surfaces of the first jaw member 1002 and/or the second jaw member 1004. Gripping portions 1010 may be adapted for contacting and bluntly dissecting tissue. Suitable gripping portions 1010 are described, for example, in connection with FIGS. 116-131. Surgical end effector 1001 may also include angled tissue engagement surfaces 1012, for transecting tissue. Suitable angled tissue engagement surfaces 1012 are described, for example, in connection with FIGS. 132-142. The first jaw member 1002 may include an interior surface 1014 and the second jaw member 1004 may include an interior surface 1016. The first 1014 and second 1016 interior surfaces may be configured to grip, pass, and/or manipulate tissue and/or surgical implements such as needles 1015 for suturing tissue. This gripping, passing, and/or manipulating functionality is described, for example, in connection with FIGS. 153-168. Furthermore, surgical end effector 1001 may also include electrodes 1017 and/or another electrically active surface for sealing blood vessels during a surgical procedure. The electrodes 1017 may be configured to deliver radio frequency (RF) energy to tissue clamped between the first jaw member 1002 and the second jaw member 1004 when in a closed position to weld/fuse the tissue, which may be transected by translating a cutting member 1018. Suitable electrodes are described, for example, in connection with FIGS. 153-168.

Referring to FIGS. 108-111, surgical end effector 1001 may be releasably attached to shaft assembly 1003. An operator or a surgeon may attach surgical end effector 1001 to shaft assembly 1003 to perform a surgical procedure. In the embodiment depicted in FIG. 108, shaft assembly 1003 includes a coupling arrangement in the form of a quick disconnect arrangement or joint 1019 that facilitates quick attachment of a distal shaft portion 1020 of the shaft assembly 1003 to a proximal shaft portion 1022 of the surgical end effector 1001. The quick disconnect joint 1019 may serve to facilitate the quick attachment and detachment of a plurality of drive train components used to provide control motions from a source of drive motions to an end effector that is operably coupled thereto.

Figure 112:
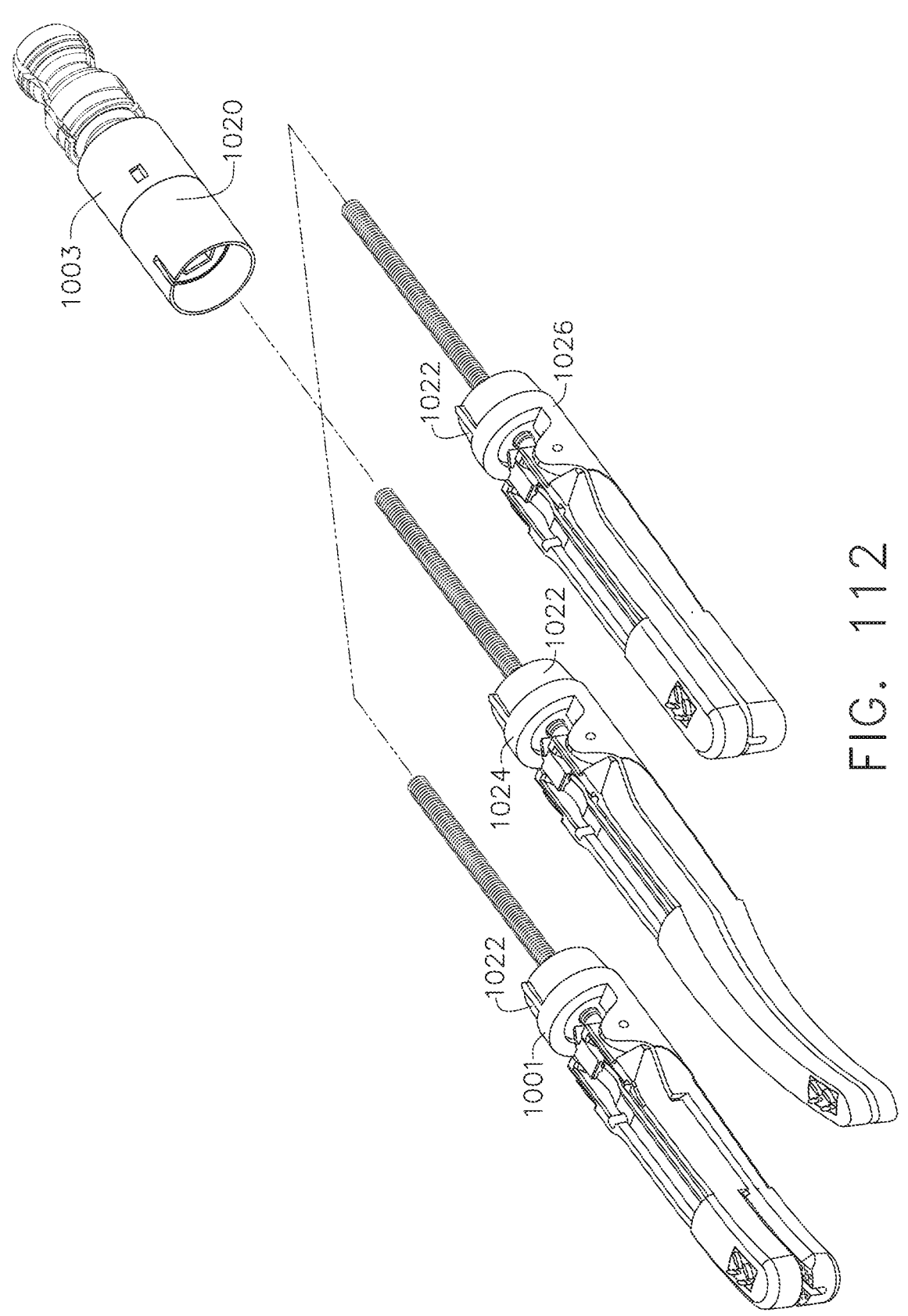
FIG. 112 is a perspective view of multiple interchangeable surgical end effectors in accordance with certain embodiments described herein.

As illustrated in FIG. 112, surgical end effector 1001 may be interchanged with other surgical end effectors suitable for use with shaft assembly 1003. For example, surgical end effector 1001 may be detached from shaft assembly 1003 and a second surgical end effector 1024 may be attached to shaft assembly 1003. In another example, the second surgical end effector 1024 may be replaced with a third surgical end effector 1026. Surgical end effectors 1001, 1024, and 1026 may include common drive train components that are operably engageable with their counter parts in the shaft assembly 1003. Yet, surgical end effectors 1001, 1024, and 1026 may each include unique operational features suitable for certain surgical tasks.

The surgical end effector 1001 may include an actuation mechanism. The actuation mechanism may comprise a closure mechanism for moving the first jaw member 1002 relative to the second jaw member 1004. The actuation mechanism may comprise a firing mechanism for transecting tissue grasped between the first jaw member 1002 and the second jaw member 1004. The closure and firing may be accomplished by separate mechanisms, which may be driven separately or contemporaneously. Alternatively, the closure and firing may be accomplished via a single mechanism. Suitable closure mechanisms and suitable firing mechanisms are described, for example, in connection with FIGS. 64-82, 83-91 and 92-96.

Figure 113:
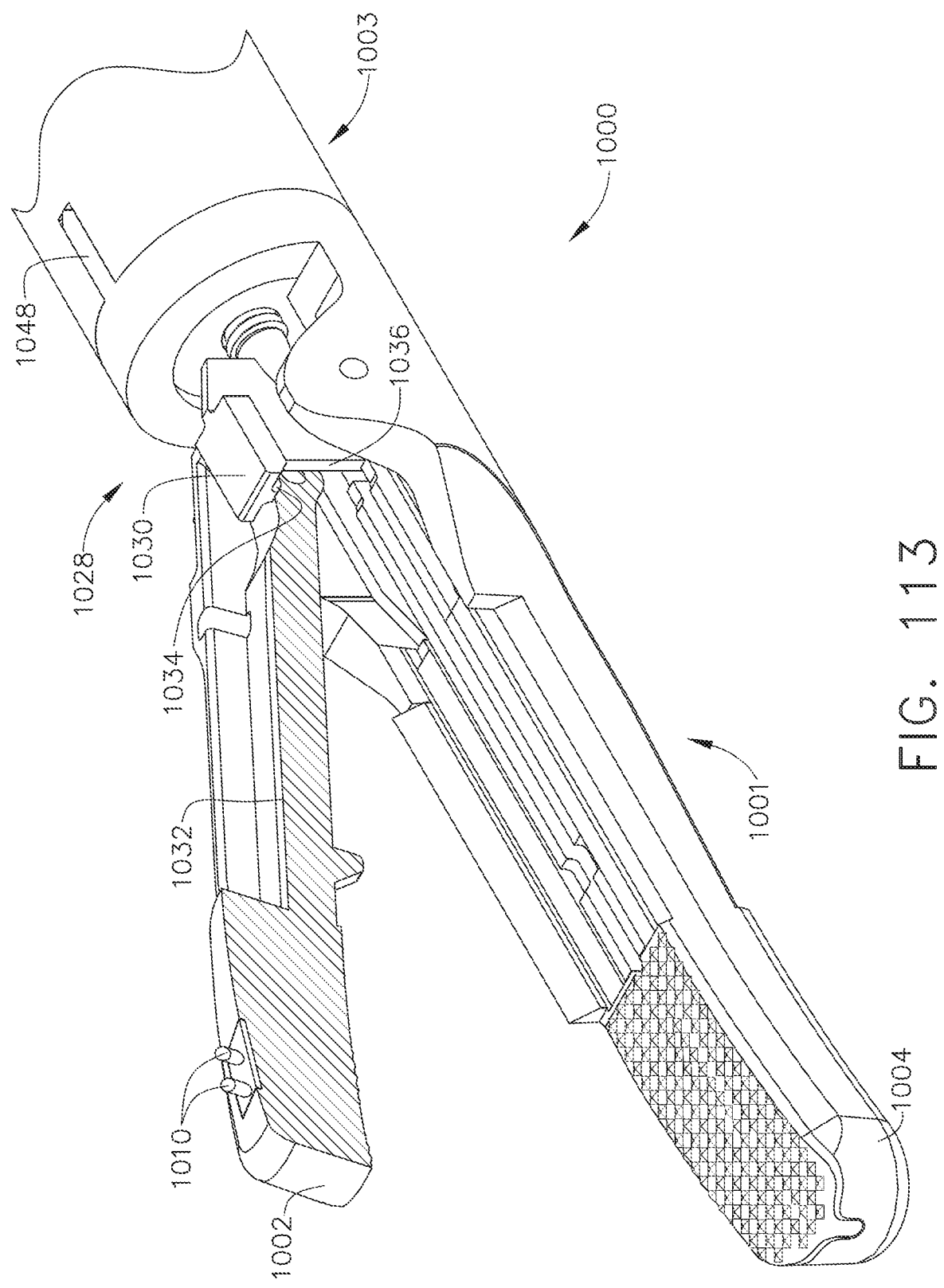
FIG. 113 is a perspective view of a surgical end effector including a cross sectional view of a jaw member in accordance with certain embodiments described herein.

Referring to FIG. 113, an actuation mechanism 1028 is shown. The actuation mechanism may include a reciprocating member 1030. The reciprocating member 1030 may define a cam slot 1032 configured to receive a cam pin 1034 coupled to the first jaw member 1002. Distal and proximal movement of the reciprocating member 1030 may cause the cam pin 1032 to translate within the cam slot 1034, which may, in turn, cause the first jaw member 1002 to pivot from an open position (e.g., proximal position of the reciprocating member 1030) to a closed (e.g., distal position of the reciprocating member 1030). In embodiments where the first 1002 and the second 1004 jaw members are movable, both jaw members 1002 and 1004 may comprise a cam pin and the reciprocating member 1030 may define a pair of cam slots or grooves. The reciprocating member 1030 may comprise an I-beam member adapted to slide over the jaw members 1002 and 1004 to close the jaw members 1002 and 1004, and/or to provide a clamping force tending to force the jaw members 1002, and 1004 together. The reciprocating member 1030 may include a cutting blade 1036. The cutting blade 1036 may be attached to the reciprocating member 1030 and situated such that it can be extended and retracted with the reciprocating member 1030. The cutting member may be extended to transect tissue or material present between the jaw members 1002, and 1004.

Referring to FIGS. 108-111, the actuation mechanism 1028 may include a rotary drive nut 1038 and a threaded rotary drive member 1040. The rotary drive member 1040 may extend proximally from the reciprocating member 1030. The reciprocating member 1030 and the rotary drive member 1040 may be formed together as one piece. Alternatively, the reciprocating member 1030 and the rotary drive member 1040 may be formed separately and welded together. Other techniques for joining the reciprocating member 1030 and the rotary drive member 1040 may be employed and are contemplated within the scope of this disclosure. The rotary drive nut 1038 may be operably supported within the proximal shaft portion 1022 of the surgical end effector 1001, which extends proximally relative to the jaw members 1002, and 1004. The rotary drive nut 1038 may be rotated around a central axis extending through the proximal shaft portion 1022, for example, as described herein above. The rotary drive member 1040 may extend proximally from the reciprocating member 1030 along the central axis through the rotary drive nut 1038. The rotary drive nut 1038 and the rotary drive member 1040 may be arranged in a mating arrangement such that rotation of the rotary drive nut 1038 around the central axis in one direction (e.g. clockwise direction) may advance the rotary drive member 1040, and rotation of the rotary drive nut 1038 around the central axis in the opposite direction (e.g. counter clockwise direction) may retract the rotary drive member 1040. This actuation mechanism and other suitable actuations mechanisms are described, for example, in connection with FIGS. 64-82, 83-91 and 92-96.

Figure 110:
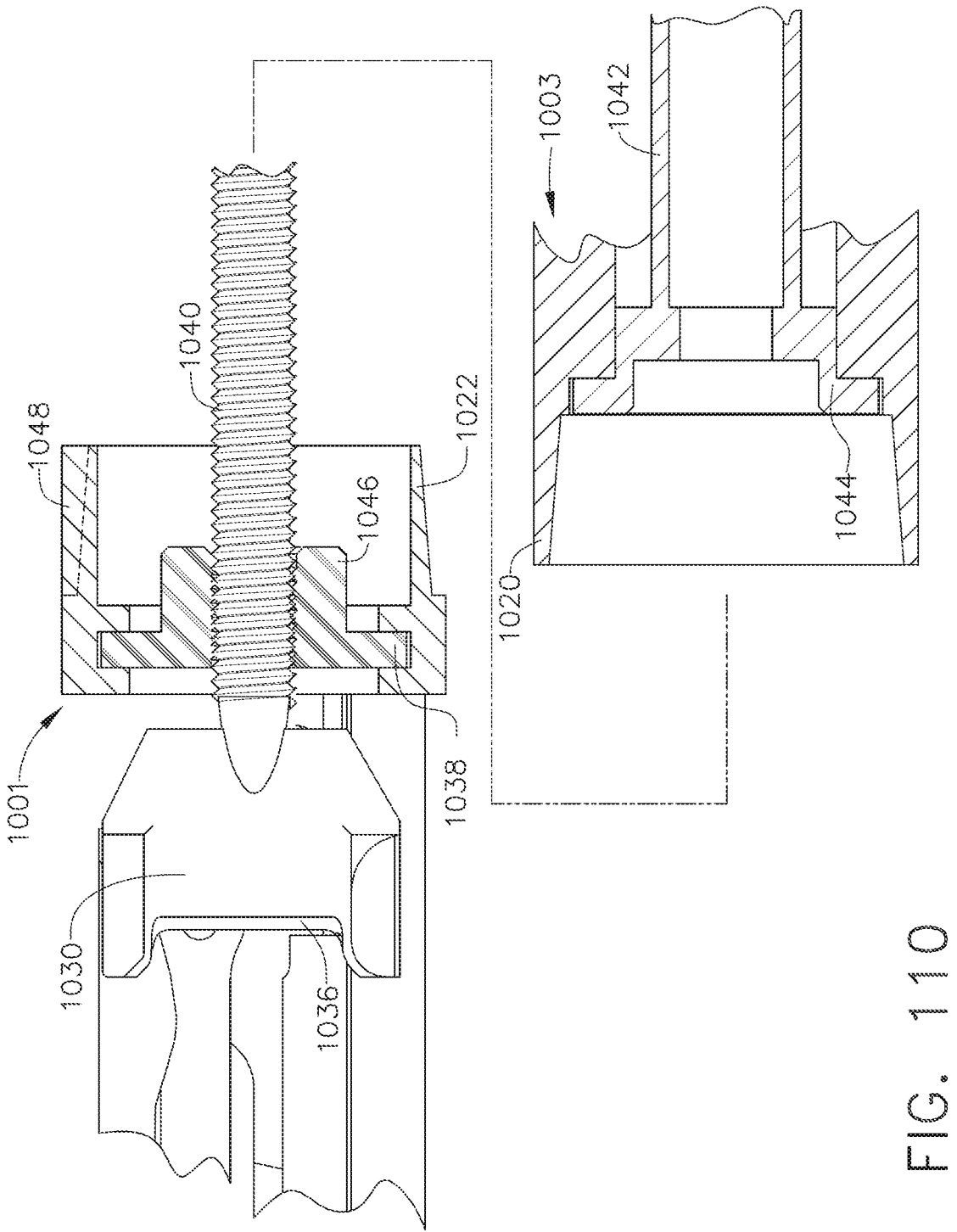
FIG. 110 is a cross-sectional view of a surgical effector detached from a shaft assembly in accordance with certain embodiments described herein.
Figure 111:
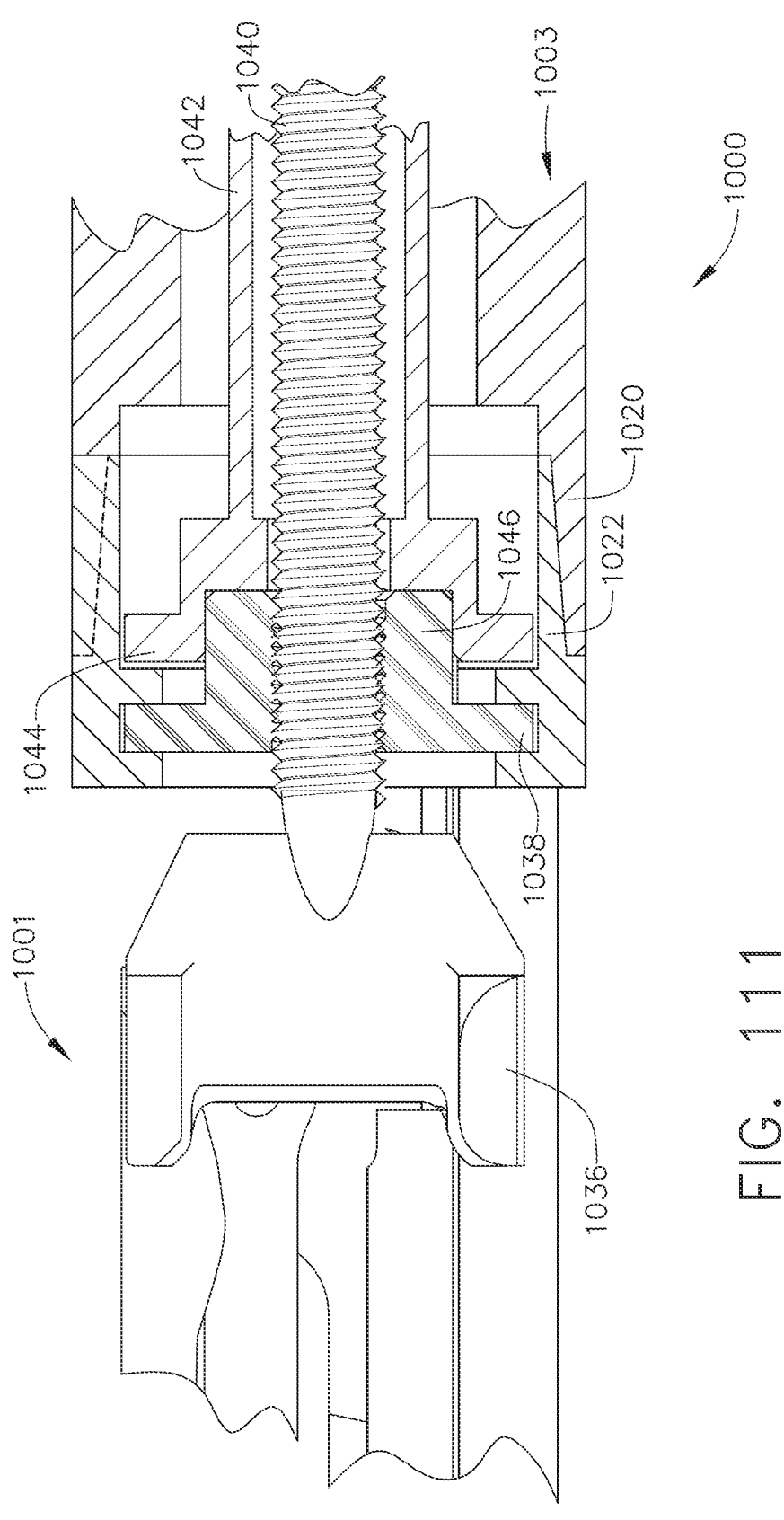
FIG. 111 is a cross-sectional view of a surgical effector attached to a shaft assembly in accordance with certain embodiments described herein.

Referring to FIGS. 108-111, the surgical tool 1000 may include a rotary drive shaft 1042 disposed longitudinally through shaft assembly 1003. The rotary drive shaft 1042 may include a rotary drive head 1044 at a distal portion thereof. The rotary drive nut 1038 may comprise an actuation coupler 1046 for mating arrangement with the rotary drive head 1044 such that when coupled, the rotary drive head 1044 may transmit rotary motions to the actuation coupler 1046. The rotary drive shaft 1042 may be selectively moved axially between multiple discrete positions. For example, the rotary drive shaft 1042 may be extended axially to bring the rotary drive head 1044 into operable engagement with the actuation coupler 1046 as depicted in FIG. 111. Alternatively, the rotary drive shaft 1042 may be retracted axially to disengage the rotary drive head 1044 from the actuation coupler 1046. Such arrangement may allow for a quick and efficient attachment and detachment of a plurality of surgical end effectors to shaft assembly 1003.

Referring to FIGS. 108-110, surgical end effector 1001 is shown detached from shaft assembly 1003. The proximal shaft portion 1022 of surgical end effector 1001 is disengaged from the distal shaft portion 1020 of the shaft assembly 1003. As depicted in FIG. 108, the proximal shaft portion 1022 of the surgical end effector 1001 may include a tapered end for mating arrangement with a funneling end on the distal shaft portion 1020 of the shaft assembly 1003. The rotary drive shaft 1042 may include a hollow distal portion that extends distally along a central axis through the rotary drive head 1044 and terminates at a distal opening thereof. The hollow distal portion may receive a proximal portion of the rotary drive member 1040 when the surgical end effector 1001 is attached to the shaft assembly 1003. The rotary drive member 1040 may rotate freely in the hollow distal portion of the rotary drive shaft 1042. As depicted in FIG. 110, the surgical end effector 1001 is attached to shaft assembly 1003 simply by inserting the proximal portion of the rotary drive member 1040 into the hollow portion of the rotary drive shaft 1042 and guiding the tapered end of the proximal shaft portion 1022 of the surgical end effector 1001 into a mating arrangement with the funneling end of the distal shaft portion 1020 of the shaft assembly 1003. As depicted in FIG. 111, once the surgical end effector 1001 is attached to shaft assembly 1003, the rotary drive shaft 1042 may be advanced to bring the rotary drive head 1044 into operable engagement with the actuation coupler 1046 to transmit rotary motions to the rotary drive nut 1038. Other attachment means and techniques for releasably attaching the surgical end effector 1001 to the shaft assembly 1003 are contemplated within the scope of this disclosure.

As illustrated in FIGS. 108-110, the proximal shaft portion 1022 of surgical end effector 1001 and the distal shaft portion 1020 of the shaft assembly 1003 may have aligning features to ensure that the surgical end effector 1001 and the shaft assembly 1003 are correctly aligned upon attachment. In an example embodiment, as illustrated in FIG. 108, the proximal shaft portion 1022 of surgical end effector 1001 includes a key feature 1048 and the distal shaft portion 1020 of the shaft assembly 1003 may include a slot 1050 for receiving the key feature. Other aligning means and techniques for aligning the surgical end effector 1001 to the shaft assembly 1003 are contemplated within the scope of this disclosure.

Figure 114:
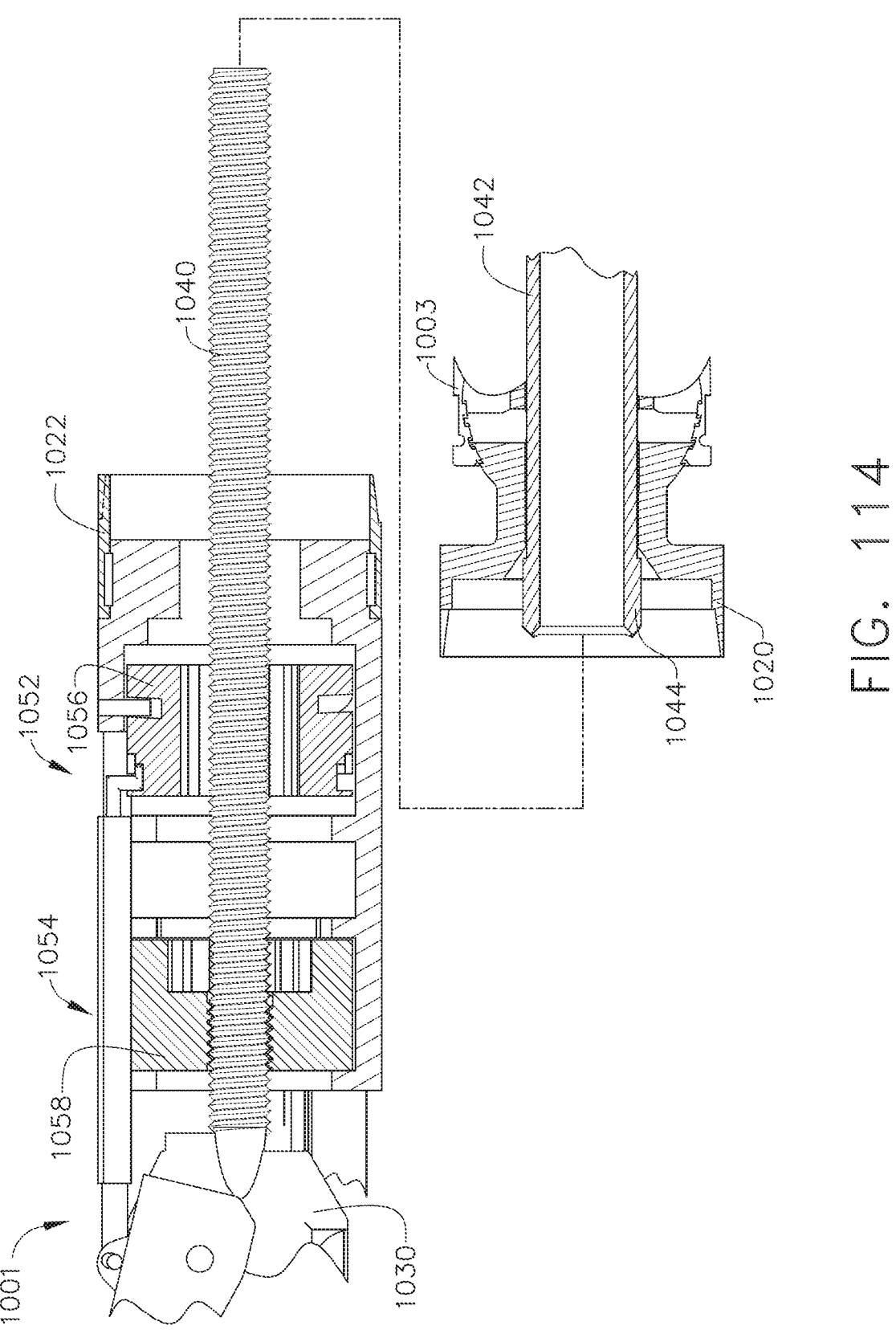
FIG. 114 is a cross-sectional view of a surgical effector detached from a shaft assembly in accordance with certain embodiments described herein.

Referring to FIG. 114, the surgical end effector 1001 may include an actuation mechanism wherein the firing and closure are performed separately. This actuation mechanism and other suitable actuation mechanisms are described, for example, in connection with FIGS. 83-91 and 92-96. In an example embodiment, as illustrated in FIG. 114, the surgical end effector 1001 comprises a closure mechanism 1052 and a firing mechanism 1054 which are driven separately. The closure mechanism 1052 includes a closure driver 1056 and the firing mechanism 1054 includes a firing driver 1058. As described above, surgical end effector 1001 may be releasably attached to shaft assembly 1003. As depicted in FIG. 114, the proximal shaft portion 1022 of surgical end effector 1001 may be detached from the distal shaft portion 1020 of the shaft assembly 1003. Once the proximal shaft portion 1022 of surgical end effector 1001 is attached to the distal shaft portion 1020 of the shaft assembly 1003, the shaft drive 1042 may be extended distally to a first discrete position to be in operable engagement with the closure driver 1056. Alternatively, the shaft drive may be extended distally to a second discrete position distal to the first discrete position to be in operable engagement with the firing driver 1058.

Figure 115:
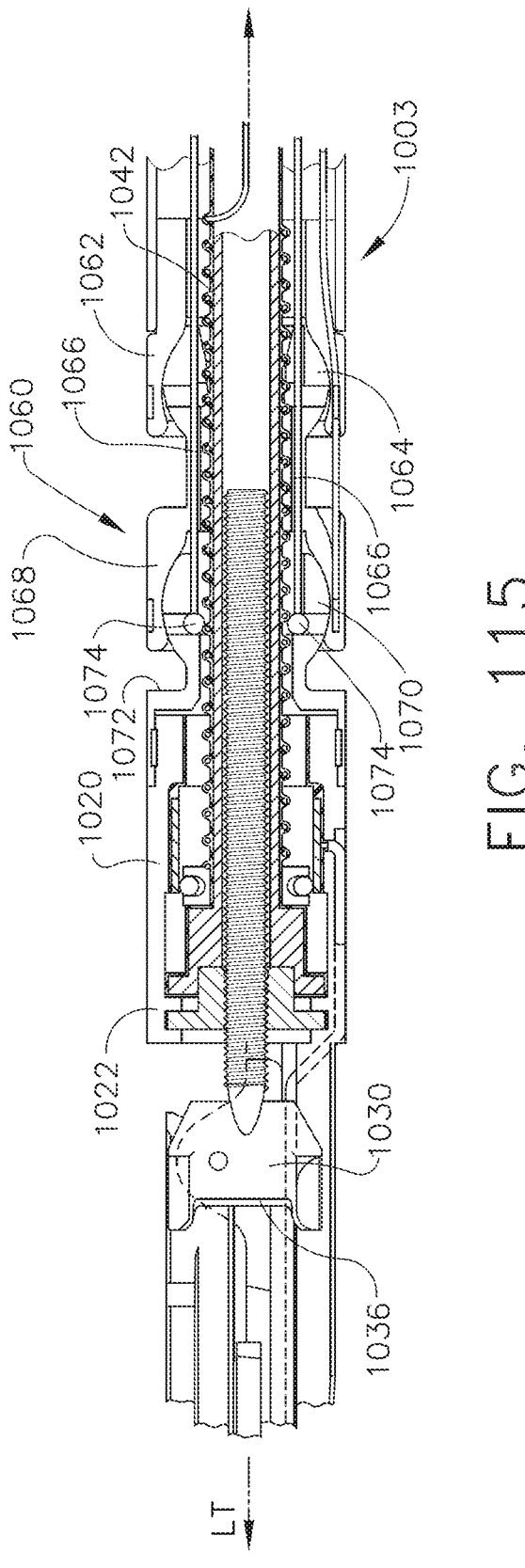
FIG. 115 is a cross-sectional view of a surgical effector attached to a shaft assembly in accordance with certain embodiments described herein.
Figure 116:
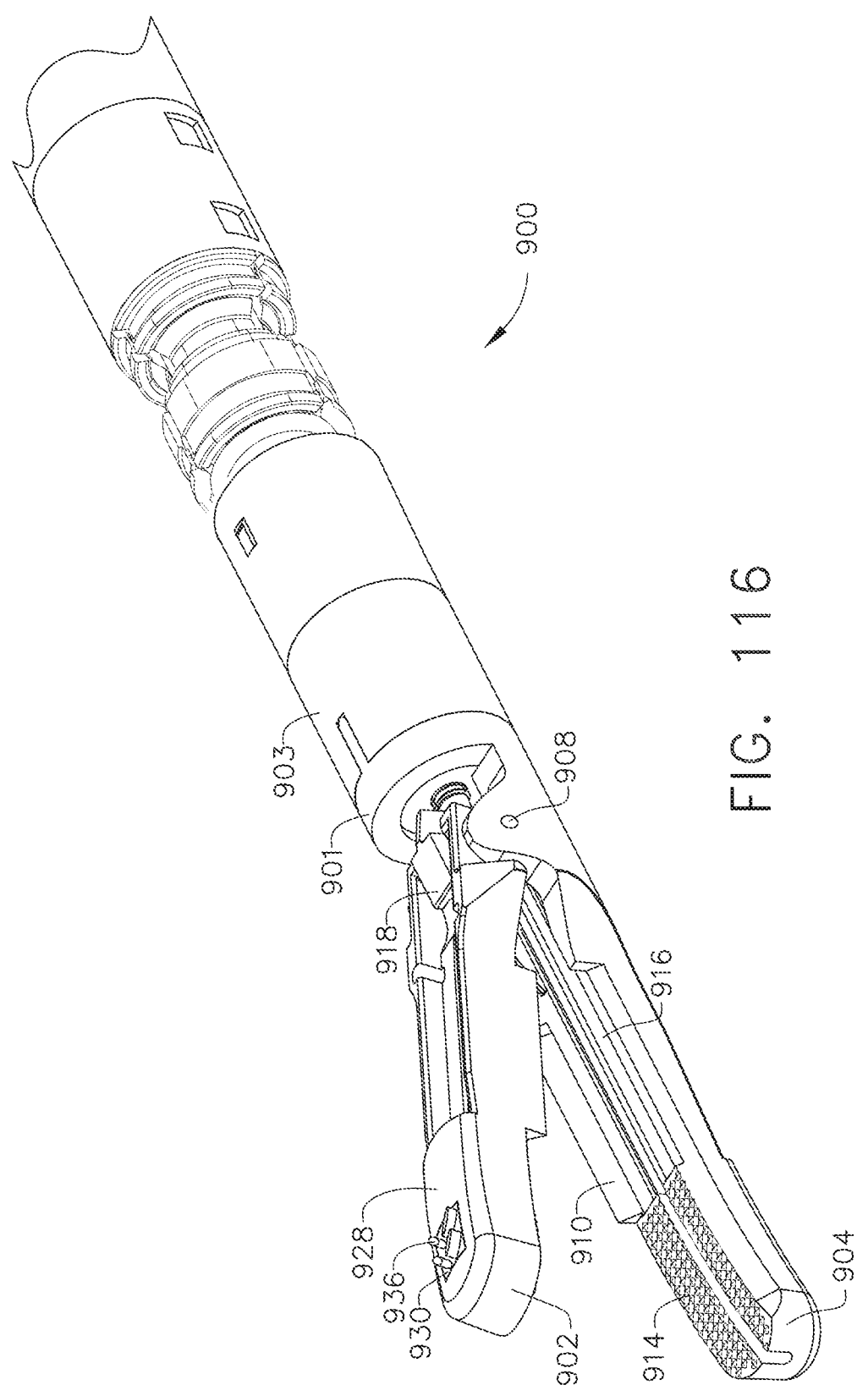
FIG. 116 is a perspective view of a surgical end effector having first and second jaws in accordance with certain embodiments described herein.

As illustrated in FIG. 115, the surgical tool 1000 may include an articulation joint 1060 for articulating the surgical end effector 1001 about a longitudinal tool axis "LT". In this example embodiment, the articulation joint 1060 is disposed proximal to the distal portion 1020 of the shaft assembly 1003. The articulation joint 1060 articulates the distal portion 1020 of the shaft assembly 1003. When the proximal portion 1022 of the surgical end effector 1001 is attached to the distal portion 1020 of the shaft assembly 1003, articulation of the distal portion 1020 of shaft assembly 1003 will cause the surgical end effector 1003 to articulate.

In an example embodiment, as illustrated in FIG. 115, the articulation joint 1060 includes a proximal socket tube 1062 that is attached to the shaft assembly 1003 and defines a proximal ball socket therein. See FIG. 115. A proximal ball member 1064 is movably seated within the proximal ball socket. As can be seen in FIG. 115, the proximal ball member 1064 has a central drive passage that enables the rotary drive shaft 1042 to extend therethrough. In addition, the proximal ball member 1064 has four articulation passages therein which facilitate the passage of four distal cables 1066 therethrough. As can be further seen in FIG. 115, the articulation joint 1060 further includes an intermediate articulation tube segment 1068 that has an intermediate ball socket formed therein. The intermediate ball socket is configured to movably support therein a distal ball member 1070 formed on a distal connector tube 1072. The cables 1066 extend through cable passages formed in the distal ball member 1070 and are attached thereto by lugs 1074. Other attachment means suitable for attaching cables to the end effector ball 1070 are contemplated within the scope of this disclosure.

Referring to FIGS. 116-120, a surgical tool 900 may include a surgical end effector extending from a shaft assembly 903. The surgical end effector 901 may be configured to perform surgical activities in response to drive motions applied thereto. The surgical end effector 901 may include a first jaw member 902, and a second jaw member 904. The first jaw member 902 may be movable relative to the second jaw member 904 between a first position and a second position. Alternatively, the first jaw member 902 and second jaw member 904 may be moveable relative to each other between a first position and a second position. The first position may be an open position and the second position may be a closed position.

Figure 120:
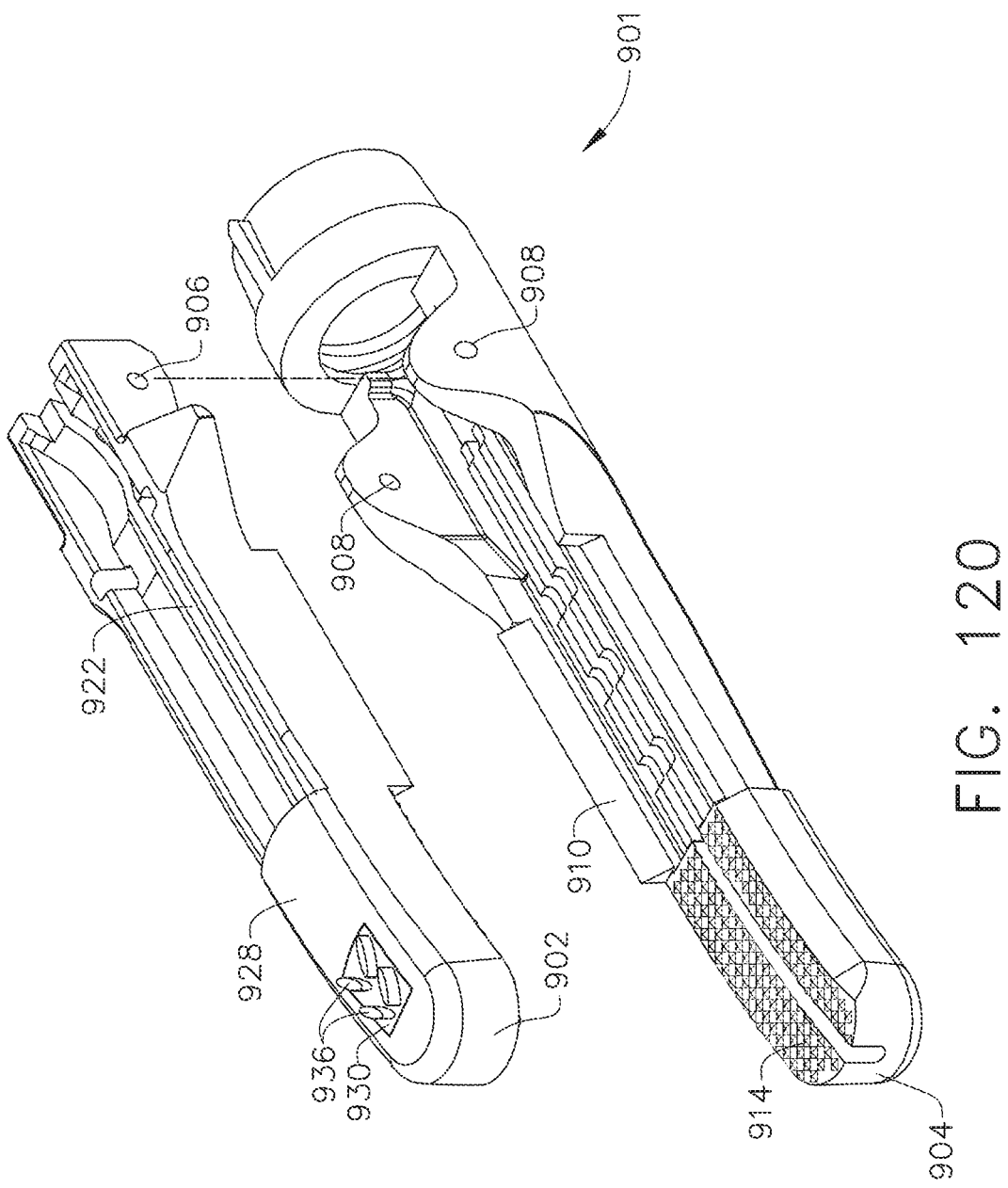

Referring to FIGS. 116-120, the first jaw member 902 may be pivotally movable relative to the second jaw member 904 between an open position and a closed position. As illustrated in FIG. 120, the first jaw member 902 may include mounting holes 906, and the second jaw member 904 may include mounting holes 908. The first jaw member 902 can be arranged relative to the second jaw member 904 such that a pivot or trunnion pin (not shown) is inserted through the mounting holes 906 of the first jaw member 902 and the mounting holes 908 of the second jaw member 904 to pivotally couple the first jaw member 902 to the second jaw member 904. Other suitable means for coupling the first jaw member 902 and the second jaw member 904 are contemplated within the scope of this disclosure.

Referring to FIGS. 116-120, surgical end effector 901 may be adapted to perform multiple functions. For example, surgical end effector 901 may include angled tissue engagement surfaces 910 for transecting tissue. Suitable tissue engagement surfaces 910 are described, for example, in connection with FIGS. 132-142. The first jaw member 902 may include an interior surface 912 and the second jaw member 904 may include an interior surface 914. The first interior surface 912 and the second interior surface 914 may be configured to grip, pass, and/or manipulate tissue and/or surgical implements such as needles 915 for suturing tissue. This gripping, passing, and/or manipulating functionality is described, for example, in connection with FIGS. 153-168.

Referring to FIGS. 116-120, the surgical end effector 901 may also include electrodes 916 and/or another electrically active surface for sealing blood vessels during a surgical procedure. The electrodes 916 may be configured to deliver radio frequency (RF) energy to tissue clamped between the first jaw member 902 and the second jaw member 904 when in a closed position to weld/fuse the tissue, which may be transected by translating a cutting member. Suitable electrodes 916 are described, for example, in connection with FIGS. 6-10 and FIGS. 153-168. The surgical end effector 901 may be releasably attached to a shaft assembly 903. An operator or a surgeon may attach surgical end effector 901 to shaft assembly 903 to perform a surgical procedure. Suitable techniques and mechanisms for releasably attaching the surgical end effector 901 to the shaft assembly 903 are described, for example, in connection with FIGS. 106-115.

Referring to FIGS. 116-120, the surgical end effector 901 may include an actuation mechanism. The actuation mechanism may comprise a closure mechanism for moving the first jaw member relative to the second jaw member. The actuation mechanism may comprise a firing mechanism for transecting tissue grasped between the first jaw member and the second jaw member. The closure and firing may be accomplished by separate mechanisms, which may be driven separately or contemporaneously. Alternatively, the closure and firing may be accomplished by a single mechanism. Suitable closure mechanisms and suitable firing mechanisms are described, for example, in connection with FIGS. 64-82, 83-91 and 92-96.

Figure 117:
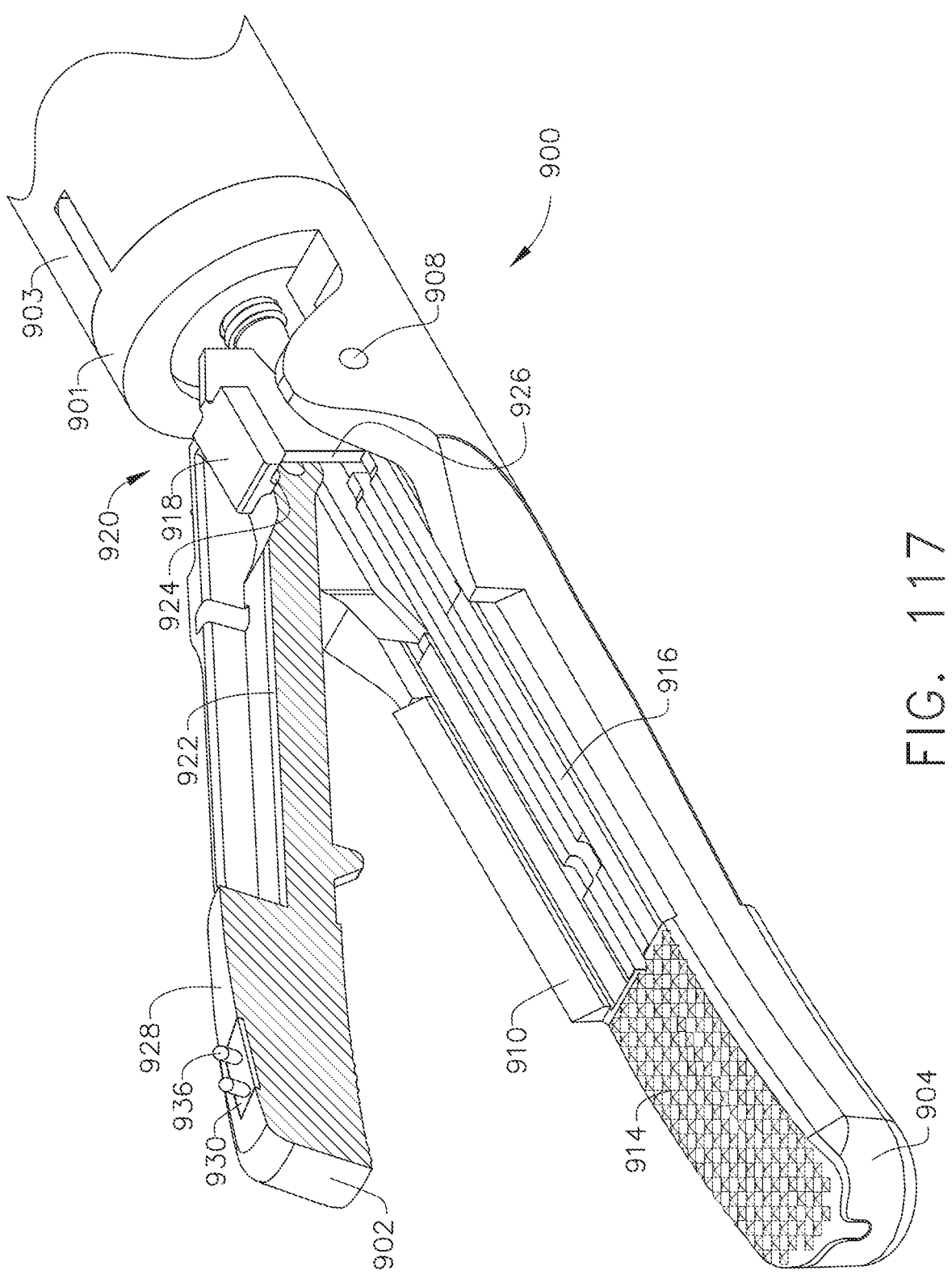
Figure 118:
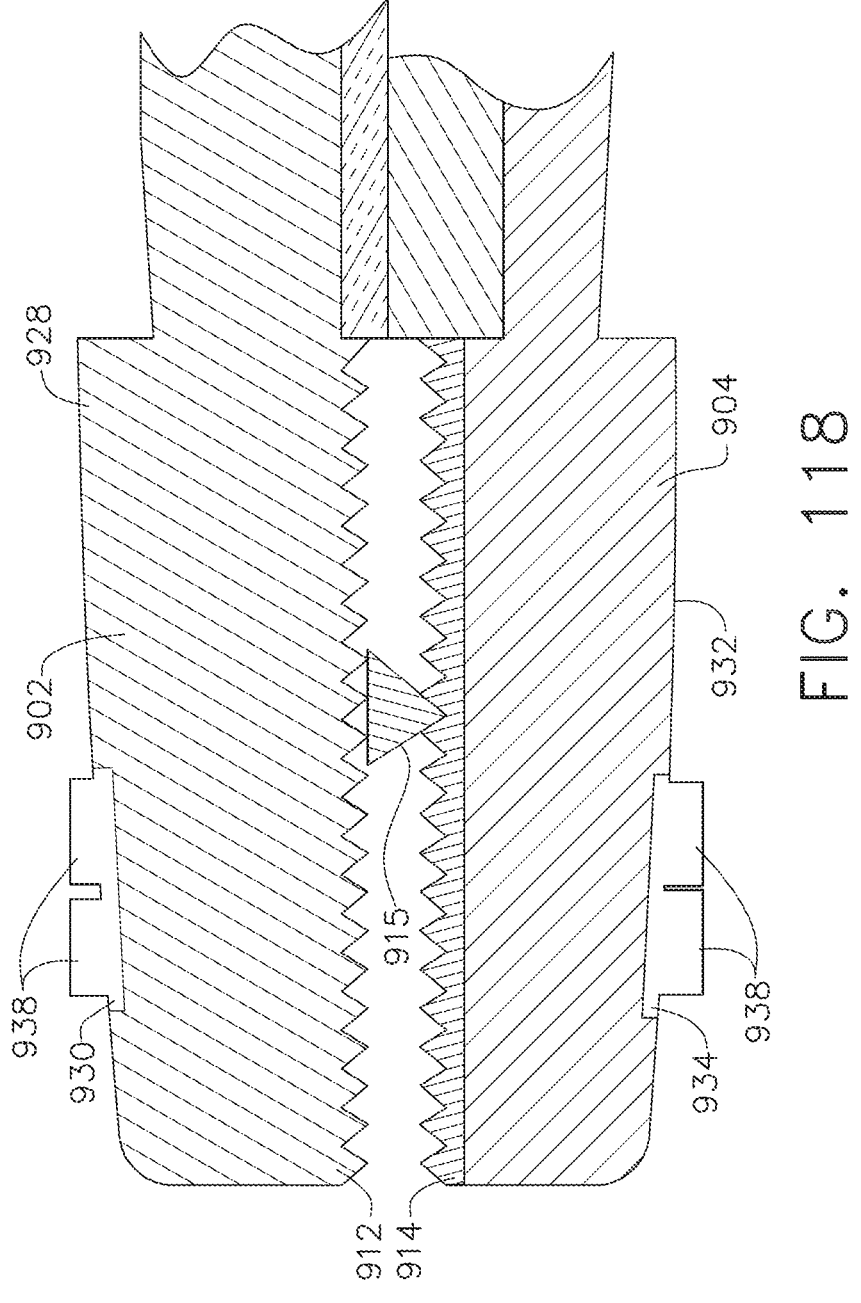
Figure 119:
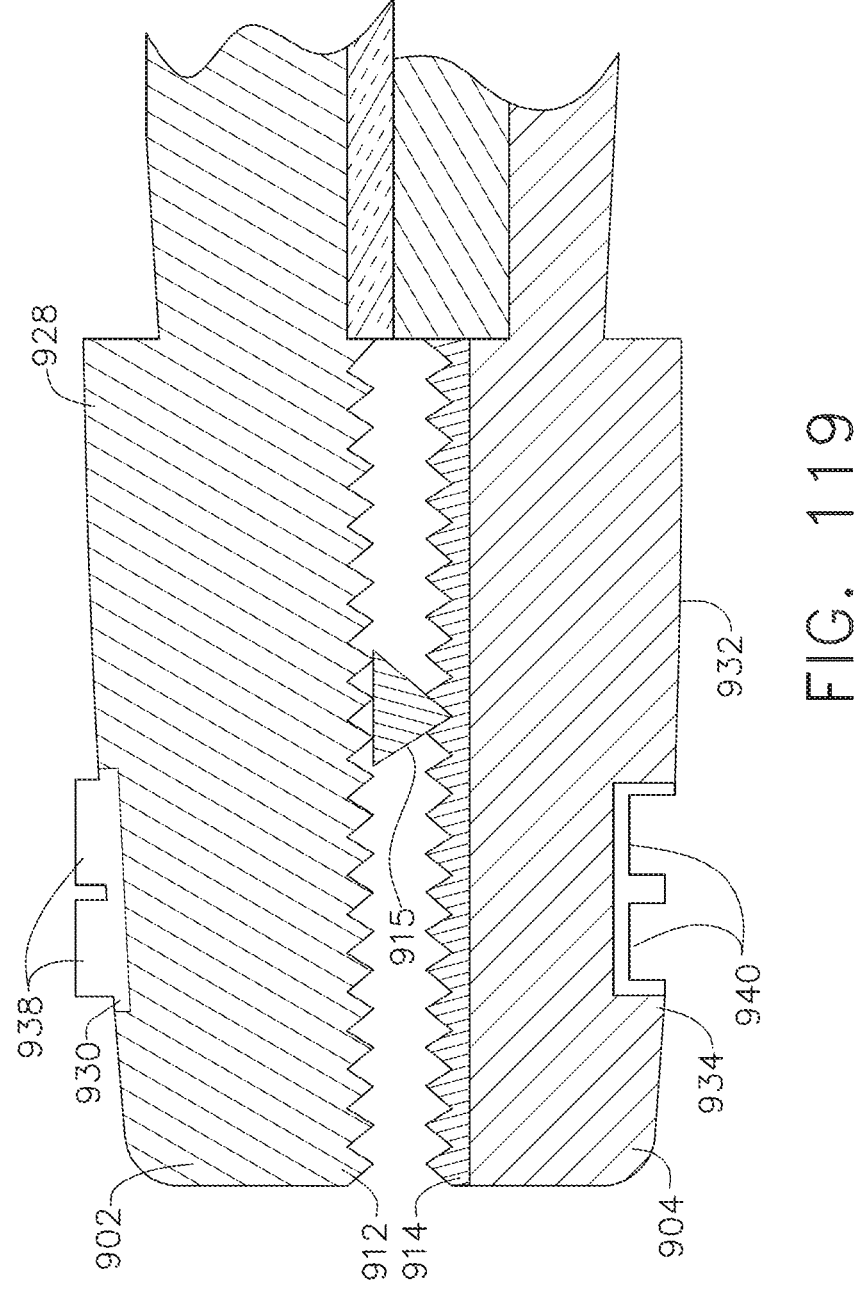

As illustrated in FIG. 117, an example actuation mechanism 920 is shown. The actuation mechanism 920 may include a reciprocating member 918 similar to the axially movable member 3016 described herein above. The reciprocating member 918, or a cam pin 924 thereof, may be received within a cam slot 922. Distal and proximal movement of the reciprocating member 918 may cause the cam pin 924 to translate within the cam slot 922, which may, in turn, cause the first jaw member 902 to pivot from an open position (e.g., proximal position of the reciprocating member 918) to a closed (e.g., distal position of the reciprocating member 918). In embodiments where the first 902 and the second 904 jaw members are movable, both jaw members may comprise cam slot 922 and the reciprocating member 918 may define a pair of cam pins. The reciprocating member 918 may comprise an I-beam member adapted to slide over the first jaw member 902 and the second jaw member 904 to close the first jaw member 902 and the second jaw member 904, and/or to provide a clamping force tending to force the first jaw member 902 and the second jaw member 904 together. The reciprocating member 918 may include a cutting blade 926. The cutting blade 926 may be attached to the reciprocating member 918 and situated such that it can be extended and retracted with the reciprocating member 918. The cutting blade 926 may be extended to transect tissue or material present between the first jaw member 902 and the second jaw member 904.

Referring to FIGS. 116-120, the first jaw member 902 may include an exterior surface 928. The exterior surface of first jaw member 902 may include a first tissue gripping portion 930. The second jaw member 904 may also include an exterior surface 932. The exterior surface 932 of second jaw member 904 may include a second tissue gripping portion 934. The first tissue gripping portion 930 and second tissue gripping portion 934 may grip tissue by contacting and temporarily adhering to tissue. The first gripping portion 930 and the second gripping portion 934 may contact and bluntly dissect tissue while the first jaw member 902 and the second jaw member 904 is moving relative to each other from the closed position to the open position.

In an example embodiment, the surgical end effector 901 may be utilized during a surgical procedure to dissect tissue. For example, the first gripping portion 930 and the second gripping portion 934 may contact and temporarily adhere to a first and second tissue portions (not shown) respectively such that when the first jaw member 902 is moved relative to the second jaw member 904 from a closed position to an open position, the first tissue portion is separated from the second tissue portion along facial planes while substantially preserving locoregional architecture and structural integrity of vessels and nerves. The first gripping portion 930 and the second gripping portion 934 may be configured to create operative space during a surgical procedure by bluntly separating (dissecting) tissue layers as the first jaw member 902 is moved relative to the second jaw member 904.

Figure 121:
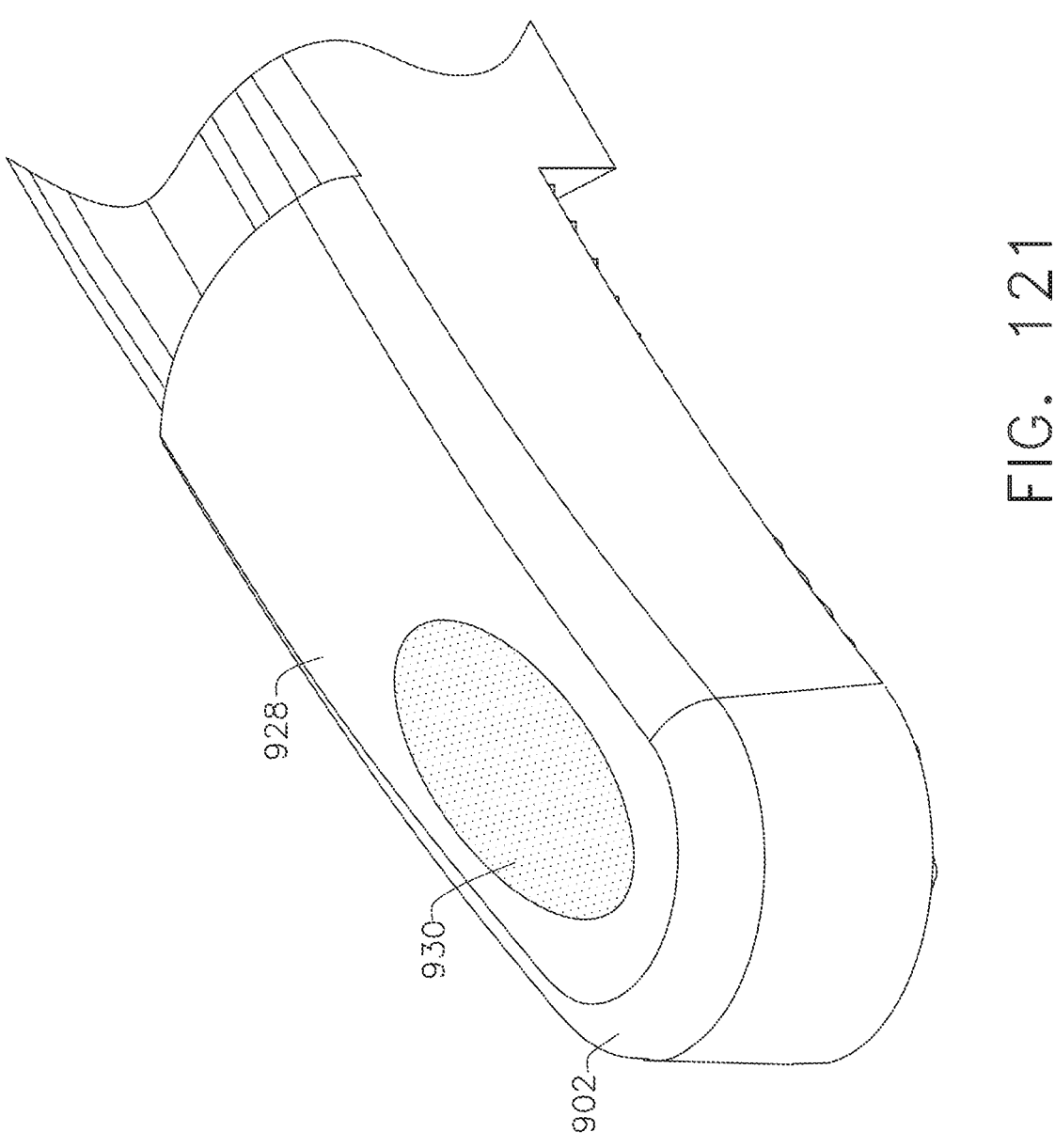

As illustrated in FIG. 121, the first gripping portion 930 and the second gripping portion 934 may be formed onto distal sections of the exterior surfaces 928 and 932 of the first and second jaw members 902 and 904 by applying a coating. In one embodiment, the first and second gripping portions 930 and 934 are attached to the exterior surfaces 928 and 932 of their respective jaw members by an adhesive. In one embodiment, the first and second gripping portions 930 and 934 are press fitted onto distal portions of the exterior surfaces 928 and 932. Other techniques and attachment means suitable for attaching or forming a gripping portion onto an exterior surface are contemplated by the current disclosure.

The first and second gripping portions 930 and 934 may include materials with high coefficient of friction to grip tissue as tissue slides relative to the first and second jaw members 902 and 904 upon moving the first and second jaw members 902 and 904 relative to each other to the open position thereby separating (dissecting) tissue layers along fascial planes while substantially preserving locoregional architecture and structural integrity of vessels and nerves. Examples of materials with high coefficient of friction that may be utilized to form the first and second gripping portions 930 and 934 include but are not limited to Silicone based elastomers, styrenic-based thermoplastic elastomers (TPE), polyisoprene, low density polyethylene, polypropylene, sanoprene, silicone, polyurethane, natural rubber, isoplast, liquid crystal polymer (LCP), etc.

The first and second gripping portions 930 and 934 may include a semi-rigid material sufficiently flexible to contour without shearing upon tissue contact. The first and second gripping portions 930 and 934 may include a non-allergenic biocompatible material. In one embodiment, the first and second gripping portions 930 and 934 may comprise a material with a low Young's modulus and high yield strain such as an elastomer. Examples of suitable elastomers include but are not limited to Silicone based elastomers, styrenic-based thermoplastic elastomers (TPE), polyisoprene, low density polyethylene, polypropylene, sanoprene, silicone, polyurethane, natural rubber, isoplast, liquid crystal polymer (LCP), etc.

Referring to FIGS. 116-120, the first and second gripping portions 930 and 934 may include gripping features 936. The gripping features 936 may be sufficiently flexible to contour without shearing upon tissue contact. The gripping features 936 may be in the form of protrusions 938. In at least one embodiment, the gripping features 936 may be in the form of depressions 940.

Figures 122, 123, 124, 125:
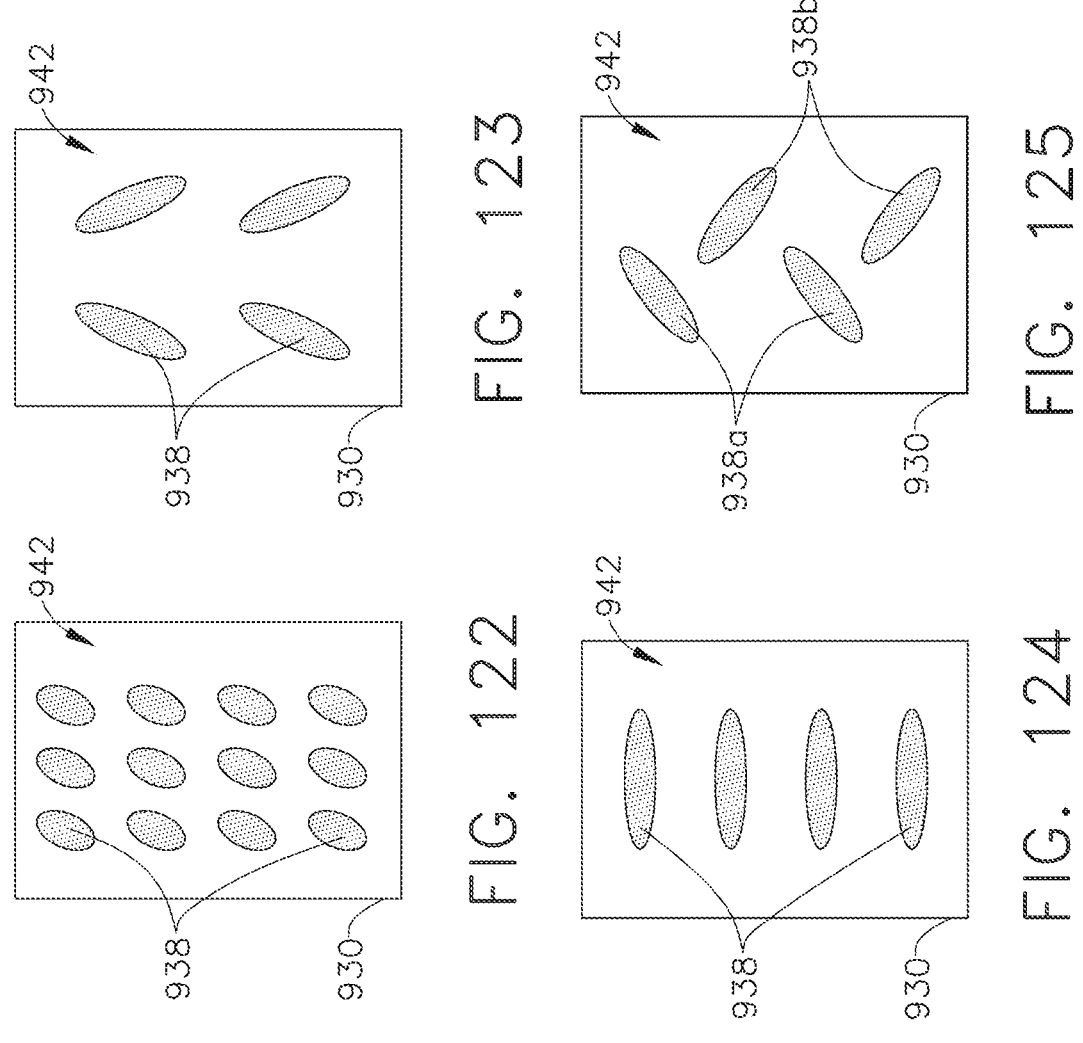

Referring to FIGS. 121-126, the gripping features 936 may be spatially arranged in a gripping pattern 942. Gripping pattern 942 may include a plurality of protrusions 938. The gripping pattern may include a plurality of depressions 940. In at least one embodiment, as illustrated in FIG. 127 the gripping pattern 942 may include a plurality of alternating protrusions 938 and depressions 940. In one embodiment, as illustrated in FIG. 123, the gripping pattern 942 may include four protrusions 938.

Figures 126, 127, 128:
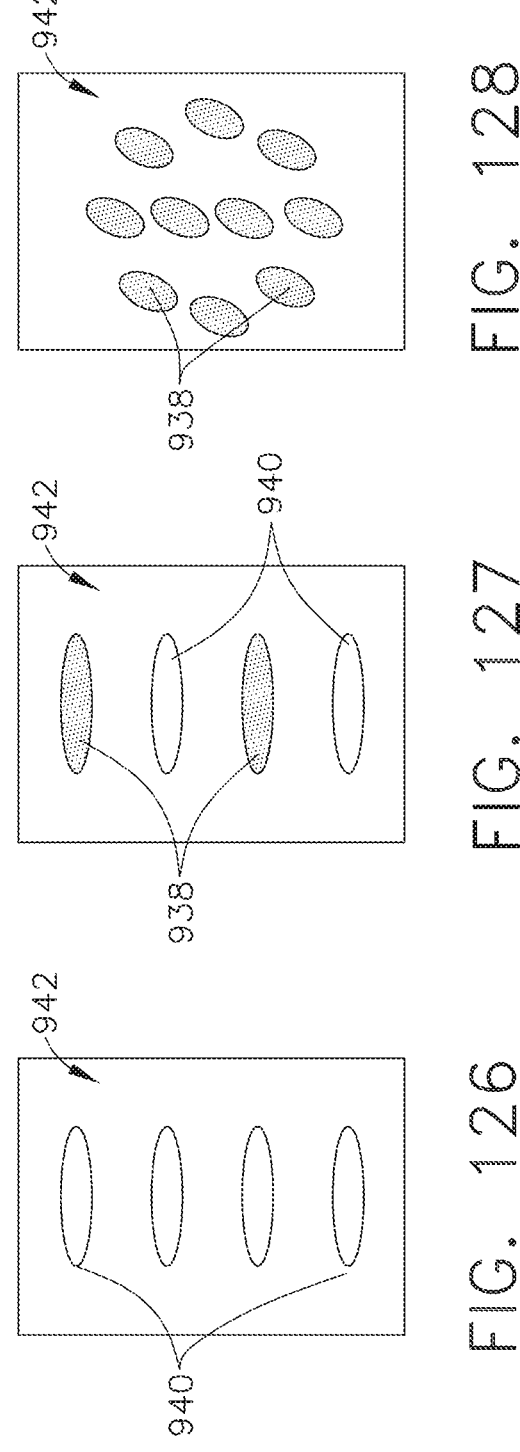

As illustrated in FIG. 128, gripping pattern 942 may include a plurality of protrusions 940 spatially arranged in a circle. Other arrangements are possible and within the scope of the present disclosure. As illustrated in FIG. 122, gripping pattern 942 may include a plurality of protrusions 938 spatially arranged in multiple rows wherein each row includes several protrusions 938 aligned along the length of the row. Each row may include alternating protrusions 938 and depressions 940.

Referring to FIG. 123-128, the gripping pattern 942 may include vertical protrusions 938 that extend horizontally on gripping portion 930. As illustrated in FIG., the vertical protrusions 938 may extend in opposing directions. In certain embodiments, as illustrated in FIG. 124, the protrusions 938 may extend in parallel rows. In at least one embodiment, as illustrated in FIG. 125, gripping pattern 942 includes a first plurality of parallel protrusions 938a, and a second plurality of parallel protrusions 938b, wherein the first plurality 938a is in a slanted arrangement with the second plurality 938b. In at least one embodiment, as illustrated in FIG. 125, the gripping portion 930 may include a herringbone pattern.

Referring to FIGS. 129-131, the gripping pattern 942 may define vertical protrusions 938 that extend horizontally on gripping portion 930 in a non linear fashion. For example, as illustrated in FIG. 129, the non-linear protrusions 938 may extend in a in a zigzag fashion. In certain embodiments, as illustrated in FIGS. 130 and 131, the non-linear protrusions 938 may extend in parallel rows. In certain embodiments, as illustrated in FIGS. 130, and 131, the non-linear protrusions 938 may extend in opposing directions.

Referring to FIGS. 132 through 137, an end effector 500 comprises a first jaw member 502A and a second jaw member 502B. The first jaw member 502A is movable relative to the second jaw member 502B between an open position (FIGS. 132 and 136) and a closed position (FIGS. 133, 134, and 137) to clamp tissue between the first jaw member 502A and the second jaw member 502B. The first jaw member 502A comprises angled tissue-contacting surfaces 504A and 506A. The second jaw member 502B comprises angled tissue-contacting surfaces 504B and 506B. The first jaw member 502A comprises a first positively-angled tissue-contacting surface 504A and a first negatively-angled tissue-contacting surface 506A. The second jaw member 502B comprises a second positively-angled tissue-contacting surface 504B and a second negatively-angled tissue-contacting surface 506B.

As used herein, the terms "positively-angled" and "negatively-angled" refer to the direction in which a tissue-contacting surface is angled relative to the body of the jaw member comprising the tissue-contacting surface and a clamping plane of the jaw member. Referring to FIG. 138, a first jaw member 502A' and a second jaw member 502B' are shown in a closed position such as to clamp tissue between the opposed jaw members 502A' and 502B'. This closed position is analogous to the closed position shown in FIGS. 133, 134, 135, 137, and 142. The first jaw member 502A' comprises a first jaw body 503A', a first tissue gripping element 507A', and a first clamping plane 505A. The second jaw member 502B' comprises a second jaw body 503B', a second tissue gripping element 507B', and a second clamping plane 505B. Generally, the tissue gripping elements and the clamping planes of the jaw members of an end effector are in an opposed orientation when the jaw members are in a closed position such as to clamp tissue between opposed jaw members.

The first jaw member 502A' comprises a first positively-angled tissue-contacting surface 504A' forming an angle (α) relative to the first clamping plane 505A and away from the first jaw body 503A' at the periphery of the first tissue gripping element 507A' of the first jaw member 502A'. The first jaw member 502A' comprises a first negatively-angled tissue-contacting surface 506A' forming an angle (α) relative to the first clamping plane 505A and toward from the first jaw body 503A' at the periphery of the first tissue gripping element 507A' of the jaw member 502A'.

Accordingly, as used herein, the term "positively-angled" is used to specify tissue-contacting surfaces that angle away from a clamping plane and that angle away from the jaw body at the periphery of the tissue gripping element of the jaw member comprising the positively-angled tissue-contacting surface. Likewise, as used herein, the term "negatively-angled" is used to specify tissue-contacting surfaces that angle away from a clamping plane and that angle toward the jaw body at the periphery of the tissue gripping element of the jaw member comprising the negatively-angled tissue-contacting surface.

Thus, the second jaw member 502B' comprises a second positively-angled tissue-contacting surface 504B' forming an angle (α) relative to the second clamping plane 505B and away from the second jaw body 503B' at the periphery of the second tissue gripping element 507B' of the second jaw member 502B'. The second jaw member 502B' comprises a second negatively-angled tissue-contacting surface 506B' forming an angle (α) relative to the second clamping plane 505B and toward from the second jaw body 503B' at the periphery of the second tissue gripping element 507B' of the second jaw member 502B'.

Referring again to FIGS. 132-134, the first jaw member 502A comprises a first jaw body 503A and a first tissue gripping element 507A, and the second jaw member 502B comprises a second jaw body 503B and a second tissue gripping element 507B. The first positively-angled tissue-contacting surface 504A of the first jaw member 502A is angled away from the first jaw body 503A at the periphery of the first tissue gripping element 507A. The first negatively-angled tissue-contacting surface 506A of the first jaw member 502A is angled toward the first jaw body 503A at the periphery of the first tissue gripping element 507A. The second positively-angled tissue-contacting surface 504B of the second jaw member 502B is angled away from the second jaw body 503B at the periphery of the second tissue gripping element 507B. The second negatively-angled tissue-contacting surface 506B of the second jaw member 502B is angled toward the second jaw body 503B at the periphery of the second tissue gripping element 507B.

When the first jaw member 502A and the second jaw member 502B are in a closed position, such as to clamp tissue between the first and second jaw members, the first positively-angled tissue-contacting surface 504A opposes the second negatively-angled tissue-contacting surface 506B. When the first jaw member 502A and the second jaw member 502B are in a closed position, such as to clamp tissue between the first and second jaw members, the first negatively-angled tissue-contacting surface 506A opposes the second positively-angled tissue-contacting surface 504B.

As shown in FIGS. 132-133 and 136-137, the first positively-angled tissue-contacting surface 504A and the first negatively-angled tissue-contacting surface 506A are disposed along substantially the entire length of the first jaw member 502A. The second positively-angled tissue-contacting surface 504B and the second negatively-angled tissue-contacting surface 506B are disposed along substantially the entire length of the second jaw member 502B.

The end effector 500 comprises an "I-beam" member 508, which in some embodiments, may function as a closure member and/or a tissue-cutting member. The I-beam member 508 may operate in a manner similar to that described herein above with respect to the axially movable member 3016 described herein above. The I-beam member 508 may be sized and configured to fit at least partially within channels in the first jaw member 502A and the second jaw member 502B. The I-beam member 508 may operably translate along the channels in the first jaw member 502A and the second jaw member 502B, for example, between a first, proximally retracted position correlating with the jaw members 502A and 502B being at an open position, and a second, distally advanced position correlating with the jaw members 502A and 502B being at a closed position. In this manner, for example, the I-beam member 508 may be configured to operably translate within the channels in the first and second jaw members 502A and 502B to close the jaw members using a camming action and/or to advance a cutting member through the first and second tissue gripping elements 507A and 507B to transect tissue clamped between the first and second jaw members 502A and 502B.

The movement of the first jaw member 502A relative to the second jaw member 502B between an open position (FIGS. 132 and 136) and a closed position (FIGS. 133, 134, and 137) to clamp tissue between the first jaw member 502A and the second jaw member 502B may be actuated with a suitable closure actuation mechanism. Translation of the I-beam member between a retracted position and an advanced position may be actuated with a suitable translation actuation mechanism. Suitable closure actuation mechanisms and suitable translation actuation mechanisms are described, for example, in connection with FIGS. 64-82, 83-91 and 92-96.

Referring to FIGS. 139 and 140, an end effector 510 comprises a first jaw member 512A and a second jaw member 512B. The first jaw member 512A is movable relative to the second jaw member 512B between an open position (FIGS. 139 and 140) and a closed position (no shown) to clamp tissue between the first jaw member 512A and the second jaw member 512B. The first jaw member 512A comprises angled tissue-contacting surfaces 514A and 516A. The second jaw member 512B comprises angled tissue-contacting surfaces 514B and 516B. The first jaw member 512A comprises a first positively-angled tissue-contacting surface 514A and a first negatively-angled tissue-contacting surface 516A. The second jaw member 512B comprises a second positively-angled tissue-contacting surface 514B and a second negatively-angled tissue-contacting surface 516B.

The first jaw member 512A comprises a first jaw body 513A and a first tissue gripping element 517A, and the second jaw member 512B comprises a second jaw body 513B and a second tissue gripping element 517B. The first positively-angled tissue-contacting surface 514A of the first jaw member 512A is angled away from a first jaw body 513A at the periphery of the first tissue gripping element 517A. The first negatively-angled tissue-contacting surface 516A of the first jaw member 512A is angled toward the first jaw body 513A at the periphery of the first tissue gripping element 517A. The second positively-angled tissue-contacting surface 514B of the second jaw member 512B is angled away from a second jaw body 513B at the periphery of the second tissue gripping element 517B. The second negatively-angled tissue-contacting surface 516B of the second jaw member 512B is angled toward the second jaw body 513B at the periphery of the second tissue gripping element 517B.

When the first jaw member 512A and the second jaw member 512B are in a closed position, such as to clamp tissue between the first and second jaw members, the first positively-angled tissue-contacting surface 514A opposes the second negatively-angled tissue-contacting surface 516B. When the first jaw member 512A and the second jaw member 512B are in a closed position, such as to clamp tissue between the first and second jaw members, the first negatively-angled tissue-contacting surface 516A opposes the second positively-angled tissue-contacting surface 514B.

The first positively-angled tissue-contacting surface 514A is disposed along a proximal portion of the length of the first jaw member 512A. The second positively-angled tissue-contacting surface 514B is disposed along a proximal portion of the length of the second jaw member 512B. The first negatively-angled tissue-contacting surface 516A is disposed along substantially the entire length of the first jaw member 512A. The second negatively-angled tissue-contacting surface 516B is disposed along substantially the entire length of the second jaw member 502B.

The end effector 510 comprises an "I-beam" member 518, which in some embodiments, may function as a closure member and/or a tissue-cutting member. The I-beam member 518 may be sized and configured to fit at least partially within channels in the first jaw member 512A and the second jaw member 512B. The I-beam member 518 may translate along the channels in the first jaw member 512A and the second jaw member 512B, for example, between a first, proximally retracted position correlating with the jaw members 512A and 512B being at an open position, and a second, distally advanced position correlating with the jaw members 512A and 512B being at a closed position. In this manner, for example, the I-beam member 518 may be configured to operably translate within the channels in the first and second jaw members 512A and 512B to close the jaw members using a camming action and/or to advance a cutting member through the first and second tissue gripping elements 517A and 517B to transect tissue clamped between the first and second jaw members 512A and 512B.

The movement of the first jaw member 512A relative to the second jaw member 512B between an open position (FIGS. 139 and 140) and a closed position (not shown) to clamp tissue between the first jaw member 512A and the second jaw member 512B may be actuated with a suitable closure actuation mechanism. Translation of the I-beam member between a retracted position and an advanced position may be actuated with a suitable translation actuation mechanism. Suitable closure actuation mechanisms and suitable translation actuation mechanisms are described, for example, in connection with FIGS. 64-82, 83-91 and 92-96.

The first jaw member 512A and the second jaw member 512B comprise a first distal textured portion 519A and second distal textured portion 519B, respectively. The first distal textured portion 519A of the first jaw member 512A is disposed distal and directly adjacent to the proximal tissue gripping element 517A of the first jaw member 512A comprising the first positively-angled tissue-contacting surface 514A. The first positively-angled tissue-contacting surface 514A does not extend distally along the length of the first jaw member 512A into the first distal textured portion 519A. The second distal textured portion 519B of the second jaw member 512B is disposed distal and directly adjacent to the proximal tissue gripping element 517B of the second jaw member 512B comprising the second positively-angled tissue-contacting surface 514B. The second positively-angled tissue-contacting surface 514B does not extend distally along the length of the second jaw member 512B into the second distal textured portion 519B. The first and second distal textured portions 519A and 519B of the first and second jaw members 512A and 512B may be opposed and may allow the end effector 510 to grip, pass, and/or manipulate surgical implements such as needles for suturing tissue, in addition to gripping tissue, for example, during dissection operations. This gripping, passing, and/or manipulating functionality is described, for example, in connection with FIGS. 116-131 and 154-164.

The first jaw member 512A and the second jaw member 512B comprise a first gripping portion 521A and second gripping portion 521B, respectively. The first gripping portion 521A is disposed on an outwardly-facing surface of the first jaw member 512A, and the second gripping portion 521B is disposed on an outwardly-facing surface of the second jaw member 512B. The gripping portions 521A and 521B may function to aid in tissue dissection as described, for example, in connection with FIGS. 116-131 and 154-164.

FIG. 141 is a perspective view of an end effector 510' similar to the end effector 510 shown in FIGS. 139 and 140, but comprising electrodes 522 located in the second tissue gripping element 517B of the second jaw member 516B and located between the second positively-angled tissue-contacting surface 514B and the second negatively-angled tissue-contacting surface 516B. The electrodes 522 may be configured to deliver RF energy to tissue clamped between the first jaw member 512A and the second jaw member 512B when in a closed position to weld/fuse the tissue, which may be transected by translating the I-beam member 518 comprising a cutting member. Although FIG. 141 shows two electrodes 522, it is understood that an end-effector in accordance with the embodiments described in this specification may comprise at least one or more electrodes comprising any suitable shape and orientation, as described, for example, in this specification. The second jaw member 516B also comprises an offset electrode 524 at the distal tip 525 configured to deliver RF energy to tissue during dissection operations, for example. In some embodiments, the first distal textured portion 519A and second distal textured portion 519B may also be electrodes configured, for example, to deliver RF energy to tissue during dissection operations. This electrode functionality is described, for example, in connection with FIGS. 154-164.

Referring to FIG. 142, an end effector 530 comprises a first jaw member 532A and a second jaw member 532B shown in a closed position clamping tissue 545 between the jaw members. The first jaw member 532A comprises a first positively-angled tissue-contacting surface 534A and a first negatively-angled tissue-contacting surface 536A. The second jaw member 532B comprises a second positively-angled tissue-contacting surface 534B and a second negatively-angled tissue-contacting surface 536B. The tissue 545 physically contacts the angled tissue-contacting surfaces 534A, 534B, 536A, and 536B. The physical contact between the tissue 545 and the angled tissue-contacting surfaces 534A, 534B, 536A, and 536B compresses the tissue 545 between the first jaw member 532A and the second jaw member 532B. As shown in FIG. 142, the clamping of the tissue between the first jaw member 532A and the second jaw member 532B compresses the tissue 545 between the mutually opposed tissue-contacting surfaces 536A and 534B, and also between the mutually opposed tissue-contacting surfaces 534A and 536B, which establishes a tortuous deformation in the compressed tissue 545. The tortuous deformation improves the clamping action of the end effector 530 on the tissue 545, which in turn, improves the welding/fusion of the tissue 545 and/or the transection of the tissue 545. The tissue 545 can be welded/fused, for example, by the application of RF energy through electrodes 542 located in the tissue gripping element of the second jaw member 532B and located between the second positively-angled tissue-contacting surface 534B and the second negatively-angled tissue-contacting surface 536B. The tissue 545 can be transected, for example, by translating the I-beam member 538, which translates the cutting member 541 through the clamped tissue 545.

In some embodiments, an end effector may comprise a first jaw member comprising a first positively-angled tissue-contacting surface and a first negatively-angled tissue-contacting surface, and a second jaw member comprising a second positively-angled tissue-contacting surface and a second negatively-angled tissue-contacting surface. The angled tissue-contacting surfaces may form angles (a) relative to a clamping plane as described, for example, in connection with FIG. 138. The magnitude of the angle ($\alpha$) between a tissue contacting surface and a clamping plane may range from 5-degrees to 85-degrees or any sub-range subsumed therein such as, for example, from 10-degrees to 80-degrees, from 20-degrees to 70-degrees, from 30-degrees to 60-degrees, from 40-degrees to 50-degrees, from 25-degrees to 50-degrees, or from 30-degrees to 45-degrees.

In some embodiments, angled tissue-contacting surfaces may independently form angles relative to respective clamping planes. The angle formed by the angled tissue-contacting surfaces may be substantially the same or different in a given end effector. For example, two opposed angled tissue-contacting surfaces (e.g., a first positively-angled tissue-contacting surface and an opposed second negatively-angled tissue-contacting surface) may both form a common angle ($\alpha_1$) relative to respective clamping planes, and two other opposed angled tissue-contacting surfaces (e.g., a first negatively-angled tissue-contacting surface and an opposed second positively-angled tissue-contacting surface) may both form a common angle ($\alpha_2$) relative to respective clamping planes, wherein $|\alpha_1| \neq |\alpha_2|$.

In some embodiments, an angled tissue-contacting surface may extend a predetermined distance normal to a respective clamping plane coincident with a horizontal tissue contacting portion of a jaw member. For example, referring to FIG. 138, the first positively-angled tissue-contacting surface 504A' extends a distance normal to the first clamping plane 505A, and the second positively-angled tissue-contacting surface 5043 extends a distance normal to the second clamping plane 505B. Likewise, the first negatively-angled tissue-contacting surface 506A' extends a distance normal to the first clamping plane 505A, and the second negatively-angled tissue-contacting surface 506B' extends a distance normal to the second clamping plane 505B. In some embodiments, an angled tissue-contacting surface may extend a distance between 0.025 inch to 0.25 inch normal to a respective clamping plane, or any sub-range subsumed therein such as, for example, 0.025 inch to 0.01 inch or 0.025 inch to 0.05 inch.

While the angled tissue-contacting surfaces shown in FIGS. 132 through 142 are illustrated as being planar surfaces, it is to be appreciated that in some embodiments, the angled tissue-contacting surfaces may be curved surfaces or a combination of planar surfaces and curved surfaces.

In some embodiments, end effectors comprising angled tissue-contacting surfaces may be configured to operably couple to robotic surgical systems such as, for example, the robotic surgical systems described in connection with, for example, FIGS. 1-45. In some embodiments, end effectors having angled tissue-contacting surfaces may be configured to operably couple to hand-held surgical devices such as, for example, the hand-held surgical devices described in connection with FIGS. 46-63.

The angled tissue-contacting surfaces described in connection with FIGS. 132 through 142 provide various advantages to end effectors configured to grip/clamp tissue, weld/fuse tissue, transect tissue, or any combination of these operations. For example, in some embodiments, as illustrated in FIGS. 132 through 142, the positively-angled tissue contacting surfaces are integral with the outer surfaces of the jaw members (i.e., formed from a single piece of material). As such, the positively-angled tissue contacting surfaces provide for a thicker jaw member structure in the thickness dimension (labeled dimension T in FIGS. 141 and 142). The thicker jaw member structure increases the strength and stiffness of the jaw members, which provides improved gripping/clamping load to tissue. In some embodiments, for example, a thicker jaw member structure provided by positively-angled tissue contacting surfaces may increase the moment of inertia of the jaw members by 20-30% relative to jaw members comprising co-planar tissue-contacting surfaces. An increased moment of inertia may provide an improved weld zone for fusing and cauterizing tissue clamped in an end effector comprising angled tissue-contacting surfaces by providing a more focused area for RF energy to enter and fuse tissue.

Any of the electrosurgical tools described herein may be energized utilizing current/energy paths extending from the generator or other signal source (such as generator 3002) through conductors, such as the supply 3012 and return 3014 conductors (see FIG. 6), through the shaft assembly to the electrode or electrodes. Within the shaft assembly, the current paths may be provided by wires that extend through the shaft assembly. Wires, however, must be configured to avoid kinking, twisting or other deformation at the various articulation and rotation joints of the tools, including the articulation joint 3500 described herein. In the illustrated embodiments, an electrosurgical tool may utilize components of the shaft assembly as current paths for energizing electrosurgical electrodes. This may eliminate the need for wires and simplify articulation and rotation of the surgical tool.

In the illustrated embodiments, a rotary connector assembly may be utilized to allow a rotary drive shaft or other internal component of the shaft assembly to provide an energized current path between a generator and the end effector and/or an electrode thereof. The rotary connector may be configured to maintain a connection between the energized current path and the end effector despite rotation of the shaft and/or end effector. In bi-polar configurations, a return path may be formed by conductive components of the shaft and end effector such as, for example, a skin of the shaft, the I-beam member or other knife, portions of the various jaw members, etc., as described herein FIGS. 143-146 illustrate one embodiment of a rotary connector assembly 1100 installed in an end effector 550 and shaft assembly 560 as described herein with respect to FIGS. 64-81. FIG. 143 is a cross-sectional view of one embodiment of the end effector 550 and shaft assembly 560 illustrating an example installation of the rotary electrode assembly 1100. FIG. 144 is an exploded view of one embodiment of the end effector 550 and shaft assembly 560 showing the rotary electrode assembly 1100 both installed on the rotary drive shaft 630 (indicated by reference numbers 1100', 1104', 1106') and exploded (indicated by reference numbers 1100, 1104, 1106). FIG. 145 is a cross-sectional view of one embodiment of the end effector 550 and shaft assembly 560 showing the rotary electrode assembly 1100 with a rotary drive head 632 in a proximal position. FIG. 146 is a cross-sectional view of one embodiment of the end effector 550 and shaft assembly 560 showing the rotary electrode assembly 1100 with the rotary drive head 632 in a distal position.

The rotary electrode assembly 1100 may be positioned within the end effector drive housing 608 and may comprise an outer contact 1102 and an inner contact 1103. The outer contact 1102 may be positioned around an inner wall 1108 of the end effector drive housing 608. In the illustrated embodiment, and in functionally similar embodiments, the outer contact 1102 may be in the shape of a cylinder or other figure of revolution. The outer contact 1102 may be in electrical communication with one or more electrodes 1112 in the end effector 550 via one or more leads, such as lead 1110. The lead 1110 may be in physical contact with the outer contact 1102 and may extend through the lower jaw member 602B to the electrode 1112 as shown. The lead 1110 may be fastened to the electrode 1112 in any suitable manner including, for example, with a solder or other similar joint. For example, multiple energized electrodes may be utilized with one lead 1110 directed to each electrode. In the illustrated embodiment, the lead 1110 may be insulated so as to avoid electrical communication with other portions of the end effector 550 and shaft assembly 560.

The inner contact 1103 may be physically coupled to the rotary drive shaft 630, for example, proximal from the hex coupling portion 634, as shown. The inner contact 1103 may be in electrical contact with the outer contact 1102. For example, the inner contact 1103 may be in physical contact with the outer contact 1102. In the illustrated embodiment and in functionally similar embodiments, the inner contact 1103 may maintain electrical contact with the outer contact 1102 as the rotary drive shaft 630 and/or the end effector 560 rotates. For example, the outer contact 1102 may be a figure of revolution such that the inner contact 1103 is in physical contact with the contact 1102 as the rotary drive shaft 630 rotates.

In the illustrated embodiment and in functionally similar embodiments, the inner contact 1103 may also be a figure of revolution. For example, as illustrated, the inner contact 1103 may comprise a ringed brush 1104 and a grooved conductor 1106. The grooved conductor 1106 may be positioned around the rotary drive shaft 630 proximal from the hex coupling portion 634. The grooved conductor 1106 may define a groove 1107 to receive the ringed brush 1104. The ringed brush 1104 may have a diameter larger than that of the groove 1107. In the illustrated embodiment and in functionally similar embodiments, the ringed brush 1104 may define a slot 1105. For example, the slot 1105 may allow the diameter of the ringed brush 1104 to expand and contract. For example, the diameter of the ringed brush 1104 may be expanded in order to place it over the remainder of the grooved conductor 1106 and into the slot 1107. Also, when the inner contact 1103 is placed within the outer contact 1102, its diameter may be contracted. In this way, the tendency of the ringed brush 1104 to resume its original diameter may cause the ringed brush 1104 to exert an outward force on the outer contact 1102 tending to keep the ringed brush 1104 and outer contact 1102 in physical and electrical contact with one another.

The inner contact 1103 may be in electrical communication with a suitable shaft component, thus completing the current path from the electrode 1112 to a generator, such as the generator 3002 described herein above with respect to FIG. 6 and/or an internal generator. In the illustrated embodiment, the inner contact 1103, and particularly the grooved conductor 1106, is in physical and electrical contact with a coiled wire component 1114 wrapped around the rotary drive shaft 630. The coiled wire component 1114 may extend proximally through the shaft where it may be coupled directly or indirectly to the generator. As described herein, the coiled wire component 1114 may also act as a spring to provide rigidity to the rotary drive shaft 630 around an articulation joint, for example, as described herein with respect to FIGS. 31-31 and spring 3612. In some embodiments, the rotary drive shaft 630 may comprise an outer insulated sleeve. The inner contact 1103 may be in electrical contact with the outer insulated sleeve in addition to or instead of the coiled wire component 1114. An example insulated sleeve 1166 is described herein with respect to FIG. 151. Another example of a potential insulated sleeve is the constraining member 3660 described herein above with respect to FIG. 45.

In the illustrated embodiment, the a current return path from the electrode 1112 may be provided by various components of the end effector 550 and shaft assembly 560 including, for example, the jaw members 602A, 602B, the end effector drive housing 608 and other shaft members extending proximally. Accordingly, portions of the energized current path may be electrically isolated from other components of the end effector 550 and shaft assembly 560. For example, as described above, the lead 1110 between the outer contact 1102 and electrode 1112 may be surrounded by an electrical insulator 1111, as shown. Also, the outer contact 1102 and inner contact 1103 may be isolated from other components of the end effector 550 and shaft assembly 560. For example, an insulator 1118 may be positioned to electrically isolate the outer contact 1102 from the end effector drive housing 608. An insulator 1116 may be positioned to isolate the outer contact 1102 and inner contact 1103 from the rotary drive shaft 630. The insulator 1118 may be an additional component or, in some embodiments, may be provided as a TEFLON or other insulating coating. As illustrated in FIGS. 145-146, the insulator 1116 may extend proximally, also isolating the coiled wire component 1114 from both the rotary drive shaft 630 and from other components of the shaft assembly 560 such as, for example, the end effector drive housing 608.

In the embodiment illustrated in FIGS. 145-146, the outer contact 1102 may be extended proximally and distally such that electrical contact between the outer contact 1102 and inner contact 1103 is maintained with the rotary drive shaft 630 and rotary drive head 632 in different proximal and distal positions. For example, in FIG. 145, the rotary drive shaft 630 and rotary drive head 632 are pulled proximally such that the male hex coupling portion 636 of the drive shaft head 632 is received by hex shaft coupling portion 609 of the end effector drive housing 608. In this position, rotation of the rotary drive shaft 630 may cause rotation of the end effector drive housing 608 and end effector 550, as described herein. Additionally, as illustrated in FIG. 145, the inner contact 1103 may be in physical and electrical contact with the outer contact 1102. In FIG. 146, the rotary drive shaft 630 and rotary drive head 632 are pushed distally such that the hex coupling portion 634 of the rotary drive head 632 receives the threaded rotary drive nut 606. In this position, rotation of the rotary drive shaft 630 may cause rotation of the threaded rotary drive nut 606 that, in turn, causes rotation of the threaded rotary drive member 604 and distal and/or proximal translation of the I-beam member 620. Additionally, as illustrated in FIG. 146, the inner contact 1103 may be in physical and electrical contact with the outer contact 1102.

FIGS. 147-148 are cross-sectional views of one embodiment of the end effector 550 and shaft assembly 560 where a longitudinal length of the outer contact 1102 is selected such that the rotary connector assembly 1100 alternately creates and breaks an electrical connection limited by the longitudinal position of the inner contact 1103. For example, in FIG. 147, the rotary drive shaft 630 and rotary drive head 632 are positioned proximally such that the male hex coupling portion 636 is received into the hex shaft coupling portion 609 of the distal shaft portion 608. As illustrated, the inner contact 1103 (and specifically the ring brush 1104) may contact not the contact 1102, but instead may contact the insulator 1118. In this way, there may not be a completed electrical connection between the electrode 1112 and the generator when the rotary drive shaft 630 and rotary drive head 632 are in the proximal position shown in FIG. 147. When the rotary drive shaft 630 and rotary drive head 632 are positioned distally to contact the threaded drive nut 606, as illustrated in FIG. 148, the inner contact 1103 may be in electrical (and physical) contact with the contact 1102, completing the current path between the electrode 1112 and generator. The configuration illustrated in FIGS. 147-148 may be useful in various different contexts. For example, it may be undesirable to energize the electrode 1112 when the jaw members 602A, 602B are open. In the illustrated embodiment, the jaw members 602A, 602B are closed by the rotary drive shaft 630 when the shaft 630 is positioned distally (FIG. 148) and not when the shaft 630 is positioned proximally (FIG. 147). Accordingly, in the configuration of FIGS. 147-148, the current path from the generator to the electrode 1112 is complete only when the rotary drive shaft 630 and rotary drive head 632 are positioned distally.

In some of the embodiments described herein, the end effector 550 may be removable from the end effector drive housing 608 and, for example, may be interchangeable with other end effectors (not shown). Examples of mechanisms for implementing interchangeable electrodes are provided herein with respect to FIGS. 106-115. In such implementations, the lead 1110 may comprise an end effector portion and a shaft portion connected by a connector assembly. FIGS. 149-150 illustrate one embodiment of the end effector 550 and shaft assembly 560 showing a configuration including the lead portions 1130, 1132 and connector assembly 1120. For example, as illustrated in FIGS. 149-150 and as described herein, a proximal portion 603 of the jaw member 602B may be received within the end effector drive housing 608. The proximal portion 603 of the jaw member 602B is illustrated within the end effector drive housing 608 in FIG. 149 and separated from the end effector drive housing 608 in FIG. 150. The connector assembly 1120 may comprise an end effector side-lead 1122 and a shaft-side lead 1124. The respective leads may be brought into physical and electrical contact with one another when the proximal portion 603 is received into the distal shaft portion 608, as illustrated in FIG. 149. In various embodiments, the connector assembly 1120 may be configured so as to maintain electrical isolation of the energized current path from other components of the end effector 550 and shaft 560. For example, insulation 1126, 1128 may electrically isolate the connector leads 1122, 1124. In the illustrated embodiment and in functionally similar embodiments, the insulation 1126, 1128 may take the form of plastic or other insulating shrink tubes positions over all or part of the leads 1122, 1124. In some embodiments, the insulation 1126, 1128 may comprise a TEFLON or other insulating coating applied to portions of the leads 1122, 1124 and/or surrounding material.

FIG. 151 illustrates a cross-sectional view of an alternate embodiment of an end effector 1140 and shaft assembly 1142 showing another context in which a rotary connector assembly 1147 may utilized. The end effector 1140 may comprise jaw members 1146A, 1146B that may operate similar to the jaw members 3008A, 3008B, 602A, 602B, etc., described herein above. For example, the jaw members 1146A, 1146B may be actuated by an I-beam member 1156 that, in the illustrated embodiment, may comprise a cutting edge 1148 for severing tissue between the jaw members 1146A, 1146B. The I-beam member 1156 may be driven distally and proximally by rotation of a threaded I-beam member shaft 1154. The I-beam member shaft 1154 may be rotated via a main drive shaft 1149. For example, the main drive shaft 1149 may be coupled to a gear 1150. The gear 1150 may be in mechanical communication with a gear 1152 coupled to the I-beam member shaft 1154 as illustrated.

The end effector 1140 may comprise an electrode 1158 that may operate in a manner similar to that of electrode 1112, etc., described herein above. An insulated lead 1160 may be electrically coupled to the electrode 1158 and may extend proximally to an outer contact 1162. The outer contact 1162 may be positioned on an inner wall of a shaft member 1141 in a manner similar to that in which the contact 1102 is coupled to the inner wall 1108 of the end effector drive housing 608. A inner contact 1164 (e.g., brush) may be positioned around the main drive shaft 1149 such that the brush 1164 is in electrical contact with the contact 1162. The brush 1164 may also be in electrical contact with a conductive sleeve 1166 positioned around the main drive shaft 1149. The sleeve 1166 may be electrically isolated from the main drive shaft 1149 and from the remainder of the shaft 1142, for example, by insulators 1168, 1170.

It will be appreciated that the rotary electrode assembly 1100 may be utilized with any of the end effector and/or shaft assembly embodiments described herein. For example, FIG. 152 illustrates a cross-sectional view of one embodiment of the end effector and shaft assembly of FIGS. 83-91 illustrating another example installation of a rotary electrode assembly 1100 including the outer contact 1102 and inner contact 1103 as described herein.

FIGS. 153-168 illustrate various embodiments of an electrosurgical end effector 700 comprising a proximal tissue treatment zone 706 and a distal tissue treatment zone 708. The proximal tissue treatment zone 706 utilizes various electrodes and cutting edges to treat tissue, for example, as described herein above with respect to end effector 3000 shown in FIGS. 6-10. Treatment provided by the proximal tissue treatment zone 706 may include, for example, clamping, grasping, transsection, coagulation, welding, etc. The distal tissue treatment zone 708 may also comprise one or more electrodes 742 and may be utilized to apply treatment to tissue and, in some embodiments, to perform other surgical tasks such as grasping and manipulating suturing needles and/or other surgical implements.

FIG. 153 illustrates one embodiment of the end effector 700. The end effector 700 may be utilized with various surgical tools including those described herein. As illustrated, the end effector 700 comprises a first jaw member 720 and a second jaw member 710. The first jaw member 720 may be movable relative to the second jaw member 710 between open positions (shown in FIGS. 153-156) and closed positions (shown in FIGS. 166 and 165). For example, the jaw members 720, 710 may be pivotably coupled at a pivot point 702. The jaw members 710, 720 may be curved with respect to a longitudinal tool axis "LT," as illustrated. In some embodiments, the jaw members 710, 720 may be instead straight, as illustrated with respect to jaw members 3008A, 3008B shown in FIGS. 6-8. In use, the end effector 700 may be transitioned from an open position to a closed position to capture tissue between the jaw members 720, 710. The tissue captured between the jaw members 720, 710 may be clamped or grasped along portions of the jaw members 710,720 for application of one or more tissue treatments such as transection, welding, dissection, and electrocauterization.

The proximal tissue treatment zone 706 of the end effector 700 may treat tissue in a manner similar to that described above with respect to the end effector 3000. Tissue between the jaw members 720, 710 in the proximal tissue treatment zone 706 may be secured in place, for example, by teeth 734a, 734b. See, e.g., FIGS. 154-159. In the proximal tissue treatment zone 706, the jaw members 720, 710 may each define respective longitudinal channels 812, 810. An I-beam member 820 (FIGS. 155 and 159) may traverse distally and proximally within the longitudinal channels 812, 810, for example, as described herein above with respect to the end effector 3000 and axially movable member 3016. In some embodiments, distal and proximal translation of the I-beam member 820 may also transition the jaw members 720, 710 between open and closed positions. For example, the I-beam member 820 may comprise flanges positioned to contact cam surfaces of the respective jaw members 720, 710, similar to the manner in which flanges 3016A, 3016B contact cam surfaces 3026A, 3026B in the embodiment described with respect to FIGS. 6-10. The I-beam member 820 may also define a distally directed cutting element 822 that may transect tissue between the jaw members 720, 710 as the I-beam member 820 advances distally. In some embodiments, the jaw members 720, 710 may comprise tissue-contacting surfaces 730a, 730b, 732a, 732b similar to the tissue-contacting surfaces 504A, 504B, 506A, 506B described herein above with respect to FIGS. 132-137.

The proximal tissue treatment zone 706 may additionally comprise various electrodes and/or current paths for providing electrosurgical (RF) and/or other energy to tissue. The second jaw member 710 may comprise a supply electrode 848 positioned around the channel 810. See e.g., FIGS. 153-155 and 157. The supply electrode 848 may be in electrical communication with a generator for providing RF energy, such as the generator 3002 described herein above. For example, the supply electrode 848 may be coupled to one or more supply connector leads 846. The supply connector leads 846 may extend distally through a shaft assembly to a tool interface 302 and/or handle 2500 and ultimately to a generator, such as the generator 3002 or an internal generator, as described herein. The supply electrode 848 may be electrically insulated from other elements of the end effector 700. For example, referring to FIGS. 10, the supply electrode (indicated on either side of the channel 810 by 848a and 848b) may be positioned on an insulating layer 844 (again indicated on either side of the channel 810 by 844a, 844b). The insulating layer 844 may be made of any suitable insulating material, such as ceramic, TEFLON, etc. In some embodiments, the insulating layer 844 may be applied as a coating to the jaw member 710. The supply electrode 848 may operate in conjunction with a return path to apply bipolar RF energy to tissue, such as tissue 762 shown in FIG. 159. Current provided via the supply electrode 848 may flow through the tissue 762 and return to the generator via the return path. The return path may comprise various electrically conducting components of the end effector 700. For example, in some embodiments, the return path may comprise bodies of the first and second jaws 720, 710, the I-beam member 820, the tissue-contacting surfaces 730a, 730b, 732a, 732b, etc.

In the illustrated embodiments, the supply electrode 848 is offset from the return path. For example, the supply electrode 848 is positioned such that when the jaw members 720, 710 are in the closed position illustrated in FIG. 159, the electrode 848 is not in electrical contact (e.g., physical contact) with conductive portions of the end effector 700 that may serve and a return path for RF current. For example, the first jaw member 720 may comprise an opposing member 878 (indicated in FIG. 159 as 878a and 878b on either side of the channel 812) positioned opposite the electrode 848 such that upon closure of the jaw members 720, 710, the electrode 848 is in direct contact with the opposing member 878 and not with any other portions of the end effector 700. The opposing member 878 may be electrically insulating. In this way, it may be possible to close the jaw members 720, 710 without shorting the supply electrode 848 to the return path. In some embodiments, the opposing member 878 may be selectively insulating. For example, the opposing member 878 may comprise a positive temperature coefficient (PTC) body, as described above, that is conductive below a temperature threshold (e.g., about 100° C.) and insulating at higher temperatures. In this way, the opposing member 878 may form part of the return path, but only until its temperature exceeds the temperature threshold. For example, if the supply electrode 848 were to be electrically shorted to an opposing member 878 comprising PTC or a similar material, the short would quickly drive the temperature of the opposing member 878 about the threshold, thus relieving the short.

The distal tissue treatment zone 708 may define distal grasping surfaces 790a, 790b positioned on jaw members 710, 720, respectively. The distal grasping surfaces 790a, 790b may be positioned distally from the proximally treatment zone 706. The distal grasping surfaces 790a, 790b may, in some embodiments, be configured to grasp and hold tissue. For example, the distal grasping surfaces 790a, 790b may comprise grip elements 741 for increasing friction between the grasping surfaces 790a, 790b and tissue and/or surgical implements, as described herein below. The grip elements 741 may comprise any suitable texture defined by the surfaces 790a, 790b, a friction enhancing coating applied to the surfaces 790a, 790b, etc.

In some embodiments, the distal tissue treatment zone 708 may also be configured to apply monopolar and/or bipolar electrosurgical (e.g., RF) energy. For example, the surface 790a may be and/or comprise a distal supply electrode 742. For example, the surface 790*a* itself may be made from a conductive material and therefore be the distal supply electrode 742. In some embodiments, as described herein, the conductive electrode 742 may comprise a conductive material coupled to an insulating layer 845. The insulating layer 845 may be a dielectric layer and/or a coating applied to the jaw member 710. The distal supply electrode 742 may be in electrical contact with a generator, such as the generator 3002 described herein above and/or an internal generator. In some embodiments, the distal supply electrode 742 may be in electrical contact with the supply electrode 848 of the proximal tissue treatment zone 706. In this way, the distal supply electrode 742 may be energized when the proximal supply electrode 848 is energized. In some embodiments, the distal supply electrode 742 may be energized independent of the proximal supply electrode 848. For example, the distal supply electrode 742 may be coupled to the generator via a dedicated supply line (not shown).

A return path for electrical energy provided by the distal supply electrode 742 may also comprise any suitable conductive portion of the end effector including, for example, the jaw member 710, the jaw member 720, the I-beam member 820, etc. In some embodiments, the distal grasping surface 790*b* may also form a distal return electrode 748 that may be part of the return path from the distal supply electrode 742. For example, the distal return electrode 748 may be in electrical contact with the jaw member 720 that may, in turn, be in electrical contact with a generator such as the generator 3000. The distal return electrode 748 may be formed in any suitable manner. For example, the surface 790*b* may be conductive, thus forming the electrode 748. In some embodiments, a conductive material may be applied to the surface 790*b*, where the conductive material makes up the electrode 748.

In the illustrated embodiments, the distal supply electrode 742 is not offset. For example, the distal supply electrode 742 is aligned with the return electrode 748. Accordingly, the end effector 700 may be configured such that the distal supply electrode 742 does not come into contact with the return electrode 748 when the jaw members 720, 710 are in the closed position. For example, a gap 780 may exist between the distal supply electrode 742 and the distal return electrode 748 when the jaw members 720, 710 are in a closed position. The gap 780 is visible in FIGS. 160, 161, 162, 163, 164 and 165.

In various embodiments, the gap 780 may be generated as a result of the dimensions (e.g., thickness) of various components of the proximal tissue treatment zone 706. For example, the opposing member 878 and the proximal supply electrode 848 may extend towards the axis LT such that when the electrode 848 and member 878 are in physical contact with one another (e.g., when the jaw members 720, 710 are in the closed position), the distal grasping surfaces 790*a*, *b* are not in physical contact with one another. Any suitable combination of the opposing member 878, the supply electrode 848 and the insulating layer 844 may be utilized to bring about this result.

Figure 160:
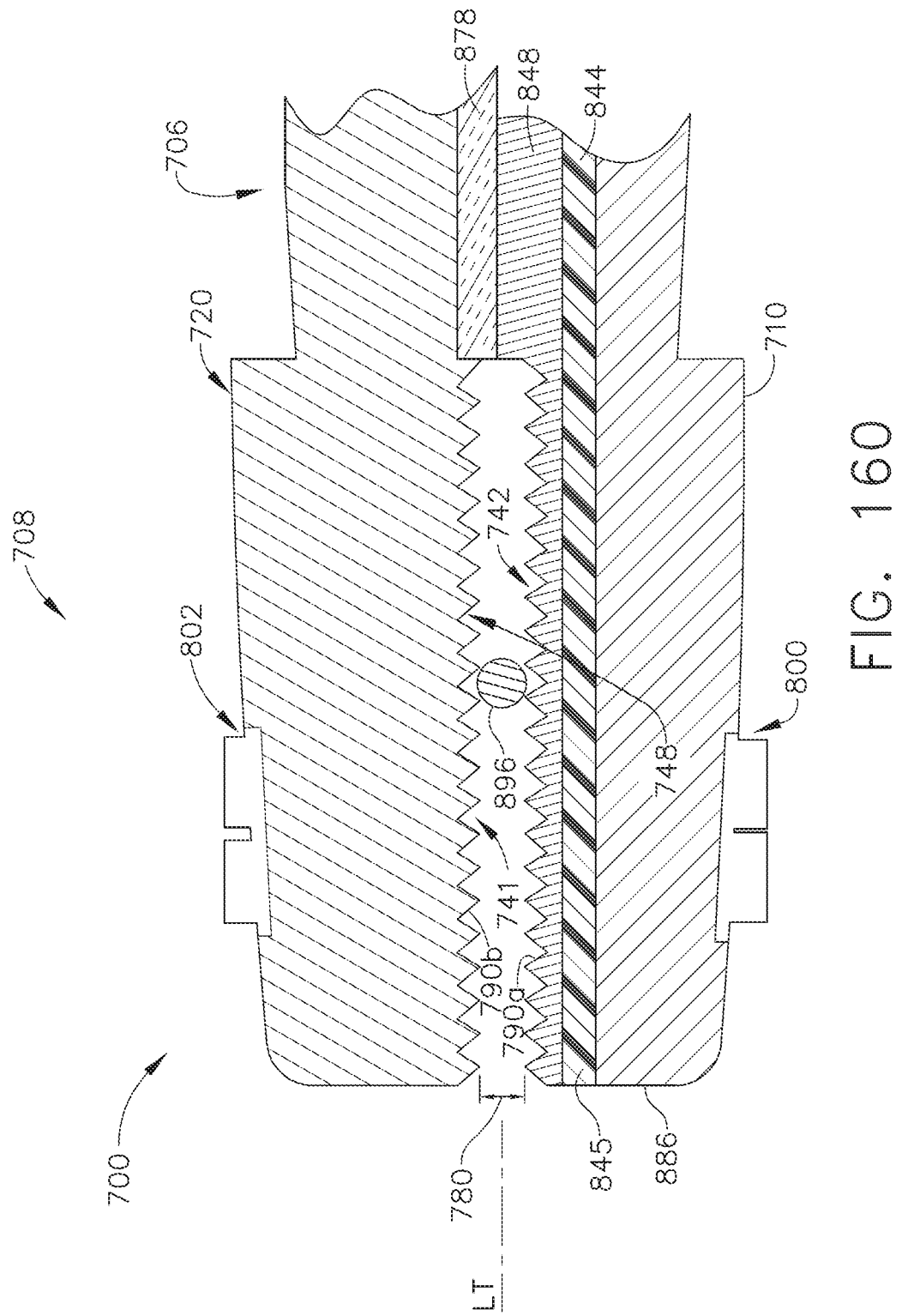
Figure 161:
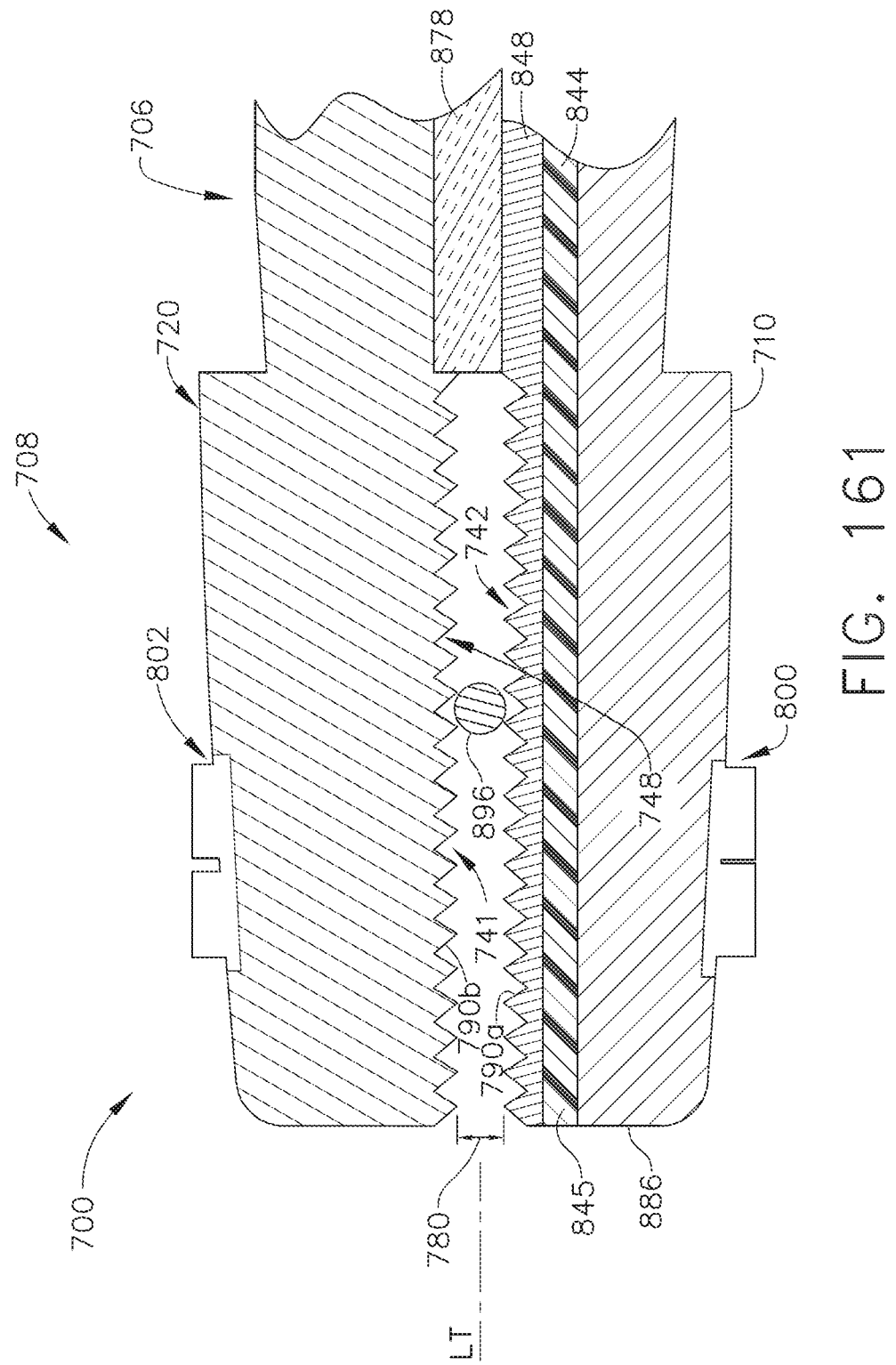
Figure 162:
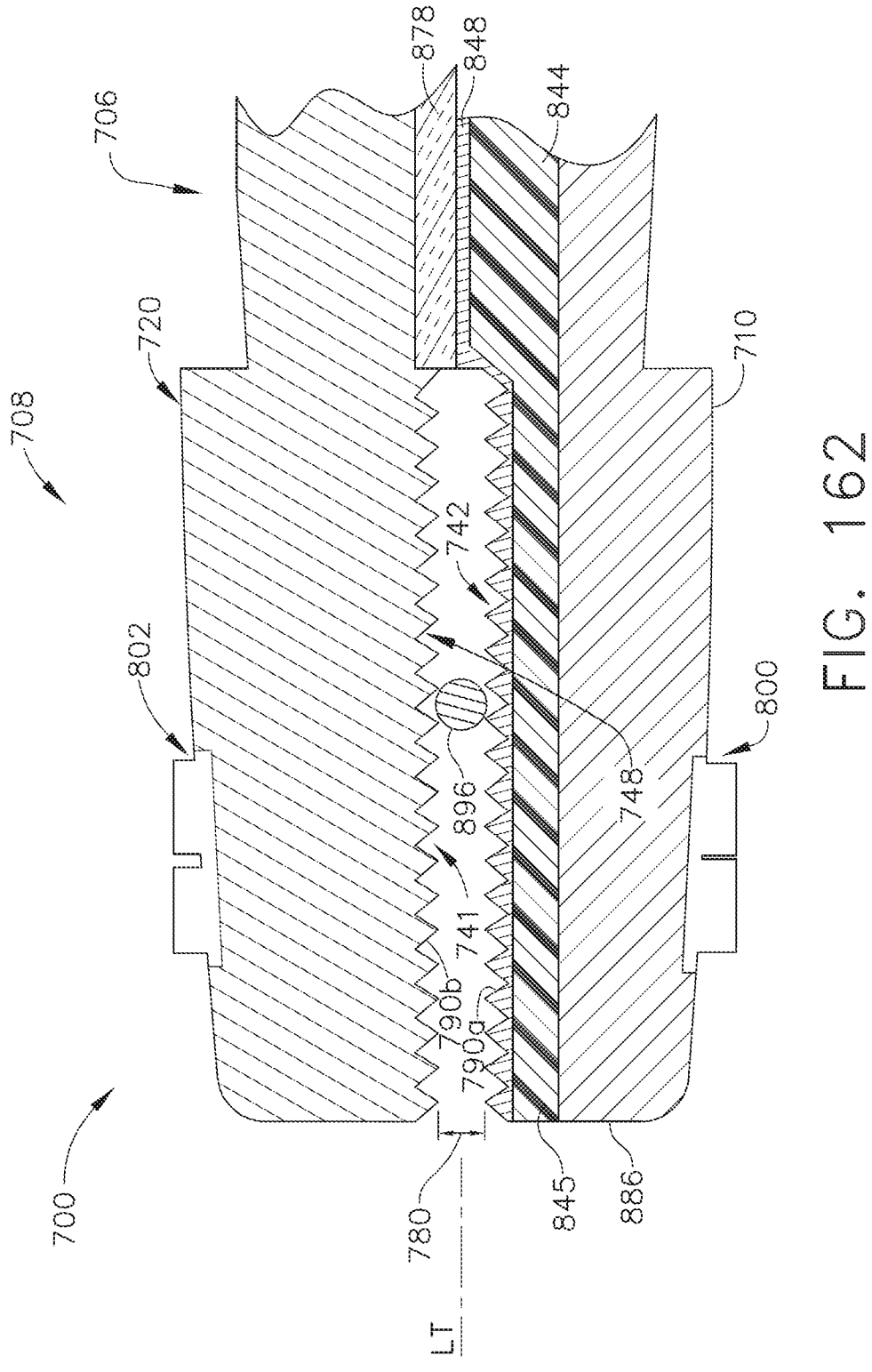
Figure 163:
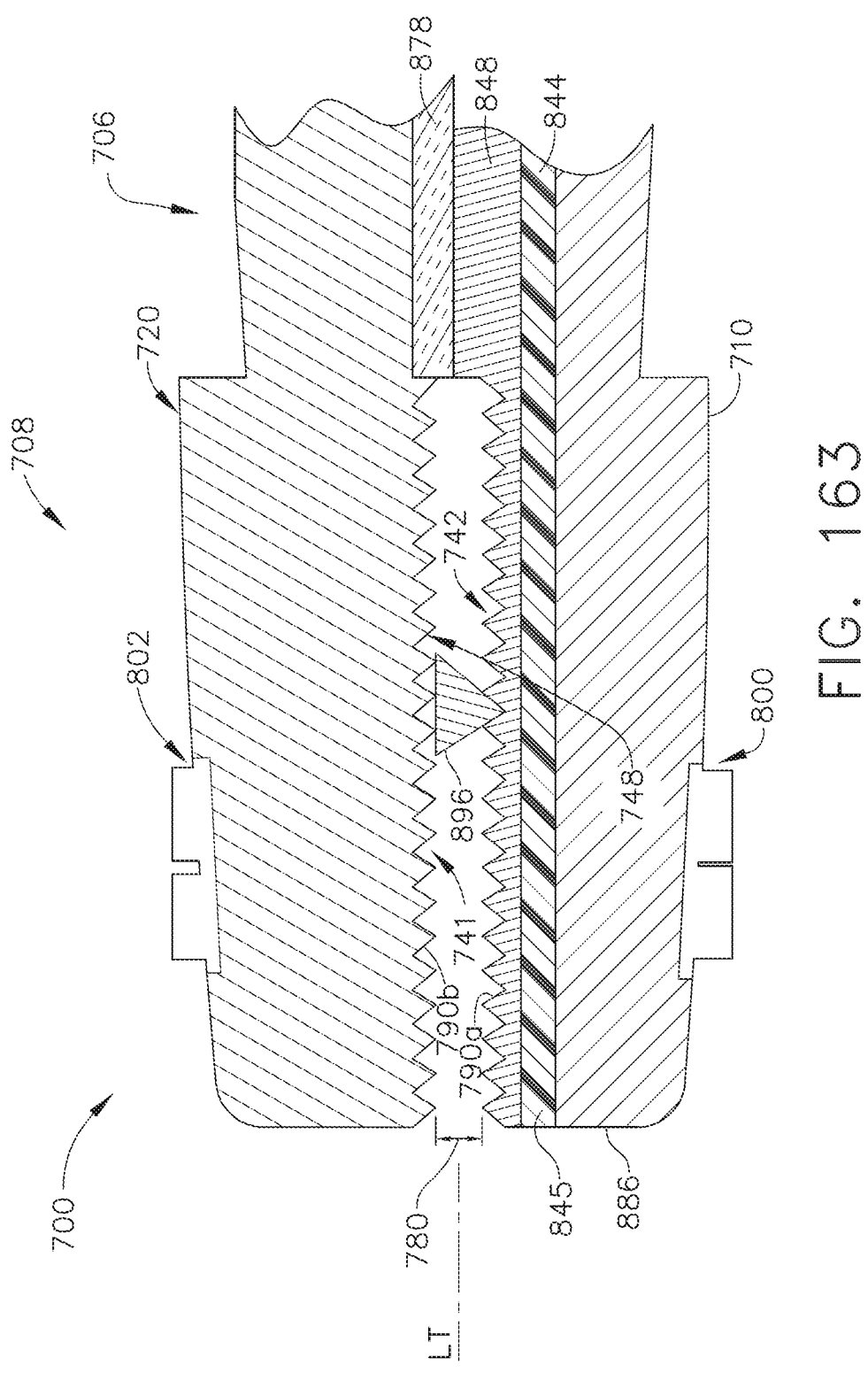
Figure 164:
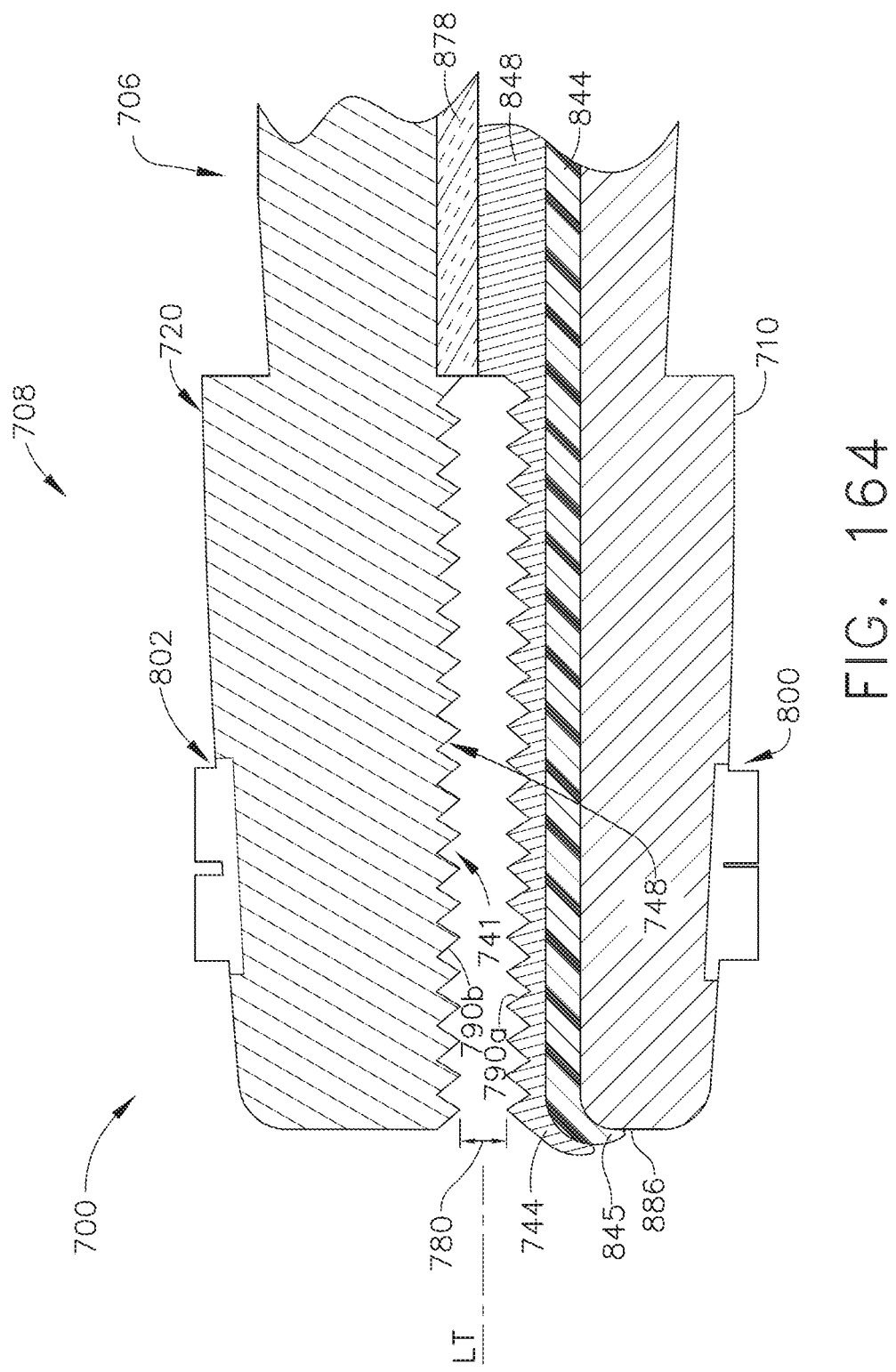

Referring now to FIGS. 160, 163 and 164, the insulating layer 844 and the insulating layer 845 may be continuous (e.g., form a continuous insulating layer). Similarly, the proximal supply electrode 848 and distal supply electrode 742 may be continuous (form a continuous electrode). The opposing member 878 is also illustrated. As illustrated, the electrode 848 (e.g., the portion of the continuous electrode in the proximal zone 706) is thicker than the electrode 742. Accordingly, when the electrode 848 contacts the opposing member 878, the thickness of the electrode 848 may prevent the distal grasping surfaces 790*a*, *b* from contacting one another, thus forming the gap 780. FIG. 161 illustrates an alternative embodiment of the end effector 700 where the electrode 742 and the electrode 848 are of the same thickness. The thickness of the opposing member 878, however, is selected such that when the electrode 848 contacts the opposing member 878, the distal grasping surfaces 790*a*, *b* do not contact one another, forming the gap 780. FIG. 162 illustrates another embodiment where the insulating layer 844 is thicker than the insulating layer 845, thus preventing contact between the distal grasping surfaces 790*a*, *b* and forming the gap 780.

In some embodiments, the distal supply electrode 742 may extend distally to a portion of a distal edge 886 of the jaw member 710. For example, FIG. 153 shows a distal electrode portion 744. The distal electrode portion 744 may be utilized by a clinician to apply electrosurgical energy to tissue that is not necessarily between the jaw members 720, 710. In some embodiments, the distal electrode portion 744 may be utilized to provide bipolar and/or monopolar cauterization. In bi-polar embodiments, the distal electrode portion 744 may utilize a return path similar to the return paths described herein. In some embodiments, the respective jaw members may comprise external depressions and/or protrusions 800, 802 similar to the protrusions described herein with respect to FIGS. 116-131. The depressions and/or protrusions 800, 802 may be conductive and may provide possible return paths for current passed via the distal electrode portion 744. In some embodiments where the distal electrode portion 744 is present, the insulating layer 845 may extend distally under the distal electrode portion, as shown in FIG. 164.

Figure 165:
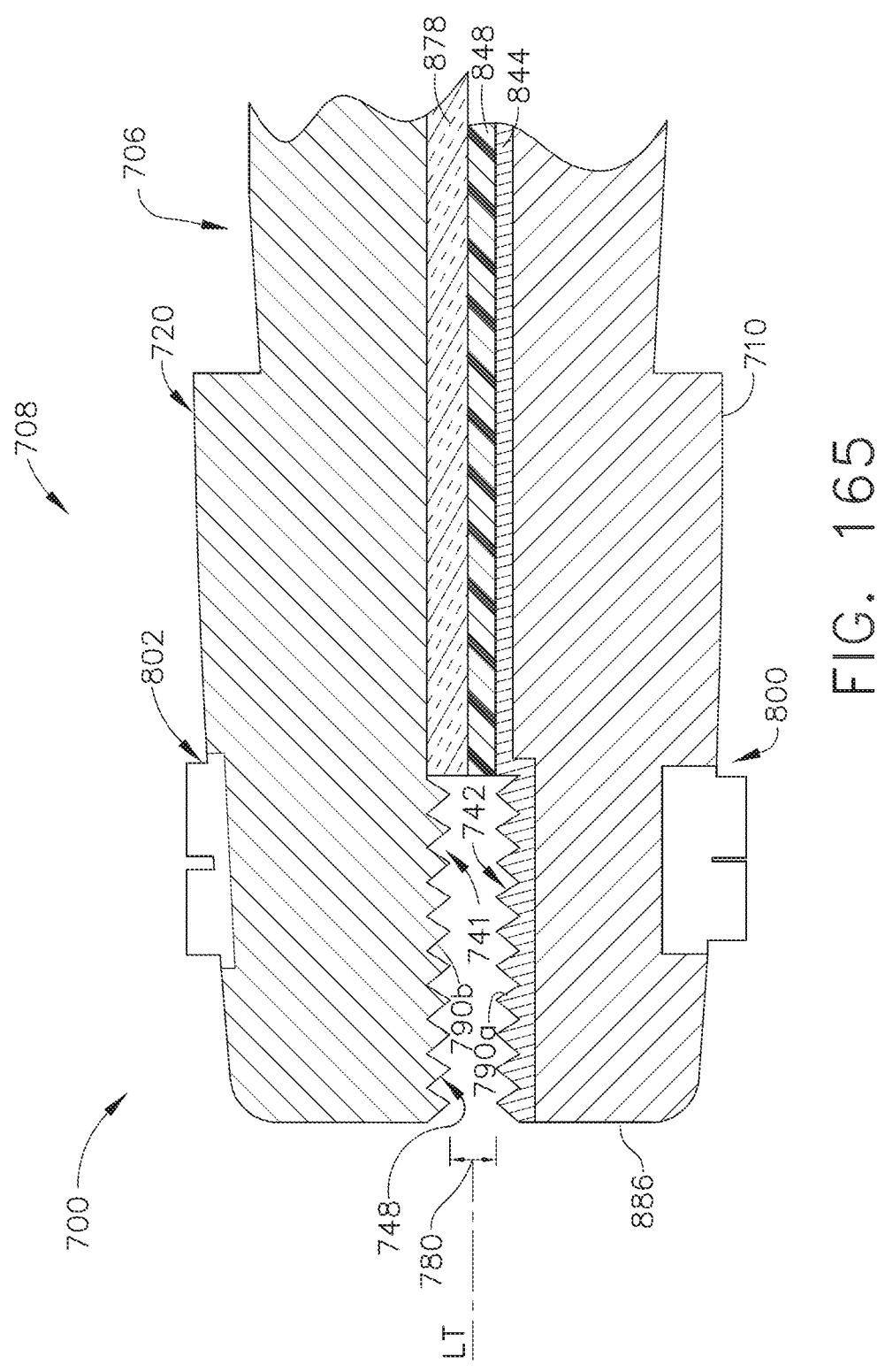

It will be appreciated that the length of the respective tissue treatment zones 706, 708 may vary with different implementations. For example, FIG. 165 shows an embodiment where the distal tissue treatment zone 708 is relatively shorter than the zone 708 shown in the other figures. For example, in FIG. 165, the distal tissue treatment zone 708 extends proximally by a lesser distance from the distal tip of the end effector 700 than the zones 708 illustrated elsewhere.

In some embodiments, the distal tissue treatment zone 708 may be utilized as a general surgical grasper. For example, the distal grasping surfaces 790*a*, *b* may be utilized to grasp and manipulate tissue. Also, in some embodiments, the distal grasping surfaces 790*a,b*, may be utilized to grasp and manipulate artificial surgical implements such as needles, clips, staples, etc. For example, FIGS. 160, 161, 162 and 163 show a surgical implement 896 secured between the distal grasping surfaces 790*a*, *b*. In FIGS. 160, 161 and 162 the surgical implement 896 has a round cross-section (e.g., a suturing needle). In FIG. 163, the surgical implement 896 has a non-round cross-section (e.g., a trailing end of a suturing needle, a clip, etc.). When used as a grasper, the distal treatment zone 708 may or may not apply electrosurgical energy to objects between the tissue surfaces 790*a*, *b*. For example, it may not be desirable to apply electrosurgical energy to a needle or other surgical implement.

It will be appreciated that, as described above, some components of the proximal tissue treatment zone 706 may be common and/or continuous with some components of the distal tissue treatment zone 708. For example, FIG. 167 illustrates one embodiment of the jaw member 710 with the electrodes 878, 742 removed to illustrate the insulating layers 845, 844. As illustrated, the insulating layers 845, 844 define a common, continuous layer 899. A distal portion of the continuous layer 899 may make up the insulating layer

845 while a proximal portion of the insulating layer 899 may make up the insulating layer 844. The insulating layer 844, as illustrated, defines a notch 897 corresponding to the channel 810, as shown, such that the I-beam member 820 may traverse the channel 810 without contacting the continuous layer 899. Also, as illustrated, the insulating layer 845 defines a distal portion 843 that extends over a part of the distal end 886 of the jaw member 710. The distal portion 843, for example, may be positioned under the distal electrode portion 744.

FIG. 166 illustrates an embodiment of the jaw member 710, as illustrated in FIG. 167, with the electrodes 742, 848 installed. As illustrated, the proximal supply electrode may comprise regions 850*a*, 850*b*, 850*c* and the opposing member 878 may comprise corresponding regions 864*a*, 864*b*, 864*c*. Regions 850*a* and 850*b* are positioned on either side of the channel 810. Region 850*c* is positioned distal from a distal-most portion of the channel 810. FIG. 168 illustrates an alternate embodiment where the third region 850*c* is omitted. Accordingly, first and second regions 850*a*, 850*b* of the electrode 848 extend distally to the distal supply electrode 742.

Non-Limiting Examples

In various embodiments, a surgical instrument can comprise an end effector and a shaft assembly coupled proximal to the end effector. The end effector comprises a first jaw member, a second jaw member, and a closure mechanism configured to move the first jaw member relative to the second jaw member between an open position and a closed position. The shaft assembly comprises an articulation joint configured to independently articulate the end effector in a vertical direction and a horizontal direction. The surgical instrument also comprises at least one active electrode disposed on at least one of the first jaw member and the second jaw member. The at least one active electrode is configured to deliver RF energy to tissue located between the first jaw member and the second jaw member when in the closed position.

In various embodiments, a surgical instrument can comprise an end effector and a shaft assembly coupled proximal to the end effector. The end effector comprises a first jaw member, a second jaw member, and a closure mechanism configured to move the first jaw member relative to the second jaw member between an open position and a closed position. The shaft assembly comprises a head rotation joint configured to independently rotate the end effector. The surgical instrument also comprises at least one active electrode disposed on at least one of the first jaw member and the second jaw member. The at least one active electrode is configured to deliver RF energy to tissue located between the first jaw member and the second jaw member when in the closed position.

A surgical tool can comprise an end effector, comprising a first jaw member, a second jaw member and a closure mechanism configured to move the first jaw member relative to the second jaw member between an open position and a closed position. The surgical tool further comprises a shaft assembly proximal to the surgical end effector, wherein the surgical end effector is configured to rotate relative to the shaft assembly, and a rotary drive shaft configured to transmit rotary motions. The rotary drive shaft is selectively movable axially between a first position and a second position relative to the shaft assembly, wherein the rotary drive shaft is configured to apply the rotary motions to the closure mechanism when in the first axial position, and wherein the rotary drive shaft is configured to apply the rotary motions to the end effector when in the second axial position. In addition, the closure mechanism of the surgical tool comprises an I-beam member configured to translate in an axial direction to cam the first jaw member toward to the second jaw member. The I-beam member is connected to a threaded rotary drive member coupled to a rotary drive nut, wherein the rotary drive shaft is configured to engage with the rotary drive nut to transmit rotary motions to the rotary drive nut. Rotary motions of the rotary drive nut actuate translation of the threaded rotary drive member and the I-beam in the axial direction. Furthermore, the first jaw member and the second jaw member comprise channels configured to slidably engage with the I-beam member, wherein rotary motions of the rotary drive nut actuate translation of the I-beam in the channels between a proximally retracted position and a distally advanced position.

A surgical tool can comprise an end effector, comprising a first jaw member, a second jaw member, and a first actuation mechanism configured to move the first jaw member relative to the second jaw member between an open position and a closed position. The surgical tool further comprises a shaft assembly proximal to the surgical end effector, and a rotary drive shaft configured to transmit rotary motions. The rotary drive shaft is selectively moveable between a first position and a second position relative to the shaft assembly, wherein the rotary drive shaft is configured to engage and selectively transmit the rotary motions to the first actuation mechanism when in the first position, and wherein the rotary drive shaft is configured to disengage from the actuation mechanism when in the second position. In addition, the first actuation mechanism comprises an I-beam member configured to translate in an axial direction to cam the first jaw member toward to the second jaw member, the I-beam member connected to a threaded rotary drive member coupled to a rotary drive nut, wherein the rotary drive shaft is configured to engage with the rotary drive nut to transmit rotary motions to the rotary drive nut, and wherein rotary motions of the rotary drive nut actuate translation of the threaded rotary drive member and the I-beam in the axial direction. Furthermore, the first jaw member and the second jaw member comprise channels configured to slidably engage with the I-beam member, and wherein rotary motions of the rotary drive nut actuate translation of the I-beam in the channels between a proximally retracted position and a distally advanced position.

A surgical tool can comprise an end effector comprising a first jaw member, and a second jaw member, wherein the first jaw member is movable relative to the second jaw member between an open position and a closed position. The surgical tool also comprises first and second actuation mechanisms, and a clutch member configured to selectively engage and transmit rotary motion to either the first or the second actuation mechanism. In addition, the first actuation mechanism comprises an I-beam member configured to translate in an axial direction to cam the first jaw member toward the second jaw member, the I-beam member connected to a threaded rotary drive member coupled to a rotary drive nut, wherein the clutch member is configured to engage with the rotary drive nut to transmit rotary motions to the rotary drive nut, and wherein rotary motions of the rotary drive nut actuates translation of the threaded rotary drive member and the I-beam in the axial direction. Furthermore, the first jaw member and the second jaw member comprise channels configured to slidably engage with the I-beam member, and wherein rotary motions of the rotary drive nut actuate translation of the I-beam in the channels between a proximally retracted position and a distally advanced position.

A surgical tool can comprise an interchangeable end effector, a handle assembly and a shaft assembly. The interchangeable end effector comprises a first jaw member including a first electrode and a second jaw member including a second electrode. The first jaw member is moveable relative to the second jaw member between a first position and a second position. The handle assembly is proximal to said surgical end effector. The shaft assembly extends between the handle assembly and the interchangeable end effector. The shaft assembly comprises a rotary drive shaft configured to transmit rotary motions. The rotary drive shaft is selectively axially moveable relative to the shaft assembly between a plurality of discrete positions. A coupling arrangement can releasably attach the interchangeable end effector to the shaft assembly.

A surgical tool can comprise an interchangeable end and a shaft assembly. The interchangeable end may comprise a first jaw member including a first electrode, a second jaw member including a second electrode, a closure mechanism configured to move the first jaw member relative to the second jaw member between a first position and a second position, and an actuation driver configured to drive the closure mechanism. The shaft assembly extends proximal to the interchangeable end effector and comprises a rotary drive shaft configured to transmit rotary motions to the actuation driver. A coupling arrangement can releasably attach the interchangeable end effector to the shaft assembly.

A surgical tool can comprise, an interchangeable end effector and a shaft assembly. The end effector comprises a first jaw member including a first electrode, a second jaw member including a second electrode, a closure mechanism configured to move the first jaw member relative to the second jaw member between a first position and a second position, and an actuation driver configured to drive the closure mechanism. The shaft assembly extends proximal to the interchangeable end effector and comprises a rotary drive shaft configured to transmit rotary motions. The interchangeable end effector is releasably attached to the shaft assembly. The rotary drive shaft is selectively extendable axially to operably engage and transmit the rotary motions to the actuation driver.

A surgical end effector can comprise a first jaw member and a second jaw member. The first jaw member defines an exterior surface on a distal portion thereof. The second jaw member defines an exterior surface on a distal portion thereof. The first jaw member is moveable relative to the second jaw member between a first position and a second position. At least one of the exterior surfaces of the first and second jaw members includes a tissue gripping portion.

A surgical tool can comprise a surgical end effector, a handle assembly and a drive shaft. The surgical end effector comprises a first jaw member defining an exterior surface on a distal portion thereof and a second jaw member defining an exterior surface on a distal portion thereof. The first jaw member is moveable relative to the second jaw member between a first position and a second position. At least one of the exterior surfaces of the first and second jaw members includes a tissue gripping portion. The handle assembly is proximal to said surgical end effector. The drive shaft extends between said surgical end effector and said handle assembly and is configured to move the first jaw relative to the second jaw between the first position and the second position in response to actuation motions in the handle.

A surgical tool can comprise an actuation system, a surgical end effector and a shaft assembly. The actuation system is for selectively generating a plurality of control motions. The surgical end effector is operably coupled to said actuation system and comprises a first jaw member and a second jaw member. The first jaw member defines an exterior surface on a distal portion thereof. The second jaw member defines an exterior surface on a distal portion thereof. The first jaw member is movably supported relative to the second jaw member between an open position and a closed position in response to closure motions generated by said actuation system. At least one of the exterior surfaces of the first and second jaw members includes a tissue adhering portion. The shaft assembly is for transmitting said plurality of control motions to the surgical end effector.

An end effector can comprise a first jaw member and a second jaw member. The first jaw member is movable relative to the second jaw member between an open position and a closed position. The first jaw member comprises a first positively-angled tissue-contacting surface. The second jaw member comprises a second positively-angled tissue-contacting surface. At least one of the first jaw member and the second jaw member comprises at least one active electrode disposed on the jaw member adjacent to the positively-angled tissue-contacting surface. The at least one active electrode is configured to deliver RF energy to tissue located between the first jaw member and the second jaw member when in the closed position.

An end effector can comprise a first jaw member and a second jaw member. The first jaw member is movable relative to the second jaw member between an open position and a closed position. The first jaw member comprises a first positively-angled tissue-contacting surface and a first negatively-angled tissue-contacting surface. The second jaw member comprises a second positively-angled tissue-contacting surface and a second negatively-angled tissue-contacting surface. The first positively-angled tissue-contacting surface opposes the second negatively-angled tissue-contacting surface when the first and second jaw members are in the closed position. The first negatively-angled tissue-contacting surface opposes the second positively-angled tissue-contacting surface when the first and second jaw members are in the closed position.

An end effector can comprise a first jaw member and a second jaw member. The first jaw member is movable relative to the second jaw member between an open position and a closed position. The first jaw member comprises a first proximal tissue-contacting portion, a first distal textured portion adjacent to the first proximal tissue-contacting portion, a first positively-angled tissue-contacting surface disposed along the first proximal tissue-contacting portion, and at least one first electrode located in the first proximal tissue-contacting portion adjacent to the first positively-angled tissue-contacting surface. The second jaw member comprises a second proximal tissue-contacting portion, a second distal textured portion adjacent to the second proximal tissue-contacting portion, a second positively-angled tissue-contacting surface disposed along the second proximal tissue-contacting portion, and at least one second electrode located in the second proximal tissue-contacting portion adjacent to the second positively-angled tissue-contacting surface. The at least one first electrode and the at least one second electrode are in a bipolar configuration to deliver RF energy to tissue located between the first jaw member and the second jaw member when in the closed position.

A surgical tool can comprise an end effector. The end effector can comprise first and second jaw members, a shaft assembly, a rotatable drive shaft, a first electrical contact and a second electrical contact. The first and second jaw members are pivotable relative to one another from an open position to a closed position. An electrode is positioned on the first jaw member. The shaft assembly extends proximally from the end effector, is at least partially hollow, and defines an inner wall. The rotatable drive shaft extends proximally within the shaft assembly. The first electrical contact is coupled to the inner wall of the shaft assembly and positioned around at least a portion of the drive shaft. The second electrical contact is coupled to and rotatable with the drive shaft. The second electrical contact is positioned to be electrically connected to the first electrical contact as the drive shaft rotates.

A surgical end effector for use with a surgical tool can comprise a first jaw member and a second jaw member. The second jaw member is pivotable relative to the first jaw member from a first open position to a closed position, where the first and second jaw members are substantially parallel in the closed position. The second jaw member comprises an offset proximal supply electrode and a distal supply electrode. The offset proximal supply electrode is positioned to contact an opposing member of the first jaw member when the first and second jaw members are in the closed position. The distal supply electrode is positioned distal of the offset proximal electrode and is aligned with a conductive surface of the first jaw member when the first and second jaw members are in the closed position. When the first and second jaw members are in the closed position, the proximal supply electrode is in contact with the opposing member and the distal supply electrode is not in contact with the conductive surface of the first jaw member.

A surgical end effector for use with a surgical tool can comprise first and second jaw members pivotable from a first open position to a closed position. The first and second jaw members define a proximal tissue treatment region and distal tissue treatment region. The second jaw member comprises, in the proximal tissue treatment region, an offset proximal supply electrode positioned such that when the jaw members are in the closed position the proximal supply electrode is in physical contact with the first jaw member and is not in electrical contact with the first jaw member. The second jaw member further comprises, in the distal tissue treatment region, a distal supply electrode positioned such that when the jaw members are in the closed position, the distal supply electrode is aligned with a conductive surface of the first jaw member. When the jaw members are in the closed position, the jaw members define a physical gap between the distal supply electrode and the conductive surface of the first jaw member.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although the present invention has been described herein in connection with certain disclosed example embodiments, many modifications and variations to those example embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention claimed is:

1. A surgical system, comprising:
an end effector, comprising:
a first jaw; and
a second jaw movable relative to said first jaw between an open position and a closed position;
an elongate shaft;
an articulation joint, wherein said end effector is rotatable relative to said elongate shaft about said articulation joint, and wherein said end effector is rotatable about said articulation joint along a plurality of articulation planes;
a beam movable within said end effector between a proximal position and a distal position, wherein said beam is configured to set a spacing between said first jaw and said second jaw when said beam is in said proximal position, wherein said beam is configured to maintain said spacing between said first jaw and said second jaw as said beam moves toward said distal position, and wherein said beam comprises a first engagement member configured to moveably engage said first jaw and a second engagement member configured to moveably engage said second jaw;
a pulling assembly operably coupled to said beam, wherein said pulling assembly extends distally through said elongate shaft into said articulation joint, and wherein said pulling assembly is configured to apply a tensile force to said beam; and
a pushing assembly operably coupled to said beam, wherein said pushing assembly extends distally through said elongate shaft into said articulation joint, wherein said pushing assembly is configured to apply a compressive force to said beam, and wherein said pushing assembly comprises a tube surrounding at least a portion of said pulling assembly.

2. The surgical system of claim 1, wherein said pulling assembly comprises an elongate cable.

3. The surgical system of claim 1, wherein said pushing assembly comprises a spring.

4. The surgical system of claim 3, wherein said spring defines a cylindrical outer profile.

5. The surgical system of claim 1, wherein said tube comprises cuts defined therein.

6. The surgical system of claim 1, wherein said tube comprises a pattern of recesses.

7. The surgical system of claim 1, wherein said end effector further comprises a staple cartridge, wherein said staple cartridge comprises a plurality of staples removably stored therein.

8. The surgical system of claim 7, wherein said staples are deployable from said staple cartridge based on said beam moving toward said distal position.

9. The surgical system of claim 1, wherein said beam comprises a proximal end, and wherein said pulling assembly and said pushing assembly are coupled to said proximal end of said beam.

10. The surgical system of claim 1, wherein said pushing assembly is movable distally relative to said elongate shaft to push said beam distally through said end effector.

11. A surgical system, comprising:
an end effector, comprising:
a first jaw; and
a second jaw movable relative to said first jaw between an open position and a closed position;
an elongate shaft;
an articulation joint, wherein said end effector is rotatable relative to said elongate shaft about said articulation joint, and wherein said end effector is rotatable about said articulation joint along a plurality of articulation planes;
a beam movable within said end effector between a proximal position and a distal position, wherein said beam is configured to set a spacing between said first jaw and said second jaw when said beam is in said proximal position, wherein said beam is configured to maintain said spacing between said first jaw and said second jaw as said beam moves toward said distal position, and wherein said beam comprises a first engagement member configured to moveably engage said first jaw and a second engagement member configured to moveably engage said second jaw;
a pulling assembly operably coupled to said beam, wherein said pulling assembly extends through said articulation joint, and wherein said pulling assembly is configured to apply a tensile force to said beam, wherein said pulling assembly comprises an elongate cable; and
a pushing assembly operably coupled to said beam, wherein said pushing assembly extends through said articulation joint, and wherein said pushing assembly is configured to apply a compressive force to said beam, and wherein said pushing assembly comprises an inner lumen surrounding said elongate cable.

12. A surgical stapling system, comprising:
an end effector, comprising:
an elongate channel;
an anvil rotatable relative to said elongate channel between an open position and a clamped position; and
a staple cartridge removably positioned in said elongate channel, wherein said staple cartridge comprises a plurality of staples removably stored therein;
an elongate shaft;
an articulation joint, wherein said end effector is rotatable relative to said elongate shaft about said articulation joint, and wherein said end effector is rotatable about said articulation joint along a plurality of articulation planes;
a beam member movable between a starting position and an ending position, wherein said beam member is configured to set a spacing between said elongate channel and the anvil when said beam member is in said starting position, wherein said beam member is configured to maintain said spacing and prevent said anvil from moving to said open position as said beam member moves toward said ending position, and wherein said beam member comprises a first flange configured to moveably engage said anvil and a second flange configured to moveably engage said elongate channel;
a tension assembly operably coupled to said beam member, wherein said tension assembly extends through said elongate shaft into said articulation joint, and wherein said tension assembly is configured to apply a tensile force to said beam member; and
a compression assembly operably coupled to said beam member, wherein said compression assembly extends through said elongate shaft into said articulation joint, wherein said compression assembly is configured to apply a compressive force to said beam member, and wherein said compression assembly comprises a tube surrounding at least a portion of said tension assembly.

13. The surgical stapling system of claim 12, wherein said tension assembly comprises an elongate cable.

14. The surgical stapling system of claim 13, wherein said compression assembly comprises an inner lumen surrounding said elongate cable.

15. The surgical stapling system of claim 12, wherein said compression assembly comprises a spring.

16. The surgical stapling system of claim 15, wherein said spring defines a cylindrical outer profile.

17. The surgical stapling system of claim 12, wherein said tube comprises cuts defined therein.

18. The surgical stapling system of claim 12, wherein said tube comprises a pattern of recesses.

19. The surgical stapling system of claim 12, wherein said staples are deployable from said staple cartridge based on said beam member moving toward said ending position.

20. A surgical fastening system, comprising:
an end effector, comprising:
an elongate channel;
an anvil, wherein said elongate channel and said anvil are configurable relative to one another between an open configuration and a closed configuration; and
a fastening cartridge removably positioned in said elongate channel, wherein said fastening cartridge comprises a plurality of fasteners removably stored therein;
an elongate shaft;
an articulation pivot, wherein said end effector is rotatable relative to said elongate shaft about said articulation pivot, and wherein said end effector is rotatable about said articulation pivot along a plurality of articulation planes;
a beam movable between a first position and a second position, wherein said beam is configured to maintain a gap between said fastener cartridge and said anvil when said beam is in said first position, wherein said beam is configured to maintain said gap as said beam moves toward said second position, and wherein said beam comprises a first arm configured to moveably engage said anvil and a second arm configured to moveably engage said elongate channel;
a pulling assembly operably coupled to said beam, wherein said pulling assembly extends through said elongate shaft into said articulation pivot, and wherein said pulling assembly is configured to apply a tensile force to said beam; and a pushing assembly operably coupled to said beam, wherein said pushing assembly extends through said elongate shaft into said articulation pivot, wherein said pushing assembly is configured to apply a compressive force to said beam, and wherein said pushing assembly comprises a tube surrounding at least a portion of said pulling assembly.

21. The surgical fastening system of claim 20, wherein said fasteners are deployable from said fastener cartridge based on said beam moving toward said second position.

* * * * *